US012753389B2

(12) United States Patent
Ghaffari et al.

(10) Patent No.: US 12,753,389 B2
(45) Date of Patent: Oct. 6, 2026

(54) METHODS OF CULTURING QUIESCENT HEMATOPOIETIC STEM CELLS AND TREATMENT METHODS

(71) Applicant: ICAHN SCHOOL OF MEDICINE AT MOUNT SINAI, New York, NY (US)

(72) Inventors: Saghi Ghaffari, New York, NY (US); Raymond Liang, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 985 days.

(21) Appl. No.: 17/612,487

(22) PCT Filed: May 26, 2020

(86) PCT No.: PCT/US2020/034574
§ 371 (c)(1),
(2) Date: Nov. 18, 2021

(87) PCT Pub. No.: WO2020/243105
PCT Pub. Date: Dec. 3, 2020

(65) Prior Publication Data

US 2022/0243177 A1 Aug. 4, 2022

Related U.S. Application Data

(60) Provisional application No. 62/931,126, filed on Nov. 5, 2019, provisional application No. 62/852,790, filed on May 24, 2019.

(51) Int. Cl.

| | |
|---|---|
| ***C12N 5/0789*** | (2010.01) |
| ***A61K 35/28*** | (2015.01) |
| ***A61P 7/00*** | (2006.01) |
| ***A61P 35/02*** | (2006.01) |

(52) U.S. Cl.
CPC ............ *C12N 5/0647* (2013.01); *A61K 35/28* (2013.01); *A61P 7/00* (2018.01); *A61P 35/02* (2018.01); *C12N 2501/125* (2013.01); *C12N 2501/145* (2013.01); *C12N 2501/2303* (2013.01); *C12N 2501/26* (2013.01)

(58) Field of Classification Search
CPC .......... C12N 5/0647; A61K 35/28; A61P 7/00
See application file for complete search history.

(56) References Cited

PUBLICATIONS

Leeman, Dena S., et al. "Lysosome activation clears aggregates and enhances quiescent neural stem cell activation during aging." Science 359.6381 (2018): 1277-1283. (Year: 2018).*
Cao, Yan, et al. "Autophagy regulates the cell cycle of murine HSPCs in a nutrient-dependent manner." Experimental Hematology 43.3 (2015): 229-242. (Year: 2015).*
Mercier, Francois E., Christine Ragu, and David T. Scadden. "The bone marrow at the crossroads of blood and immunity." Nature Reviews Immunology 12.1 (2012): 49-60. (Year: 2012).*
Zhao, Meng, et al. "Megakaryocytes maintain homeostatic quiescence and promote post-injury regeneration of hematopoietic stem cells." Nature medicine 20.11 (2014): 1321-1326. (Year: 2014).*
Grassinger, Jochen, et al. "Phenotypically identical hemopoietic stem cells isolated from different regions of bone marrow have different biologic potential." Blood, The Journal of the American Society of Hematology 116.17 (2010): 3185-3196. (Year: 2010).*
International Search Report and Written Opinion for corresponding PCT Application No. PCT/US2020/034574, filed May 26, 2020, dated Sep. 3, 2020.
Leeman et al., "Lyosome Activation Clears Aggregates and Enhances Quiescent Neural Stem Cell Activation During Aging", Science AAAS vol. 359:6381 (Mar. 16, 2010), pp. 1277-1283. Supplementary materials, 63 pages.
Zhang et al., "Anti-Leukemic Effects of the V-ATPase Inhibitor Archazolid A", Oncotarget vol. 6:41 (Dec. 22, 2015), pp. 43508-43528.

* cited by examiner

*Primary Examiner* — Teresa E Knight
*Assistant Examiner* — Michael Angelo Riga
(74) *Attorney, Agent, or Firm* — Troutman Pepper Locke LLP (Rochester)

(57) ABSTRACT

The present disclosure relates to a method of culturing quiescent hematopoietic stem cells. This method involves providing a culture medium and introducing, into the culture medium, quiescent hematopoietic stem cells to culture the stem cells and maintain quiescence of the stem cells. The culture medium comprises a vacuolar-$H^+$ adenosine triphosphate ATPase ("v-ATPase") inhibitor. Also disclosed are methods of treating a subject for a hematological disorder, methods of culturing leukemic stem cells, and methods of enhancing the hematopoietic reconstitution ability of a population of human hematopoietic stem cells.

16 Claims, 65 Drawing Sheets

Specification includes a Sequence Listing.

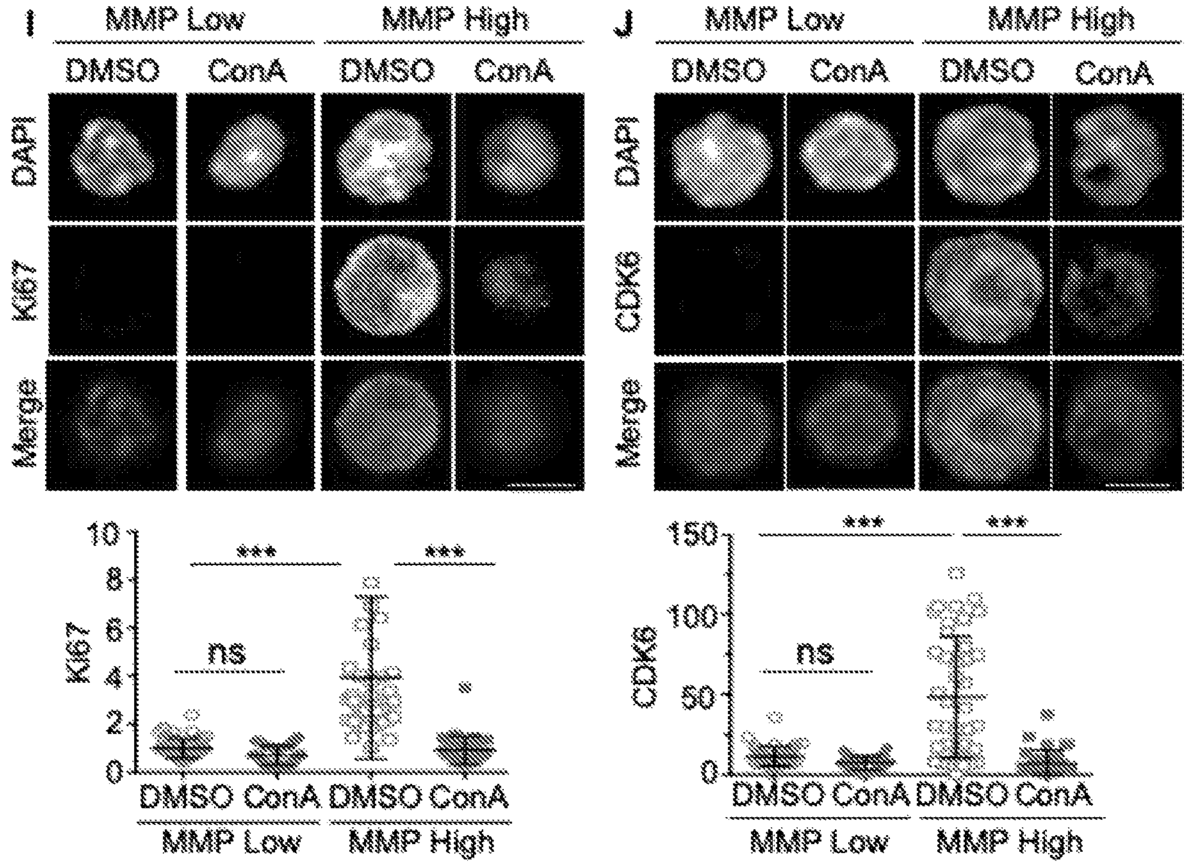
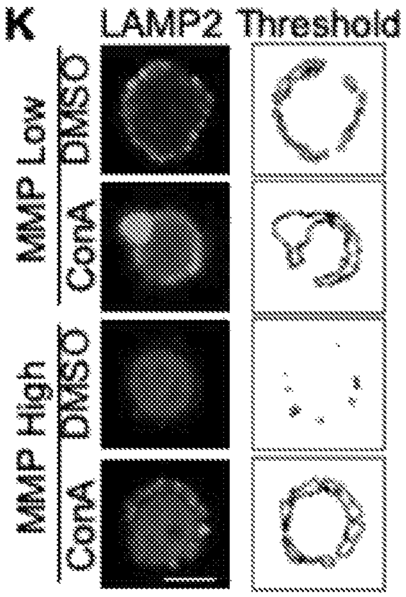
FIGs. 10I-K

% hCD45+ cells of total PB MNCs at 3, 5, 7 months post transplantation

% hCD45+ cells of total hCD45+ cells and mCD45+ cells in MNCs of BM, PB and spleen at 8 month

SEQUENCE LISTING

<160> NUMBER OF SEQ ID NOS: 32

<210> SEQ ID NO 1
<211> LENGTH: 20
<212> TYPE: DNA
<213> ORGANISM: Artificial
<220> FEATURE:
<223> OTHER INFORMATION: Gaa forward primer

<400> SEQUENCE: 1
ctacgcagga ggtcgtgtga 20

<210> SEQ ID NO 2
<211> LENGTH: 20
<212> TYPE: DNA
<213> ORGANISM: Artificial
<220> FEATURE:
<223> OTHER INFORMATION: Gaa reverse primer

<400> SEQUENCE: 2
tctgaaggcc tgcgcaatca 20

<210> SEQ ID NO 3
<211> LENGTH: 20
<212> TYPE: DNA
<213> ORGANISM: Artificial
<220> FEATURE:

<223> OTHER INFORMATION: Ctsb forward primer

<400> SEQUENCE: 3
ctcttgttgg gcatttgggg 20

<210> SEQ ID NO 4
<211> LENGTH: 20
<212> TYPE: DNA
<213> ORGANISM: Artificial
<220> FEATURE:
<223> OTHER INFORMATION: Ctsb reverse primer

<400> SEQUENCE: 4
atgctccaga gggatagcca 20

<210> SEQ ID NO 5
<211> LENGTH: 20
<212> TYPE: DNA
<213> ORGANISM: Artificial
<220> FEATURE:
<223> OTHER INFORMATION: Ctsbd forward primer

<400> SEQUENCE: 5
actcaaggta tcgcagggtg 20

<210> SEQ ID NO 6
<211> LENGTH: 20
<212> TYPE: DNA
<213> ORGANISM: Artificial
<220> FEATURE:
<223> OTHER INFORMATION: Ctsbd reverse primer

<400> SEQUENCE: 6
ttggcaaagc cgaccctatt 20

<210> SEQ ID NO 7
<211> LENGTH: 19
<212> TYPE: DNA
<213> ORGANISM: Artificial
<220> FEATURE:
<223> OTHER INFORMATION: HEXA forward primer

<400> SEQUENCE: 7
gactgcaacc tgcgctatg 19

<210> SEQ ID NO 8
<211> LENGTH: 20
<212> TYPE: DNA
<213> ORGANISM: Artificial
<220> FEATURE:
<223> OTHER INFORMATION: HEXA reverse primer

<400> SEQUENCE: 8
gtaatatcgc cgaaacgcct 20

<210> SEQ ID NO 9
<211> LENGTH: 20
<212> TYPE: DNA
<213> ORGANISM: Artificial
<220> FEATURE:
<223> OTHER INFORMATION: SMPD1 forward primer

<400> SEQUENCE: 9
accttaaccc tggctaccga 20

-continued

<210> SEQ ID NO 10
<211> LENGTH: 20
<212> TYPE: DNA
<213> ORGANISM: Artificial
<220> FEATURE:
<223> OTHER INFORMATION: SMPD1 reverse primer

<400> SEQUENCE: 10
gttggcctgg gtcagattca 20

<210> SEQ ID NO 11
<211> LENGTH: 20
<212> TYPE: DNA
<213> ORGANISM: Artificial
<220> FEATURE:
<223> OTHER INFORMATION: HK1 forward primer

<400> SEQUENCE: 11
ccgagctgaa ggatgaccaa 20

<210> SEQ ID NO 12
<211> LENGTH: 19
<212> TYPE: DNA
<213> ORGANISM: Artificial
<220> FEATURE:
<223> OTHER INFORMATION: HK1 reverse primer

<400> SEQUENCE: 12 cccctttct gagccgtcc 19

<210> SEQ ID NO 13
<211> LENGTH: 20
<212> TYPE: DNA
<213> ORGANISM: Artificial
<220> FEATURE:
<223> OTHER INFORMATION: LDH A forward primer

<400> SEQUENCE: 13
aacttggcgc tctacttgct 20

<210> SEQ ID NO 14
<211> LENGTH: 25
<212> TYPE: DNA
<213> ORGANISM: Artificial
<220> FEATURE:
<223> OTHER INFORMATION: LDH A reverse primer

<400> SEQUENCE: 14
ggactttgaa tcttttgaga ccttg 25

<210> SEQ ID NO 15
<211> LENGTH: 20
<212> TYPE: DNA
<213> ORGANISM: Artificial
<220> FEATURE:
<223> OTHER INFORMATION: Pkm2 forward primer

<400> SEQUENCE: 15
tcgcatgcag cacctgatag 20

<210> SEQ ID NO 16
<211> LENGTH: 20
<212> TYPE: DNA
<213> ORGANISM: Artificial
<220> FEATURE:
<223> OTHER INFORMATION: Pkm2 reverse primer

<400> SEQUENCE: 16
gaggtctgtg gagtgactgg 20

<210> SEQ ID NO 17
<211> LENGTH: 20
<212> TYPE: DNA
<213> ORGANISM: Artificial
<220> FEATURE:
<223> OTHER INFORMATION: Pgk1 foward primer

<400> SEQUENCE: 17
ggtgttgcca aaatgtcgct 20

<210> SEQ ID NO 18
<211> LENGTH: 20
<212> TYPE: DNA
<213> ORGANISM: Artificial
<220> FEATURE:
<223> OTHER INFORMATION: Pgk1 reverse primer

<400> SEQUENCE: 18
cagcagcctt gatcctttgg 20

<210> SEQ ID NO 19
<211> LENGTH: 20
<212> TYPE: DNA
<213> ORGANISM: Artificial
<220> FEATURE:
<223> OTHER INFORMATION: Aldoa forward primer

<400> SEQUENCE: 19
aacccagctg aataggctgc 20

<210> SEQ ID NO 20
<211> LENGTH: 19
<212> TYPE: DNA
<213> ORGANISM: Artificial
<220> FEATURE:
<223> OTHER INFORMATION: Aldoa reverse primer

<400> SEQUENCE: 20
catgggtcac cttgcctgg 19

<210> SEQ ID NO 21
<211> LENGTH: 18
<212> TYPE: DNA
<213> ORGANISM: Artificial
<220> FEATURE:
<223> OTHER INFORMATION: Glut1 forward primer

<400> SEQUENCE: 21
tcaacacggc cttcactg 18

<210> SEQ ID NO 22
<211> LENGTH: 22
<212> TYPE: DNA
<213> ORGANISM: Artificial
<220> FEATURE:
<223> OTHER INFORMATION: Glut1 reverse primer

<400> SEQUENCE: 22
cacgatgctc agataggaca tc 22

<210> SEQ ID NO 23
<211> LENGTH: 21

<212> TYPE: DNA
<213> ORGANISM: Artificial
<220> FEATURE:
<223> OTHER INFORMATION: Glut4 forward primer

<400> SEQUENCE: 23
gtaacttcat tgtcggcatg g 21

<210> SEQ ID NO 24
<211> LENGTH: 20
<212> TYPE: DNA
<213> ORGANISM: Artificial
<220> FEATURE:
<223> OTHER INFORMATION: Glut4 reverse primer

<400> SEQUENCE: 24
agctgagatc tggtcaaacg 20

<210> SEQ ID NO 25
<211> LENGTH: 20
<212> TYPE: DNA
<213> ORGANISM: Artificial
<220> FEATURE:
<223> OTHER INFORMATION: Beta-actin forward primer

<400> SEQUENCE: 25
ccctaaggcc aaccgtgaaa 20

<210> SEQ ID NO 26
<211> LENGTH: 20
<212> TYPE: DNA
<213> ORGANISM: Artificial
<220> FEATURE:
<223> OTHER INFORMATION: Beta-actin reverse primer

<400> SEQUENCE: 26
cagcctggat ggctacgtac 20

<210> SEQ ID NO 27
<211> LENGTH: 20
<212> TYPE: DNA
<213> ORGANISM: Artificial
<220> FEATURE:
<223> OTHER INFORMATION: Mt10983 forward primer

<400> SEQUENCE: 27
agctcaatct gcttacgcca 20

<210> SEQ ID NO 28
<211> LENGTH: 20
<212> TYPE: DNA
<213> ORGANISM: Artificial
<220> FEATURE:
<223> OTHER INFORMATION: Mt10983 reverse primer

<400> SEQUENCE: 28
tgtgaggcca tgtgcgatta 20

<210> SEQ ID NO 29
<211> LENGTH: 20
<212> TYPE: DNA
<213> ORGANISM: Artificial
<220> FEATURE:
<223> OTHER INFORMATION: Cox1 forward primer

<400> SEQUENCE: 29

-continued gccccagata tagcattccc 20

<210> SEQ ID NO 30
<211> LENGTH: 20
<212> TYPE: DNA
<213> ORGANISM: Artificial
<220> FEATURE:
<223> OTHER INFORMATION: Cox1 reverse primer

<400> SEQUENCE: 30
gttcatcctg ttcctgctcc 20

<210> SEQ ID NO 31
<211> LENGTH: 21
<212> TYPE: DNA
<213> ORGANISM: Artificial
<220> FEATURE:
<223> OTHER INFORMATION: NucActb forward primer

<400> SEQUENCE: 31
agctcagtaa cagtccgcct a 21

<210> SEQ ID NO 32
<211> LENGTH: 22
<212> TYPE: DNA
<213> ORGANISM: Artificial
<220> FEATURE:
<223> OTHER INFORMATION: NucActb reverse primer

<400> SEQUENCE: 32
cagagagctc accattcacc at 22

METHODS OF CULTURING QUIESCENT HEMATOPOIETIC STEM CELLS AND TREATMENT METHODS

This invention was made with government support under grant numbers R01CA205975 and R01HL136255 awarded by the National Institutes of Health. The government has certain rights in the invention.

This application is a national stage application under 35 U.S.C. § 371 of International Application No. PCT/US2020/034574, filed May 26, 2020, which claims priority benefit of U.S. Provisional Patent Application No. 62/931,126, filed Nov. 5, 2019, and U.S. Provisional Patent Application Ser. No. 62/852,790, filed May 24, 2019, which are hereby incorporated by reference in their entirety.

FIELD

Disclosed herein are methods of culturing quiescent hematopoietic stem cells and treatment methods involving cultured quiescent hematopoietic stem cells.

BACKGROUND

Hematopoietic stem cells ("HSCs") have a unique property to maintain blood homeostasis and to generate over 600 billion cells daily throughout life (Orkin et al., "Hematopoiesis: An Evolving Paradigm for Stem Cell Biology," *Cell* 132: 631-644 (2008) and Till et al., "A Direct Measurement of the Radiation Sensitivity of Normal Mouse Bone Marrow Cells," *Radiat. Res.* 14: 213-222 (1961)). This potential is sustained through the capacity of HSCs to self-renew and produce multipotent progenitors ("MPPs"). In turn, MPPs generate lineage-restricted progenitors, which produce short-lived mature cells that populate blood and are constantly replenished. HSCs also generate blood in response to loss or damage as it occurs with hemorrhage or infection (Seita et al., "Hematopoietic Stem Cell: Self-Renewal Versus Differentiation," *Wiley Interdiscip. Rev. Syst. Biol. Med.* 2: 640-653 (2010)). These functions are manifested by the ability of HSCs to restore all blood lineages in lethally irradiated mice (Till et al., "A Direct Measurement of the Radiation Sensitivity of Normal Mouse Bone Marrow Cells," *Radiat. Res.* 14: 213-222 (1961)).

Despite their immense in vivo repopulating capacity, HSCs remain quiescent for most of their lifetime, a feature shared with most adult stem cells (Bigarella et al., "Stem Cells and the Impact of ROS Signaling," *Development* 141: 4206-4218 (2014) and Chandel et al., "Metabolic Regulation of Stem Cell Function in Tissue Homeostasis and Organismal Ageing," *Nat. Cell Biol.* 18: 823-832 (2016)). HSC quiescence and in vivo self-renewal capacity are directly linked (Nakamura-Ishizu et al., "The Analysis, Roles and Regulation of Quiescence in Hematopoietic Stem Cells," *Development* 141: 4656-4666 (2014)). Tracking histone 2B-green fluorescent label retention in mice has provided the most direct evidence of an association between HSC quiescence and self-renewal capacity (Qiu et al., "Divisional History and Hematopoietic Stem Cell Function During Homeostasis," *Stem Cell Reports* 2 :473-490 (2014) and Wilson et al., "Hematopoietic Stem Cells Reversibly Switch From Dormancy to Self-Renewal During Homeostasis and Repair," *Cell* 135: 1118-1129 (2008)). Quiescence is proposed to protect HSCs from replicative and metabolic stress that would otherwise alter their health and longevity (Bigarella et al., "Stem Cells and the Impact of ROS Signaling," *Development* 141: 4206-4218 (2014) and Chandel et al., "Metabolic Regulation of Stem Cell Function in Tissue Homeostasis and Organismal Ageing," *Nat. Cell Biol.* 18: 823-832 (2016)). This is evident with aging, when quiescence is compromised leading to an increased pool of immune-phenotypically defined HSCs that are defective in stem cell potential and lineage commitment (Signer et al., "Mechanisms that Regulate Stem Cell Aging and Life Span," *Cell Stem Cell* 12: 152-165 (2013)). As a consequence, with age the overall HSC's regenerative capacity declines, which has implications for age-associated blood disorders (Rossi et al., "Stem Cells and the Pathways to Aging and Cancer," *Cell* 132: 681-696 (2008)). The underpinning mechanisms that maintain HSC quiescence are incompletely understood and whether quiescence can be restored in old HSC is undetermined.

Quiescence is intimately coupled with cellular metabolism that becomes profoundly modulated with HSC commitment (Bigarella et al., "Stem Cells and the Impact of ROS Signaling," *Development* 141: 4206-4218 (2014) and Chandel et al., "Metabolic Regulation of Stem Cell Function in Tissue Homeostasis and Organismal Ageing," *Nat. Cell Biol.* 18: 823-832 (2016)). However, the metabolic signature of HSC quiescence remains unresolved. It is postulated that quiescent HSCs restrict mitochondrial respiration and rely mainly on glycolysis for their maintenance (Simsek et al., "The Distinct Metabolic Profile of Hematopoietic Stem Cells Reflects Their Location in a Hypoxic Niche," *Cell Stem Cell* 7: 380-390 (2010); Takubo et al., "Regulation of Glycolysis by pdk Functions as a Metabolic Checkpoint for Cell Cycle Quiescence in Hematopoietic Stem Cells," *Cell Stem Cell* 12: 49-61 (2013); and Unwin et al., "Quantitative Proteomics Reveals Posttranslational Control as a Regulatory Factor in Primary Hematopoietic Stem Cells," *Blood* 107: 4687-4694 (2006)). Mitochondrial metabolism, on the other hand, is thought to promote HSC commitment and differentiation in part through enhanced production of reactive oxygen species (ROS) (Chen et al., "TSC-mTOR Maintains Quiescence and Function of Hematopoietic Stem Cells by Repressing Mitochondrial Biogenesis and Reactive Oxygen Species," *J. Exp. Med.* 205: 2397-2408 (2008); Mortensen et al., "The Autophagy Protein Atg7 is Essential for Hematopoietic Stem Cell Maintenance," *J. Exp. Med.* 208: 455-467 (2011); Tai-Nagara et al., "Mortalin and DJ-1 Coordinately Regulate Hematopoietic Stem Cell Function Through the Control of Oxidative Stress," *Blood* 123: 41-50 (2014); and Yalcin et al., "ROS-Mediated Amplification of AKT/mTOR Signaling Pathway Leads to Myeloproliferative Syndrome in Foxo3$^{(-/-)}$ Mice," *EMBO J.* 29: 4118-4131 (2010)), while lysosomal degradation and clearance of mitochondria by a selective form of autophagy—known as mitophagy—may be required for the maintenance of the HSC pool, in part by reducing ROS levels, as HSCs are greatly sensitive to oxidative stress (Ito et al., "Self-Renewal of a Purified Tie2$^{+}$ Hematopoietic Stem Cell Population Relies on Mitochondrial Clearance," *Science* 354: 1156-1160 (2016)). Lysosomes are a major component of organelle degradation and cellular recycling (Luzio et al., "The Biogenesis of Lysosomes and Lysosome-Related Organelles," *Cold Spring Harbor Perspectives In Biology* 6: a016840 (2014) and Saftig et al., "Lysosome Biogenesis and Lysosomal Membrane Proteins: Trafficking Meets Function," *Nat. Rev. Mol. Cell Biol.* 10: 623-635 (2009)). However, whether lysosomes have any specific function in HSC beyond mediating autophagy is unknown.

The present disclosure is directed to overcoming deficiencies in the art.

SUMMARY

One aspect of the disclosure relates to a method of culturing quiescent hematopoietic stem cells. This method involves providing a culture medium and introducing, into the culture medium, quiescent hematopoietic stem cells to culture the stem cells and maintain quiescence of the stem cells. The culture medium comprises a vacuolar-$H^+$ adenosine triphosphate ATPase ("v-ATPase") inhibitor.

Another aspect relates to a method of treating a subject for a hematological disorder. This method involves selecting a subject in need of treatment for a hematological disorder and administering, to the selected subject, quiescent hematopoietic stem cells of the present disclosure to treat the hematological disorder in the subject.

A further aspect relates to a method of treating a subject for a hematological disorder. This method involves selecting a subject in need of treatment for a hematological disorder and contacting hematopoietic stem cells in the selected subject with a vacuolar-H+ adenosine triphosphate ATPase ("v-ATPase") inhibitor. According to this aspect, contacting hematopoietic stem cells in the selected subject represses lysosomal activation in the contacted stem cells to treat the hematological disorder in the subject.

Yet another aspect relates to a method of treating a subject for a hematological disorder. This method involves selecting a subject in need of treatment for a hematological disorder and administering to the selected subject a vacuolar-$H^+$ adenosine triphosphate ATPase ("v-ATPase") inhibitor. According to this aspect, administering the v-ATPase to the selected subject treats the hematological disorder in the selected subject.

Another aspect relates to a method of culturing leukemic stem cells. This method involves isolating a population of Lin-$CD34^+$ cells from a subject, where the subject has leukemia, and culturing the isolated population of Lin-$CD34^+$ cells in a culture medium comprising a vacuolar-$H^+$ adenosine triphosphate ATPase ("v-ATPase") inhibitor. Culturing the isolated population of Lin-$CD34^+$ cells in the presence of the v-ATPase inhibitor can be carried out to maintain quiescence of the cells. The isolated population of Lin-$CD34^+$ cells may be cultured in the presence of an ATPase activator to activate dormant leukemic stem cells. In some embodiments, the population of Lin-$CD34^+$ cells is a population of Lin-$CD34^+CD38^-$ cells.

Another aspect relates to a method of culturing leukemic stem cells. This method involves isolating a population of Lin-$CD34^+$ cells from a subject, where the subject has leukemia, and culturing the isolated population of Lin-$CD34^+$ cells in a culture medium comprising an adenosine triphosphate ATPase ("ATPase") activator. Culturing the isolated population of Lin-$CD34^+$ cells in the presence of the ATPase activator can be carried out to activate dormant leukemic stem cells. In some embodiments, the population of Lin-$CD34^+$ cells is a population of Lin-$CD34^+CD38^-$ cells.

A further aspect relates to a method of enhancing the hematopoietic reconstitution ability of a population of human hematopoietic stem cells. This method involves providing an ex vivo population of human hematopoietic stem cells and contacting the population of human hematopoietic stem cells with an amount of a vacuolar-$H^+$ adenosine triphosphate ATPase ("v-ATPase") inhibitor effective to enhance the hematopoietic reconstitution ability of the population of human hematopoietic stem cells.

Hematopoietic stem cells produce all blood cells throughout life. This capacity is maintained by quiescence of HSCs, which become compromised with age. Quiescent HSCs are thought to rely on cytoplasmic glycolysis for their energy, but it remains unknown if mitochondrial oxidative phosphorylation contributes to the maintenance of HSC quiescence.

Mitochondrial activity has been observed to be readily detectable and heterogeneous in phenotypically defined populations of HSCs (Rimmele et al., "Mitochondrial Metabolism in Hematopoietic Stem Cells Requires Functional FOXO3," *EMBO Rep.* 16: 1164-1176 (2015); Sukumar et al., "Mitochondrial Membrane Potential Identifies Cells with Enhanced Stemness for Cellular Therapy," *Cell Metab.* 23: 63-76 (2016); and Vannini et al., "Specification of Haematopoietic Stem Cell Fate Via Modulation of Mitochondrial Activity," *Nat. Comm.* 7: 13125 (2016), which are hereby incorporated by reference in their entirety). Thus, mitochondrial metabolism may be implicated in regulating HSC quiescence.

The experimental results described herein take advantage of the heterogeneous mitochondrial activity within the phenotypically defined HSCs (Rimmele et al., "Mitochondrial Metabolism in Hematopoietic Stem Cells Requires Functional FOXO3," *EMBO Rep.* 16: 1164-1 176 (2015), which is hereby incorporated by reference in its entirety) and confirm that the majority (approximately 75%) of (LSK $CD150^+CD48^-$) HSCs contain active mitochondria (primed HSC). In addition, using a combinatorial approach that includes single-cell transcriptomics and high-resolution confocal imaging, it is shown that most, if not all, of HSCs' attributes (including self-renewal) segregate with the minor (<25%) subpopulation that display relatively low mitochondrial membrane potential (MMP; quiescent HSCs). Using intrinsic properties of primary HSCs, the molecular signature of quiescence is disclosed and primed "MMP-high" rather than quiescent "MMP-low" HSCs are shown to rely mainly on glycolysis as their source of energy. MMP-low HSCs, on the other hand, are shown to be enriched in lysosomes that maintain their quiescence. Lysosomal activation is further shown to disrupt quiescence, activate mTOR signaling, enhance glucose uptake, and prime young MMP low HSCs, which are all processes that become highly compromised in aging HSCs. Overall, the examples provided herein indicate that the coordinated exit from quiescence and priming of HSCs relies on both mitochondrial and lysosomal activation, and lysosomal inhibition restores youthful properties including quiescence in aging HSCs.

BRIEF DESCRIPTION OF THE DRAWINGS

FIG. 1A illustrates the gating strategy (n=4 mice) used to identify Lin-$CD48^-$, LSK $CD48^-$, and HSC (LSK $CD150^+CD48^-$) populations with the indicated cell surface markers (left panels). Representative flow contour plots of MMP (TMRE) and ROS (DCF) levels in indicated bone marrow populations are also shown (middle and bottom right panels; Mean±SEM of frequencies of cells in each quadrant are indicated; n=4 mice). Representative histograms of ROS levels (MFI of DCF) in indicated populations (top, right panels, n=4) and in MMP-low and MMP-high HSC subpopulations (bottom, right panels) are shown (n=2). FIG. 1B illustrates the gating strategy used for FACS sorting and analysis of LT-HSCs (LSK $CD150^+CD48^-$) within 25% bottom and top TMRE ("MMP-low" and "MMP-high," respectively) expressing HSCs. FIG. 1C shows representative histograms of TMRE staining in HSCs of bone marrow cells treated with or without Verapamil (25 μM, 50 μM). Frequencies of MMP fractions are displayed. FIG. 1D shows limiting dilution analysis for LTC-IC derived from freshly isolated MMP-low and MMP-high HSCs. FIG. 1E is a schematic diagram showing limiting dilution analysis of long-term in vivo competitive repopulation unit ("CRU") assay of freshly isolated MMP-low and MMP-high (CD45.1 donor) HSCs transplanted into lethally irradiated recipient (CD45.2) mice at a dose of 7 or 15 cells per mouse with $2\times10^5$ CD45.2 total bone marrow competitor cells (n=10). Results of limiting dilution assay ("LDA") are displayed; mice exhibiting <1% reconstitution at 16 weeks post-transplant were considered nonresponders (using 37% non-responder threshold, see dotted lines); CRU frequency and P values are displayed. FIGS. 1F-1G are graphs showing the contribution of donor-derived (CD45.1) cells to peripheral blood (PB) of primary (FIG. 1F) or secondary (FIG. 1G) recipient mice (CD45.2) in a long-term CRU assay at the 15-cell dose. All data are expressed as Mean±SEM (*P<0.05, P<0.01, *P<0.001).

FIGS. 2A-2B are graphs showing the lineage output of donor-derived (CD45.1) cells to peripheral blood (PB) of primary (FIG. 2A) or secondary (FIG. 2B) recipient mice (CD45.2) in a long-term CRU assay at the 15-cell dose. FIGS. 2C-2D are representative flow plots displaying the expression of endothelial protein C receptor ("EPCR") (FIG. 2C) and MMP (TMRE) levels (FIG. 2D). Quantification of EPCR fluorescence levels based on geometric mean in MMP-low and MMP-high HSCs (right). Gating of MMP fractions are identical to those seen in FIG. 1B. Converse analysis in FIG. 2D, with histograms comparing MMP levels in $EPCR^+$ and $EPCR^-$ HSCs (left) and quantification of MMP (TMRE) fluorescence (right). All data are expressed as Mean±SEM (***P<0.001) (n=3). FIG. 2E shows the results of one representative experiment showing DAPI staining and in vivo BrdU labeling of MMP-low and MMP-high HSCs (n=4).

FIG. 3A shows the cell cycle analysis (top) and quantification (bottom) of Pyronin Y and Hoechst stained MMP-low and MMP-high HSCs (LSK $CD150^+$ $CD48^-$) (n=3). FIG. 3B shows the results of single cell division assays showing the fraction of MMP-low and MMP-high $GFP^+$ HSCs undergoing the indicated number of divisions at 60 hours (n=4). FIG. 3C is a schematic of H2B-GFP label-retaining dilution of the GFP signal with each cell division. FIG. 3D shows a representative plot of H2B-GFP levels (solid line) in HSCs from 14-week doxycycline (DOX)-chased mouse against background (black) HSCs with no tetracycline-inducible construct (n=4). FIG. 3E shows histograms of H2B-GFP label retention (left) and quantification (right) in MMP-low and MMP-high HSCs (n=4). FIG. 3F shows MMP levels in H2B-$GFP^+$/$GFP^-$ HSCs (left) and geometric mean quantification (right). FIG. 3G shows the quantification of MMP fractions within label-retaining and non- label-retaining cells. Data are presented as mean±SEM (*p<0.05, p<0.01, and *p<0.001).

FIG. 4A is a schematic representation of captured single HSCs and the subsequent sequencing steps. FIG. 4B shows the number of distinct genes expressed in each MMP-low versus MMP-high HSCs (mean±SEM;***p<0.001). FIG. 4C shows the results of an in silico cell-cycle gene expression analysis. FIGS. 4D-4E show GO-term enrichment displaying "biological process" terms (FIG. 4D) or ChEA analysis (FIG. 4E) using significantly upregulated MMP-low (top) and MMP-high (bottom) HSCs as determined by MAST. FIG. 4F shows t-SNE dimensional reduction displaying relative position of MMP-low (red; light grey) and MMP-high (blue; dark grey) HSCs. FIG. 4G shows clustering of t-SNE plots with name of cluster labeled. FIG. 4H shows hierarchical clustering. FIG. 4I shows pathway analysis of catabolic and biosynthetic processes (p values, 2-sample 2-tailed Z-test).

FIG. 5A shows a boxplot representing median and quartile range of normalized expression of Cdk6 determined by single-cell RNAseq. FIG. 5B shows the results of pathway analysis of TCA, ETC, transcription initiation, lysosomal and autophagy related processes (analyses as in FIG. 4I). FIG. 5C shows representative confocal images of DAPI stained nuclei of indicated groups (top, bar=5 μm). Quantification of nuclear area, each point representing an individual MMP-low or MMP-high HSC (bottom). FIG. 5D shows principal component analysis (PCA) plots displaying relative positions of clusters determined by t-SNE. FIG. 5E shows in silico cell cycle staging of individual HSC and their relative positions on the PCA plot. FIG. 5F shows SCORPIUS analysis of the trajectory inference for linear trajectories. SCORPIUS takes as input scaled expression matrix (imputed, normalized) and list of clusters for each cell. It then counts Spearman correlation distances between cells and plots multi-dimensional scaling. SCORPIUS clusters the data with k-means clustering, and finds the shortest path through the cluster center. After that it refines the trajectory with the principal curves algorithm. FIG. 5G shows normalized ATP levels from MMP-low and MMP-high HSCs (top) and from MMP-low and MMP-high LSK and total c-Kit cells (bottom). c-Kit×3 denotes samples with three times the cell number of c-Kit cells used as a control for the sensitivity of the assay (n=3). FIG. 5H is a graph showing qRT-PCR analysis of metabolic markers in MMP-low and MMP-high HSCs (n=3). FIG. 5I is a graph showing the cell viability of glucose (2NBDG) uptake in freshly isolated MMP-low and MMP-high HSCs incubated with 2NBDG for 2 hours in glucose, pyruvate, glutamine-free medium is displayed. FIG. 5J is a graph showing the viability of cells treated as in FIG. 5I. All data are expressed as Mean±SEM (*P<0.05, P<0.01, *P<0.001).

FIG. 6A shows glucose analog (2NBDG) uptake in freshly isolated MMP-low and MMP-high HSCs incubated with 2NBDG for 2 hours in (glucose, pyruvate, glutamine)-free medium. Histograms (left) show quantification of 2NBDG uptake (mean fluorescence intensity [MFI]±SEM) (middle) and percentage of 2NBDG+ cells (right) (n=6). FIG. 6B shows glucose uptake (as in A) in HSCs treated or not with Glut1 inhibitor (STF-31, 10 mM) for 6 hours (n=3). FIG. 6C oxygen consumption rates ("OCR") and extracellular acidification rates ("ECARs") in freshly isolated MMP-low and MMP-high LSK cells (n=3). FIG. 6D is a graph showing cell viability of MMP-low and MMP-high HSCs cultured with 10 mM CHC or DMSO control for 6 hours (n=3). FIG. 6E shows glucose uptake in freshly isolated MMP-low and MMP-high HSCs treated for 18 hours with dimethyl alpha ketoglutarate (MOG; 1 mM) and methyl pyruvate (MP; 1 mM) or 2-DG (30 mM) or DMSO. Histograms (left) show quantification (MFI±SEM) (middle) and percentage of 2NBDG+ cells (right). Data are presented as mean ±SEM (*p<0.05, p<0.01, and *p<0.001).

FIG. 7A shows viability FAGS Profiles (left) of MMP-low and MMP-high HSCs cultured with or without 2-DG (50 mM) for the indicated time (middle); percentage of live cells (right, n=3). FIG. 7B is a schematic of mice (top) treated with 2-DG (750 mg/kg) every other day for 6 days; histogram of MMP (TMRE) levels (bottom left) and quantification (bottom right) (n=3). FIG. 7C are histograms showing glucose uptake in MMP-low and MMP-high HSCs from (FIG. 7B); histograms (top) and quantification (bottom). FIG. 7D shows a schematic of long-term in vivo competitive repopulation assay (top) and analysis (bottom); 2 days after transplantation, mice were treated with 2-DG (1,000 mg/kg) or PBS every other day for 30 days (n=7 mice in each group). FIG. 7E is a graph showing the lineage output as a percentage of distribution of total CD45.1 donor-derived cells in competitively repopulated mice—from (FIG. 7D). Data are presented as mean±SEM (*P<0.05, <0.01, *P<0.001).

FIG. 8A shows a workflow of mitochondrial content analysis by mtDNA. qPCR quantification of mtDNA copy number normalized to nuclear DNA (mitochondrial abundance) in indicated cells (right, n=3). FIG. 8B is a graph showing MMP levels normalized to mitochondrial abundance (n=3). FIG. 8C is a graph showing the average volume of mitochondria (TOM20) in MMP-low and MMP-high HSCs corresponding to FIG. 9A. FIG. 8D are representative IF confocal images of MMP-low and MMP-high HSCs displaying either PINK1 (left) or PARKIN (right) colocalization with mitochondria (TOM20). Colocalization was quantified based on Manders' Overlap coefficient (correlation comparing MMP-low and MMP-high HSCs (bottom, bar=5 μm). FIG. 8E is a box plot representing median and quartile range of scaled expression of Foxo3 from single cell-RNA sequencing comparing MMP-low and MMP-high HSCs. FIG. 8F shows representative IF confocal images of Foxo3 immunostaining in MMP-low and MMP-high HSCs (top) and quantification of nuclear Foxo3 fluorescence intensity (bottom, bar=5 μm, n=3). FIGS. 8G-8I show representative IF confocal images (left) and quantification of relative fluorescence intensity (n=3) of lysosomes based on LAMP1 (FIG. 8G bar=5 μm), LAMP2 (FIG. 8H), or LysoTracker Green (FIG. 8I) in live cells comparing in MMP-low and MMP-high HSCs (right, bar=5 μm). All data are expressed as Mean±SEM (*P<0.0, P<0.01, *P<0.001).

FIGS. 9A-9E are representative immunofluorescent confocal images of TOM20 (FIGS. 9A, 9B, and 9D), DRP1 (FIG. 9B), pDRP1 (FIG. 9C), LAMP1 (FIGS. 9D and 9E), and DAPI (FIGS. 9A-9E) from freshly isolated MMP-low and MMP-high HSCs. (FIGS. 9A, 9B, and 9D), DRP1 (FIG. 9B), pDRP1 (FIG. 9C), LAMP1 (FIGS. 9D and 9), LC3 (FIG. 9E), and DAPI (FIGS. 9A-9E). FIG. 9A shows TOM20 (top; bar, 2 mm) and quantification (bottom). FIG. 9B shows colocalization of TOM20 with DRP1 (top; bar, 5 mm) and quantification (bottom). FIG. 9C shows confocal images (left) and quantification of phospo-Drp1 (S616) total fluorescence (right; n=3, bar, 5 mm). FIG. 9D shows colocalization of TOM20 with LAMP1 (top; bar, 5 mm) in HSCs treated with leupeptin (100 mM) or DMSO control for 4 h; quantification (bottom). FIG. 9E shows colocalization of LC3 with LAMP1 (left; bar, 5 mm) in HSCs after 4-h treatment with leupeptin (100 mM) or DMSO control;

quantification and LC3 flux (right). FIG. 9F shows qRT-PCR analysis of lysosomal enzymes in freshly isolated MMP-low and MMP-high HSCs (normalized to b-actin) (n=3). Data are presented as mean±SEM (*p<0.05, p<0.01, *p<0.001).

FIGS. 10A-10K demonstrate that suppression of lysosomal activity enhances HSC quiescence and potency ex-vivo. FIGS. 10A-10E show representative confocal IF images of mTOR (FIG. 10A) and mTOR pathway-related proteins including p4EBP1 (FIG. 10B), RHEB (FIG. 10C), and RAGA/B (FIG. 10D), in freshly isolated MMP-low and MMP-high HSCs (top) and quantification of indicated protein fluorescence intensity (bottom, bar=5 μm) (n=5). FIG. 10E shows representative confocal IF images of TFEB in freshly isolated MMP-low and -MMP high HSCs (top) and quantification of indicated protein fluorescence intensity (bottom, bar=5 μm) (n=3). FIG. 10F shows representative confocal IF images of mTOR and LAMP1 and their colocalization in MMP low and MMP-high HSCs (left) and colocalization quantification (right), arrow shows colocalization of mTOR and LAMP1 respectively (n=3, bar=5 μm). FIG. 10G shows representative histograms of MMP levels in DMSO or ConA (100 nM) treated cells for 0,12, and 24 hours. Quantification of MMP based on geo. mean of TMRE levels (right)at each time point (corresponding to FIGS. 11A-11B). FIG. 10H shows a representative photomicrograph of LTC-IC-derived colonies generated from MMP-low and MMP-high HSCs treated with control DMSO or ConA (40 nM) for two days in culture. FIGS. 10I-10J show representative IF images of Ki67 (FIG. 10I, top left) and CDK6 (FIG. 10J, top right) and quantification of nuclear localized Ki67 (bottom left) and CDK6 (bottom right) in MMP-low and MMP-high HSCs treated with control DMSO or ConA (40 nM) for 18 hours; and analyzed by confocal microscopy (bar=5 μm) (n=3). FIG. 10K shows representative confocal images of IF staining of LAMP2 in MMP-low and MMP-high HSCs treated with control DMSO vs ConA (40 nM) for 18 hours (bar=2.5 μm) (n=3). All data are expressed as Mean±SEM (*P<0.05, P<0.01, *P<0.001).

FIG. 11A is a schematic of lysosomal inhibition by concanamycin A (ConA) or DMSO control on lineage cells (top). FACS profiles of HSCs treated with ConA (100 nM) or DMSO for the indicated time (bottom left) and quantification of HSC frequency (bottom right) (n=5). FIG. 11B is a graph showing the frequency of MMP-low HSCs generated from (FIG. 11A). FIG. 11C is a graph showing the results of a single-cell division assay of MMP-low and MMP-high HSCs cultured with DMSO or ConA (40 nM) for 60 h (n=3). FIG. 11D is a graph showing the results of □ a limiting dilution analysis of LTC-IC in MMP-low and MMP-high HSCs treated for 2 days in culture with ConA (40 nM) or DMSO. FIG. 11E shows a schematic illustration of an in vivo competitive repopulation assay (top). 3,000 FACS-sorted MMP-low and MMP-high (CD45.1 donor) HSCs were cultured in vitro in ConA (40 nM) or DMSO for 4 days, after which 50 cells from each group were injected into lethally irradiated recipient (CD45.2) mice along with $2\times10^5$ CD45.2 total bone marrow cells (n=7 in each group). Shown is the contribution of donor-derived (CD45.1) cells to the peripheral blood (PB) of primary recipient mice (CD45.2) over 16 weeks in an in vivo competitive repopulation assay (bottom). FIG. 11F is a graph showing the lineage output as a percentage of distribution of total CD45.1 donor-derived cells in primary recipients from FIG. 11E. Data are presented as mean±SEM (*P<0.05, P<0.01, *P<0.001).

FIG. 12A are images showing the effect of ConA treatment on lysosomal acidity measured in freshly isolated MMP-low and MMP-high HSCs incubated in StemSpan medium with ConA (40 nM) or DMSO control, or in amino acid-depleted media (Starvation, positive control) for 5 hours. After the indicated treatments, cells were stained with Lyso-Tracker green (1 μM; top) or Lysosensor blue (1 μM; bottom) at 37° C. for 30 minutes. Slides were viewed using a scanning confocal microscope. FIGS. 12B-12C show representative IF confocal images of mTOR pathway-related proteins RHEB (FIG. 12B), p4EBP1 and RAGA/B (FIG. 12CC) in MMP-low and MMP-high HSCs (left) treated with ConA (40 nM), rapamycin (Rapa, 40 nM) or DMSO control for 18 hours and their quantification of fluorescence intensity (right) (bar=5 μm) (n=3). FIG. 12D are plots showing mRFP-EGFP-LC3B bone marrow cells (n=3) cultured in StemSpan medium with either DMSO control, ConA (40 nM), Leupeptin (Leu,100 μM) or chloroquine (CQ, 40 μM) or −starved amino acid-depleted medium, for 3 hours. MMP-low and MMP-high HSCs were then analyzed for autophagosomes ($RFP^{+}GFP^{+}$) formation (corresponding to FIG. 13B). FACS profiles (top) and quantification of autophagosomes (bottom) in MMP-low and MMP-high LT-HSCs. Results adjusted to DMSO control in MMP-low HSCs (one representative of three experiments is shown). FIG. 12E shows representative high resolution IF confocal images of freshly isolated MMP-low and MMP-high HSCs treated with DMSO or ConA (40 nM); co-localization of TOM20 with LAMP1 (left, bar=5 μm); and quantification of TOM20 area (top right), LAMP1 (middle right) and colocalization of TOM20 with LAMP1 are shown (bottom right) respectively. All data are expressed as Mean±SEM (*P<0.05, P<0.01, *P<0.001).

FIG. 13A shows representative confocal images of mTOR and LAMP2 (left; bar, 5 mm; arrow shows co-localization) and quantification (right; n=3) in freshly isolated MMP-low and MMP-high HSCs treated with DMSO or ConA (40 nM) for 18 hours. FIG. 13B shows the fold change in MMP-low versus MMP-high HSCs fractions with autolysosomes ($RFP^{+}GFP^{-}$) (n=3; normalized to control; nd, not detected); analysis of mRFP-EGFP-LC3B BM cells cultured in DMSO or ConA (40 nM), leupeptin (100 mM), or chloroquine (40 mM) or amino acid-depleted media (starvation) for 3 hours. FIG. 13C shows representative confocal images of LC3 and LAMP1 in MMP-low and MMP-high HSCs cultured in DMSO, ConA (40 nM), leupeptin (100 mM), or chloroquine (40 mM) for 18 hours (left); quantification (right; bar, 5 mm; n=3). FIG. 13D shows representative super-resolution confocal images of TOM20, LAMP1 and their co-localization in freshly isolated MMP-low and MMP-high HSCs treated with DMSO or ConA (40 nM) (bar, 5 mm). FIG. 13E shows representative histograms (top) and quantification (bottom) of glucose uptake in MMP-low and MMP-high HSCs treated with STF-31 (10 and 20 mM), ConA (25 and 50 nM), or DMSO for 18 hours (n=2). FIG. 13F is a graph showing glycolysis (ECAR) in MMP-low and MMP-high HSCs cultured in DMSO or ConA (40 nM) for 18 hours. Data are presented as mean±SEM (n=2; *p<0.05, p<0.01, and *p<0.001).

FIG. 14A is a graph showing glucose (2NBDG) uptake in freshly isolated MMP-low and MMP-high HSCs treated with STF-31 (10, 20 μM), ConA (25 nM, 50 nM) or DMSO control for 18 hours followed by 2 hour-incubation with 2NBDG in glucose-free medium; % 2NBDG+ cells (top) and cell viability (bottom) are displayed corresponding to FIG. 13E (Mean±SEM; n=2 experiments, each with three technical replicates of HSCs pooled from 8 mice; *P<0.05, P<0.01, *P<0.001). In FIG. 14B, OXPHOS and glycolysis levels were measured by oxygen consumption rates (OCR, top) and extracellular acidification rates (ECARs, bottom) respectively, after 18 hours in MMP-low and MMP-high HSCs treated with or without ConA (40 nM) using Mito Stress or glycolysis stress test Kits from a pool of 11 mice. One representative experiment from three independent experiments is shown. FIG. 14C is a schematic illustration of a model showing that MMP-low HSCs are enriched in quiescent HSCs that exhibit punctate mitochondrial (Mito) morphology, are enriched in large lysosomes and undergo inefficient lysosomal clearance of mitochondria. Acidification and activation of lysosomes primes HSC via possibly amino acids (and mTORC1 activation). Lysosomes maintain HSC quiescence by sequestering and storing old and defective organelles and proteins; the lysosomal degradation and release of metabolites coincide with, and participate, in HSC activation and priming.

FIG. 15A shows representative histograms (top) and quantification (bottom) of MMP levels (geometric MFI of TMRE) comparing young and aging HSCs (n=3). FIG. 15J shows representative confocal images of mTOR pathway such as p4EBP1 and RAG AB in MMP-low and MMP-high HSCs from aging mice treated with ConA (40 nM) or DMSO for 18 hours (bar=2.5 μm) corresponding to FIG. 16D. FIG. 15L shows representative confocal images of mTOR pathway such as REHB (top) and quantification (bottom) in MMP-low and MMP-high HSCs (bar=2.5 μm) form young vs. aging mice (n=3). FIG. 15M shows representative confocal images (top) of mTOR pathway such as RHEB (FIG. 13H) and quantification (bottom) in MMP-low and MMP-high HSCs from aging mice treated with ConA (40 nM) or DMSO for 18 hours. FIG. 15Q is a graph showing the results of an experiment where 12 replicates at 3 dilutions ranging from 100 cells to 400 cells were deposited on the stromal layer in each well of a 96-well plate. The number of wells containing clonogenic cells after 5 weeks was determined by plating the entire contents of each well in the clonogenic assays. All confocal microscopy image quantification data are expressed as Mean±SEM (*P<0.05, P<0.01, *P<0.001) (n=3).

FIG. 18A shows CD177 expression on LSK CD150$^+$CD48$^-$ HSCs versus CD150 (left panel) and probed with TMRE (right panel). FIG. 18B shows CD177 expression on LSK CD150$^+$CD48$^-$ HSCs in 25% MMP-low HSCs (left panel) and 25% MMP-high HSCs (right panel).

FIG. 21A is a schematic of long-term in vivo competitive repopulation assay. FACS-sorted (5000) aged MMP-low and -high (CD45.2) long-term (LT) HSCs were cultured in vitro in DMSO control or Con A (40 nM) for 4 days after which 100 cells from each group were injected into lethally irradiated recipient (CD45.1) mice along with $2\times10^5$ CD45.1 total bone marrow competitor cells (n=7). FIG. 21B is a graph showing contribution of donor-derived (CD45.2) cells to the peripheral blood (PB) of primary recipient mice (CD45.1) in a long-term competitive repopulation assay. FIG. 21C is a graph showing lineage output as a percentage of total CD45.2 donor-derived cells in primary recipients. Data expressed as Mean±SEM (P<0.01, *P<0.001). Note only ConA-treated old HSCs and not control-treated HSCs generate over 1% chimerism in transplanted animals after 21 weeks.

FIGS. 24A-24 show that CD34 high fraction of cord blood CD38-CD45RA-CD90$^+$ HSCs are highly enriched for LT-HSC marker CD49f and show very low MMP profile. FIG. 24A shows the results of a gating strategy for highly primitive CD49f$^+$ HSCs.

FIG. 25A is a graph showing MMP-low or MMP-high (25% lowest or highest of the parental population) CD34$^+$ CD38$^-$CD45RA$^-$CD90$^+$ HSCs (CD90$^+$) HSCs were analyzed for their ability to form long-term colonies in vitro by limiting dilution; LTC-IC (long-term culture—initiating cells) frequency by LDA (limiting dilution analysis). FIG. 25B is a graph showing total number of LTC-IC CFC (colony forming cells) generated from 150 initially seeded cells (from MMP-low vs -high HSCs). Bars represent mean (SD); student's t-test, *p<0.05, **p<0.01.

FIG. 26A is a graph showing analysis of engraftment (the percentage of human CD45$^+$ cells in total PB MNCs) of immunocompromised NSG mice transplanted with MMP-low or -high UCB CD34$^+$CD38$^-$ CD45RA$^-$CD90$^+$ (CD90$^+$) HSCs 3, 5, 7 months post transplantation. FIG. 26B is a graph showing the engraftment ratio (the percentage of human CD45$^+$ cells in total human and mouse CD45$^+$MNCs) in BM, PB, or spleen 7 months post transplantation. Lineage analysis were performed only for transplants with engraftment ratio above 1%. Bars represent mean (SD); *P<0.05, **P<0.01, student's t-test (D, E), Mann-Whitney test (A, B).

DETAILED DESCRIPTION

Figures 1A, 1B:
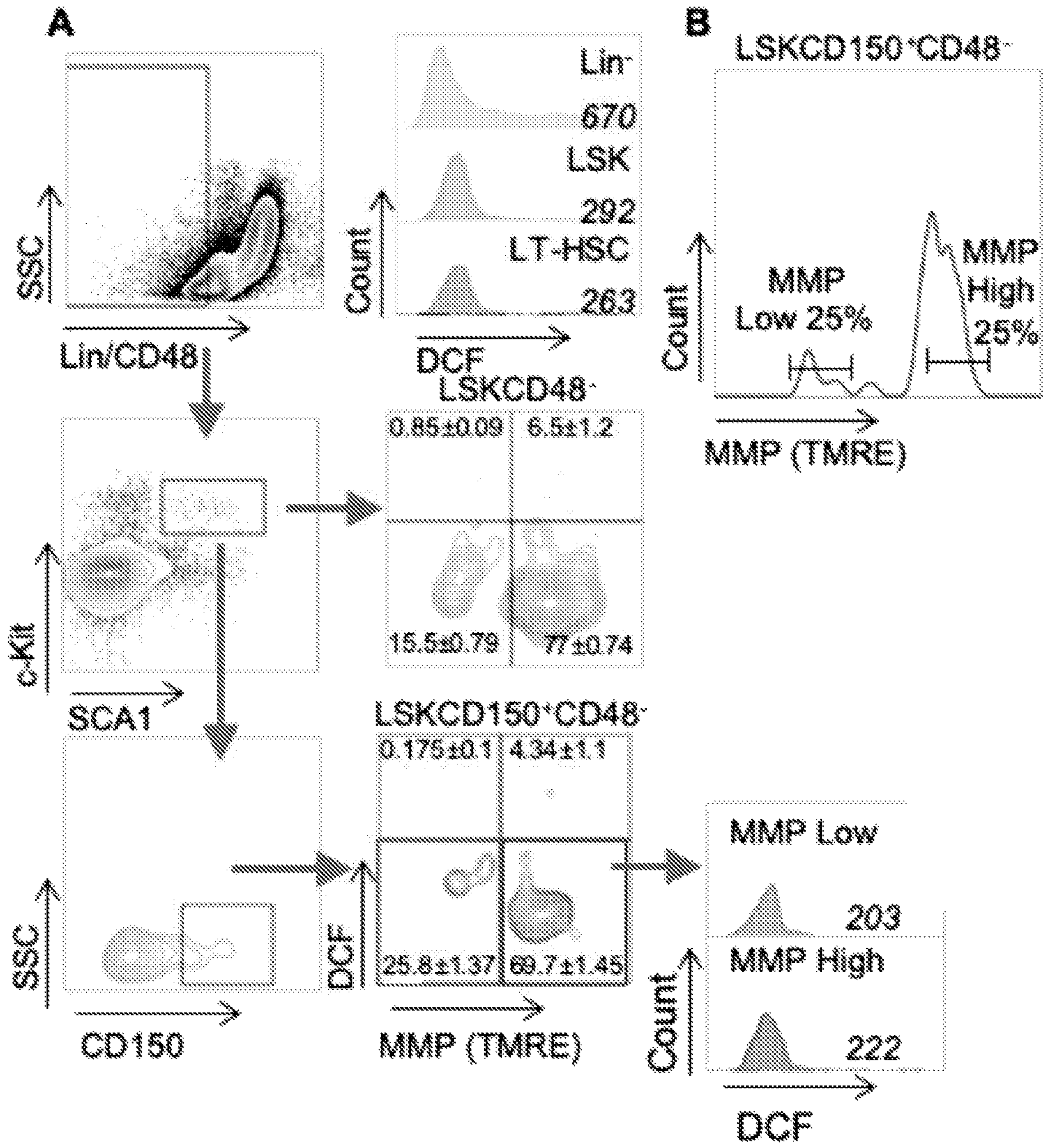
FIGS. 1A-1G demonstrate that MHC-low MHCs are enriched in in vivo competitive repopulation units.

The present disclosure relates to the identification, enrichment, and maintenance of blood forming stem cells. In particular, disclosed herein are methods of culturing quiescent hematopoietic stem cells ("HSCs") and treatment methods involving cultured quiescent hematopoietic stem cells.

One aspect relates to a method of culturing quiescent hematopoietic stem cells. This method involves providing a culture medium and introducing, into the culture medium, quiescent hematopoietic stem cells to culture the stem cells and maintain quiescence of the stem cells. The culture medium comprises a vacuolar-H$^+$ adenosine triphosphate ATPase ("v-ATPase") inhibitor.

As used herein, the term "stem cell" refers to a cell which is an undifferentiated cell capable of (i) long term self-renewal or the ability to generate at least one identical copy of the original cell, (ii) differentiation at the single cell level into multiple, and in some instances only one, specialized cell type, and/or (iii) in vivo functional regeneration of tissues. Stem cells are subclassified according to their developmental potential as totipotent, pluripotent, multipotent, and oligo/unipotent.

As used herein, the term "self-renewal" refers to the ability to produce replicate daughter stem cells having differentiation potential that is identical to those from which they arose. A similar term used in this context is "proliferation."

HSCs are functionally defined by their capacity for self-renewal, to maintain or expand the stem cell pool; multi-lineage differentiation, to generate and/or regenerate the mature lympho-hematopoietic system; and ultimately to home to the appropriate microenvironment in vivo where, through self-renewal and multi-lineage differentiation, they can restore normal hematopoiesis in a myeloablated host. As HSCs differentiate they give rise to committed hematopoietic progenitor cells with limited self-renewal capacity and an increasingly restricted lineage potential. The earliest HSC cell-fate decision involves differentiation into either a common lymphoid or a common myeloid progenitor ("CLP" and "CMP," respectively), establishing the major lymphoid and myeloid divisions of the lympho-hematopoiteic system. As the name implies, the CLP gives rise to the mature lymphoid B, T, and NK cells; and the CMP gives rise to both megakaryocyte-erythrocyte progenitors (MEPs) and granulocyte-monocyte progenitors (GMPs) that further differentiate into the mature myeloid megakaryocytic, erythroid, granulocytic and monocytic lineages.

Methods of identifying and subsequently separating differentiated cells from their undifferentiated counterparts can be carried out by methods well known in the art. Cells can be identified by selectively culturing cells under conditions whereby undifferentiated cells have a specific phenotype identifiable by fluorescence activated cell sorting ("FACS"). Similarly, differentiated cells can be identified by morphological changes and characteristics that are not present on their undifferentiated counterparts, such as cell size and the complexity of intracellular organelle distribution. Methods of identifying differentiated cells by their expression of specific cell-surface markers such as cellular receptors and transmembrane proteins may also be used. Monoclonal antibodies against these cell-surface markers can be used to identify differentiated cells. Detection of these cells can be achieved through, e.g., FACS.

From the standpoint of transcriptional upregulation of specific genes, differentiated cells often display levels of gene expression that are different from undifferentiated cells. Reverse-transcription polymerase chain reaction, or RT-PCR, also can be used to monitor changes in gene expression in response to differentiation. Whole genome analysis using microarray technology also can be used to identify differentiated cells.

Accordingly, once differentiated cells are identified, they can be separated from their undifferentiated counterparts, if necessary. The methods of identification detailed above also provide methods of separation, such as FACS, preferential cell culture methods, magnetic beads, and combinations thereof In one embodiment, FACS is used to identify and separate cells based on cell-surface antigen expression.

In some embodiments, HSCs are lineage negative (Lin$^-$). Various lineage-specific markers may be used to distinguish lineage-positive (Lin$^+$) from lineage negative (Lin$^-$) cells. Suitable lineage-specific markers include, but are not limited to, CD5 (lymphocytes), Cd11b (leukocytes), CD19 (B-cells), CD45R (lymphocytes), 7-4 (neutrophils), Ly-6G-Gr-1 (granulocytes), and TER119 (erythroid cells).

HSCs may be further phenotypically defined using various cell surface markers including, e.g., CD150 (Signaling Lymphocyte Activation Molecule 1; SLAMF1), CD48 (Signaling Lymphocyte Activation Molecule 2; SLAMF2), CD34, CD59, CD90, CD38, c-kit (CD117), CD41, CD14, Sca-1 (stem cell antigen-1), EPCR (endothelial protein C receptor), and EMCN.

In some embodiments, the HSCs are $Lin^-/Sca-1^+/c-kit^+$ (LSK). In accordance with this embodiment, the HSCs may be further phenotypically defined as LSK $CD150^+/CD48^-$ stem cells.

Methods described herein can be practiced using stem cells (i.e., HSCs) of vertebrate species, such as humans, non-human primates, domestic animals, livestock, and other non-human mammals. The HSCs may be mammalian stem cells. For example, the HSCs may be murine, human, bovine, ovine, porcine, feline, equine, murine, canine, lapine, etc.

In some embodiments, the HSCs are murine HSCs. In accordance with this embodiment, the HSCs may be $CD48^-$ (Signal Lymphocyte Activation Molecule 2; $SLAMF2^-$), $CD34^+$, $CD59^+$, $CD90^+$, $CD41^+$, $CD14^+$, $EPCR^+$, $CD150^+$, $CD34^{low/-}$, $Sca-1^+$, $CD90/Thy1^{+/low}$, $CD38^+$, $c-Kit^+$ ($CD117^+$), and/or $Lin^-$.

In some embodiments, the murine HSCs are LSK $CD150^+CD48^-CD74^+$.

In some embodiments, the murine HSCs are LSK $CD150^+CD48^-CD177^+$.

In other embodiments, the HSCs are human HSCs. In accordance with this embodiment, the HSCs may be $CD34^+$, $CD59^+$, $CD90/Thy1^+$, $CD38^{low/-}$, $c-Kit^{-/low}$, $Lin^-CD34^-CD38^-CD90^+CD45RA^-$, and/or $EPCR^+(CD201)^+$.

In some embodiments, the human HSCs are $CD74^+$ or LSK $CD150^+CD48^-CD74^+$.

In some embodiments, the human HSCs are $CD177^+$ or LSK $CD150^+CD48^-CD177^+$.

In carrying out the methods described herein, the HSCs may be peripheral blood cells, cord blood cells, bone marrow cells, amniotic fluid cells, aorta-gonad mesonephros ("AGM"), placental blood cells, or mixtures thereof.

In one embodiment, the method involves providing a culture medium comprising a v-ATPase inhibitor and introducing, into the culture medium, quiescent HSCs to culture the stem cells and maintain quiescence of the stem cells.

In another embodiment, the method involves providing a culture medium and introducing, into the culture medium, quiescent hematopoietic stem cells and a v-ATPase inhibitor, to culture the stem cells in the presence of a v-ATPase inhibitor. The v-ATPase inhibitor may be added to the culture medium concurrently with, or subsequent to introducing the hematopoietic stem cells into the culture medium.

In some embodiments, supplements to keep maintain/expand stem cells, more particularly HSCs, include those cellular factors disclosed herein or components thereof that allow maintenance/expansion of said stem cells. This may be indicated by the number of stem cells present in a given sample.

In carrying out methods described herein, HSCs can be maintained and expanded in culture medium that is available to and well-known in the art. Such media include, but are not limited to, Dulbecco's Modified Eagle's Medium® ("DMEM"), DMEM F12 Medium®, Eagle's Minimum Essential Medium®, F-12K Medium®, Iscove's Modified Dulbecco's Medium®, RPMI-1640 Medium®, and serum-free medium for culture and expansion of HSCs SFEM®. Thus, in some embodiments, the medium is a serum-free culture medium. Many media are also available as low-glucose formulations, with or without sodium pyruvate.

Also contemplated is supplementation of cell culture medium with mammalian sera. Sera often contain cellular factors and components for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at 55-65° C. if deemed necessary to inactivate components of the complement cascade.

Suitable culture mediums may comprise sodium, potassium, calcium, magnesium, phosphorus, chlorine, amino acids, vitamins, cytokines, growth factors, hormones, antibiotics, serum, fatty acids, saccharides, or the like.

Additional supplements also can be used advantageously to supply the cells with the trace elements for optimal growth and expansion. Such supplements include, without limitation, insulin, transferrin, sodium selenium, and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids. However, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Suitable cytokines may include, without limitation, interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon alpha (IFNα), interferon beta (IFNβ), interferon gamma (IFNγ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (Flt3), leukemia inhibitory factor (LIF), oncostatin M (OM), erythropoietin (EPO), and thrombopoietin (TPO). For example, the culture medium may further comprise a cytokine selected from the group consisting of SCF, Flt3, TPO, IL-3, and combinations thereof. Thus, in some embodiments, the culture medium further comprise SCF and TPO.

Suitable growth factors to be added to the culture system may include, without limitation, transforming growth factor β(TGFβ), macrophage inflammatory protein-1 alpha (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1), Wnt protein, angiopoietin-like protein 2,3,5 or 7 (Angpt 2, 3, 5 or 7), insulin-like growth factor (IGF), insulin-like growth factor binding protein (IGFBP), and Pleiotrophin.

In addition, recombinant cytokines or growth factors having an artificially modified amino acid sequence may be included in the culture system and may include, for example and without limitation, IL-6/soluble IL-6 receptor complex and Hyper IL-6 (IL-6/soluble IL-6 receptor fusion protein).

Hormones also can be advantageously used in the cell cultures described herein and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine.

Lipids and lipid carriers also can be used to supplement cell culture media, depending on the type of cell and the fate of the differentiated cell. Such lipids and carriers can include, but are not limited to, cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, and oleic acid unconjugated and conjugated to albumin, among others.

Also contemplated is the use of feeder cell layers. Feeder cells are used to support the growth of fastidious cultured cells, such as ES cells. Feeder cells are normal cells that have been inactivated by γ-irradiation. In culture, the feeder layer serves as a basal layer for other cells and supplies cellular factors without further growth or division of their own (Lim & Bodnar, "Proteome Analysis of Conditioned Medium from Mouse Embryonic Fibroblast Feeder Layers which Support the Growth of Human Embryonic Stem Cells," *Proteomics* 2(9): 1187-1203 (2002), which is hereby incorporated by reference in its entirety). Examples of feeder layer cells are typically human diploid lung cells, mouse embryonic fibroblasts, and Swiss mouse embryonic fibroblasts, but can be any post-mitotic cell that is capable of supplying cellular components and factors that are advantageous in allowing optimal growth, viability, and expansion of stem cells.

Cells in culture can be maintained either in suspension or attached to a solid support, such as extracellular matrix components. Stem cells often require additional factors that encourage their attachment to a solid support, such as type I and type II collagen, chondroitin sulfate, fibronectin, "superfibronectin" and fibronectin-like polymers, gelatin, poly-D and poly-L-lysine, thrombospondin, and vitronectin. HSCs can also be cultured in low attachment flasks, such as, but not limited to, Corning Low attachment plates.

Once established in culture, cells can be used fresh or frozen and stored as frozen stocks, using, for example, DMEM with 40% FCS and 10% DMSO. Other methods for preparing frozen stocks for cultured cells are also available to those skilled in the art.

Applicants have surprisingly found that phenotypically defined LSK $CD150^{+}/CD48^{-}$ HSCs comprise a sub-population of mitochondrial membrane potential low ("MMP-low") quiescent HSCs with high long term culture-initiating cell potential (and in vivo repopulating and self-renewal potential).

As used herein, the term "quiescent" refers to cells in the $G_0$ phase of the cell cycle. "Quiescent" cells may also include cells in a phase of the cell cycle referred to as "$G_0/G_1$," where the cells have some of the characteristics of cells in the $G_1$ phase, but have not fully entered $G_1$ phase, nor have they completely transitioned from $G_0$ phase. Thus, in some embodiments of the methods described herein, at least 90% of the stem cells are quiescent. For example, at least 90%, 91%, 92%, 93%, 94%, 95%, 96%, 97%, 98%, 99%, 99.5%, 99.5%, or 100% of the stem cells are quiescent.

In some embodiments of the methods described herein, at least 50%, 60%, 70%, 80%, or 90% of the stem cells are quiescent. For example, at least 80%, 81%, 82%, 83%, 84%, 85%, 86%, 87%, 88%, 89%, 90%, 91%, 92%, 93%, 94%, 95%, 96%, 98%, 99%, 99.5%, 99.9%, or 100% of the stem cells are quiescent. In one embodiment, at least 50%, 60%, 70%, 80%, 90%, or 100% of the stem cells are in $G_0$ phase. In another embodiment, at least 50%, 60%, 70%, 80%, 90%, or 100% of the stem cells are in $G_0/G_1$ phase.

Applicants have further unexpectedly found that treatment of quiescent HSCs with a v-ATPase inhibitor enhances quiescent HSC maintenance. Thus, treatment of quiescent HSCs with a v-ATPase inhibitor is effective to maintain the quiescent HSCs in $G_0$ phase. In some embodiments, treatment of quiescent HSCs with a v-ATPase inhibitor is effective to expand the number of quiescent HSCs in $G_0$ phase. For example, treatment of MMP-low quiescent HSCs in $G_0$ phase with a v-ATPase inhibitor is effective to maintain the quiescent HSCs in $G_0$ phase and to expand the number of quiescent HSCs in $G_0$ phase. In another example, treatment of MMP-high quiescent HSCs in $G_0/G_1$ phase with a v-ATPase inhibitor is effective to maintain the quiescent HSCs in $G_0$ phase and to increase the number of quiescent HSCs in $G_0$ phase.

The term "inhibitor" as used herein with reference to an inhibitor of V-ATPase means a molecule that inhibits the normal function of a V-ATPase (e.g., pumping protons across a vacuolar membrane). Suitable v-ATPase inhibitors are described, e.g., in Dröse et al., "Semisynthetic Derivatives of Concanamycin A and C, as Inhibitors of V- and P-Type ATPases: Structure-Activity Investigations and Developments of Photoaffinity Probes," *Biochemistry* 40: 2816-2825 (2001); Huss & Wieczorek, "Inhibitors of V-ATPases: Old and New Players," *J. Exp. Biol.* 212: 341-346 (2009); U.S. Patent Application Publication No. 2011/0237497 to Xu et al.; and U.S. Patent Application Publication No. 2008/0317857 to Farina et al., which are hereby incorporated by reference in their entirety. Suitable v-ATPase inhibitors may be selected from the group consisting of salicylihalamide A, bafilomycin A1, bafilomycin B1, bafilomycin C1, bafilomycin D, concanamycin A, concanamycin C, disulfiram, elaiophylin, 3R,4S,5R-3-O-(β-D-2-deoxyrhamnopyranosyl)-4-methyl-6-octenic acid δ-lactone (prelactone C-glycoside), 3R,4S,5R-3-hydroxy-4-methyl-6-octenic acid δ-lactone (prelactone C), 4R,5S,6R-3-O-(α-L-deoxyfucopyranosyl)-4-ethyl-hexanoic acid δ-lactone (prelactone E-glycoside), 21-deoxyconcanamycin A, 21-deoxyconcanolide A, 23-O-benzoyl-21-deoxyconcanolide A, 9-O-benzoyl-21-deoxyconcanolide A, 9-O-oleoyl-21-deoxyconcanamycin A, 3'-O-(4-azidobenzoyl)-concanamycin C, 3',4'-di-O-(4-azidobenzoyl)-concanamycin C, 3'-O-(9-anthracenoyl)-concanamycin C, 9-O-([3,5-$^{3}$H]-4-azidobenzoyl)-21-deoxy-concanamycin A, 3'-O-(9-anthracenoyl)-4',9-di-O-(4-azidobenzoyl)-concanamycin C, 3'-O-[3-(anthracen-9-yl)-propionoyl]-9-O-(4-azidobenzoyl)-concanamycin A, 3'-O-[3-(anthracen-9-yl)-propionoyl]-9-O-acetyl-21-(4-azidobenzoylperoxy)-concanamycin A, 16-demethyl-21-deoxyconcanolide A, 9,23-di-O-acetyl-16-demethyl-21-deoxyconcanolide A, 21,23-dideoxy-23-epi-chloro-concanolide A, 9-O-[p-(trifluoroethyldiazirinyl)-benzoyl]-21,23-dideoxy-23-epi-[$^{125}$I]iodo-concanolide A, Archazolid A, Archazolid B, Archazolid C, Archazolid D, 15-dehydro-archazolid A, 1-descarbamoyl-archazolid A, 7-O-p-Nitrobenzoate-archazolid A, 7-O-TB S-archazolid A, oximidine I, oximidine II, obatamide A, apicularen A, cruentaren, INDOL0 (Nadler et al., "(2Z,4E)-5-(5,6-dichloro-2-indolyl)-2-methoxy-N-(1,2,2,6,6-pentamethylpiperidin-4-yl)-2,4-pentadienamide, a Novel, Potent and Selective Inhibitor of the Osteoclast VATPase," *Bioorg. Med. Chem. Lett.* 8: 3621-3626 (1998), which is hereby incorporated by reference in its entirety), Lobatamide A, Lobatamide B, Lobatamide C, Lobatamide D, Lobatamide E, Lobatamide F, and combinations thereof.

In one embodiment, the v-ATPase inhibitor is concanamycin A.

In the methods described herein, stem cells are maintained in a culture medium to preserve quiescence of the stem cells. Maintenance may be for a period of time over a few hours, a few or several days, a week or weeks, a month or months, or even longer. For example, stem cells may be maintained over a period of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more days. In another example, stem cells are maintained for at least 1, 2, 3, 4, 5, 6, 7, 8, 9, 10, 11, 12, 13, 14, 15, 16, 17, 18, 19, 20, or more weeks. In practicing the methods described herein, the stem cells may be maintained in in vitro or ex vivo cell culture.

In some embodiments of the methods described herein, the stem cells may be stored. For example, stem cells may be stored by cryopreservation. Methods of cryopreserving stem cells are well known in the art (see, e.g., Berz et al., "Cryopreservation of Hematopoietic Stem Cells," *Am. J. Hematol.* 82(6): 463-472 (2007) and Duchez et al., "Cryopreservation of Hematopoietic Stem and Progenitor Cells Amplified ex vivo from Cord Blood CD34+ Cells," *Transfusion* 53(9): 2012-2019 (2013), which are hereby incorporated by reference in its entirety). The stem cells may be stored for a period of time over a few hours, a few or several days, a week or weeks, a month or months, a year or years, or longer. For example, stem cells may be stored for at least 1, 2, 3, 4, 5, 6, 7, 8, 9, 10, 11, or 12 months. In some embodiments, stem cells are stored for at least 1, 2, 3, 4, or 5 years.

Another aspect relates to an isolated population of quiescent hematopoietic stem cells obtained from any one of methods described herein above.

In certain embodiments, isolated populations of HSCs are quiescent and display low mitochondrial membrane potential. Such populations may be achieved, for example, by obtaining a population of HSCs, the HSCs having particular phenotypic markers, contacting the HSCs with an agent capable of distinguishing stem cells with a low mitochondrial membrane potential from stem cells with a high mitochondrial membrane potential, and separating, based on said contacting, the cells with a low mitochondrial membrane potential from the cells with a high mitochondrial membrane potential, to produce an enriched population of quiescent HSCs.

As described herein, the HSCs may be cultured or preserved in a medium comprising a V-ATPase inhibitor.

In certain other embodiments, isolated populations of HSCs achieved, for example, by obtaining a population of HSCs, the HSCs having particular phenotypic markers, contacting the HSCs with an agent capable of distinguishing stem cells that are lysosome enriched from stem cells that are lysosome depleted, and separating the lysosome enriched stem cells from the lysosome depleted stem cells, to produce an enriched population of quiescent HSCs. As described herein, the HSCs may be cultured or preserved in a medium comprising a V-ATPase inhibitor.

As discussed supra, separating HSCs can be carried out by standard methods, such as flow cytometry and/or fluorescence-activated cell sorting.

Agents capable of distinguishing stem cells with a low mitochondrial membrane potential from stem cells with a high mitochondrial membrane potential include, without limitation, tetramethlrhodamine ethyl ester perchlorate ("TMRE"), tetramethylrhodamine methyl ester ("TMRM"), JC-1, MitoTracker™, and combinations thereof.

Agents capable of distinguishing stem cells that are lysosome enriched from stem cells that are lysosome depleted include, without limitation, an anti-LAMP1 antibody, an anti-LAMP2 antibody, LysoTracker™, and derivatives and combinations thereof A further aspect relates to a method of treating a subject for a hematological disorder. This method involves selecting a subject in need of treatment for a hematological disorder and administering, to the selected subject, quiescent hematopoietic stem cells of the isolated population described herein to treat the hematological disorder in the subject.

As used herein, a "subject" is, e.g., a patient, and encompasses any animal, but preferably a mammal. In one embodiment, the subject is a human subject. Suitable human subjects include, without limitation, children, adults, and elderly subjects.

In other embodiments, the subject may be bovine, ovine, porcine, feline, equine, murine, canine, lapine, etc.

The selected subject may be in need of long-term culture initiating cells. In some embodiments, the selected subject has undergone radiation therapy, chemotherapy, and or a bone marrow transplant. In other embodiments, the selected subject is in need of a bone marrow transplant. In certain embodiments, the selected subject has an autoimmune cytopenia (e.g., thrombocytopenia purpura, pure red cell aplasia, and autoimmune neurtropenia).

In some embodiments, the hematopoietic stem cells are derived from the selected subject. Thus, the hematopoietic stem cells may be bone marrow, peripheral blood, pluripotent adult progenitor cell-derived cells, or mixtures thereof. In accordance with this embodiment, the hematopoietic stem cells are autologous HSCs.

In other embodiments, the hematopoietic stem cells are derived from a donor who is not the subject. Thus, the hematopoietic stem cells may be bone marrow, peripheral blood, pluripotent adult progenitor cell-derived cells, amniotic fluid cells, placental blood cells, cord blood cells, or mixtures thereof In accordance with this embodiment, the hematopoietic stem cells are allogenic HSCs.

In some embodiments, the selected subject may be in need of treatment for a non-malignant blood disorder, a metabolic storage disorder, or a cancer. The non-malignant blood disorder may be an immunodeficiency selected from any one or more of SCID, fanconi's anemia, aplastic anemia, and congenital hemoglobinopathy. The metabolic storage disease may be selected from any one or more of Hurler's disease, Hunter's disease, or mannosidosis. The cancer may be a hematological malignancy. Exemplary hematological malignancies include, but are not limited to, acute leukemia, chronic leukemia, lymphoma, multiple myeloma, myelodysplastic syndrome, myeloproliferative neoplasm, myelofibrosis, or non-hematological cancer. In some embodiments, the chronic leukemia is myeloid or lymphoid. In other embodiments, the lymphoma is Hodgkin's or non-Hodgkin's lymphoma. In further embodiments, the non-hematological cancer is breast carcinoma, colon carcinoma, neuroblastoma, or renal cell carcinoma.

In some embodiments, the selected subject has lost hematopoietic stem cells. For example, the selected subject may have been treated with a chemotherapeutic and/or radiation therapy. Thus, in some embodiments, the selected subject has reduced blood cell levels as compared to blood cell levels prior to treatment with the chemotherapeutic and/or radiation therapy. In accordance with this embodiment, the treatment is sufficient to restore normal blood cell levels in the selected subject.

Yet another aspect relates to a method of treating a subject for a hematological disorder. This method involves selecting a subject in need of treatment for a hematological disorder and contacting hematopoietic stem cells in the selected subject with a v-ATPase inhibitor, where the contacting represses lysosomal activation in the contacted stem cells to treat the hematological disorder in the subject.

As described above, the subject may be a mammal. In accordance with this embodiment, the subject may be a human. For example, the subject may be an elderly human.

In some embodiments, the hematological disorder is selected from the group consisting of neutropenia, lymphopenia, thrombocytopenia, anemia (Diamond-Blackfin anemia, fanconi's anemia, aplastic anemia), hemoglobinopathies, myelodysplasia, myelofibrosis, lymphomas, and leukemias.

Suitable v-ATPase inhibitors are described above.

To carry out "treating" methods described herein, isolated and purified cell populations may be present within a composition adapted for and suitable for delivery, i.e., physiologically compatible. Accordingly, the present disclosure contemplates compositions comprising HSCs cultured according to methods described herein. Such compositions may further comprise one or more buffers (e.g., neutral buffered saline or phosphate buffered saline), carbohydrates (e.g., mannose, sucrose, or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents, and/or preservatives.

In other embodiments, the HSC populations are present within a composition adapted for or suitable for freezing or storage.

The purity of the cells for administration to a subject may be about 100%. In other embodiments, purity of the cells is about 95% to about 100%. In some embodiments, purity is about 85% to about 95%. Particularly, in the case of admixtures with other cells, the percentage can be about 10%-15%, about 15%-20%, about 20%-25%, about 25%-30%, about 30%-35%, about 35%-40%, about 40%-45%, about 45%-50%, about 60%-70%, about 70%-80%, about 80%-90%, or about 90%-95%. Alternatively, isolation/purity can be expressed in terms of cell doublings where the cells have undergone, for example, about 10-20, about 20-30, about 30-40, about 40-50, or more cell doublings.

The number of cells in a given volume can be determined by well-known and routine procedures and instrumentation. The percentage of the cells in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

The choice of formulation for administering the composition for a given application will depend on a variety of factors. Prominent among these will be the species of subject, the nature of the disorder, dysfunction, or disease being treated and its state and distribution in the subject, the nature of other therapies and agents that are being administered, the optimum route for administration, survivability via the route, the dosing regimen, and other factors that will be apparent to those skilled in the art. In particular, for instance, the choice of suitable carriers and other additives will depend on the exact route of administration and the nature of the particular dosage form.

For example, cell survival can be an important determinant of the efficacy of cell-based therapies. This is true for both primary and adjunctive therapies. Another concern arises when target sites are inhospitable to cell seeding and cell growth. This may impede access to the site and/or engraftment there of therapeutic cells. Thus, measures may be taken to increase cell survival and/or to overcome problems posed by barriers to seeding and/or growth.

Final formulations may include an aqueous suspension of cells/medium and, optionally, protein and/or small molecules, and will typically involve adjusting the ionic strength of the suspension to isotonicity (i.e., about 0.1 to 0.2) and to physiological pH (i.e., about pH 6.8 to 7.5). The final formulation will also typically contain a fluid lubricant, such as maltose, which must be tolerated by the body. Exemplary lubricant components include glycerol, glycogen, maltose, and the like. Organic polymer base materials, such as polyethylene glycol and hyaluronic acid as well as non-fibrillar collagen, such as succinylated collagen, can also act as lubricants. Such lubricants are generally used to improve the injectability, intrudability, and dispersion of the injected material at the site of injection and to decrease the amount of spiking by modifying the viscosity of the compositions. This final formulation is by definition the cells described herein in a pharmaceutically acceptable carrier.

The compositions may subsequently be placed in a syringe or other injection apparatus for precise placement at a preselected site. The term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200 μ I.D.) or even 30 gauge (150 μ ID.) may be desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be more complex.

The desired isotonicity of the compositions may be accomplished using sodium chloride, or other pharmaceutically acceptable agents such as dextrose, boric acid, sodium tartrate, propylene glycol, or other inorganic or organic solutes. Sodium chloride may be preferred for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity.

Viscous compositions are normally prepared from solutions by adding thickening agents.

A pharmaceutically acceptable preservative or stabilizer can be employed to increase the life of cell/medium compositions. If such preservatives are included, it is well within the purview of the skilled artisan to select compositions that will not affect the viability or efficacy of the cells.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells/medium in the required amount of the appropriate solvent with various amounts of the other ingredients, as desired.

In some embodiments, cells/medium are formulated in a unit dosage injectable form, such as a solution, suspension, or emulsion. Pharmaceutical formulations suitable for injection of cells/medium are sterile aqueous solutions and dispersions. Carriers for injectable formulations can be a solvent or dispersing medium containing, for example, water, saline, phosphate buffered saline, polyol (e.g., glycerol, propylene glycol, liquid polyethylene glycol, and the like), and suitable mixtures thereof.

The skilled artisan can readily determine the amount of cells and optional additives, vehicles, and/or carrier in compositions to be administered in methods disclosed herein. Typically, any additives (in addition to the cells) are present in an amount of 0.001 to 50 wt % in solution, such as in phosphate buffered saline. The active ingredient is present in the order of micrograms to milligrams, such as about 0.0001 to about 5 wt %, about 0.0001 to about 1 wt %, about 0.0001 to about 0.05 wt % or about 0.001 to about 20 wt %, about 0.01 to about 10 wt %, or about 0.05 to about 5 wt %.

In some embodiments, stem cells are encapsulated for administration, particularly where encapsulation enhances the effectiveness of the therapy, or provides advantages in handling and/or shelf life. Also, encapsulation in some embodiments provides a barrier to a subject's immune system.

A wide variety of materials may be used in various embodiments for microencapsulation. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers.

Techniques for microencapsulation that may be used for administration are known to those of skill in the art and are described, for example, in Chang et al., "Encapsulation for Somatic Gene Therapy," *Ann. NY Acad. Sci.* 18(875): 146-158 (1999); Matthew et al., "Microencapsulated Hepatocytes: Prospects for Extracorporeal Liver Support," *Trans. Ann. Soc. Artif. Inter. Organs* 37(3): M328-30 (1991); Cai et al., "Microencapsulated Hepatocytes for Bioartificial Liver Support," *Artif. Organs* 12(5): 288-93 (1988); Chang, "Blood Substitutes Based on Modified Hemoglobin Prepared by Encapsulation or Crosslinking: An Overview," *Biomater. Artif. Cells Immobilization Biotechnol.* 20: 159-79 (1992), and in U.S. Pat. No. 5,639,275 (which, e.g., describes a biocompatible capsule for long-term maintenance of cells that stably express biologically active molecules), all of which are hereby incorporated by reference in their entirety. Additional methods of encapsulation are described in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943, all of which are hereby incorporated by reference in their entirety.

Certain embodiments incorporate cells (and any other desirable components, e.g., protein and/or small molecules) into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments, cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

Compositions (e.g., compositions containing cells and other desirable components) can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of cells/medium appropriate to be used in accordance with various embodiments described herein will depend on numerous factors. It may vary considerably for different circumstances. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells/medium to be effective; and such characteristics of the site such as accessibility to cells/medium and/or engraftment of cells. Additional parameters include co-administration with other factors (such as growth factors and cytokines). The optimal dose in a given situation also will take into consideration the way in which the cells/medium are formulated, the way they are administered, and the degree to which the cells/medium will be localized at the target sites following administration. Finally, the determination of optimal dosing necessarily will provide an effective dose that is neither below the threshold of maximal beneficial effect nor above the threshold where the deleterious effects associated with the dose outweighs the advantages of the increased dose.

The optimal dose of cells for some embodiments will be in the range of doses used for autologous, mononuclear bone marrow transplantation. For fairly pure preparations of cells, optimal doses in various embodiments will range from about $10^4$ to about $10^8$ cells/kg of recipient mass per administration. In some embodiments, the optimal dose per administration will be between about $10^5$ to about $10^7$ cells/kg. In many embodiments the optimal dose per administration will be about $5\times10^5$ to about $5\times10^6$ cells/kg. By way of reference, higher doses in the foregoing are analogous to the doses of nucleated cells used in autologous mononuclear bone marrow transplantation. Some of the lower doses are analogous to the number of $CD34^+$ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, cells/medium may be administered in an initial dose, and thereafter maintained by further administration. Cells/medium may be administered by one method initially, and thereafter administered by the same method or one or more different methods. The levels can be maintained by the ongoing administration of the cells/medium. Various embodiments administer the cells/medium either initially or to maintain their level in the subject or both by intravenous injection. In a variety of embodiments, other forms of administration are used, dependent upon the patient's condition and other factors, discussed elsewhere herein.

Human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regimens can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer the cells/medium.

In some embodiments cells/medium are administered to a subject in one dose. In others, cells/medium are administered to a subject in a series of two or more doses in succession. In some other embodiments where cells/medium are administered in a single dose, in two doses, and/or more than two doses, the doses may be the same or different, and they are administered with equal or with unequal intervals between them.

Cells/medium may be administered in many frequencies over a wide range of times. In some embodiments, they are administered over a period of less than one day. In other embodiments, they are administered over two, three, four, five, or six days. In some embodiments, they are administered one or more times per week, over a period of weeks. In other embodiments, they are administered over a period of weeks for one to several months. In various embodiments, they may be administered over a period of months. In others they may be administered over a period of one or more years. Generally, lengths of treatment will be proportional to the length of the disease process, the effectiveness of the therapies being applied, and the condition and response of the subject being treated.

The term "treatment" or "treating" as used herein refers to the administration of medicine or the performance of medical procedures with respect to a subject, for either prophylaxis (prevention) or to cure or reduce the extent of or likelihood of occurrence or recurrence of the infirmity or malady or condition or event in the instance where the subject or patient is afflicted. The term may also mean the administration of medicine or the performance of medical procedures as therapy, prevention, or prophylaxis of a hematological disorder.

Yet another aspect relates to a method of treating a subject of a hematological disorder. This method involves selecting a subject in need of treatment for a hematological disorder and administering to the selected subject a vacuolar-$H^+$ adenosine triphosphate ATPase ("v-ATPase") inhibitor. According to this aspect, administering the v-ATPase to the selected subject treats the hematological disorder in the selected subject.

In some embodiments, this method is effective to convert primed HSCs to quiescent HSCs in the selected subject. As described herein, converting primed HSCs to quiescent HSCs may be effective to improve HSC quality in the selected subject.

In some embodiments, this method is effective to increase the population quiescent HSCs with high long term culture-initiating cell potential in the selected subject.

Another aspect relates to a method of culturing leukemic stem cells. This method involves isolating a population of Lin-$CD34^+$ cells from a subject, where the subject has leukemia, and culturing the isolated population of Lin-$CD34^+$ cells in a culture medium comprising a vacuolar-$H^+$ adenosine triphosphate ATPase ("v-ATPase") inhibitor.

Culturing the isolated population of Lin-$CD34^+$ cells in the presence of the v-ATPase inhibitor can be carried out to maintain quiescence of the cells.

The population of Lin-$CD34^+$ cells may be a population of MMP-low leukemic stem cells.

The population of Lin-$CD34^+$ cells may be $CD38^+$or $CD38^-$. In some embodiments, the population of Lin-$CD34^+$ cells is a population of Lin-$CD34^+CD38^-$ cells.

In some embodiments, the method further involves culturing the population of Lin-$CD34^+$ cells with an ATPase activator, where the leukemic stem cells are cultured in the absence of the v-ATPase inhibitor. In accordance with this embodiment, the ATPase activator is sufficient to activate dormant leukemic stem cells. The ATPase activator may be one or more amino acids.

Another aspect relates to a method of culturing leukemic stem cells. This method involves isolating a population of Lin-$CD34^+$ cells from a subject, where the subject has leukemia, and culturing the isolated population of Lin-$CD34^+$ cells in a culture medium comprising an adenosine triphosphate ATPase ("ATPase") activator. Culturing the isolated population of Lin-$CD34^+$ cells in the presence of the ATPase activator can be carried out to activate dormant leukemic stem cells.

The population of Lin-$CD34^+$ cells may be a population of MMP-low leukemic stem cells.

The population of Lin-$CD34^+$ cells may be $CD38^+$or $CD38^-$. In some embodiments, the population of Lin-$CD34^+$ cells is a population of Lin-$CD34^+CD38^-$ cells.

The ATPase activator may be one or more amino acids.

In some embodiments, the population of MMP of Lin-$CD34^+$ cells is a population of Lin-$CD34^+CD38^-$ cells.

In some embodiments, the culturing is carried out to maintain the quiescence of the isolated population of cells.

In some embodiments, the method further involves culturing the isolated population of cells in the absence of the v-ATPase inhibitor to induce progression through the cell cycle.

In some embodiments, the method further involves culturing the isolated population of cells in the presence of a therapeutic agent.

A further aspect relates to a method of enhancing the hematopoietic reconstitution ability of a population of human hematopoietic stem cells. This method involves providing an ex vivo population of human hematopoietic stem cells and contacting the population of human hematopoietic stem cells with an amount of a vacuolar-$H^+$ adenosine triphosphate ATPase ("v-ATPase") inhibitor effective to enhance the hematopoietic reconstitution ability of the population of human hematopoietic stem cells.

In some embodiments, the hematopoietic stem cells are derived from peripheral blood cells, cord blood cells, bone marrow cells, amniotic fluid cells, placental blood cells, aorta-gonad mesonephros (AGM), induced pluripotent stem cells, embryonic stem cells, or mixtures thereof In some embodiments, contacting the population of human hematopoietic stem cells with an amount of a vacuolar-$H^+$ adenosine triphosphate ATPase ("v-ATPase") inhibitor increases the frequency of long-term culture initiating cells in the population of human hematopoietic stem cells compared to a population of human hematopoietic stem cells that is not contacted by the v-ATPase inhibitor.

In some embodiments, the method of enhancing the hematopoietic reconstitution ability of a population of human hematopoietic stem cells further involves culturing the population of human hematopoietic stem cells in the presence of the v-ATPase inhibitor. Culturing may take place over a few minutes to a few hours, or longer. For example, in some embodiments, culturing the population of human hematopoietic stem cells in the presence of the v-ATPase inhibitor is carried out for at least 1, 2, 3, or 4 hours.

In some embodiments, the contacted population of human hematopoietic stem cells is stored, e.g., until a particular use for the cells is needed, or to transport the cells. In one embodiment, storage involves freezing the cells.

The method according to this aspect may further involve selecting a subject in need of hematopoietic stem cell transplantation and introducing the contacted population of hematopoietic stem cells into the selected subject. According to one embodiment, the selected subject is conditioned for a bone marrow transplantation prior to said introducing.

In one embodiment, the contacted population of hematopoietic stem cells is autologous to the selected subject. In another embodiment, the contacted population of hematopoietic stem cells is allogenic to the selected subject.

According to one embodiment, the selected subject according to this aspect is a human subject. In some embodiments, the selected subject has a condition selected from the group consisting of an auto-immune disease, multiple sclerosis, cancer, solid tumor, hematological disorder, and hematological cancer. Specific hematological disorders may include, for example and without limitation, neutropenia, lymphopenia, thrombocytopenia, anemia, thalassemia, sickle cell disease, hemoglobinopathy, myeloma, myelodysplasia, myeloproliferative neoplasm, myelofibrosis, lymphomas, and leukemia.

According to one embodiment, the population of hematopoietic stem cells is from a human subject, and may be from an infant, a child, an adolescent, an adult, or a geriatric adult.

Another aspect relates to a population of enhanced human hematopoietic stem cells obtained from the methods described herein.

A further aspect relates to a method of promoting hematopoietic reconstitution of hematopoietic stem cells in a human subject in need thereof. This method involves administering to the human subject the population of enhanced human hematopoietic stem cells described herein.

The present technology may be further illustrated by reference to the following examples.

EXAMPLES

The following examples are provided to illustrate embodiments of the present technology but are by no means intended to limit its scope.

Example 1—Materials and Methods for Examples 2-7

Table 1 below identifies key reagents and resources used in Examples 2-7.

TABLE 1

| Key Reagents and Resources | | |
|---|---|---|
| REAGENT OR RESOURCE | SOURCE | IDENTIFIER |
| Antibodies | | |
| Anti-Mouse APC-c-Kit | BD Bioscience | Cat# 553356, RID: AB_398536 |
| Anti-Mouse APC/CY7-CD48 | BD Bioscience | Cat# 561242, RID: AB_10644381 |
| Streptavidin APC/CY7 | BD Bioscience | Cat# 554063, RID: AB_10054651 |
| Anti-Mouse APC CD8 | eBioscience | Cat# 17-0081-83, RID: AB_469336 |
| Anti-Mouse APC CD4 | eBioscience | Cat# 17-0042-82, RID: AB_469323 |
| Anti-Mouse BrdU | BD Biosciences | Cat# 347580, RRID: AB_400326 |
| Anti-Rabbit polyclonal CDK6 | Novus biological | Cat# NBP1-87262, RRID: AB_11031374 |
| Anti-Mouse monoclonal DLP1 | BD Trans. Lab | Cat# 611112, RRID: AB_398423 |
| Anti-Mouse FITC CD45.1 | BD PharMingen | Cat# 553775, RRID: AB_395043 |
| Anti-Mouse FITC-CD48 | Invitrogen | Cat# 11-0481-82, RID: AB_465077 |
| Anti-Rabbit polyclonal FOXO3a | Cell Signaling | Cat# 12829, RRID: AB_2636990 |
| Anti-Mouse Alexa Fluor 488 IgG | Invitrogen | Cat# A28175, RRID: AB_2536161 |
| Anti-Rabbit Alexa Fluor 594 IgG | Invitrogen | Cat# A-11012, RRID: AB_141359 |
| Anti-Rat Alexa Fluor 488 goat IgG | Abcam | Cat# ab150157, RID: AB_2722511 |

TABLE 1-continued

| Key Reagents and Resources | | |
|---|---|---|
| REAGENT OR RESOURCE | SOURCE | IDENTIFIER |
| Alexa Fluor 488 goat anti-rabbit IgG | Invitrogen | Cat# A-11008, RRID: AB_143165 |
| Anti-Mouse monoclonal Ki67 | Cell Signaling | Cat# 9449, RRID: AB_2715512 |
| Anti-Mouse eFluor 450-Ly-6G (GR-1) | eBioscience | Cat# 48-5931-82, RRID: AB_1548788 |
| Anti-Mouse Pacific blue Ly-6A/E-SCA1 | BioLegend | Cat# 108119, RRID: AB_493274 |
| Anti-Mouse monoclonal LAMP1 | Santa Cruz biotechnology | sc-20011, RRID: AB_626853 |
| Anti-Rat monoclonal LAMP2 | Santa Cruz biotechnology | Cat# sc-20004, RRID: AB_626857 |
| Anti-Rabbit polyclonal mTOR | Cell Signaling | Cat# 2983, RRID: AB_2105622 |
| Anti-Mouse monoclonal PARKIN | Abcam | Cat# ab77924, RRID: AB_1566559 |
| Anti-Rabbit polyclonal PINK1 | Abcam | Cat# ab23707, RRID: AB_447627 |
| Anti-Mouse PE/CY7-CD150 | BioLegend | Cat# 115914, RRID: AB_439797 |
| Anti-Mouse PE-CD45R (B220) | eBioscience | Cat# 12-0452-82, RRID: AB_465671 |
| Anti-Rabbit polyclonal pDRP1 (S616) | Cell Signaling | Cat# 3455, RRID: AB_2085352 |
| Anti-Mouse monoclonal RHEB | Santa Cruz biotechnology | Cat# sc-271509, RRID: AB_10659102 |
| Anti-Mouse monoclonal RAGA/B | Millipore | MABS1182 |
| Anti-Mouse monoclonal TFEB | Santa Cruz biotechnology | Cat# sc-166736, RRID: AB_2255943 |
| Anti-Rabbit polyclonal TOM20 | Santa Cruz biotechnology | Cat# sc-11415, RRID: AB_2207533 |
| Anti-Mouse monoclonal TOM20 | Santa Cruz biotechnology | Cat# sc-17764, RRID: AB_628381 |
| Culture Media | | |
| Stem Span SFEM | StemCell Technologies | 09650 |
| Fetal Bovine Serum | Invitrogen | 16000-044 |
| MyeloCult M5300 | StemCell Technologies | 05350 |
| MethoCult GF M3434 | StemCell Technologies | 03444 |
| RPMI 1640 | MyBioSource | MBS652918 |
| DMEM (1X) | GIBCO | A14430-01 |
| Pen Strep | GIBCO | 15140-122 |
| Recombinant Proteins and Cytokines | | |
| Recombinant Retronectin | Novaprotein | CH38 |
| Recombinant Mouse SCF | R&D Systems | 455-M |
| Recombinant Human TPO | R&D Systems | 288-TP |
| Recombinant Mouse IL-3 | R&D Systems | 403-ML |
| Recombinant Mouse IL-6 | R&D Systems | 406-ML |
| Recombinant Mouse FLT3 | R&D Systems | 308-FKN |
| Recombinant Mouse IL11 | R&D Systems | 308418-ML |
| Erythropoietin (EPO) | Amgen, Inc. | NDC55513 |
| Staining | | |
| 7-amino-actinomycin D | BD Biosciences | 100-5759 |
| Chloromethyl-dichlorodihydrofluoresceindiacetate | Invitrogen | C6827 |
| 4',6-Diamidino-2-Phenylindole, Dihydrochloride (DAPI) | Sigma | D9542 |
| Hoechst 33342 | Invitrogen | 62249 |
| LysoTracker-Green DND 26 | Invitrogen | L7526 |
| LysoSensor Blue DND-167 | Invitrogen | L7533 |
| Propidium Iodide (PI) | Sigma | P4170 |
| Pyronin Y | Sigma | 83200 |
| Tetramethylrhodamine ethyl ester perchlorate (TMRE) | Sigma | 87917 |
| Reagents | | |
| ATP Bioluminescence Assay Kit HS II | Roche diagnostics | 11699709001 |
| a-Cyano-4-hydroxycinnamic acid | Sigma | C2020 |
| Chloroquine | Sigma | C6628 |
| Concanamycin A | Santa Cruz Biotech | SC20211 |
| Carbonyl cyanide 3-chlorophenylhydrazone | Sigma | C2759 |

TABLE 1-continued

| Key Reagents and Resources | | |
|---|---|---|
| REAGENT OR RESOURCE | SOURCE | IDENTIFIER |
| Doxycycline hyclate (Dox) | Sigma | D9891 |
| 2-Deoxy-Glucose | Sigma | D8375 |
| Dimethyl 2-oxoglutarate | Sigma | 349631-5G |
| EasySep Mouse hematopoietic progenitor | StemCell Technologies | 19856A |
| 16% Formaldehyde Solution (w/v) Methanol-free | Thermo Scientific | 28908 |
| Hydrocortisone | StemCell Technologies | 07904 |
| Leupeptin | Sigma | L2884 |
| Methypyrurvate | Sigma | 371173 |
| 2-NBD-Glucose | Invitrogen | N13195 |
| Oligomycin | Sigma | 75351 |
| PowerUp SYBR ® Green Master Mix | Applied Biosystems | A25742 |
| QIAamp DNA Micro kit | QIAGEN | 56304 |
| Quant-iT Picogreen ds DNA Assay kit | Invitrogen | P11496 |
| Rapamycin | Cell Signaling | 9904S |
| RNeasyMicroPlus Kit | QIAGEN | 74004 |
| m-Slide-VI- flat ibitreat | Ibidi | 80626 |
| STF-31 | Sigma | SML1108 |
| SuperScript II reverse transcriptase kit | Invitrogen | 18080-044 |
| Seahorse XF Glycolysis Stress Test Kit | AgilentSeahorse | 103020-100 |
| Seahorse XF Cell Mito Stress Test Kit | AgilentSeahorse | 103015-100 |
| Triton X-100 | PerkinElmer | N930-0260 |
| Mounting Medium With DAPI - Aqueous, Fluoroshield | Abcam | Ab104139 |
| Experimental Models: Organisms/Strains | | |
| Mouse: C57BL/6J | TheJackson Laboratory | Stock No: 000664 |
| Mouse: Tg(UBC-GFP)30Scha/J | The Jackson Laboratory | Stock No: 004353 |
| Mouse: Tg(tetO-HIST1H2BJ/GFP)47Efu/J | The Jackson Laboratory | Stock No: 002014 |
| Mouse CAG-RFP-GFP-LC3 | Dr. Fangming Lin, Columbia University | N/A |
| Single-Cell RNA Sequencing (scRNA-seq) | | |
| C1 Single-Cell Auto Prep Kit | Clontech | 635027 |
| C1Single-Cell Auto Prep kit | Clontech | 100-6201 |
| SMART-Seq v4 Ultra Low Input RNA kit | Clontech | P11496 |
| Software | | |
| Flowjo Software | FlowJo | N/A |
| FCS Express 7 | De Novo Software | N/A |
| FACSDIVA | BD | N/A |
| GraphPad Prism 6 | GraphPad Software | N/A |
| ImageJ | https://imagej.nih.gov/ | N/A |
| Arivis Vision4D | Arivis | N/A |

Mice: Mice were of C57BL/6 background. For all experiments, unless noted, 8-12 week-old mice were used. For analysis of single cell division assay, UBC-GFP mice were used unless noted. For analysis of label-retaining HSCs that show successive dilution of the GFP signal with each cell division, H2B-GFP mice generated as described in Qiu et al., "Divisional History and Hematopoietic Stem Cell Function during Homeostasis," *Stem Cell Reports* 2: 473-490 (2014) (which is hereby incorporated by reference in its entirety) were used. Non-doxycycline treated mice were used to determine background expression of H2B-GFP. To determine the frequency of HSCs with autophagosome/autolysosome content 8-10 week old CAG- RFP-GFP-LC3 mice were used. Mice 65-72 week-old were used in aging experiments and compared to young 8-12 week-old mice.

Flow Cytometry and Cell Sorting: Flow cytometry analysis and FACS sorting of hematopoietic stem and progenitor cells ("HSPC") was performed with freshly isolated bone marrow ("BM") (Rimmele et al., "Mitochondrial Metabolism in Hematopoietic Stem Cells Requires Functional FOXO3,"*EMBO Rep.* 16: 1164-1176 (2015), which is hereby incorporated by reference in its entirety). BM was extracted from femur and tibia by flushing with ice cold IMDM+2% FBS. Cell suspensions were filtered through a 70 mm cell strainer, treated with RBC lysis buffer, washed, and incubated with the following antibodies: lineage cocktail consisted of biotinylated hematopoietic multilineage monoclonal antibodies (StemCell Technologies) containing CD5 (lymphocytes), CD11b (leukocytes), CD19 (B cells), CD45R (lymphocytes), 7/4 (neutrophils), Ly-6G-Gr-1 (granulocytes), and TER119 (erythroid cells). Cells were also stained with V450-SCA1, APC-c-Kit, FITC, or APC/CY7-CD48, and PE/CY7-CD150 prior to washing followed by incubation with APC/CY7-streptavidin to isolate or identify progenitors ($Lin^{-}Sca1^{-}$ $c\text{-}Kit^{+}$) and HSCs (LSK $CD150^{+}$ $CD48^{-}$). All samples were also stained with DAPI to exclude dead cells.

To measure mitochondrial membrane potential ("MMP"), Tetramethylrhodamine ethyl ester perchlorate ("TMRE", 100 nM), which specifically accumulates within the mitochondrial matrix of live cells, was used in accordance with the manufacturer's instructions. In brief, cells were stained with the probe at 37° C. for 15 minutes post antibody staining, followed by washing and flow cytometry analysis or FACS purification. Probe responsiveness to MMP changes were tested using controls carbonyl cyanide 3-chlorophenylhydrazone ("CCCP") and oligomycin, which decreased and increased fluorescence of TMRE respectively. MMP-low and MMP-high thresholds were determined as the lowest and highest 25% TMRE intensity HSCs. Reactive oxygen species ("ROS") were measured using chloromethyl-dichlorodihydrofluorescein diacetate ("CM-$H_2$DCFDA") fluorescent probe as described in Rimmele et al., "Mitochondrial Metabolism in Hematopoietic Stem Cells Requires Functional FOXO3,"*EMBO Rep.* 16: 1164-1176 (2015); Yalcin et al., "ROS-Mediated Amplification of AKT/mTOR Signalling Pathway Leads to Myeloproliferative Syndrome in Foxo3(−/−) Mice," *EMBO J.* 29: 4118-4131 (2010); and Yalcin et al., "Foxo3 Is Essential for the Regulation of Ataxia Telangiectasia Mutated and Oxidative Stress-mediated Homeostasis of Hematopoietic Stem Cells," *J. Biol. Chem.* 283: 25692-25705 (2008), which are hereby incorporated by reference in their entirety. Flow cytometry acquisition was performed on the BD LSRII, while cell sorting was performed on the BD Influx. All flow cytometry analyses and quantification were done using FlowJo 10 (Treestar).

Competitive In Vivo Long-Term Reconstitution Assay: MMP-low and MMP-high HSCs (LSK$CD150^{+}CD48^{-}$, LT-HSC; $MMP^{low/high}$) were FACS purified from CD45.1 mice and transplanted at the indicated dose of test cells with $2\times10^{5}$ CD45.2 bone marrow cells into lethally irradiated CD45.2 recipients (12 Gy as a split dose, 6.5 and 5.5 Gy, 4 hours apart). Donor (CD45.1) and recipient (CD45.2) mice were 8-12 weeks old. HSC frequency was determined by the limiting dilution assay (Hu & Smith, "ELDA: Extreme Limiting Dilution Analysis for Comparing Depleted and Enriched Populations in Stem Cell and Other Assays," *J. Immunol. Methods* 347:7 0-78 (2009), which is hereby incorporated by reference in its entirety) based on the number of mice with <1% reconstitution (CD45.1) at 16 weeks.

To assay the effect of HSC lysosomal inhibition in a in vivo competitive long-term reconstitution assay: FACS-sorted MMP-low and -high LT-HSCs (CD45.1) were treated with Concanamycin A (ConA,40 nM) or DMSO control in 96 well plates containing StemSpan with SCF (100 ng/ml) and TPO (20 ng/ml) for 4 days, after which 50 cells from each group were mixed with $2\times10^{5}$ CD45.2 total bone marrow cells and injected into lethally irradiated CD45.2 recipients and reconstituted peripheral blood was monitored up to four months.

To assay the effect of glycolytic inhibition of HSCs in a competitive in vivo long-term reconstitution assay: FACS-sorted MMP-low and MMP-high LT-HSCs (CD45.1) were mixed with $2\times10^{5}$ CD45.2 total bone marrow cells and injected into lethally irradiated CD45.2 recipients. After 2 days mice were divided into four groups, MMP-low and MMP-high groups treated with PBS or 2-Deoxy-Glucose (2-DG, 1000 mg/kg) every other day for 30 days. Reconstitution of donor CD45.1 cells and lineage distribution were monitored monthly by staining blood cells with antibodies against CD45.1, CD4, CD8 (T), B220 (B), CD11b and Gr-1 (myeloid) cells. For secondary transplantations, $2\times10^{6}$ BM cells from primary recipients were transplanted into lethally irradiated secondary recipients. Donor CD45.1 cells contribution and lineage distribution were tracked from the peripheral blood by flow cytometry.

LT-HSCs Maintenance Assay: FACS-purified MMP-low and MMP-high HSCs cells were cultured in serum-free Stemspan medium supplemented with SCF (10 ng/mL) and TPO (20 ng/mL), cultured as single or 1,000 yells or 2,000 cells/well, and treated with ConA (10-100 nM), or 2-Deoxy-Glucose (2-DG; 5-60 mM), α-Cyano-4-hydroxycinnamic acid (CHC, 10 mM), or 0.5% DMSO, incubated at 37° C. for the indicated time. Cells were then washed twice in PBS, re-suspended in PBS containing 1 μg/ml DAPI, and analyzed by flow cytometry after DAPI exclusion.

For measuring MMP and proliferation, lineage negative bone marrow (BM) cells were enriched with the EasySep Mouse hemato- poietic progenitor kit. Lineage negative (1 3 106) cells (isolated separately from four mice) were seeded onto 6 well plates in Stem-Span medium containing SCF (100 ng/ml) and TPO (20 ng/ml). Cells were treated with ConA (100nM) or the DMSO control and analyzed at 0, 6, 12 and 24 hour-time points by flow cytometry for HSC (LSKCD150+CD48−) frequencies or MMP-low and MMP-high HSCs frequencies or MMP (TMRE).

Long Term Culture-Initiating Cell ("LTC-IC") Assay: Long-term cultures were initiated as described in Lemieux et al., "Characterization and Purification of a Primitive Hematopoietic Cell Type in Adult Mouse Marrow Capable of Lymphomyeloid Differentiation in Long-Term Marrow 'Switch' Cultures," *Blood* 86: 1339-1347 (1995), which is hereby incorporated by reference in its entirety. Briefly, freshly FACS-purified MMP-low and MMP-high HSCs (100-400 cells) were treated with Con A (40 nM) or vehicle control (DMSO) for 48 hours, cells were washed and co-cultured on preestablished S17 stromal feeders in MyeloCult M5300 containing freshly added hydrocortisone ($10^{-6}$ M) for 5 weeks, after which colony-forming cells ("CFC") were quantified in secondary semi-solid cultures (Lemieux et al., "Characterization and Purification of a Primitive Hematopoietic Cell Type in Adult Mouse Marrow Capable of Lymphomyeloid Differentiation in Long-Term Marrow 'Switch' Cultures," *Blood* 86: 1339-1347 (1995), which is hereby incorporated by reference in its entirety). The frequency of long-term culture-initiated cells ("LTC-ICs") was determined by limiting dilution and applying Poisson distribution statistics as described in Hu & Smyth, "ELDA: Extreme Limiting Dilution Analysis for Comparing Depleted and Enriched Populations in Stem Cell and Other Assays," *J. Immunol. Methods* 347: 70-78 (2009), which is hereby incorporated by reference in its entirety.

Single Cell Division Assay: Single cell cultures were carried out as previously described (Bernitz et al., "Hematopoietic Stem Cells Count and Remember Self-Renewal Divisions," *Cell* 167(5): 1296-1309 (2016), which is hereby incorporated by reference in its entirety). Single MMP-low and MMP-high HSCs (LSKCD150$^+$CD48$^-$) isolated from GFP-transgenic mice were FACS sorted into individual wells of round-bottomed 96-well plates. Single cells were visually confirmed under light microscope and cultured in serum free Stemspan medium. Wells were supplemented with SCF (100 ng/ml) and TPO (20 ng/ml) (both from R&D system), were incubated at 37° C. in a humidified atmosphere with 5% $CO_2$, and the number of cells per well was monitored daily. The final number of cell divisions per well was assessed at the indicated time points in each experiment. Treatments with concanamycin A ("ConA") (40-100 nM) or DMSO control were added at the start of culture and left in the wells for the duration of the experiment unless otherwise stated. More than 200 cells per condition were analyzed. Cell Cycle Analysis—Pyronin Y staining. Pyronin Y staining was performed as described in Rimmele et al., "Mitochondrial Metabolism in Hematopoietic Stem Cells Requires Functional FOXO3," *EMBO Rep.* 16: 1164-1176 (2015) and Yalcin et al., "Foxo3 Is Essential for the Regulation of Ataxia Telangiectasia Mutated and Oxidative Stress-mediated Homeostasis of Hematopoietic Stem Cells," *J. Biol. Chem.* 283: 25692-25705 (2008), which are hereby incorporated by reference in their entirety. FACS-purified MMP-low and MMP-high LT-HSCs were stained with Hoechst 33342 (20 mg/ml) at 37° C. for 45 minutes, followed by staining with pyronin Y (1 mg/ml) for an additional 15 minutes at 37° C. Cells were then washed in cold PBS, and resuspended in IMDM+2% FBS. Samples were immediately analyzed by flow cytometry.

Cell Cycle Analysis—BrdU staining. BrdU (5-bromo-2-deoxyuridine) incorporation was measured as previously described in Yalcin et al., "Foxo3 Is Essential for the Regulation of Ataxia Telangiectasia Mutated and Oxidative Stress-mediated Homeostasis of Hematopoietic Stem Cells," *J. Biol. Chem.* 283 :25692-25705 (2008), which is hereby incorporated by reference in its entirety. Briefly, mice were injected intravenously with 2mg of BrdU. At 19 hours post injection (Cheshier et al., "In Vivo Proliferation and Cell Cycle Kinetics of Long-Term Self-Renewing Hematopoietic Stem Cells," *Proc. Natl. Acad. Sci.* 96: 3120-3125 (1999), which is hereby incorporated by reference in its entirety), freshly isolated bone marrow MMP-low and MMP-high HSCs were FACS-purified, sorted and incubated with mouse anti-BrdU antibody and 7-amino-actinomycin D for flow cytometry analysis.

Immunofluorescence Staining, Imaging, and Analysis—Laser Scanning Confocal Microscopy: FACS purified MMP-low and MMP-high HSCs (in average pooled from three mice) were seeded into retronectin-coated channel slides (Ibidi Cat# 80626) and fixed for 15 minutes with 10% formalin (1,000 cells). After washing with PBS, cells were permeabilized in PBS+0.25% Triton™ X-100 for 15 minutes and blocked for 1 hour in 3% BSA. Fixed and permeabilized cells were then incubated with primary antibodies (1:150) in PBS+1% BSA overnight at 4° C., washed and stained with fluorescence-conjugated secondary antibodies (1:1,000) for 1 hour at room temperature. Slides were sealed with mounting medium with DAPI. Images were captured using a Zeiss LSM880 Airyscan confocal microscope using a 100× objective (N.A. 1.46).

For analysis by immunofluorescence staining, MMP-low and MMP-high HSCs were FACS-purified and incubated in StemSpan medium containing SCF (100 ng/ml) and TPO (20 ng/ml) for the indicated time with the indicated compounds at 37° C. in a humidified atmosphere with 5% $CO_2$. After treatment, cells were processed for confocal imaging as described above.

To test lysosome acidity in MMP-low and MMP-high HSCs, FACS-sorted MMP-low and MMP-high HSCs were incubated in Stem-Span media with SCF (10 ng/mL) and TPO (20 ng/mL) or amino acid free medium (starvation) containing ConA (40 nM) or DMSO control for 5 hr; and then cells were incubated with 1 mM Lysotracker green (LTR) or 1mM Lysosensor Blue diluted in above medium for 30 min (37° C., 5% $CO_2$). Cells were rapidly washed with warm PBS (37° C.) three times, mounted and images were captured using a Zeiss LSM880 confocal microscope using a 40× objective (N.A. 1.4).

Immunofluorescence Staining, Imaging, and Analysis—Super Resolution Confocal Microscopy: Images were acquired with a Zeiss LSM 880 confocal microscope equipped with Airyscan Super Resolution Imaging module, using a 100×/1.46 Alpha Plan Apochromat objective lens (Zeiss MicroImaging, Jena, Germany) with "optimal" (Nyquist) XY scaling. Z stacks through the entire cell were acquired at an 0.018 mm (at least 20 optical sections) using a pixel dwell time of >50 microseconds and field dimensions of 300×300 mm (20 MMP-low and 20 MMP-high HSCs analyzed). This was followed by Airyscan image processing (set at auto but rarely over 6.2) and analyses using ZEN image acquisition and processing software (ZEN blue/black). Maximum intensity projections shown in the figures were also obtained using ZEN Blue software.

Lysosomal Localization of Mitochondria. FACS-sorted MMP-low and MMP-high HSCs (LSKCD150$^+$CD48$^-$ MMP-low/-high) were treated with DMSO control or leupeptin (100 mM) for 4 hours. HSCs were then fixed and imaged for TOM20 (mitochondria) and LAMP1 (lysosomes).

Autophagic Vacuole Formation. Accumulation of autophagy substrates, Translocase of outer membrane 20 (TOM20) or Map11c3a (LC3), was determined in the presence of amino acid-containing (DMSO) or -starved amino acid-depleted media, v-ATPase inhibitor concanamycin A (ConA 40nM), inhibitor of autophagosome-autolysosome fusion chloroquine (CQ, 40 mM), or protease inhibitor, leupeptin (100 mM) following guidelines outlined for study of autophagy (Klionsky et al., "Guidelines for the Use and Interpretation of Assays for Monitoring Autophagy (3rd Edition)," *Autophagy* 12(1): 1-222 (2016) and Martinez-Lopez et al., "Autophagy Proteins Regulate ERK Phosphorylation," *Nat. Commun.* 4: 2799 (2013), which are hereby incorporated by reference in their entirety). In brief, FACS-sorted MMP-low and MMP- high HSCs were cultured in the presence or absence of indicated inhibitors for 4, 5, or 18 hours following which cells were subjected to immunofluorescence assays for TOM20, LC3 and/or LAMP1 or LAMP2 as described above. Analyses were performed to quantify the turnover of indicated protein in lysosomes by evaluating the accumulation of TOM20 or LC3 in the presence versus absence of an inhibitor. TOM20 and LC3 flux were determined by subtracting the colocalized value of inhibitor-untreated TOM20 or LC3 with LAMP1 from corresponding inhibitor-treated values. Images were captured using a Zeiss LSM880 Airyscan confocal microscope using 100 X objectives (Leica), and percentage colocalization was calculated using the JACoP plugin (NIH ImageJ).

Image Analysis. All images were analyzed with FIJI or NIH ImageJ software (Schindelin et al., "Fiji: An Open-Source Platform for Biological-Image Analysis," *Nat. Methods* 9(7): 676-682 (2012), which is hereby incorporated by reference in its entirety) unless otherwise specified. Brightness and contrast settings were set during capture and not altered for analysis.

Fluorescence Intensity: Channel displaying the protein of interest were isolated and quantified on a per cell basis using the raw integrated density metric generated by the measure command. For nuclear intensity, DAPI thresholds were used to delimit the nucleus and mapped back onto the channel displaying the protein of interest to determine fluorescence intensity within the nucleus only.

Mitochondrial and Lysosome Morphology: Freshly isolated HSCs were analyzed for mitochondrial morphology. Each individual HSC (150 total) was analyzed by using Arivis Vision 4D software and classified as either fragmented or not fragmented in accordance with number of surfaces. Cells that fulfilled the definition of 'fragmented' contained 3 or more individual mitochondrial surfaces (Kask et al., "Fluorescence-intensity Distribution Analysis and Its Application in Biomolecular Detection Technology," *Proc. Natl. Acad. Sci. USA* 96(24): 13756-13761 (1999), which is hereby incorporated by reference in its entirety). Lysosomes' fluorescence intensity or area profiling was calculated using ImageJ software enabling the detection of fluorescently labeled mitochondrial boundaries (lysosomal marker LAMP1), as reflected by sharp increases or decreases in fluorescence intensity. Channels displaying fluorescence for either mitochondria or lysosomes were thresholded with the IsoData option to delimit the boundaries of mitochondrial networks and lysosome morphology. The resulting outlines were measured using the analyzed particles option to determine the size of distinct particles representing mitochondrial networks or lysosomes. More than 50 cells/condition/experiment were analyzed for lysosomes.

Co-Localization: Cells were manually selected and channels containing the two proteins of interest were separated and analyzed using the Colocalization plugin (Fiji); more than 30 cells/condition/experiment were analyzed. The Colocfunction auto-thresholds and returns a value for Mander's correlation coefficients. Level of colocalization between two proteins was determined by averaging over all cells analyzed per group. Percentage colocalization was calculated using the JACoP plugin (NIH ImageJ).

Single-Cell RNAseq Library Generation: Single cell cDNA libraries were generated from FACS-purified MMP-low and MMP-high HSCs with the SMART-Seq v4 Ultra Low Input RNA kit, the Fluidigm C1 system and the Nextera XT library preparation kit (Illumina) following the manufactures' protocols. In brief, sorted cells in 35% suspension reagent at 600 cells/μL were loaded into the 5-10 μm Fluidigm IFC and visually inspected to confirm one cell per capture site at 20× with a fluorescent microscope. Debris, multiple cells, and dead cells (Calcein negative) were excluded for subsequent library preparation. The captured cells were then subjected to cDNA synthesis on the C1 system and quantified the next day using the Quant-iT Picogreen dsDNA Assay kit. cDNA was tagmented, amplified, pooled, and cleaned up with the Nextera XT kit. Single-cell cDNA libraries were then quantified with the Bioanalyzer (Agilent) and subjected to sequencing on the Illumina High-Seq. 254 single-cell cDNA libraries were multiplexed over 3 lanes (~84 samples/lane) with 100 nt single-end sequencing.

Single-Cell RNAseq Processing: Raw sequencing reads were trimmed with Trimmomatic v.0.36 (Bolger et al., "Trimmomatic: A Flexible Trimmer for Illumina Sequence Data," *Bioinformatics* 30(15): 2114-2120 (2014), which is hereby incorporated by reference in its entirety) to exclude adapters and bed quality reads and mapped with STAR-2.5.3a (STAR: ultrafast universal RNA-seq aligner) on reference database containing mouse genome (GRCm38) and ERCC sequences. Matrix of gene counts was obtained with feature Counts (Liao et al., "Feature Counts: An Efficient General Purpose Program for Assigning Sequence Reads to Genomic Features," *Bioinformatics* 30: 923-930 (2014), which is hereby incorporated by reference in its entirety), which is an efficient general-purpose program for assigning sequence reads to genomic features. The count matrix was then processed to discard cells and genes not meeting following criteria:

1. Total number of reads per cell>600,000
2. Number of genes detected in cell (at least one mapped read)>5,500
3. Percentage of mitochondrial reads per cell<6%
4. Number of cells in which the gene was detected (at least two mapped reads)≥2

As a result, a set of 16,203 genes and 224 cells were used for further analysis.

Next, size factor normalization was performed, implemented in scran v1.0.3 R package (Lun et al., "A Step-by-Step Workflow for Low-Level Analysis of Single-Cell RNA-Seq Data With Bioconductor," F1000Res 5: 2122 (2016), which is hereby incorporated by reference in its entirety) for genes and spike-ins and natural logarithm transformation of the data. After that a regression on total counts and cell cycle was done with the help of Seurat v2.0 (Butler et al., "Integrating Single-Cell Transcriptomic Data Across Different Conditions, Technologies, and Species," *Nat. Biotechnol.* 36: 411- 420 (2018), which is hereby incorporated by reference in its entirety). Finally, 5,625 highly variable genes were selected based on z-score of their expression using Seurat and used for downstream analyses.

Single-Cell RNAseq Analysis—Differential Expression (MAST): Lists of genes, differentially expressed between groups of cells were obtained by MAST (Model-based Analysis of Single Cell Transcriptomics) R package (Finak et al., "MAST: A Flexible Statistical Framework for Assessing Transcriptional Changes and Characterizing Heterogeneity in Single-Cell RNA Sequencing Datam," *Genome Biol.* 16:278 (2015), which is hereby incorporated by reference in its entirety) version 1.6.1, using genes which were detected in either of the groups of cells at a minimum 25% percentage level (see Liang et al., "Restraining Lysosomal Activity Preserves Hematopoietic Stem Cell Quiescence and Potency," *Cell Stem Cell* 26: 359-376 (2020), which is hereby incorporated by reference in its entirety).

Single-Cell RNAseq Analysis—Clustering (t-SNE, PCA): Clusterization was carried out on seven first statistically significant principal components by implementing Seurat graph-based k-nearest neighbors algorithm of clustering. The results were visualized with t-SNE (see Liang et al., "Restraining Lysosomal Activity Preserves Hematopoietic Stem Cell Quiescence and Potency," *Cell Stem Cell* 26: 359-376 (2020), which is hereby incorporated by reference in its entirety).

Single-Cell RNAseq Analysis—Pathway Analysis: WikiPathways R package, REACTOME db and KEGG db (Scialdone et al., "Computational Assignment of Cell-Cycle Stage From Single-Cell Transcriptome Data," *Methods* 85: 54-61 (2015), which is hereby incorporated by reference in its entirety) were used to retrieve genes, included in the explored pathways. The pathway score for every cell was counted as a mean expression of genes included in the pathway and expressed in the cell. For every pathway, a two sample two-tailed z-test with Bonferroni correction and for the mean of pathway scores between MMP-high and MMP-low cells was performed. To compare pathway scores in different clusters, Kruskal-Wallis rank sum test was performed. After that a post hock Dunn test with Bunferroni correction was done (see Liang et al., "Restraining Lysosomal Activity Preserves Hematopoietic Stem Cell Quiescence and Potency," *Cell Stem Cell* 26: 359-376 (2020), which is hereby incorporated by reference in its entirety).

Single-Cell RNAseq Analysis—Cell Cycle Staging: Cyclone (Scialdone et al., "Computational Assignment of Cell-Cycle Stage From Single-Cell Transcriptome Data," *Methods* 85: 54-61 (2015), which is hereby incorporated by reference in its entirety) was used to assign putative cell cycle phases (S/G2M or G0/G1) to each cell based on a random forest trained on cell cycle marker genes (see Liang et al., "Restraining Lysosomal Activity Preserves Hematopoietic Stem Cell Quiescence and Potency," *Cell Stem Cell* 26: 359-376 (2020), which is hereby incorporated by reference in its entirety).

Metabolic Assays. Oxygen consumption rates ("OCR") and extracellular acidification rates ("ECAR") were measured using a 96-well Seahorse Bioanalyzer XF 96 according to manufacturer's instructions using Seahorse Mito Stress Test or Glycolysis Stress Test kit (Agilent Technologies). In brief, MMP-low and MMP-high LSK cells isolated from a pool of at least 11 mice (40,000 cells per well) were sorted and treated with or without ConA (40 nM) for 18 hours in StemSpan media with SCF (10 ng/mL) and TPO (20 ng/mL). Cells were washed and suspended in XF basic medium with 11 mM glucose, 1 mM sodium pyruvate and 2 mM glutamine (pH 7.4 at 37° C.). The injection port A on the sensor cartridge was loaded with 1 mM oligomycin (Oligo), 2 mM FCCP was loaded into port B and 0.5 mM rotenone/antimycin (ROT/AA) A was loaded into port C. During sensor calibration, the cells were incubated in the 37oC non-CO2 incubator. The plate was immediately placed onto the calibrated XF96 extracellular flux analyzer for the Mito Stress Test. For the glycolysis stress test, cells were suspended in XF basic medium in 1 mM glutamine (pH 7.4 at 37° C.). The injection port A on the sensor cartridge was loaded with 10 mM glucose. Then, 2 mM oligomycin was loaded into port B and 50 mM 2-DG into port C. During sensor calibration, cells were incubated in the 37° C. non-$CO_2$ incubator. The plate was immediately placed in the calibrated XF96 extracellular flux analyzer for the glycolysis stress test.

Glucose Uptake Assay: For measurement of glucose uptake, freshly FACS-purified MMP-low and MMP-high HSCs (at least 2,000 cells pooled in average from 8 mice) were cultured immediately in 100 mL of glucose, glutamine, pyruvate free medium containing 100 or 200 μM 2-(n-(7-nitrobenz-2-oxa-1,3-diazol-4-yl amino)-2-deoxyglucose (2-NBD-Glucose, 2NBDG) for 2 hours. Cells were then washed multiple times in PBS, re-suspended in PBS containing 1 μg/ml DAPI, and analyzed by flow cytometry for 2-NBD glucose fluorescence in the FITC channel. In some experiments cells were cultured in StemSpan medium (StemCell Technology) supplemented with SCF (100 ng/ml) and TPO (20 ng/ml), treated with or without STF-31 (10, 20 mM), ConA (25, 50 nM), dimethyl alpha ketoglutarate (MOG, 1 mM), methyl pyruvate (MP, 1 mM) or DMSO, incubated at 37° C. in a humidified atmosphere with 5% $CO_2$ for 6 or 18 hours before removing culture medium from each well, washing extensively and adding 100 mL of glucose, glutamine, pyruvate free medium containing 100 or 200 mM of 2 NBDG for 2 hours before washing cells multiple times in PBS and analyzing by flow cytometry. Quantification of 2NBDG uptake was measured by the geometric mean fluorescence intensity ("MFI") as well as % of $2NBDG^+$ cells.

In vivo Glycolytic Inhibition. To assess the effect of inhibition of glycolysis on MMP in HSCs, mice received intraperitoneal injections of either PBS or 2-DG 750 mg/kg every other day for 6 days after which total BM cells (107) cells were isolated and MMP analyzed by flow cytometry in HSCs.

CAG-RFP-EGFP-LC3 Assay. Total BM cells from CAG-RFP-EGFP-LC3 mice were cultured in StemSpan with SCF (10 ng/mL) and TPO (20 ng/mL) at $8\times10^6$ cells/ mL. Cells were either incubated with ConA (40 nM), chloroquine (CQ, 40 mM), leupeptin (100 mM) or DMSO control, or -starved amino acid-depleted RPMI 1640 media for 3 hours to induce autolysosome accumulation. Both GFP and mRFP are expressed in a single transgene, both green and red fluorescence is emitted from the same LC3 molecule, with 1:1 stoichiometry, thus allowing a more-accurate quantification of autophagosomes and autolysosomes measured by flow cytometry 3 hours post-treatment. Given the fluorescent incompatibility, only frequency of HSC with autophagosome ($RFP^+GFP^+$-LC3) or autolysosome formation ($RFP^+$-LC3) normalized to conditions with MMP-low against MMP-high HSCs was determined.

ATP Assay: FACS-purified MMP-low and MMP-high HSCs were collected and ATP levels were quantified with ATP Bioluminescence Assay Kit HS II (Roche) in accordance with the manufacturer's recommendations, as described in Rimmele et al., "Mitochondrial Metabolism in Hematopoietic Stem Cells Requires Functional FOXO3," *EMBO Rep.* 16: 1164-1176 (2015), which is hereby incorporated by reference in its entirety.

mtDNA Quantification: Extracted DNA from FACS-purified cells was performed using QIAamp DNA Micro kit according to kit instruction and DNA was quantified using Nanodrop. qRT-PCR was performed using PowerUp™ SYBRR Green Master Mix and CFX384 Real-Time System (BIO-RAD, see Primer sequences). Each DNA was generated from a pool of 3 mice.

Real-Time Quantitative RT-PCR: MMP-low and MMP-high HSC cells were sorted and total RNA was isolated using RNeasy MicroPlus Kit. First-strand cDNA was synthesized-using SuperScript II reverse transcriptase kit. cDNA obtained from 500 cells was used per well; RT-PCR was performed using PowerUp™ SYBR® Green Master Mix in triplicates using the indicated primers and C1000 Touch Thermal cycler CFX384 Real-Time system (Bio-Rad, see Primer sequences). All results were normalized to (β-actin RNA levels. Each cDNA was generated from a pool of 5 mice.

Statistical Analyses: Unpaired two-tailed Student's t-test was used for all experiments. One-way ANOVA with Tukey's post hoc test were used for comparisons between more than two groups. All experiments were repeated at least three times independently unless specified. $p<0.05$ was considered significant in all experiments. *$p<0.05$, $p<0.01$, *$p<0.001$.

Primers used are identified in Table 2 below.

TABLE 2

List of Primers

| Gene name | Primer sequence | SEQ ID NO. |
|---|---|---|
| Gaa-F | 5'-CTACGCAGGAGGTCGTGTGA-3' | SEQ ID NO: 1 |
| Gaa-R | 5'-TCTGAAGGCCTGCGCAATCA-3' | SEQ ID NO: 2 |
| Ctsb-F | 5'-CTCTTGTTGGGCATTTGGGG-3' | SEQ ID NO: 3 |
| Ctsb-R | 5'-ATGCTCCAGAGGGATAGCCA-3' | SEQ ID NO: 4 |
| Ctsbd-F | 5'-ACTCAAGGTATCGCAGGGTG-3' | SEQ ID NO: 5 |
| Ctsbd-R | 5'-TTGGCAAAGCCGACCCTATT-3' | SEQ ID NO: 6 |
| HEXA-F | 5'-GACTGCAACCTGCGCTATG-3' | SEQ ID NO: 7 |
| HEXA-R | 5'-GTAATATCGCCGAAACGCCT-3' | SEQ ID NO: 8 |
| SMPD1-F | 5'-ACCTTAACCCTGGCTACCGA-3' | SEQ ID NO: 9 |
| SMPD1-R | 5'-GTTGGCCTGGGTCAGATTCA-3' | SEQ ID NO: 10 |
| HK1-F | 5'-CCGAGCTGAAGGATGACCAA-3' | SEQ ID NO: 11 |
| HK1-R | 5'-CCCCTTTTCTGAGCCGTCC-3' | SEQ ID NO: 12 |
| LDH A-F | 5'-AACTTGGCGCTCTACTTGCT-3' | SEQ ID NO: 13 |
| LDH A-R | 5'-GGACTTTGAATCTTTTGAGACCTTG-3' | SEQ ID NO: 14 |
| Pkm2-F | 5'-TCGCATGCAGCACCTGATAG-3' | SEQ ID NO: 15 |
| Pkm2-R | 5'-GAGGTCTGTGGAGTGACTGG-3' | SEQ ID NO: 16 |
| Pgk1-F | 5'-GGTGTTGCCAAAATGTCGCT-3' | SEQ ID NO: 17 |
| Pgk1-R | 5'-CAGCAGCCTTGATCCTTTGG-3' | SEQ ID NO: 18 |
| Aldoa-F | 5'-AACCCAGCTGAATAGGCTGC-3' | SEQ ID NO: 19 |
| Aldoa-R | 5'-CATGGGTCACCTTGCCTGG-3' | SEQ ID NO: 20 |
| Glut1-F | 5'-TCAACACGGCCTTCACTG-3' | SEQ ID NO: 21 |
| Glut1-R | 5'-CACGATGCTCAGATAGGACATC-3' | SEQ ID NO: 22 |
| Glut4-F | 5'-GTAACTTCATTGTCGGCATGG-3' | SEQ ID NO: 23 |
| Glut4-R | 5'-AGCTGAGATCTGGTCAAACG-3' | SEQ ID NO: 24 |

TABLE 2 -continued

List of Primers

| Gene name | Primer sequence | SEQ ID NO. |
|---|---|---|
| β-actin-F | 5'-CCCTAAGGCCAACCGTGAAA-3' | SEQ ID NO: 25 |
| β-actin-R | 5'-CAGCCTGGATGGCTACGTAC-3' | SEQ ID NO: 26 |
| Mt10983-F | 5'-AGCTCAATCTGCTTACGCCA-3' | SEQ ID NO: 27 |
| Mt10983-R | 5'-TGTGAGGCCATGTGCGATTA-3' | SEQ ID NO: 28 |
| Cox1-F | 5'-GCCCCAGATATAGCATTCCC-3' | SEQ ID NO: 29 |
| Cox1-R | 5'-GTTCATCCTGTTCCTGCTCC-3' | SEQ ID NO: 30 |
| NucActb-F | 5'-AGCTCAGTAACAGTCCGCCTA-3' | SEQ ID NO: 31 |
| NucActb-R | 5'-CAGAGAGCTCACCATTCACCAT-3' | SEQ ID NO: 32 |

Figures 1C, 1D:
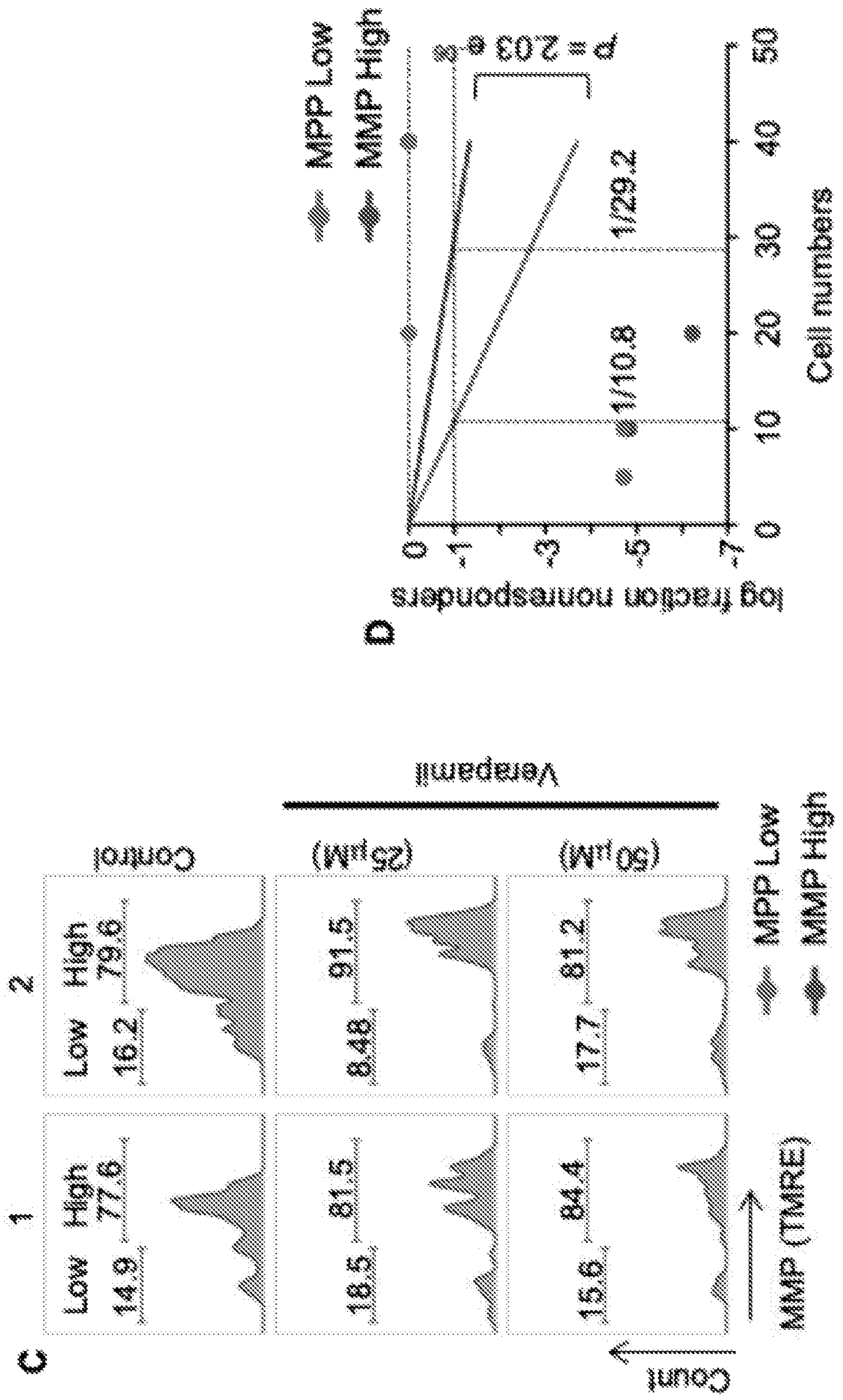

Example 2—Quiescent Immuno-Phenotypically Defined HSCs Maintain Low Mitochondrial Activity Mitochondrial activity in HSCs was measured using the cationic fluorescent probe Tetramethylrhodamine Ethyl Ester ("TMRE"), which specifically accumulates within the mitochondrial matrix dependent upon the proton concentration gradient. As previously observed (Rimmele et al., "Mitochondrial Metabolism in Hematopoietic Stem Cells Requires Functional FOXO3," *EMBO Rep.* 16: 1164-1176 (2015), which is hereby incorporated by reference in its entirety), MMP and ROS levels, which are positively correlated with mitochondrial activity, were higher in more downstream multipotent progenitors ($Lin^{-}Sca1^{+}cKit^{+}$[LSK] and $Lin^{-}/CD48^{-}$) than in phenotypically defined HSCs ($LSKCD150^{+}CD48^{-}$) with the ability to repopulate blood in a lethally irradiated mouse for a long period of time (referred to as HSCs; FIG. 1A, top panels). Notably, HSCs with similar low ROS levels were heterogeneous in their mitochondrial activity (FIG. 1A, middle and bottom panels; FIG. 1B). Within the phenotypically defined HSCs, two distinct fractions were apparent, with a majority (~75%) of HSCs displaying (on average 6 times) higher levels of TMRE (MMP-high) than the rest of the HSC population (MMP-low). The MMP-low fraction reflected lesser accumulation of TMRE rather than enhanced efflux of HSCs (FIG. 1C). As anticipated (Kim et al., "Rhodamine-123 Staining in Hematopoietic Stem Cells of Young Mice Indicates Mitochondrial Activation Rather Than Dye Efflux," *Blood* 91: 4106-4117 (1998), which is hereby incorporated by reference in its entirety), inhibition of the multidrug-resistance-associated protein ("MRP") with Verapamil did not modulate significantly TMRE levels or the proportion of MMP-low HSCs (FIG. 1C). These observations confirm (Rimmele et al., "Mitochondrial Metabolism in Hematopoietic Stem Cells Requires Functional FOXO3," *EMBO Rep.* 16: 1164-1176 (2015); Sukumar et al., "Mitochondrial Membrane Potential Identifies Cells with Enhanced Stemness for Cellular Therapy," *Cell Metab.* 23: 63-76 (2016); and Vannini et al., "Specification of Haematopoietic Stem Cell Fate Via Modulation of Mitochondrial Activity," *Nat. Comm.* 7: 13125 (2016), which are hereby incorporated by reference in their entirety) that the phenotypically defined bone marrow HSC compartment (LSK $CD150^{+}CD48^{-}$) contains metabolically diverse subpopulations with distinct mitochondrial activity that are not discriminated by their ROS levels.

Figures 1E, 1F, 1G:
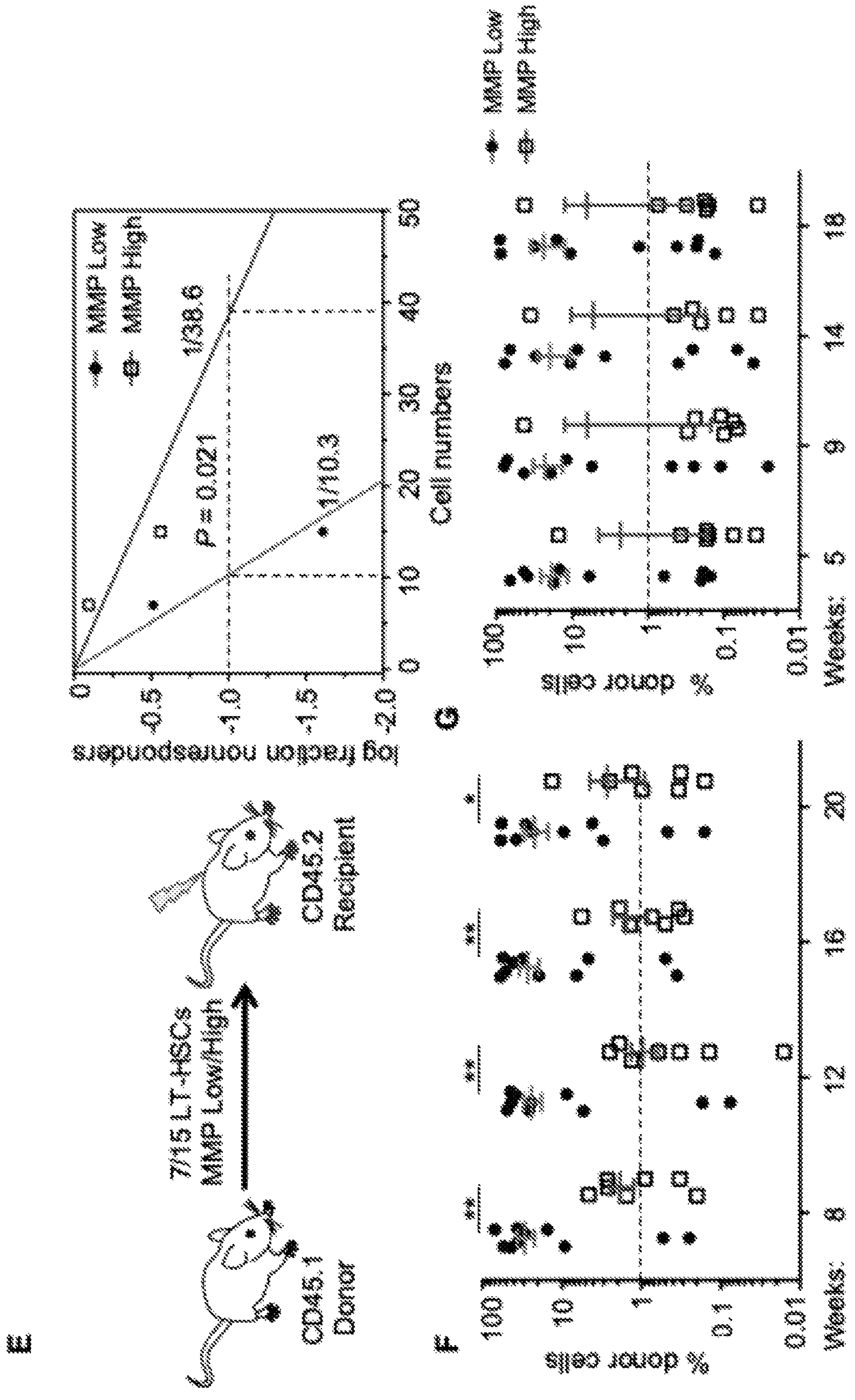

HSCs (LSK $CD150^{+}CD48^{-}$) with the lowest MMP levels (the bottom ~25%) were 2.7-fold enriched in long-term culture-initiating cell (LTC-IC) with the ability to generate colonies in vitro as compared to MMP-high (the top ~25%) HSCs (FIG. 1D). The frequency of competitive repopulating units was also 3.7-fold greater within the MMP-low than the MMP-high fraction of HSCs (LSK $CD150^{+}CD48^{-}$) at 16 weeks post-transplantation by limiting dilution analysis (FIGS. 1E-1F). Reconstitution levels were consistently more robust in MMP-low relative to MMP-high HSCs at each time-point analyzed (8.3-fold higher at 20 weeks) in lethally irradiated mice transplanted with 7 or 15 purified CD45.1 HSCs mixed with unfractionated CD45.2 ($2\times10^{5}$) competitors (FIG. 1F).

Self-renewing HSCs were also detected more robustly in mice serially transplanted with MMP-low rather than MMP-high HSCs (FIG. 1G). In fact, only one mouse injected with 15 MMP-high HSCs exhibited over 1% chimerism in the secondary transplant after 18 weeks, compared to 6 out of 10 recipients of MMP-low HSCs (FIG. 1G).

Figures 2A, 2B, 2C, 2D:
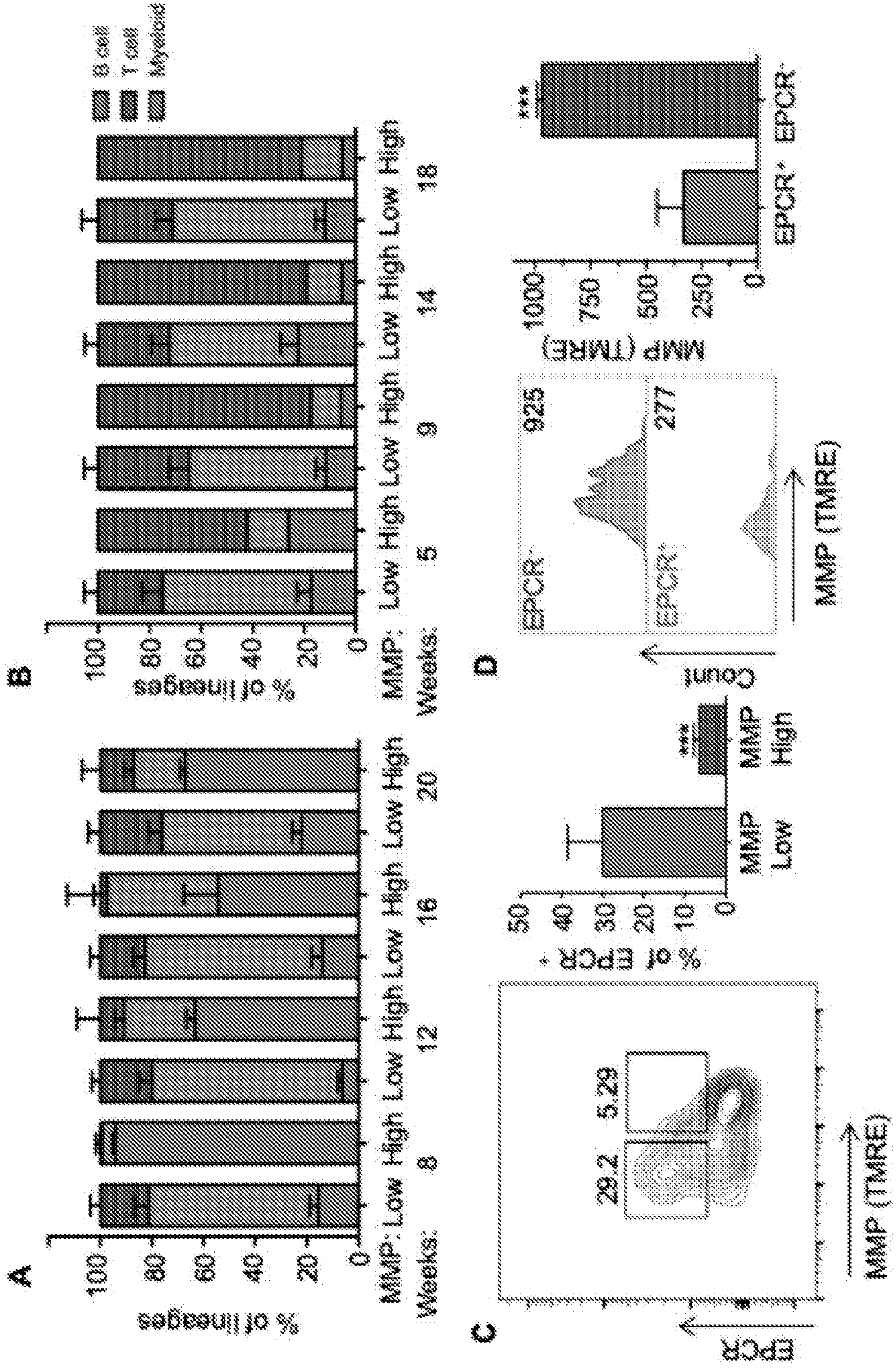
FIGS. 2A-2E show that MMP-low HSCs are quiescent and balanced in their in vivo lineage distribution.

Importantly, while MMP-low HSC-derived lineages were balanced in their composition, as defined previously (Müller-Sieburg et al., "Deterministic Regulation of Hematopoietic Stem Cell Self-Renewal and Differentiation," *Blood* 100: 1302-1309 (2002), which is hereby incorporated by reference in its entirety), up to 20 weeks post-transplantation, MMP-high HSCs were myeloid-biased (FIG. 2A). MMP-high HSCs did not produce a sufficient number of mice with over 1% chimerism in the secondary transplants for lineage analysis (FIG. 2B). The Endothelial protein C receptor ("EPCR") (FIG. 2C), an HSC marker independent of mitochondrial activity (Balazs et al., "Endothelial Protein C Receptor (CD201) Explicitly Identifies Hematopoietic Stem Cells in Murine Bone Marrow," *Blood* 107: 2317-2321 (2006), which is hereby incorporated by reference in its entirety), was also significantly more elevated in MMP-low rather than MMP-high HSCs and negatively correlated with TMRE intensity (FIGS. 2C-2D). Conversely, EPCR+ HSCs displayed significantly less mitochondrial activity than EPCR- HSCs (FIG. 2D). These findings are consistent with previous results (Sukumar et al., "Mitochondrial Membrane Potential Identifies Cells with Enhanced Stemness for Cellular Therapy," *Cell Metab.* 23: 63-76 (2016) and Vannini et al., "Specification of Haematopoietic Stem Cell Fate Via Modulation of Mitochondrial Activity," *Nat. Comm.* 7: 13125 (2016), which are hereby incorporated by reference in their entirety) and suggest that HSCs with low MMP contained the most potent in vivo competitive repopulating and self-renewing units as compared to MMP-high HSCs.

Figure 2E:
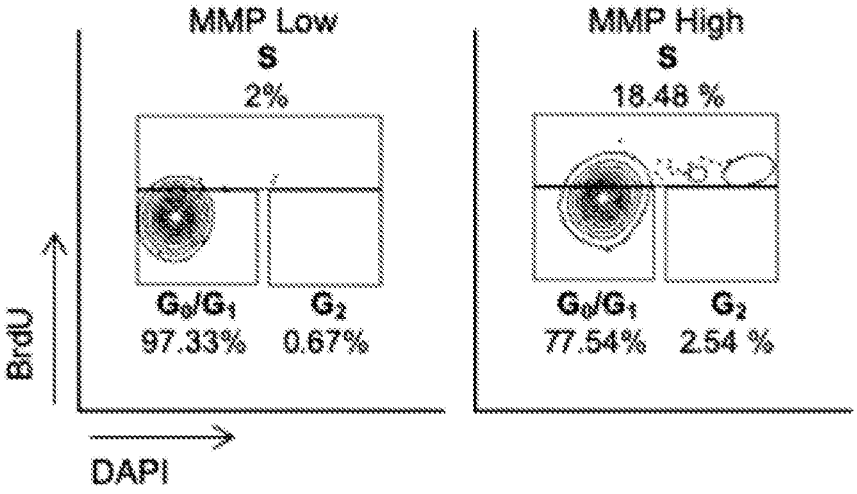
Figure 3A:
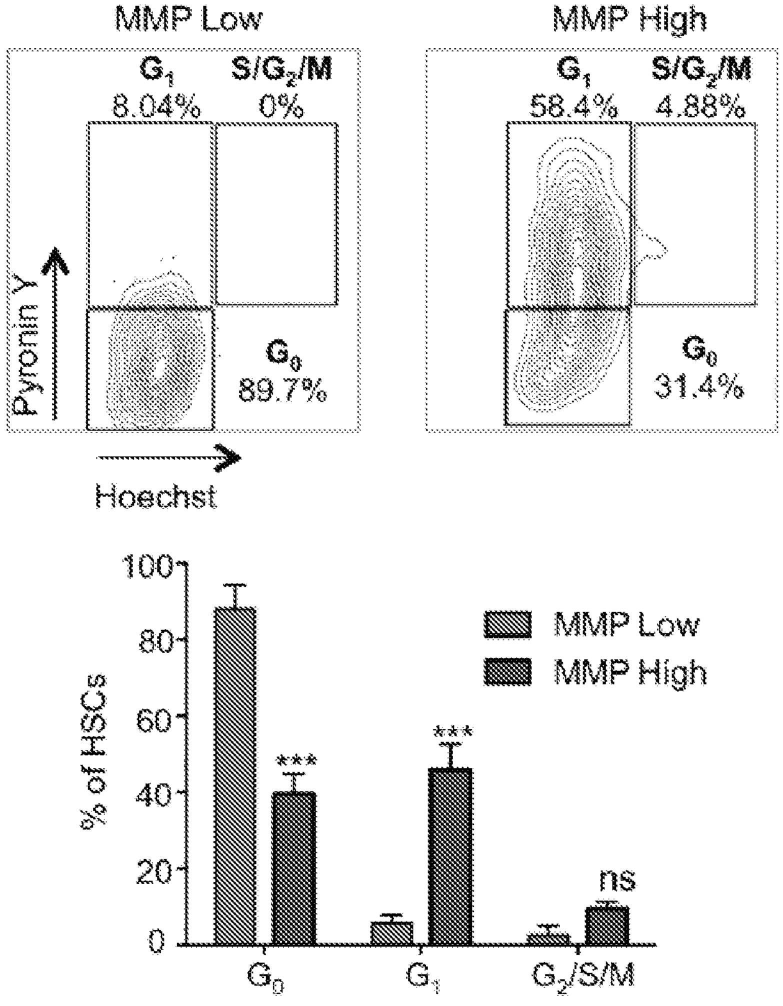
FIGS. 3A-3G show that MMP-low HSCs are enriched in label-retaining HSCs.

Since the most quiescent HSCs show the longest in vivo competitive reconstitution capacity (Ema et al., "Quantification of Self-Renewal Capacity in Single Hematopoietic Stem Cells From Normal and Lnk-Deficient Mice," *Dev. Cell* 8: 907-914 (2005) and Morrison et al., "The Long-Term Repopulating Subset of Hematopoietic Stem Cells is Deterministic and Isolatable by Phenotype," *Immunity* 1: 661-673 (1994), which are hereby incorporated by reference in their entirety), the cell cycle dynamics of MMP-low versus MMP-high HSCs were next examined using a combination of Pyronin Y, which marks RNA in live cells, and Hoechst, which labels DNA, together distinguishing quiescent ($G_0$) HSCs from non-quiescent HSCs either in $G_1$ or actively dividing HSCs in the $S/G_2/M$ phases. MMP-low fractions of HSCs were almost entirely (~90%) quiescent ($G_0$), whereas the striking majority of MMP-high HSCs (55%) had exited $G_o$ (FIG. 3A). Using bromodeoxyuridine (BrdU) labeling in vivo, it was confirmed that a greater fraction of MMP-high in contrast to MMP-low HSCs were proliferating (FIG. 2E).

Figures 3B, 3C, 3D, 3E:
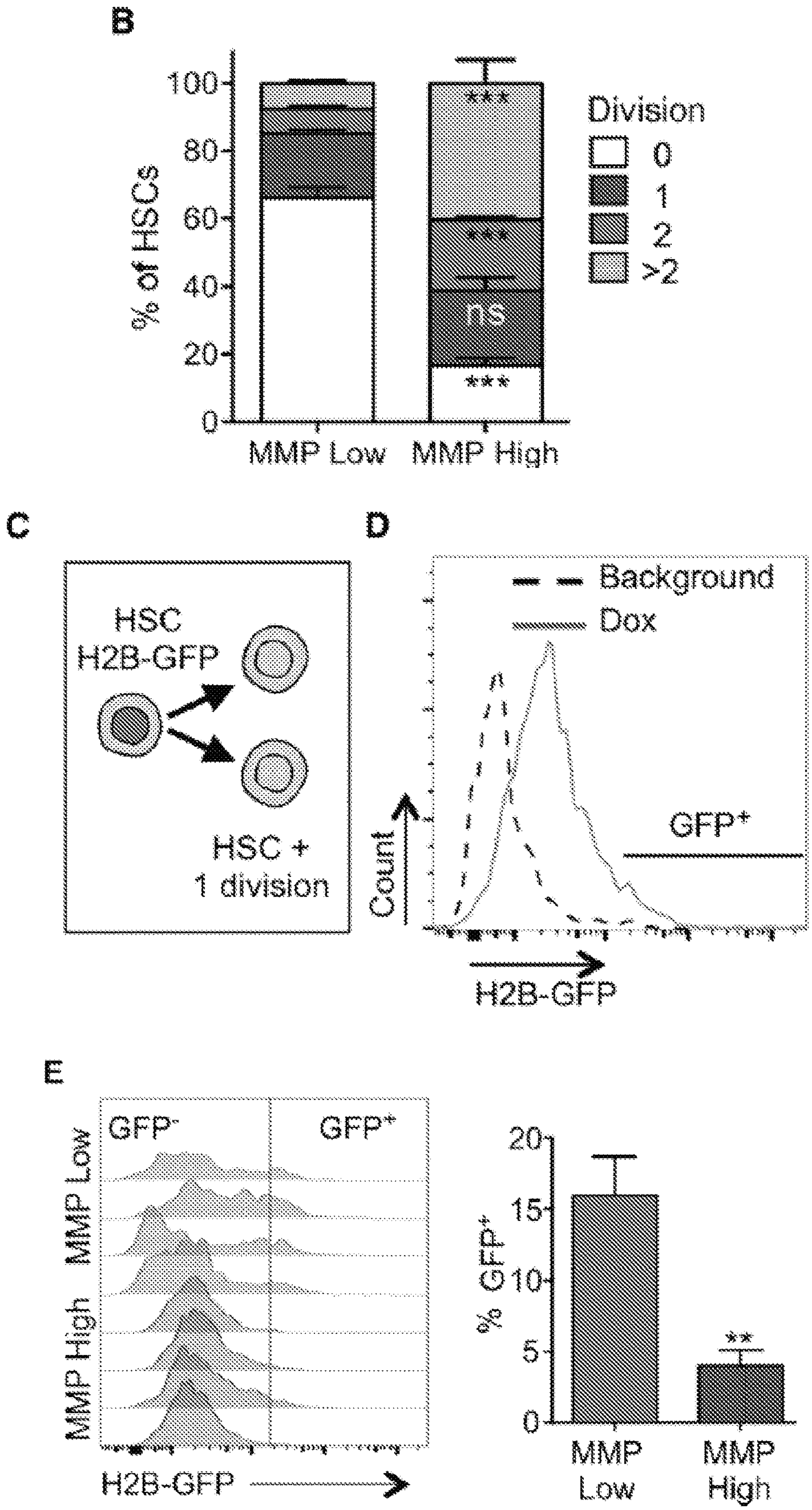

Consistent with the cell cycle results, over 60% of MMP-low $GFP^{+}$ HSCs cultured at the single-cell level did not divide during 60 hours, while over 90% of MMP-high $GFP^{+}$ HSCs divided at least once during the same period of time in culture under optimum conditions (FIG. 3B). In addition, over 40% of MMP-high $GFP^{+}$ HSCs divided more than twice as compared to less than 20% of MMP-low $GFP^{+}$ HSCs. These results further support that MMP-low HSCs are mostly quiescent in contrast to MMP-high HSCs that are primed/activated.

Figure 3F:
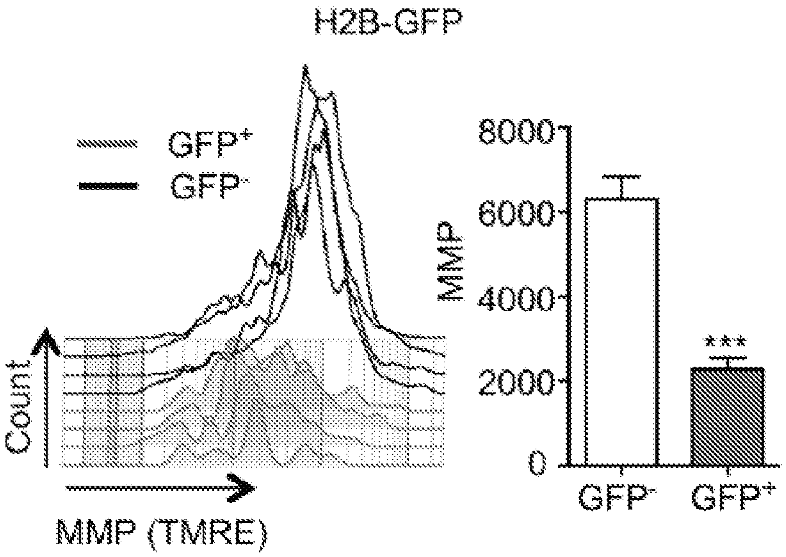
Figure 3G:
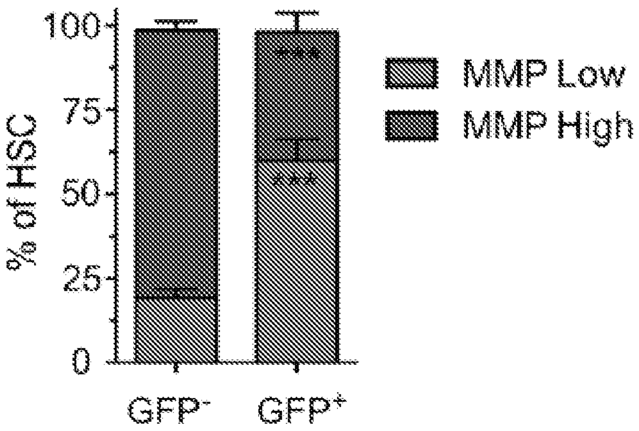

Example 3—HSCs with Low Mitochondrial Activity Are Enriched in Label-Retaining Cells To further address the relevance of mitochondrial activity under homeostasis, HSCs that retain a pulsed H2B-GFP label (known as label-retaining HSCs) were examined (Qiu et al., "MET Receptor Tyrosine Kinase Controls Dendritic Complexity, Spine Morphogenesis, and Glutamatergic Synapse Maturation in the Hippocampus," *J Neurosci.* 34(49): 16166-79 (2014) and Wilson et al., "Hematopoietic Stem Cells Reversibly Switch from Dormancy to Self-Renewal During Homeostasis and Repair," *Cell* 135(6): 1118-29 (2008), which are hereby incorporated by reference in their entirety) (FIG. 3C). Tracking H2B-GFP label identifies the quiescent non-dividing HSC population that retains the label, which is otherwise diluted by half with each division and lost over time in actively dividing cells. Consistent with previous studies (Qiu et al., "Divisional History and Hematopoietic Stem Cell Function during Homeostasis," *Stem Cell Reports* 2: 473-490 (2014) and Wilson et al., "Hematopoietic Stem Cells Reversibly Switch From Dormancy to Self-Renewal During Homeostasis and Repair," *Cell* 135: 1118-1129 (2008), which are hereby incorporated by reference in their entirety), 14-week doxycycline-chased H2B-GFP mice contained ~15% H2B-$GFP^{+}$ label-retaining HSCs within the LSK $CD150^{+}CD48^{-}$ compartment (FIG. 3D). HSCs within the MMP-low fractions contained a significantly higher proportion of label-retaining $GFP^{+}$ cells than the ones within the MMP-high fractions (FIG. 3E). Conversely, label-retaining $GFP^{+}$ HSCs maintained lower MMP than non-label-retaining cells (FIG. 3F). $GFP^{+}$ label-retaining and non-label-retaining cells were also segregated by MMP fraction, which further suggested that a significant majority of $GFP^{+}$ label-retaining cells are within the MMP-low fraction (FIG. 3G). These combined data (FIGS. 3A-3G) reinforce the notion that mitochondrial activity distinguishes between quiescent HSCs (MMP-low; dormant) and HSCs that exit quiescence and are already activated (MMP-high; primed).

These findings elicit the likelihood that quiescent ($G_0$) (FIG. 3A) and label-retaining HSCs (FIGS. 3C-3G) with low MMP are molecularly distinct from $G_0$ and label-retaining HSCs with high MMP levels. They also support the notion that gradual increase in mitochondrial activation is associated with, if not implicated in, HSC transition from quiescent MMP-Low ($G_0$) to primed MMP-high ($G_1$) state.

Figure 4A:
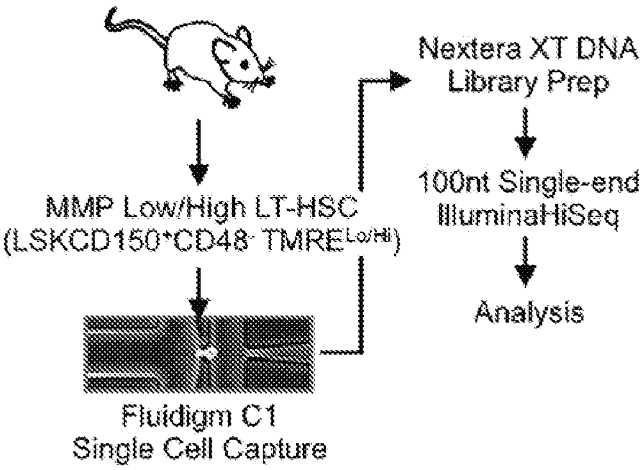
FIGS. 4A-4I demonstrate that single-cell RNAseq of MMP-low and MMP-high HSCs depicts the HSC trajectory from quiescent to a primed state.

Example 4—Single-Cell RNA-Seq ("scRNA-Seq") of MMP-Low Versus MMP-High HSCs Exposes HSC Trajectory from Quiescent to Primed State To elucidate the potential diversity of HSC identity at the single cell level in quiescent MMP-low versus primed MMP-high fractions, the transcriptome was interrogated using single-cell RNA sequencing (scRNA-seq). Using the Fluidigm C1 platform, a total of 122 MMP-low HSCs and 126 MMP-high HSCs were deemed healthy after FACS purification and were subsequently sequenced (FIG. 4A). A total of 224 cells were included for further analysis after the reads were mapped, processed, and filtered (>600,000 reads, >5,500 genes detected). Initial analysis confirmed segregation of MMP-low versus MMP-high HSCs (FIG. 4B) and revealed significant differences in the number of genes expressed in HSCs with low (~4849 genes) versus high MMP (~6,421 genes; P<0.001) (FIG. 4B; Liang et al., "Restraining Lysosomal Activity Preserves Hematopoietic Stem Cell Quiescence and Potency," *Cell Stem Cell* 26: 359-376 (2020), Table 51, which is hereby incorporated by reference in its entirety).

Figures 4B, 4C:
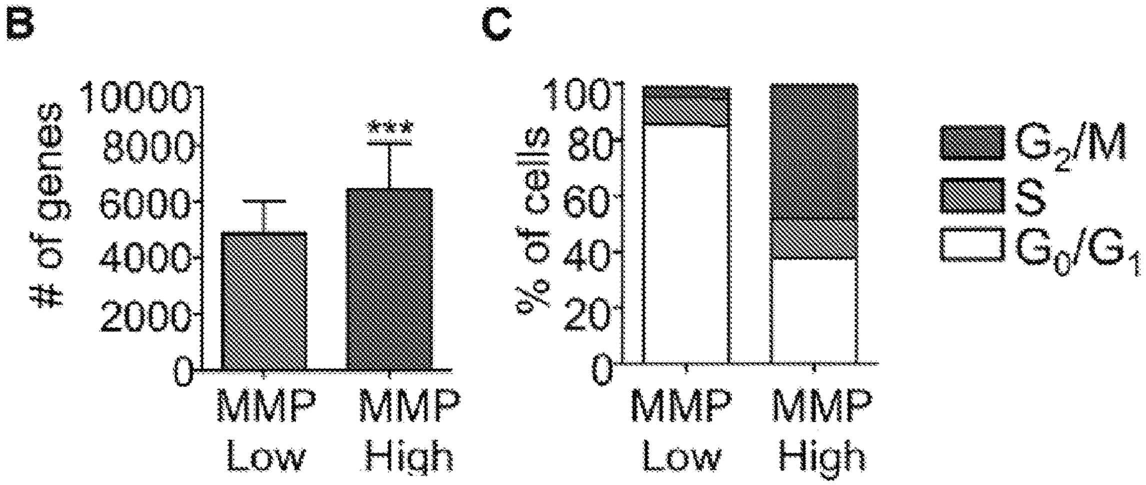
Figures 5A, 5B:
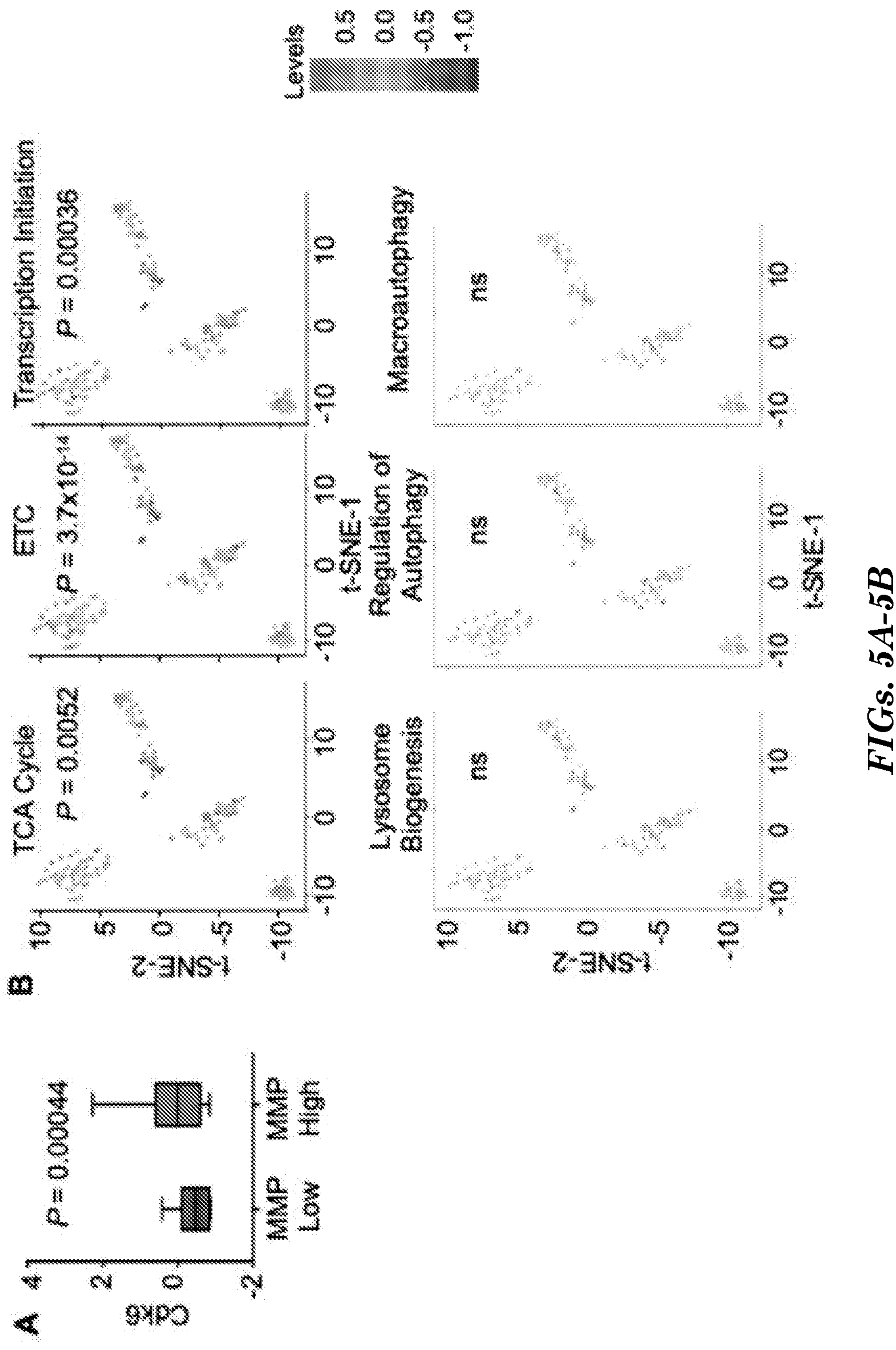
FIGS. 5A-5J demonstrate that discrete clusters within MMP-low and MMP-high HSCs depict the trajectory of HSC quiescence to activation.

Cycling analysis in silico in each cell by CYCLONE, an algorithm that stages cells based on the expression of various cell cycle genes (Scialdone et al., "Computational Assignment of Cell-Cycle Stage From Single-Cell Transcriptome Data," *Methods* 85: 54-61 (2015), which is hereby incorporated by reference in its entirety), further validated the quiescent versus primed HSC state (FIG. 4C), staging over 80% of MMP-low HSCs within $G_0/G_1$ as compared to less than 40% of MMP-high HSCs (FIG. 4C). In addition, Cdk6, which is a predictor of HSC exit from $G_0$ and initiation of the cell cycle (Laurenti et al., "CDK6 Levels Regulate Quiescence Exit in Human Hematopoietic Stem Cells," *Cell Stem Cell* 16: 302-313 (2015); Qiu et al., "Divisional History and Hematopoietic Stem Cell Function during Homeostasis," *Stem Cell Reports* 2: 473-490 (2014); and Scheicher et al., "CDK6 as a Key Regulator of Hematopoietic and Leukemic Stem Cell Activation," *Blood* 125: 90-101 (2015), which are hereby incorporated by reference in their entirety), was significantly more elevated in MMP-high HSCs than MMP-low HSCs (FIG. 5A).

Figure 4D:
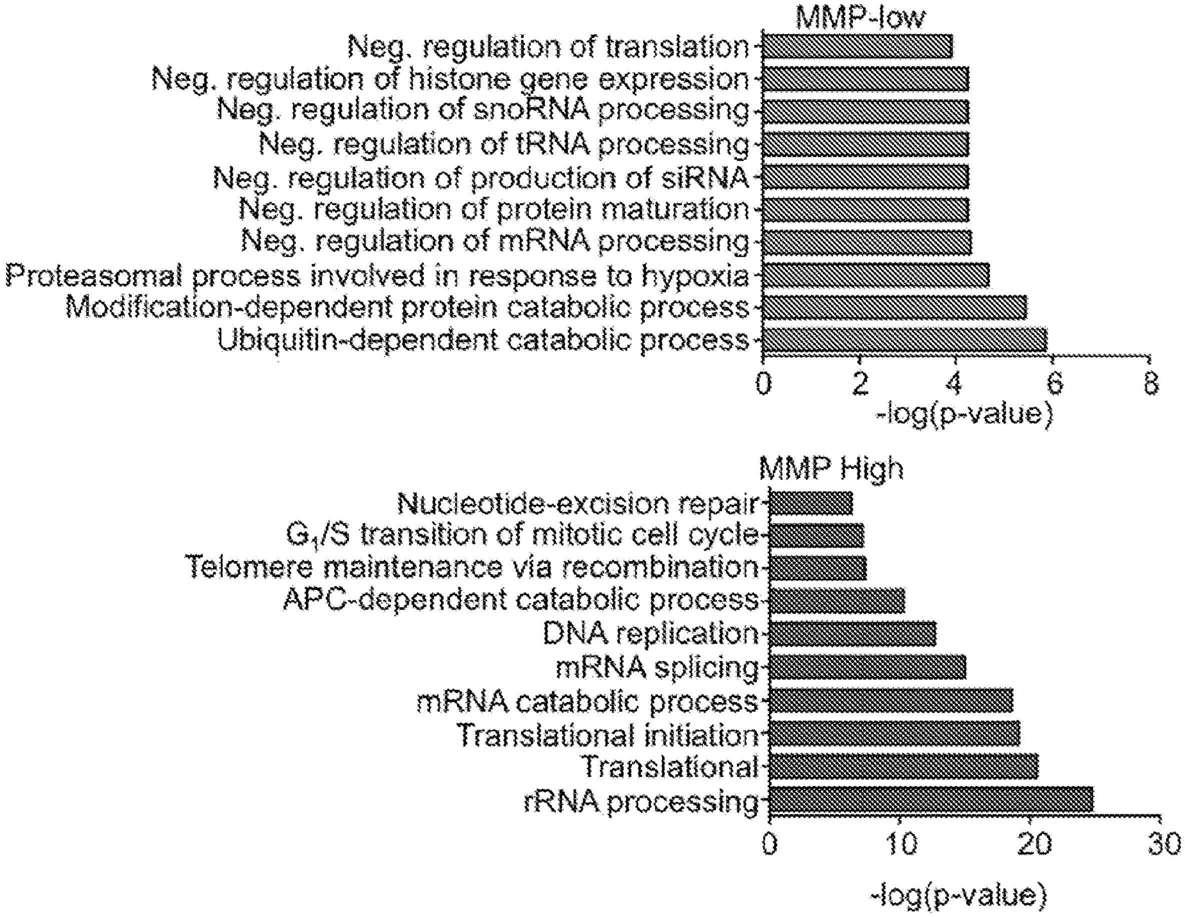
Figures 4E, 4F, 4G:
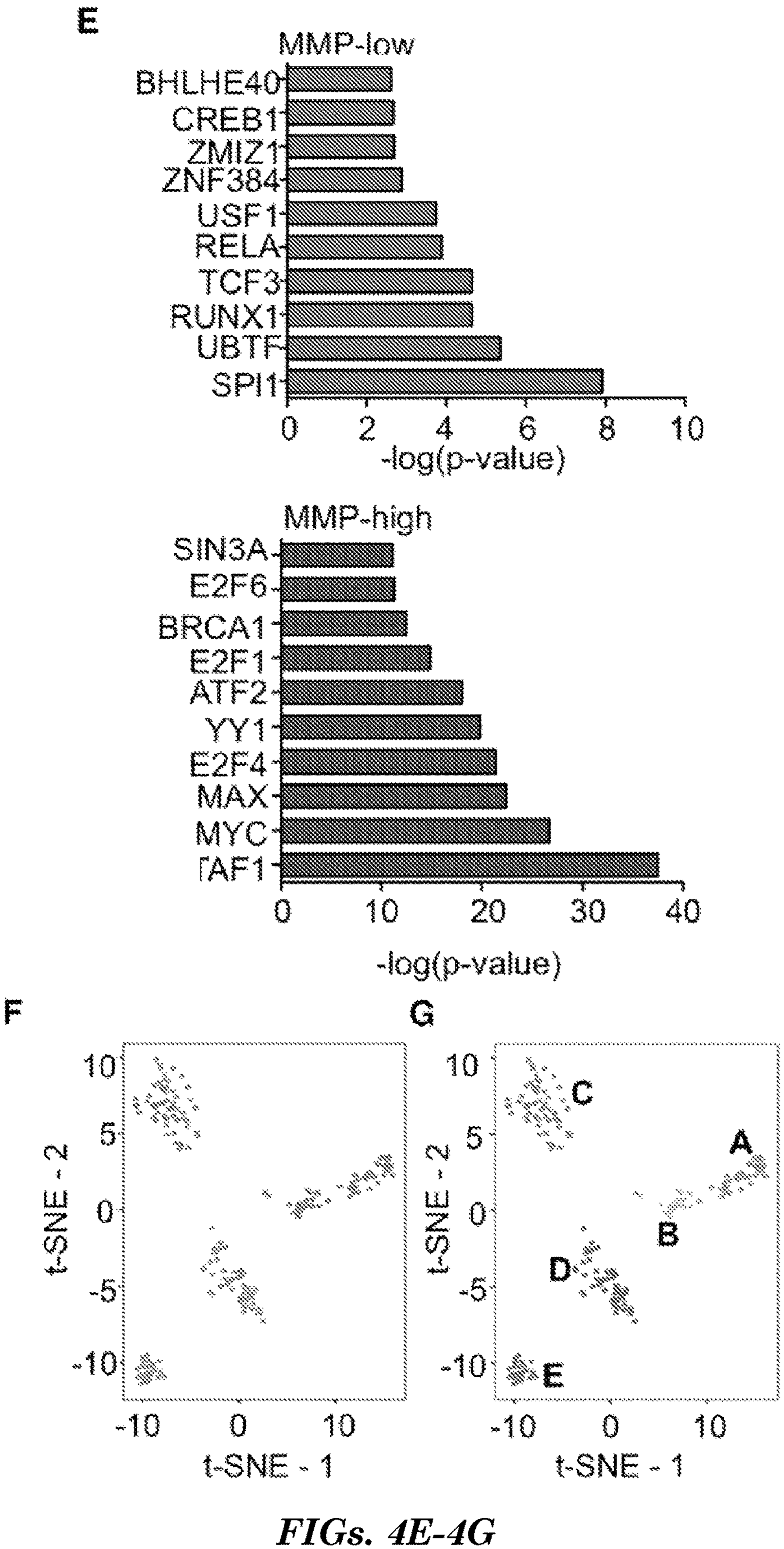

To improve the signal-to-noise ratio in identifying genes that were differentially expressed between MMP-low and MMP-high HSCs, genes that had been expressed by less than 2 cells were first filtered out. MAST (model-based analysis of single-cell transcriptomics) was then used to include only genes that were highly variable between MMP-low and MMP-high HSCs. The resulting 5,635 genes were then used for downstream analysis (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety) (Finak et al., "MAST: A Flexible Statistical Framework for Assessing Transcriptional Changes and Characterizing Heterogeneity in Single-Cell RNA Sequencing Data," *Genome Biol.* 16: 278 (2015), which is hereby incorporated by reference in its entirety). Within this list, a subset of 1,868 genes differentially expressed with statistical significance between MMP fractions of HSCs were identified. GO-term enrichment analysis revealed that genes implicated in metabolic processes as well as the negative regulation of transcription and translation including protein maturation and mRNA processing pathways were highly enriched in MMP-low HSCs, whereas MMP-high HSCs were enriched for anabolic pathways that support transcription, translation and cell cycle progression (FIG. 4D; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety). These analyses showed that genes involved in chromatin modification, DNA replication, telomere maintenance, and DNA damage repair pathways, and RNA processing as well as mitochondrial biogenesis were greatly enriched in MMP-high HSCs (FIG. 4D; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety), in line with their active nature to sustain the integrity of their genome as they replenish downstream lineages. ChEA (ChIP-X Enrichment) analysis (Lachmann et al., "ChEA: Transcription Factor Regulation Inferred From Integrating Genome-Wide ChIP-X Experiments," *Bioinformatics* 26: 2438-2444 (2010), which is hereby incorporated by reference in its entirety) identified putative transcription factors, some of which are known to be critical for HSC function were found (FIG. 4E). In agreement with the functional data, gene targets of transcription factors, including MYC and E2F, implicated in cell proliferation and mitochondrial biogenesis (Benevolenskaya et al., "Emerging Links Between E2F Control and Mitochondrial Function," *Cancer Res.* 75 :619-623 (2015) and Morrish et al., "MYC and Mitochondrial Biogenesis," *Cold Spring Harbor Perspectives In Medicine* 4 (2014), which are hereby incorporated by reference in their entirety) were enriched in MMP-high HSCs (FIGS. 4E, 5B). On the other hand, MMP-low HSCs were enriched for many transcriptional targets implicated in the maintenance of HSC quiescence, including Spi1 (PU.1), Runx1 , and RelA (FIG. 4E). This analysis also identified transcription factors greatly enriched in MMP-low HSCs, including UBTF, BHLHE40, ZMZ1, and TAF1, whose function is either unknown or poorly understood (Chen et al., "The Anti-Apoptotic and Neuro-Protective Effects of Human Umbilical Cord Blood Mesenchymal Stem Cells (hUCB-MSCs) on Acute Optic Nerve Injury Is Transient," *Brain Res.* 1532: 63-75 (2013) and Lachmann et al., "ChEA: Transcription Factor Regulation Inferred From Integrating Genome-Wide ChIP-X Experiments," *Bioinformatics* 26: 2438-2444 (2010), which are hereby incorporated by reference in their entirety) (FIG. 4E; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety). Notably, GO terms related to protein degradation through lysosomal- and proteasomal-mediated pathways were significantly enriched in MMP-low HSCs (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety).

These results depict a profile consistent with the repressive chromatin landscape maintaining HSC quiescence in MMP-low and the active chromatin supporting gene activation in MMP-high HSCs (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety) (Iwama et al., "Enhanced Self-Renewal of Hematopoietic Stem Cells Mediated by the Polycomb Gene Product Bmi-1," *Immunity* 21: 843-851 (2004) and Lu et al., "Polycomb Group Protein YY1 Is an Essential Regulator of Hematopoietic Stem Cell Quiescence," *Cell Reports* 22: 1545-1559 (2018), which are hereby incorporated by reference in their entirety). The results also support the notion that the mitochondrial activity modulates HSC chromatin landscape via the production of the precursors of histone modifiers (Ansó et al., "The Mitochondrial Respiratory Chain Is Essential for Haematopoietic Stem Cell Function," *Nat. Cell Biol.* 19(6): 614-625 (2017) and Reid et al., "The Impact of Cellular Metabolism on Chromatin Dynamics and Epigenetics," *Nat. Cell Biol.* 19: 1298-1306 (2017), which is hereby incorporated by reference in its entirety). In line with this interpretation, nuclei were compact in MMP-low HSCs than MMP-high HSCs (FIG. 5C).

Figures 4H, 4I:
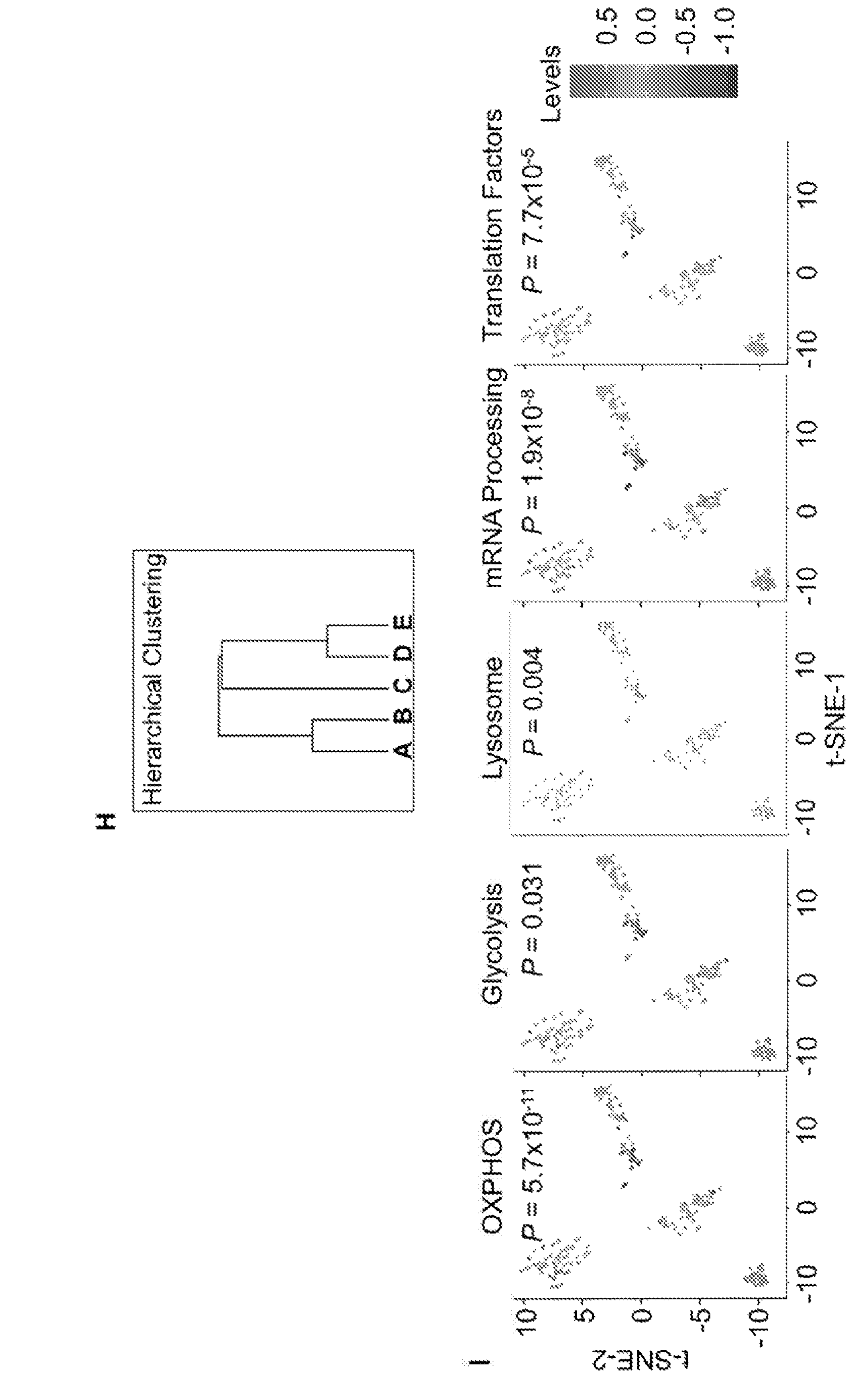
Figures 5C, 5D, 5E, 5F:
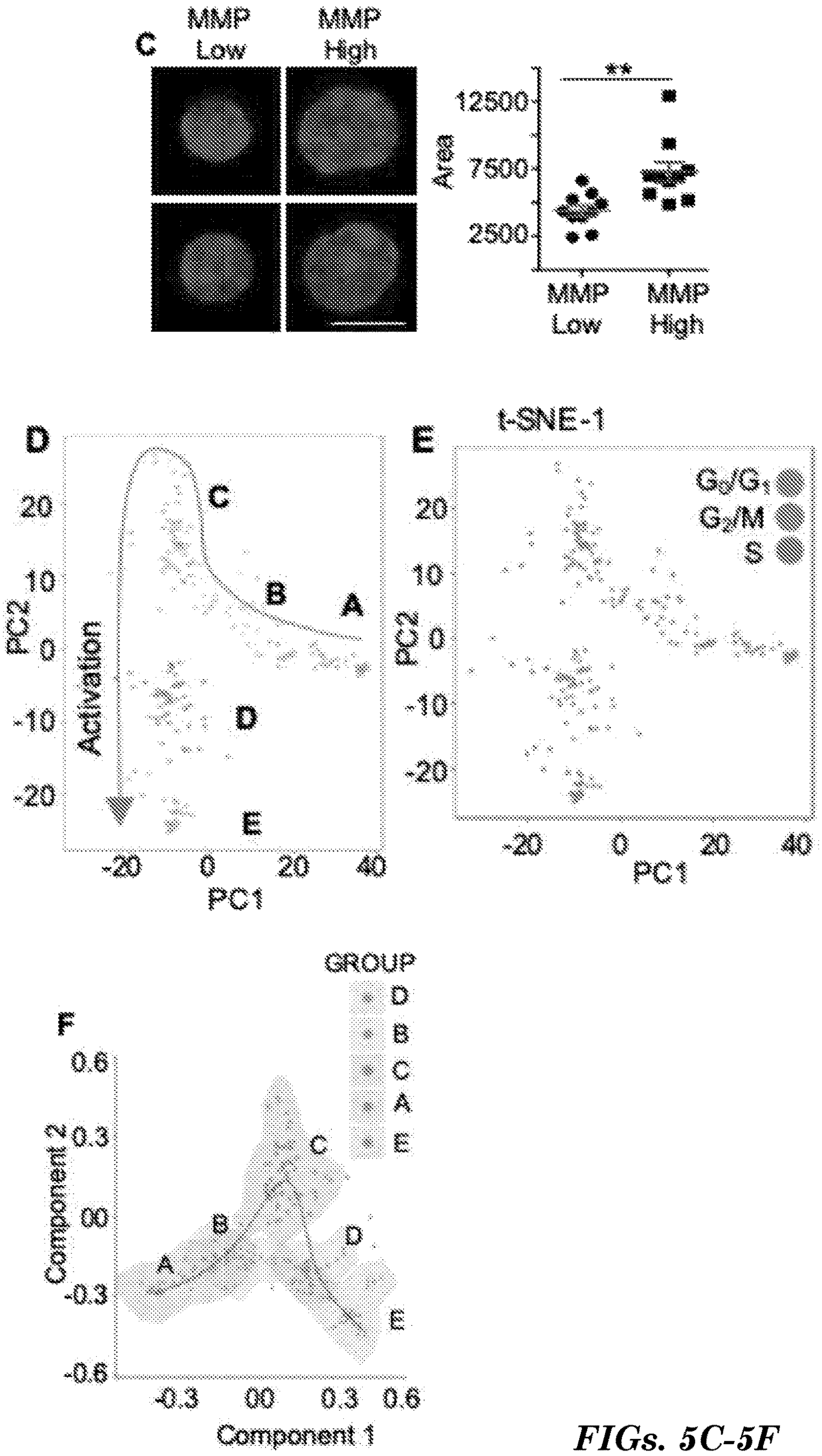

Dimensional reduction using the t-Distributed Stochastic Neighbor Embedding (t-SNE) or principal-component analysis (PCA) methods visualized similarly the heterogeneity within single-cell transcriptomes and potential distinct subpopulations within the MMP-low vs MMP-high fractions (FIGS. 4F-4G, 5D-5F). Clustering with the Seurat toolkit on the first 5 principle components resulted in 5 clusters (FIGS. 5D-5E) (Finak et al., "MAST: A Flexible Statistical Framework for Assessing Transcriptional Changes and Characterizing Heterogeneity in Single-Cell RNA Sequencing Datam" *Genome Biol.* 16: 278 (2015), which is hereby incorporated by reference in its entirety). The resulting t-SNE scatter plot distinctly separated genes in MMP-low (clusters A, B) versus MMP-high HSCs (clusters D, E; FIG. 4G). In addition, cluster C contained genes from both MMP-low and MMP-high HSCs (FIG. 4G). Clusters A and B were closely related, while clusters C, D, and E formed a distinct branch by hierarchical clustering (FIG. 4H). Within this branch, clusters D and E appeared more closely related to each other than with cluster C (FIGS. 4H, 5D). Reexamination of CYCLONE (FIGS. 4C, 5E) confirmed cell cycle staging data (FIG. 5E). GO term enrichment of genes further revealed the relationship between individual clusters (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety). Similar to the entire MMP-low HSC compartment, clusters A and B were enriched mainly for lysosomes and protein degradation pathways, including autophagy (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety). HSCs in cluster C were enriched for DNA damage repair pathways, mitochondria-localized genes, and chromatin regulators and included a subset of lysosomal genes (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety). On the other hand, HSCs in clusters D and E were highly enriched for genes related to cell-cycle progression, mitochondrial metabolism, and transcriptional and translational activation (Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety).

Altogether, these results in combination with the functional data (FIGS. 1A-1G, 2A-2E, 3A-3G; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety) suggest that HSCs switch from a quiescent state in clusters A and B to a transitional state in cluster C, which includes a mixture of MMP-low and MMP-high HSCs. This cluster relationship (A to E) was further inferred using SCORPIUS trajectory (Cannoodt et al., "Computational Methods for Trajectory Inference from Single-Cell Transcriptomics," *Eur. J. Immunol.* 46: 2496-2506 (2016), which is hereby incorporated by reference in its entirety), which clusters the data (with k-means clustering) and finds the shortest path through the cluster center (FIG. 5F). Importantly, a comparative dataset analysis suggests that MMP-low and MMP-high HSCs are greatly similar (p value=3.4e-10; Liang et al., "Restraining Lysosomal Activity Preserves Hematopoietic Stem Cell Quiescence and Potency," *Cell Stem Cell* 26: 359-376 (2020), Table S3, which is hereby incorporated by reference in its entirety) to label-retention-defined dormant HSCs (dHSCs) and activated HSCs (aHSCs) (Cabezas-Wallscheid et al., "Identification of Regulatory Networks in HSCs and Their Immediate Progeny Via Integrated Proteome, Transcriptome, and DNA Methylome Analysis," *Cell Stem Cell* 15: 507-522 (2014), which is hereby incorporated by reference in its entirety), respectively. These results suggest low levels of MMP may be an intrinsic determinant of dormancy in immune-phenotypically defined HSCs similar to the label retention transgene.

Figures 5G, 5H, 5I, 5J:
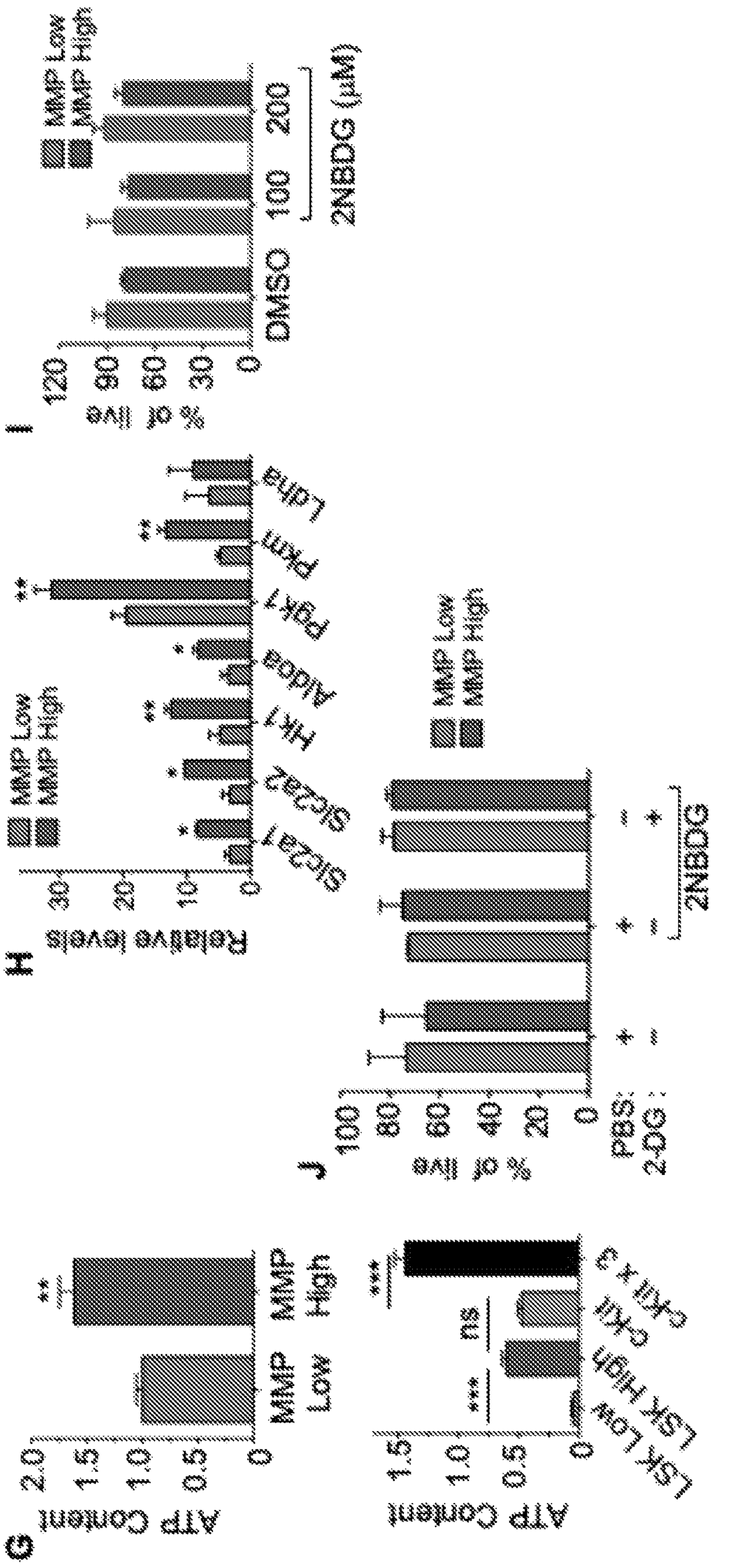

Example 5—MMP-High (Primed) but Not MMP-Low (Quiescent), HSCs Rely Readily on Glycolysis To identify metabolic pathways that may distinctively support MMP-low versus MMP-high HSCs, genes from pathways of interest were retrieved from WikiPathways and Reactome databases and pathway scores (levels) were generated for each cell as reported (Cabezas-Wallscheid et al., "Identification of Regulatory Networks in HSCs and Their Immediate Progeny Via Integrated Proteome, Transcriptome, and DNA Methylome Analysis," *Cell Stem Cell* 15: 507-522 (2014), which is hereby incorporated by reference in its entirety). All of the major metabolic pathways analyzed showed significantly greater expression within the MMP-high than in the MMP-low HSC fraction (FIG. 4I, 5B). ATP levels were also 1.5-fold lower in MMP-low than MMP-high HSCs (FIG. 5G). Cluster E was the most metabolically active, with the greatest levels in oxidative phosphorylation ("OXPHOS"), tricarboxylic acid ("TCA") cycle, and electron transfer chain ("ETC") compared to all other clusters (FIG. 4I, 5B). In contrast, cluster B showed the lowest levels of metabolic genes, even when compared to cluster A. This was also true for pathways involved in transcriptional and translational activation (FIG. 4I, 5B).

Figures 6A, 6B:
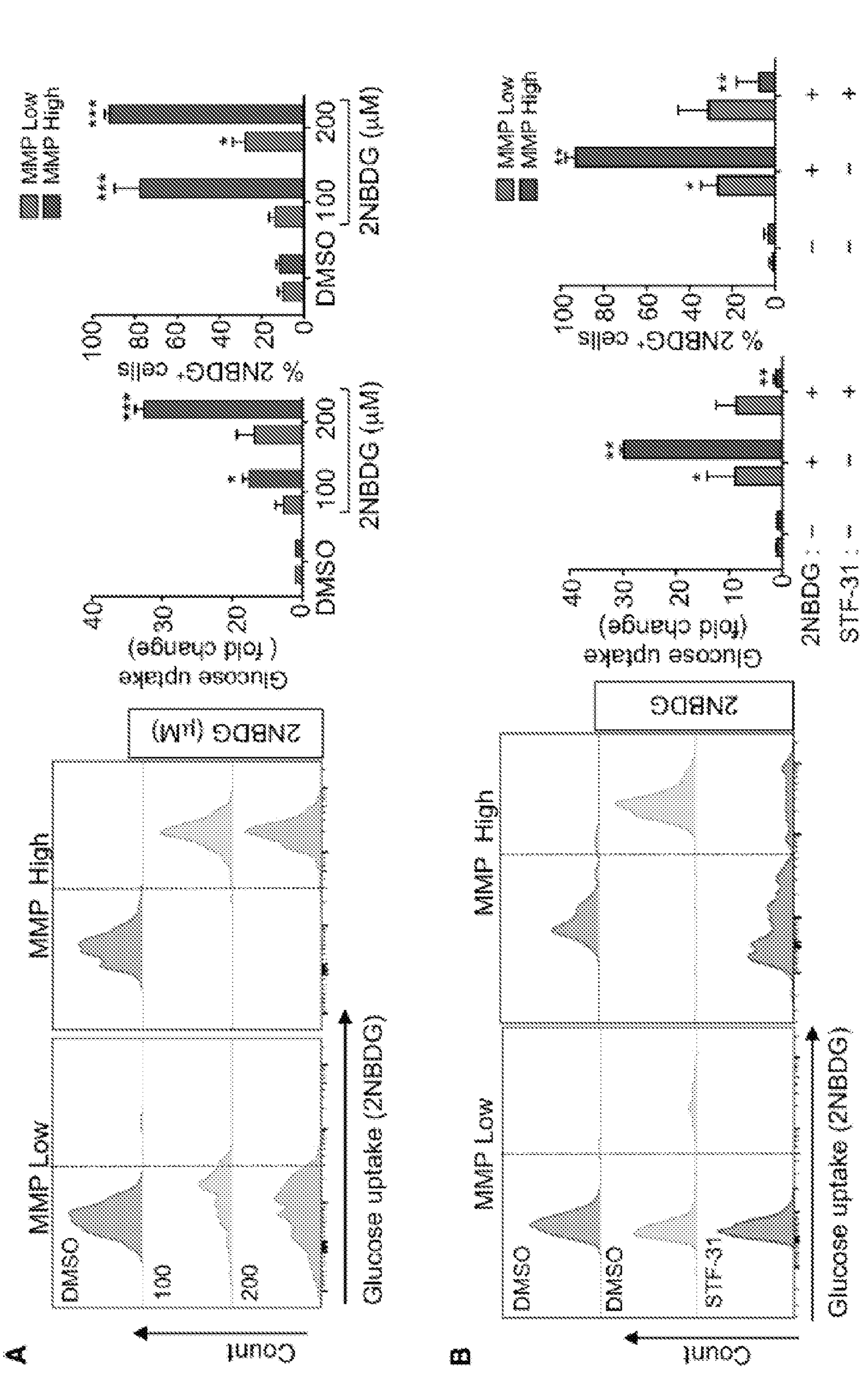
FIGS. 6A-6E demonstrate that glycolysis is more readily used in primed MMP-high HSCs than quiescent MMP-low HSCs.
Figures 6C, 6D, 6E:
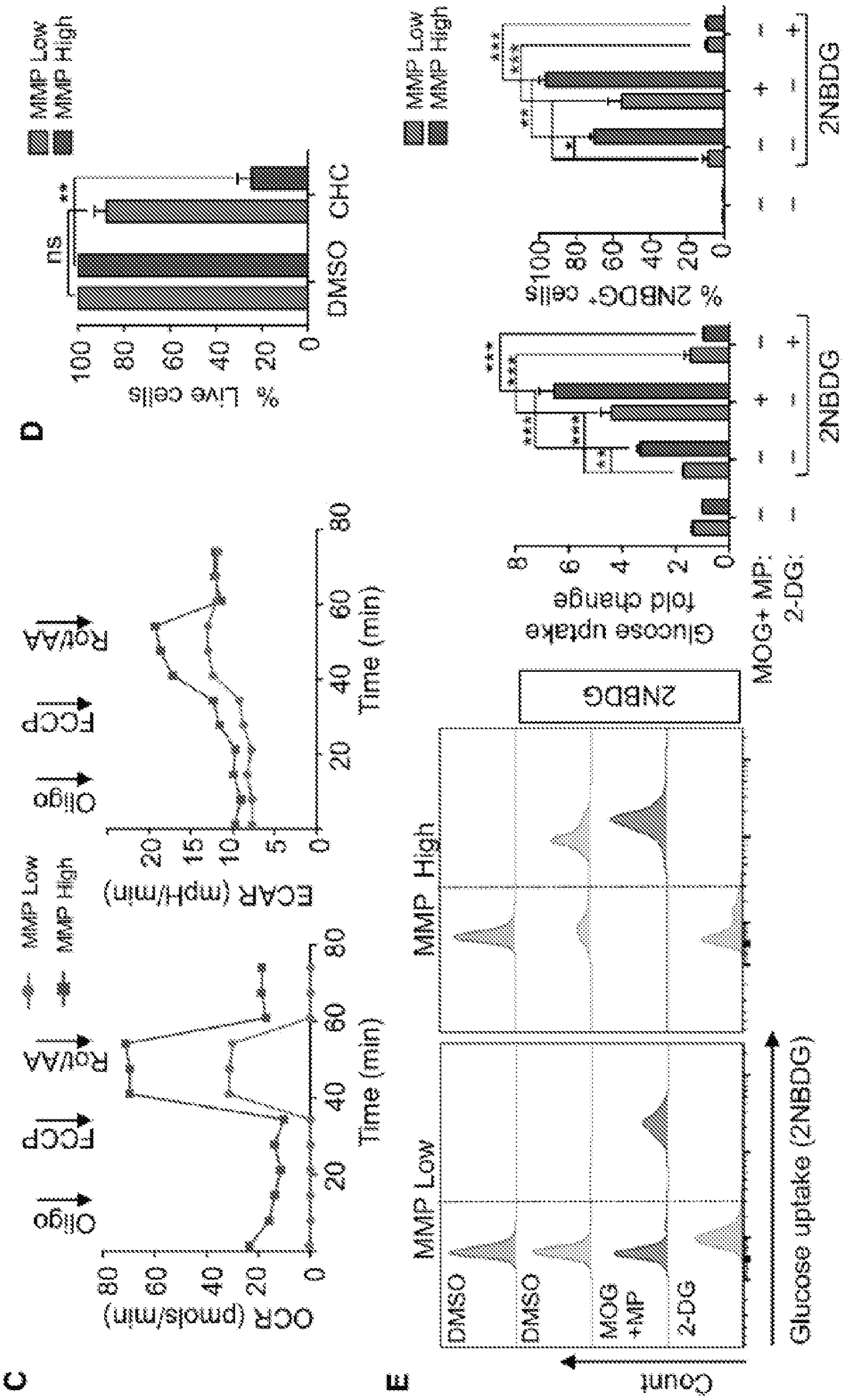

Unexpectedly, glycolytic gene expression was also enriched in the "active" cluster E and relatively low in "quiescent" clusters A and B (FIG. 4I). qRT-PCR analysis further confirmed that the expression of glycolysis-related genes, including glucose transporter 1 (Glut1, Slc2a1), which is the main glucose transporter expressed by HSCs, is greater in MMP-high HSCs than MMP-low HSCs (FIG. 5H). These unexpected findings raised the potential that despite the current consensus in HSC biology (Bigarella et al., "Stem Cells and the Impact of ROS Signaling," *Development* 141: 4206-4218 (2014) and Chandel et al., "Metabolic Regulation of Stem Cell Function in Tissue Homeostasis and Organismal Ageing," *Nat. Cell Biol.* 18: 823-832 (2016), which are hereby incorporated by reference in their entirety), glycolysis may more readily support active HSCs (in cluster E) rather than quiescent HSCs with low mitochondrial activity (in clusters A and B). To address this possibility, glucose uptake in MMP-low vs MMP-high HSCs was measured under defined metabolic [(pyruvate, glucose and glutamine)-free] conditions. Using 2NBDG (2-[N-(7-nitrobenz-2-oxa-1,3-diazol-4-yl)amino]- 2-deoxy-D-glucose), a fluorescently tagged glucose analog (Zhou et al., "2-NBDG as a Fluorescent Indicator for Direct Glucose Uptake Measurement," *J. Biochem. Biophys. Methods* 64(3): 207-215 (2005), which is hereby incorporated by reference in its entirety), it was found that MMP-high HSCs uptake 3.3-fold more glucose than MMP-low HSCs in a 2-hour in vitro assay (FIG. 6A). MMP-high HSCs also contained 3 times more $2NBDG^{+}$ cells as compared to MMP-low HSCs (FIG. 6A). Cell viability was not significantly modulated under the experimental condition (FIG. 5I). Pharmacological inhibition of Scl2a1 reduced glucose uptake in MMP-high HSCs but had no noticeable effect on MMP-low HSCs (FIG. 6B), demonstrating the sensitivity of MMP-high HSCs specifically to the glucose inhibition, although it cannot be ruled out that MMP-low HSCs use a different glucose transporter (FIG. 6B). Seahorse analysis found that higher levels of MMP are associated with both higher oxygen consumption rate (OCR) and glycolytic rate (extracellular acidification) as compared to low MMP levels in the hematopoi-etic stem and progenitor cell (HSPC) compartment (FIG. 6C). In addition, inhibiting mitochondrial transport of pyruvate, the end product of glycolysis, with CHC (a-cyano-4-hydroxycinnamate), decreased survival in MMP-high HSCs by 80% with a negligible effect on MMP-low HSCs (FIG. 6D). These results suggest that the pyruvate produced through glycolysis is required for downstream mitochondrial metabolism in MMP-high, but not MMP-low, HSCs. Importantly, activating the TCA cycle enhanced glucose uptake in both HSC fractions while it was further enhanced in MMP-high as compared to MMP-low HSCs (FIG. 6E), suggesting that increasing mitochondrial activity shifts MMP-low HSCs to use glycolysis. Overall, these combined findings indicate that in quiescent HSCs, under homeostasis, glycolysis and mitochondrial metabolism are linked such that quiescent (MMP-low) HSCs with low mitochondrial activity have no need to break down glucose to feed into the TCA cycle (FIGS. 6A-6D). Activation of the TCA cycle is associated with glycolysis in MMP-low HSCs that increase their glucose uptake (FIG. 6E).

Figures 7A, 7B:
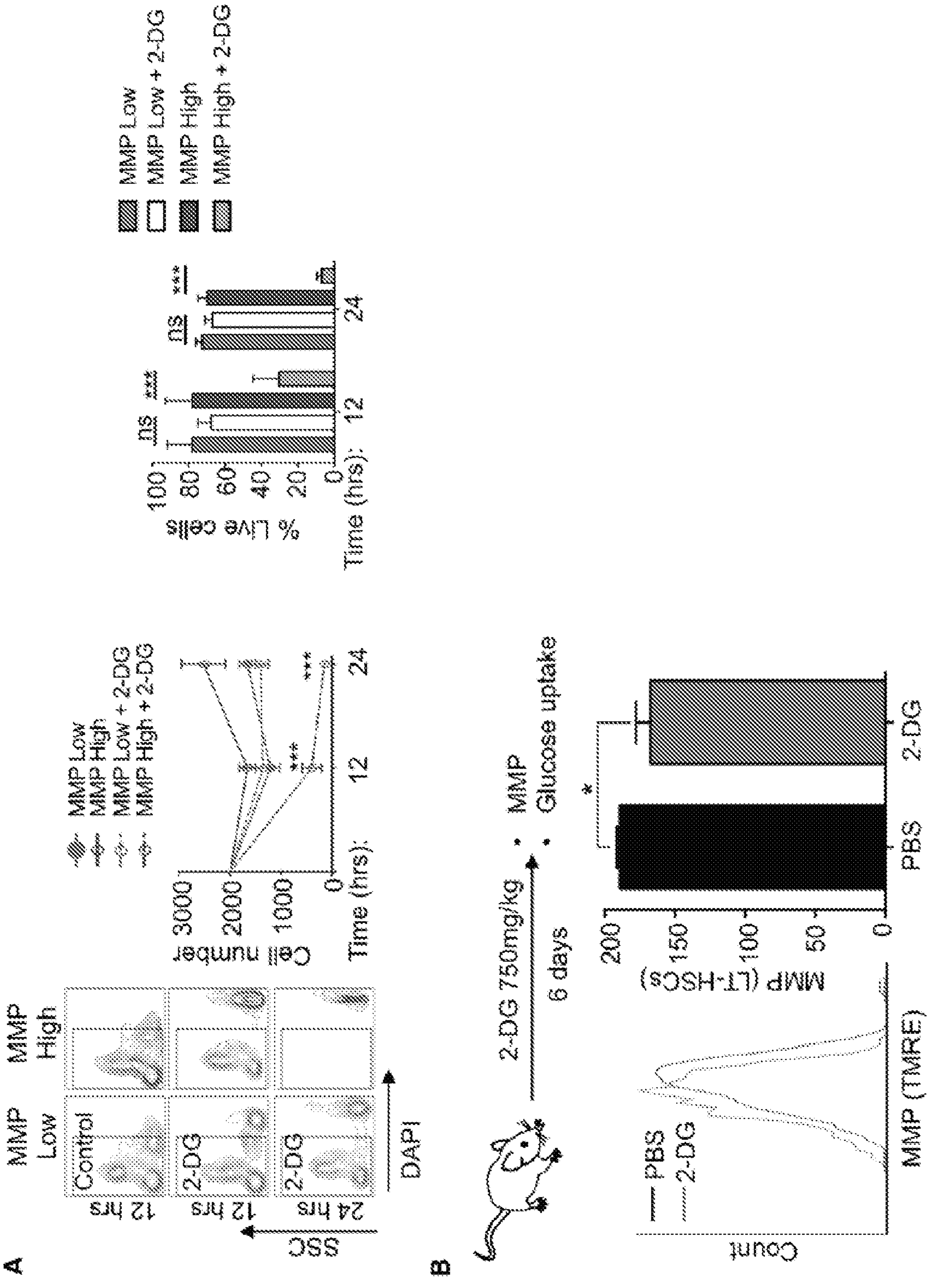
FIGS. 7A-7E show that glycolytic inhibition enhances HSC long-term competitive repopulation activity in vivo.
Figures 7C, 7D:
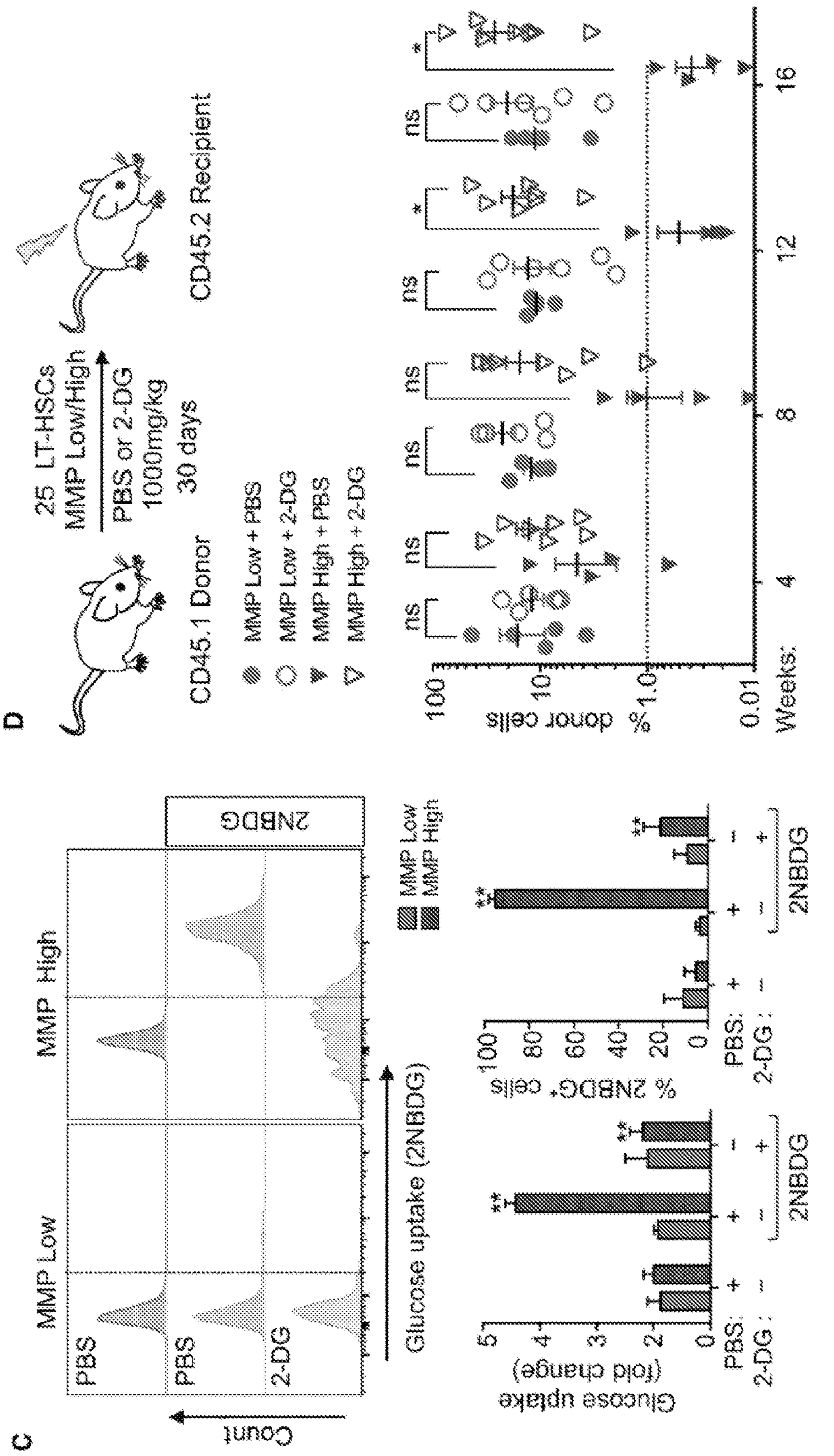
Figure 7E:
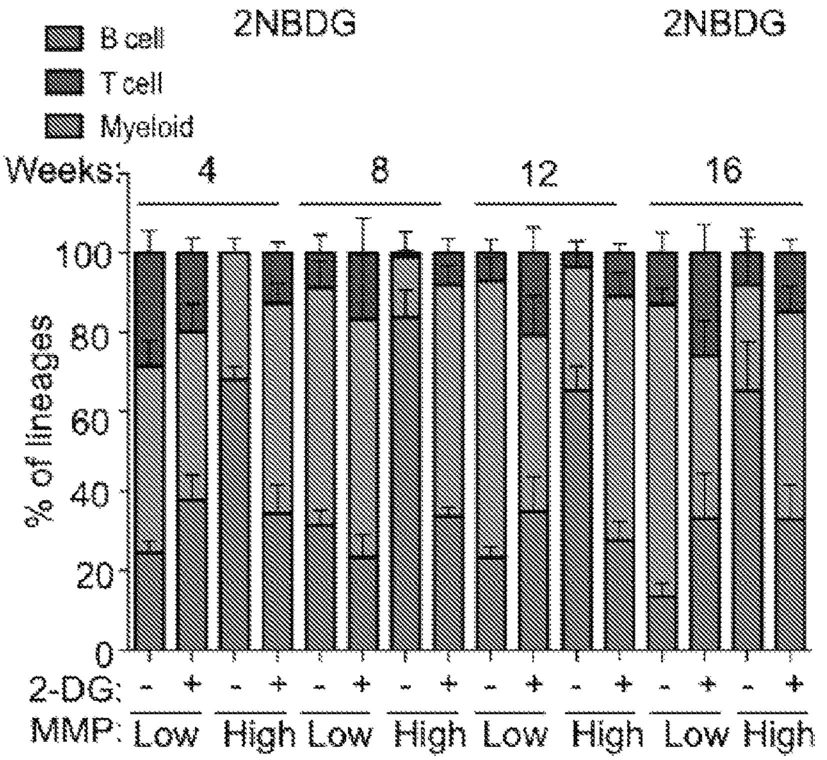

To address the degree to which glycolysis is necessary, FACS purified MMP-low and MMP-high HSCs were incubated with 2-Deoxy D-Glucose ("2DG"), a glucose analog that inhibits glycolysis via its action on hexokinase. While interference with glycolysis using 2-DG (50 mM) did not have much of an effect on MMP-low HSCs, over 60% of MMP-high HSCs died within 12 hours (FIG. 7A). This effect was even more pronounced after 24 h in MMP-high, but not MMP-low, HSCs (FIG. 7A), suggesting that MMP-high, but not MMP-low, HSCs rely readily on glycolysis for their survival. To further address the effect of inhibition of glycolysis in a more physiological HSC context, mice were treated with 2-DG in vivo and glucose uptake was measured (FIGS. 7B-7C). The 6-day in vivo 2-DG treatment slightly but significantly reduced overall MMP levels in long-term HSCs (FIG. 7B, right panel). In addition, while in vivo 2-DG treatment did not have much of an effect on the cellular viability (FIG. 5J), it reduced glucose uptake specifically in HSCs with the highest MMP levels, but not the ones with the lowest MMP levels (FIG. 7C). These intriguing results suggest that the in vivo 2-DG treatment may promote the maintenance of HSCs with lesser glycolytic needs. To further address this, MMP-low and MMP-high HSCs were transplanted in lethally irradiated mice treated with 2-DG or control for 30 days (FIGS. 7D, 7E). Remarkably, 2-DG treatment enhanced by over 70-fold the in vivo competitive repopulation ability of MMP-high HSCs (FIG. 7D), while it had only subtle effects on MMP-low HSCs after 4 months (FIG. 7D). In addition, 2-DG-treated recipients of MMP-high HSCs exhibited a balanced production of blood similar to that derived from recipients of untreated MMP-low HSCs (FIG. 7E). While in vivo 2-DG treatment clearly led to reduced glucose uptake in MMP-high HSCs (FIG. 7C), no systemic effect was detected in the blood of long-term (up to 16 weeks) transplanted mice that were maintained under normal diet (not shown). These studies highlight the importance of glycolysis in supporting active HSCs while showing that the maintenance of HSC potency relies on glycolytic restriction.

Thus, MMP-low as compared to MMP-high HSCs are mostly quiescent ($G_o$), with enhanced self-renewal and balanced lineage output, but exhibit greatly reduced ATP levels and relatively limited reliance on glycolysis.

Figures 8A, 8B, 8C:
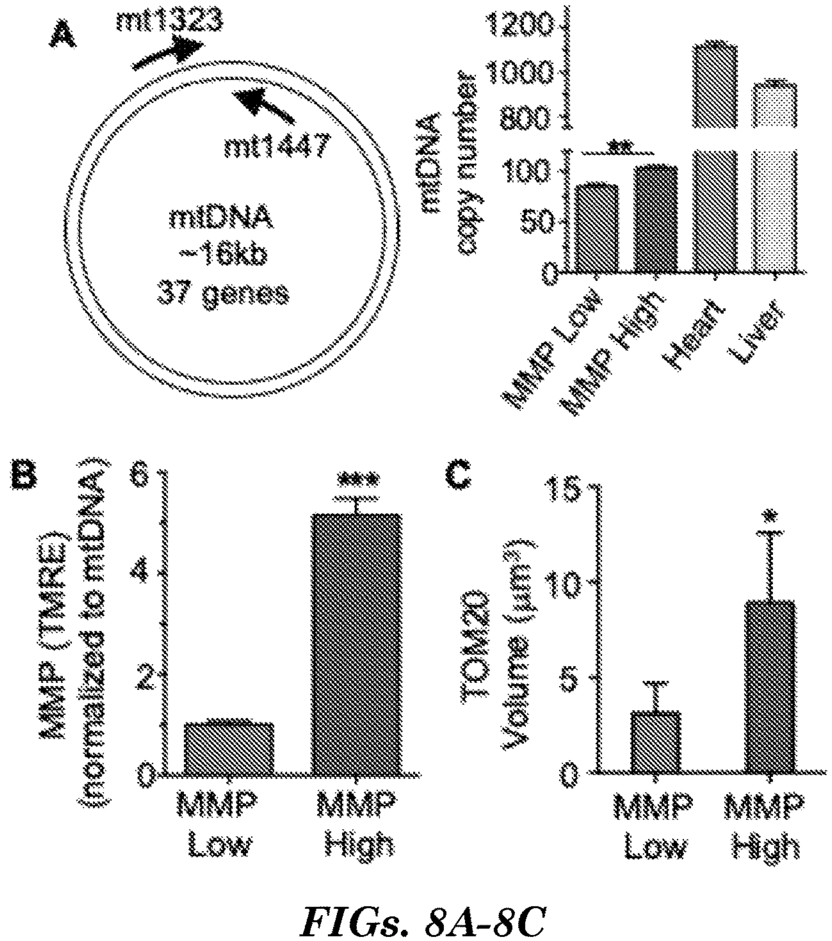
FIGS. 8A-8I demonstrate that large lysosomes are abundant in MMP-low vs. MMP-high HSCs.
Figures 9A, 9B, 9C:
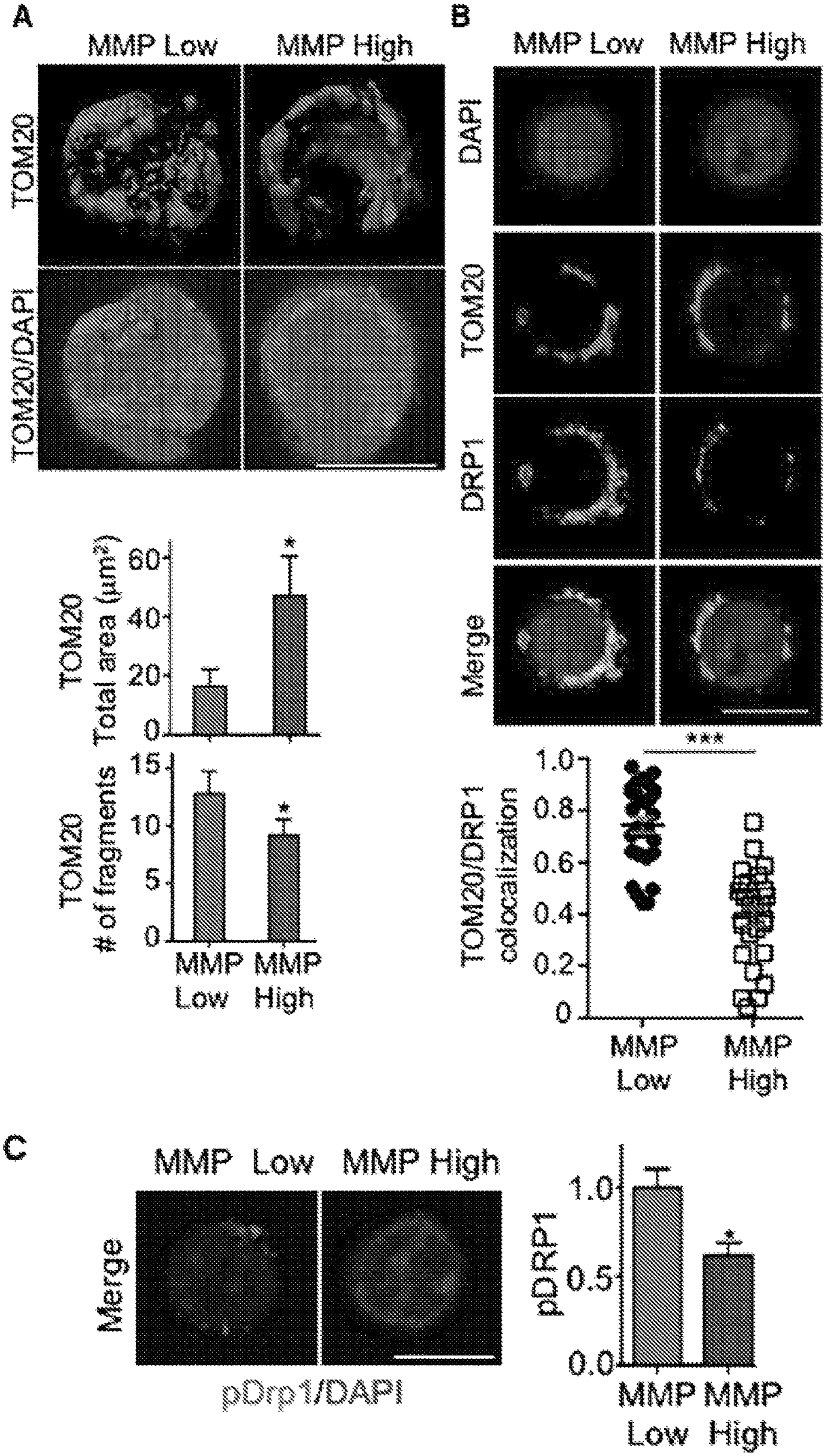
FIGS. 9A-9F demonstrate that MMP-low HSCs exhibit punctate mitochondrial networks associated with large lysosomes.
Figure 9D:
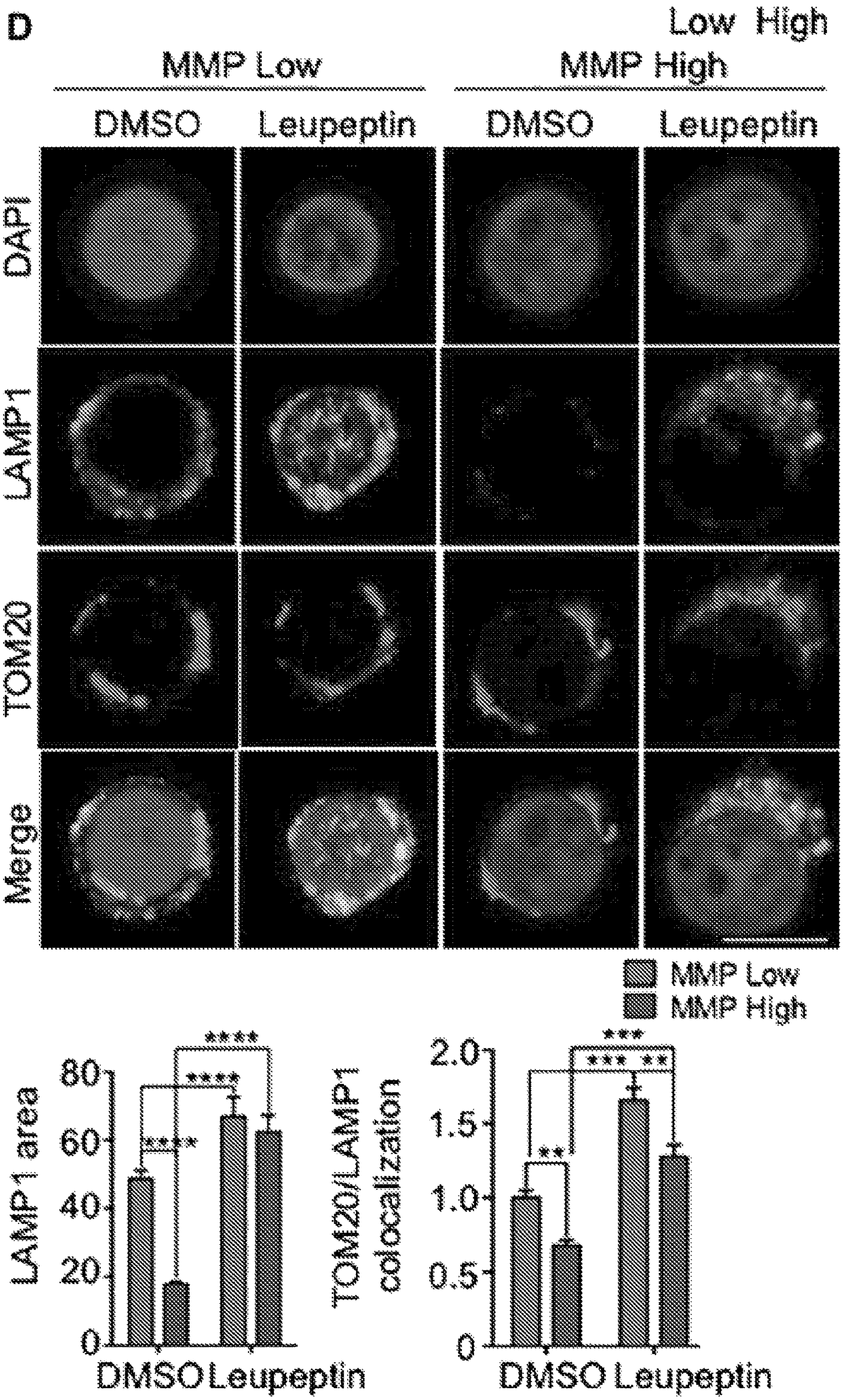

Example 6—Quiescent MMP-Low HSCs Exhibit Punctate Mitochondrial Networks Associated with an Abundance of Large Lysosomes Although mitochondrial mass was greater in HSCs relative to downstream progenitors (de Almeida et al., "Dye-Independent Methods Reveal Elevated Mitochondrial Mass in Hematopoietic Stem Cells," *Cell Stem Cell* 21: 725-729 e724 (2017); Norddahl et al., "Accumulating Mitochondrial DNA Mutations Drive Premature Hematopoietic Aging Phenotypes Distinct From Physiological Stem Cell Aging," *Cell Stem Cell* 8: 499-510 (2011); and Rimmele et al., "Mitochondrial Metabolism in Hematopoietic Stem Cells Requires Functional FOXO3," *EMBO Rep.* 16: 1164-1176 (2015), which are hereby incorporated by reference in their entirety), mitochondrial mass was slightly less in MMP-low than MMP-high HSCs (FIG. 8A). The notable distinction in MMP as compared to the slight difference in mtDNA copy numbers (FIGS. 8A-8B) suggests that mitochondrial activity is strongly repressed in MMP-low HSCs. This might be through a higher mitochondrial turnover in MMP-low relative to MMP-high HSCs (Youle et al., "Mitochondrial Fission, Fusion, and Stress," *Science* 337: 1062-1065 (2012), which is hereby incorporated by reference in its entirety). Consistent with this prediction and the scRNA-Seq results (FIG. 4I), significant differences in the morphology of mitochondrial networks were evident from the analysis of mitochondrial-specific probe the translocase of the outer membrane 20 ("TOM20") protein (FIG. 9A). Mitochondria were punctate in MMP-low as compared to hyperfused in MMP-high HSCs (FIG. 9A), an indication that MMP-low HSCs contain immature mitochondria with underdeveloped cristae providing less surface area for electron transport enzymes (Roy et al., "Mitochondrial Division and Fusion in Metabolism," *Curr. Opin. Cell Biol.* 33: 111-118 (2015), which is hereby incorporated by reference in its entirety). Also, DRP1, the mitochondrial fission GTPase, was co-localized with TOM20 to a significantly greater extent in MMP-low HSCs compared with MMP-high HSCs (FIG. 9D). Levels of the active phosphorylated (pS616) form of DRP1 (Chang et al., "Drp1 Phosphorylation and Mitochondrial Regulation," *EMBO Rep.* 8: 1088-1089 (2007), which is hereby incorporated by reference in its entirety) were also markedly increased in MMP-low HSCs (FIG. 9E), together indicating that the enhanced DRP1-mediated mitochondrial fragmentation is partly mediating the suppression of mitochondrial activity in MMP-low HSCs (FIGS. 9A, 8C).

Figures 8D, 8E, 8F:
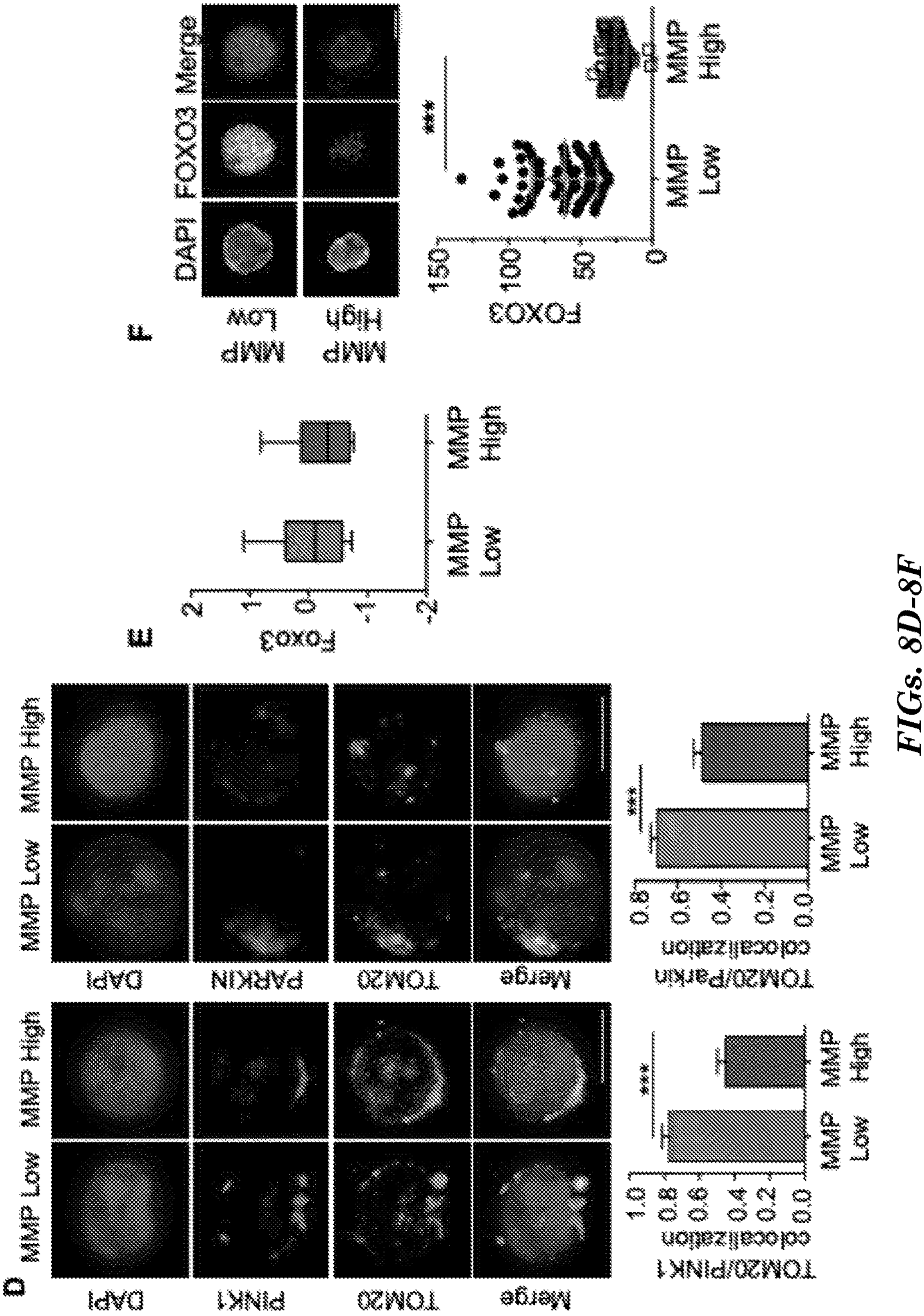
Figures 9E, 9F:
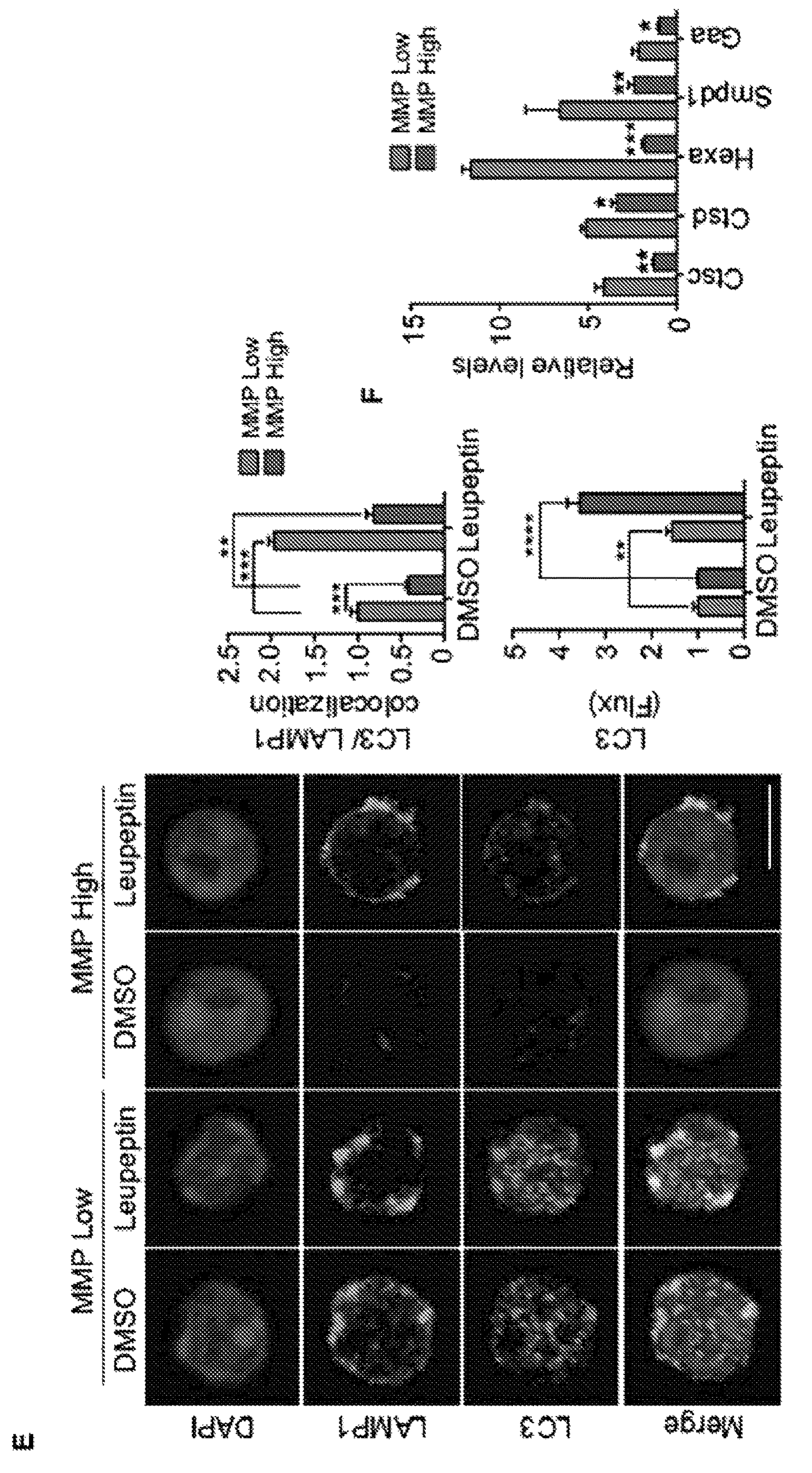

Fragmentation often precedes mitochondrial clearance by autophagy. Mitochondria (TOM20) in freshly isolated MMP- low HSCs displayed greater co-localization relative to MMP-high HSCs with PTEN-induced putative kinase 1 (PINK1) and its substrate, PARKIN, two proteins whose association with mitochondria trigger their clearance (FIG. 8D). The expression of Foxo3, a necessary transcriptional regulator of autophagy in hematopoietic cells including HSCs (Liang et al., "A Systems Approach Identifies Essential FOXO3 Functions at Key Steps of Terminal Erythropoiesis," *PLoS Genet.* (10): e1005526 (2015) and Warr et al., "FOXO3A Directs a Protective Autophagy Program in Haematopoietic Stem Cells," *Nature* 494(7437): 323-327 (2013), which are hereby incorporated by reference in their entirety) was also more abundant in the nuclei of MMP-low HSCs than MMP-high HSCs (FIGS. 8E-F). Mitochondria (TOM20) were greatly associated with the lysosomal marker lysosome membrane protein 1 (LAMP1) in freshly isolated MMP-low, but not MMP-high, HSCs (FIG. 9D). Further analysis confirmed that more autolysosomes were formed from the fusion of LC3-marked autophagosomes with lysosomes as indicated by LC3 puncta co-localization with LAMP1 in MMP-low relative to MMP-high HSCs (Yoshii & Mizushima, "Monitoring and Measuring Autophagy," *Int. J. Mol. Sci.* 18(9): 1865 (2017), which is hereby incorporated by reference in its entirety). In addition, the inhibition of targeted lysosomal degradation with the protease inhibitor leupeptin led to a greater number of autolysosomes in MMP-low as compared to MMP-high HSCs (FIG. 9E). Leupeptin treatment also enhanced similarly the co-localization of TOM20 with LAMP1 in MMP-low and MMP-high HSCs (FIG. 9D). Surprisingly, however, the increase in LC3-positive puncta in response to leupeptin, which is an indication of autophagic vacuoles that would have been otherwise degraded, was by 3.6-fold (±0.27-fold) in MMP-high HSCs versus only 1.6-fold (±0.12-fold) in MMP-low HSCs (FIG. 9E), indicating that lysosomal degradation might be less efficient in MMP-low relative to MMP-high HSCs (Klionsky et al., "Guidelines for the Use and Interpretation of Assays for Monitoring Autophagy (3rd Edition)," *Autophagy* 12(1): 1-222 (2016) and Xu & Ren, "Lysosomal Physiology," *Annu. Rev. Physiol.* 77: 57-80 (2015), which are hereby incorporated by reference in their entirety). These combined findings suggest enhanced initiation of mitochondrial clearance in MMP-low HSCs, while the downstream autolysosomal processing may be sluggish (FIGS. 9A-9E, 8C-8F). MMP-low HSCs are engaged in lysosomal processing of mitochondria while repressing mitochondrial activity partially through mitochondrial fission (FIG. 9A-9E).

Example 7♯Repression of Lysosomal Activation Enhances HSC Potency

Strikingly, and in agreement with the scRNA-seq analysis showing enrichment of lysosomal degradation proteins in MMP-low HSCs presented herein (FIG. 4I; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety), these studies further revealed that under homeostasis, lysosomes are greatly abundant in MMP-low, but not MMP-high, HSCs (FIGS. 9D-9E). Lysosomes are acidic organelles and major mediators of organelle degradation and recycling involved in endocytosis, phagocytosis, and autophagy. In addition to cargo degradtation, lysosomes reuse and store metabolites (Saftig & Klumperman, "Lysosome Biogenesis and Lysosomal Membrane Proteins: Trafficking Meets Function," *Nat. Rev. Mol. Cell Biol.* 10: 623-635 (2009), which is hereby incorporated by reference in its entirety). Although lysosomes mediate autophagy, a homeostatic mechanism critical for HSC maintenance (Ho et al., "Autophagy Maintains the Metabolism and Function of Young and Old Stem Cells," *Nature* 543 (7644): 205-210 (2017); Liu et al., "FIP200 Is Required for the Cell-Autonomous Maintenance of Fetal Hematopoietic Stem Cells," *Blood* 116(23): 4806-4814 (2010); Mortensen et al., "The Autophagy Protein Atg7 Is Essential for Hematopoietic Stem Cell Maintenance," *J. Exp. Med.* 208(3): 455-467 (2011); and Warr et al., "FOXO3A Directs a Protective Autophagy Program in Haematopoietic Stem Cells," *Nature* 494(7437): 323-327 (2013), which are hereby incorporated by reference in their entirety), their function in regulating HSCs beyond mediating autophagy- related degradation remains unknown.

Figures 8G, 8H, 8I:
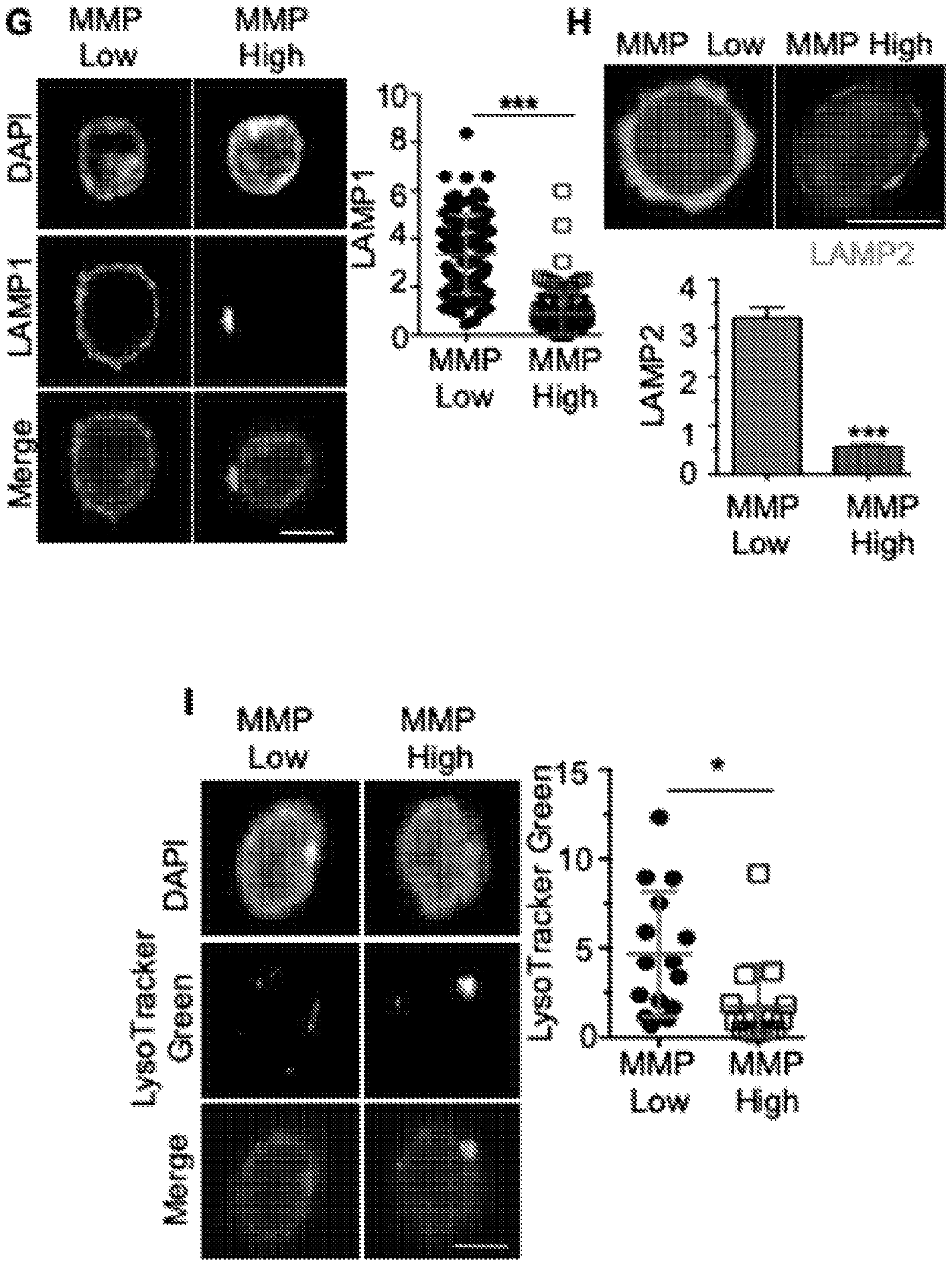

Close examination of lysosomal content by immunofluorescence staining and confocal microscopy showed that while LAMP1 was barely detected in MMP-high HSCs, LAMP1 was barely detected in MMP-high HSCs, LAMP1 was readily found in MMP-low HSCs (FIGS. 9D-9E, 8G). These intriguing results were further confirmed by another lysosomal marker, LAMP2 (FIG. 8H). Lysosomal-related genes were also elevated in MMP-low versus MMP-high HSCs (FIGS. 4I, 9F; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety). Notably, lysosomes were larger in MMP-low HSCs than MMP-high HSCs (FIGS. 9D-9E), further suggesting that lysosomal ability to degrade their content may be relatively hampered in MMP-low HSCs (Xu & Ren, "Lysosomal Physiology," *Annu. Rev. Physiol.* 77: 57-80 (2015), which is hereby incorporated by reference in its entirety). However, lysosomes in MMP-low HSCs were acidified, as confirmed by LysoTracker green staining, which is specific to acidic organelles (FIG. 8I). Inhibition of lysosomal degradation potential with leupeptin further increased the size of lysosomes in HSCs, indicating a buildup of undigested material (FIGS. 9D-9E). This effect was even more evident in lysosomes of MMP-high HSCs, which appeared bloated in treated cells (FIGS. 9D-9E). Altogether, these findings suggest that the greater numbers of enlarged lysosomes in MMP-low HSCs are curtailed in processing their content in contrast to the few lysosomes detected in MMP-high HSCs (FIGS. 9D-9E).

Figures 10A, 10B, 10C, 10D, 10E:
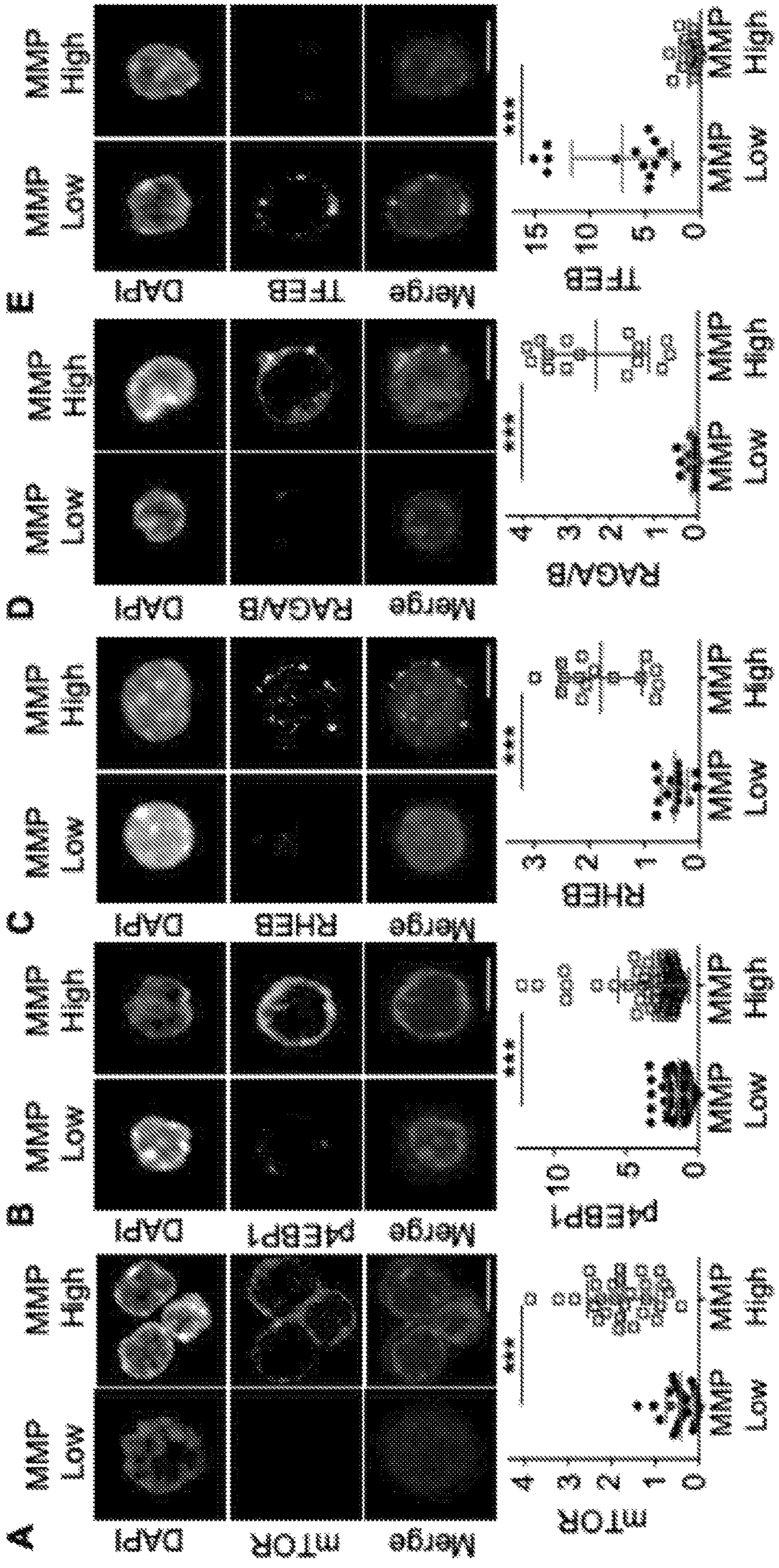
Figure 10F:
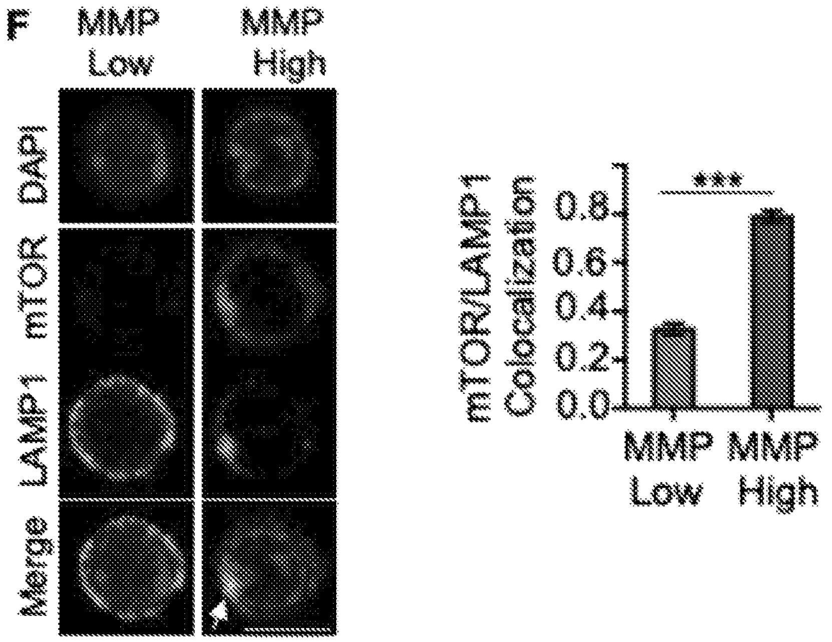

The lesser lysosomal content in MMP-high HSCs was associated with the expression, lysosomal recruitment, and activation of mTOR protein (FIGS. 10A-10F), which is necessary for the activation of gene translation and cell growth (FIGS. 4I, 5B; Liang et al., "Restraining Lysosomal Activity Preserves Hematopoietic Stem Cell Quiescence and Potency," *Cell Stem Cell* 26: 359-376 (2020), Table S2, which is hereby incorporated by reference in its entirety) (Efeyan et al., "Amino Acids and mTORC1: From Lysosomes to Disease," *Trends in Molecular Medicine* 18: 524-533 (2012), which is hereby incorporated by reference in its entirety). Activation of mTOR signaling was evident by greater downstream phosphorylation of the mTORC1 target 4EBP1 as well as higher abundance of positive upstream regulators, including RHEB and RAGA/B (FIGS. 10B-10D). Conversely, TFEB, a master regulator of lysosomal biogenesis that negatively regulates mTORC1, was expressed at greater levels in MMP-low HSCs (FIG. 10E).

Consistently, mTOR expression and activity were almost undetectable in MMP-low HSCs (FIGS. 10A-10D, 10F).

Figure 10G:
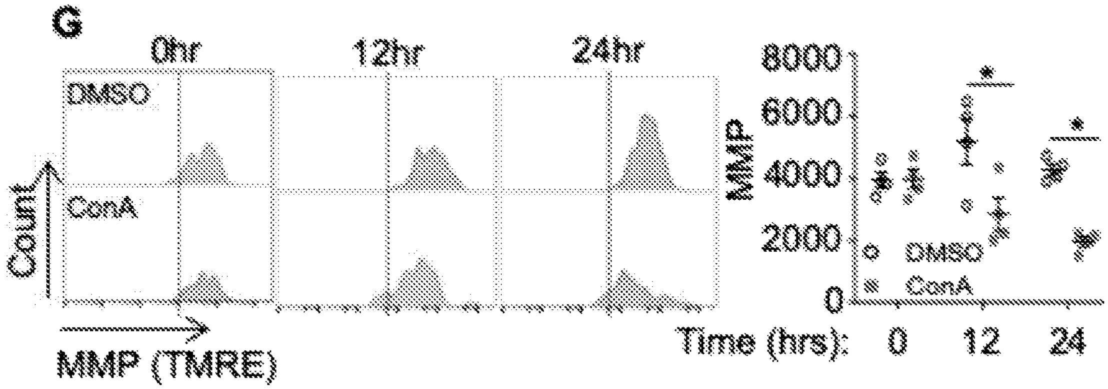
Figures 11A, 11B:
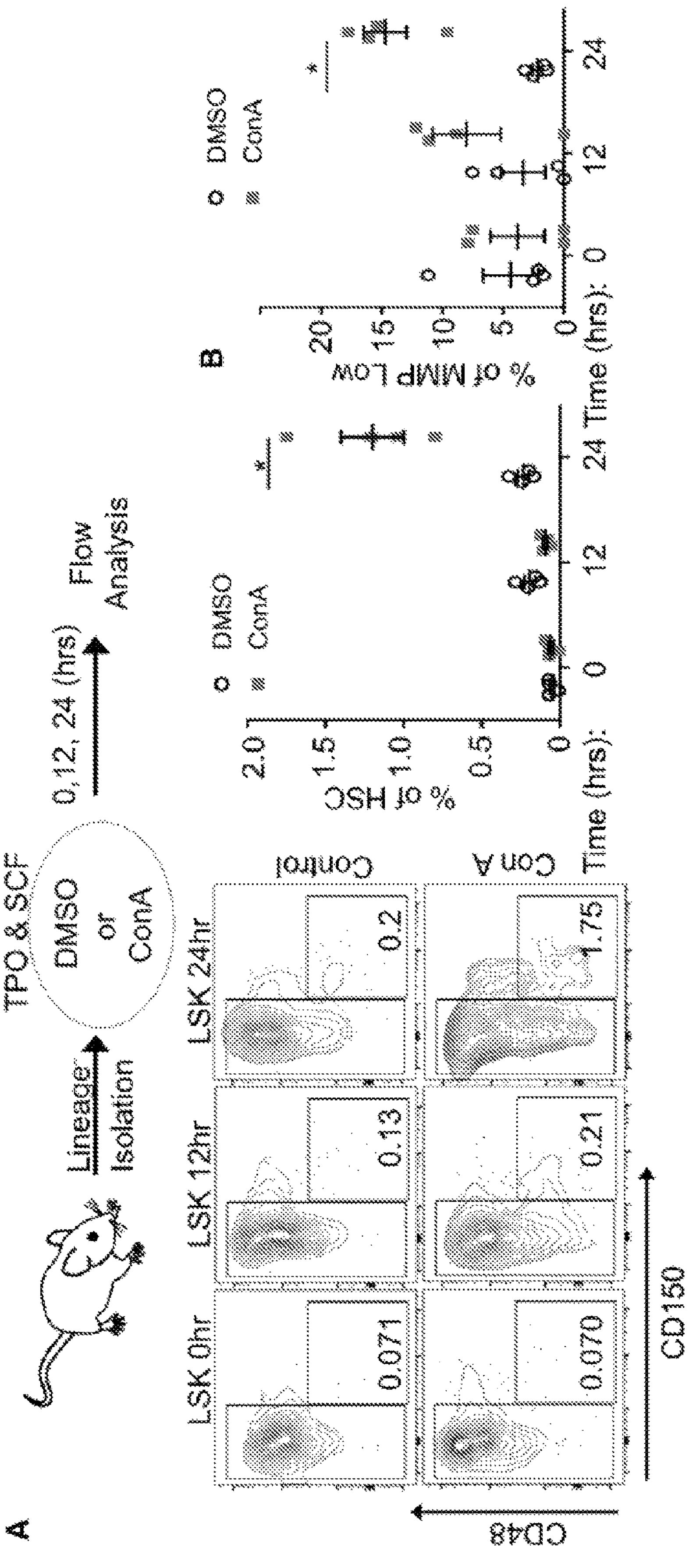
FIGS. 11A-11F demonstrate that inhibition of lysosomal activity enhances HSC competitive repopulation function in vivo.

To directly examine the potential impact of lysosomes, lysosomal activation was suppressed, which was predicted to inhibit autophagy and repress HSC function (Bigarella et al., "Stem Cells and the Impact of ROS Signaling," *Development* 141: 4206-4218 (2014) and Chandel et al., "Metabolic Regulation of Stem Cell Function in Tissue Homeostasis and Organismal Ageing," *Nat. Cell Biol.* 18: 823-832 (2016), which are hereby incorporated by reference in their entirety). Surprisingly, treatment with concanamycin-A ("ConA"), a specific inhibitor of the vacuolar $H^+$ adenosine triphosphatase ATPase ("v-ATPase") that is required for lysosomal acidification and amino acid release (Abu-Remaileh et al., "Lysosomal Metabolomics Reveals V-ATPase- and mTOR-Dependent Regulation of Amino Acid Efflux from Lysosomes," *Science* 358: 807-813 (2017); Drose et al., "Inhibitory Effect of Modified Bafilomycins and Concanamycins on P- and V-Type Adenosinetriphosphatases," *Biochemistry* 32: 3902-3906 (1993); Forgac et al., "Vacuolar ATPases: Rotary Proton Pumps in Physiology and Pathophysiology," *Nat. Rev. Mol. Cell Biol.* 8(11): 917-929 (2007); and Zoncu et al., "mTORC1 Senses Lysosomal Amino Acids Through an Inside-Out Mechanism That Requires the Vacuolar H(+)-ATPase," *Science* 334(6056): 678-683 (2011), which are hereby incorporated by reference in their entirety), which are hereby incorporated by reference in their entirety), led to improved frequency of HSCs recovered from 24-hour in vitro culture of bone marrow lineage-negative cells (FIGS. 11A-11B, 10G). While the overall levels of MMP increased within 12 hours, ConA treatment led to a relative decrease of MMP in recovered cells (FIG. 10G). In addition, a twenty-four-hour ConA treatment was associated with greater retention of the MMP-low HSC fraction (FIG. 11B).

Figure 10H:
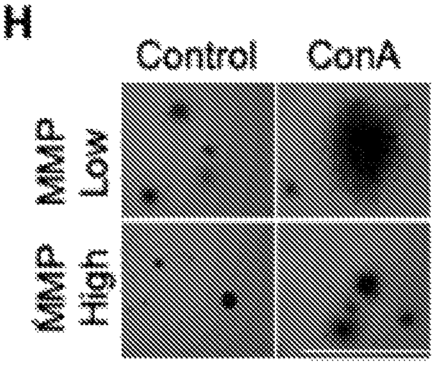
Figures 11C, 11D:
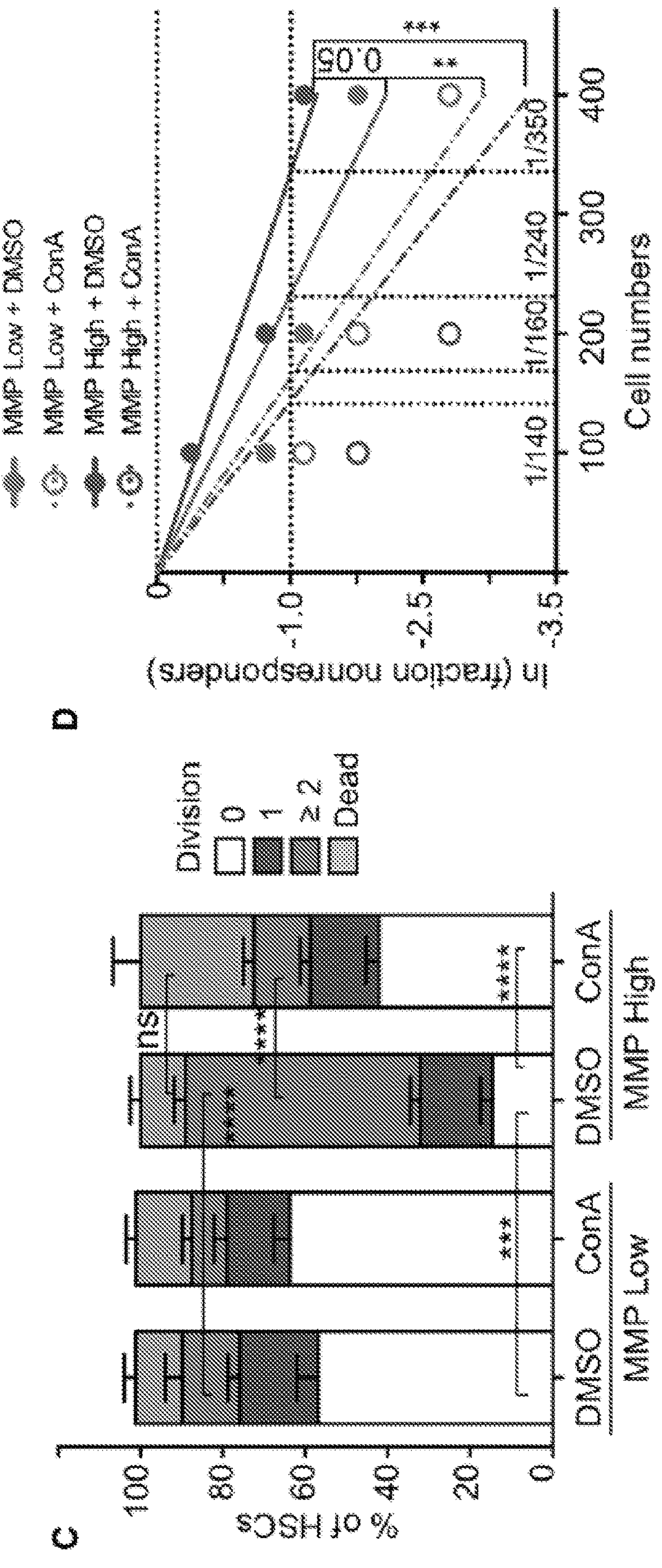
Figures 11E, 11F:
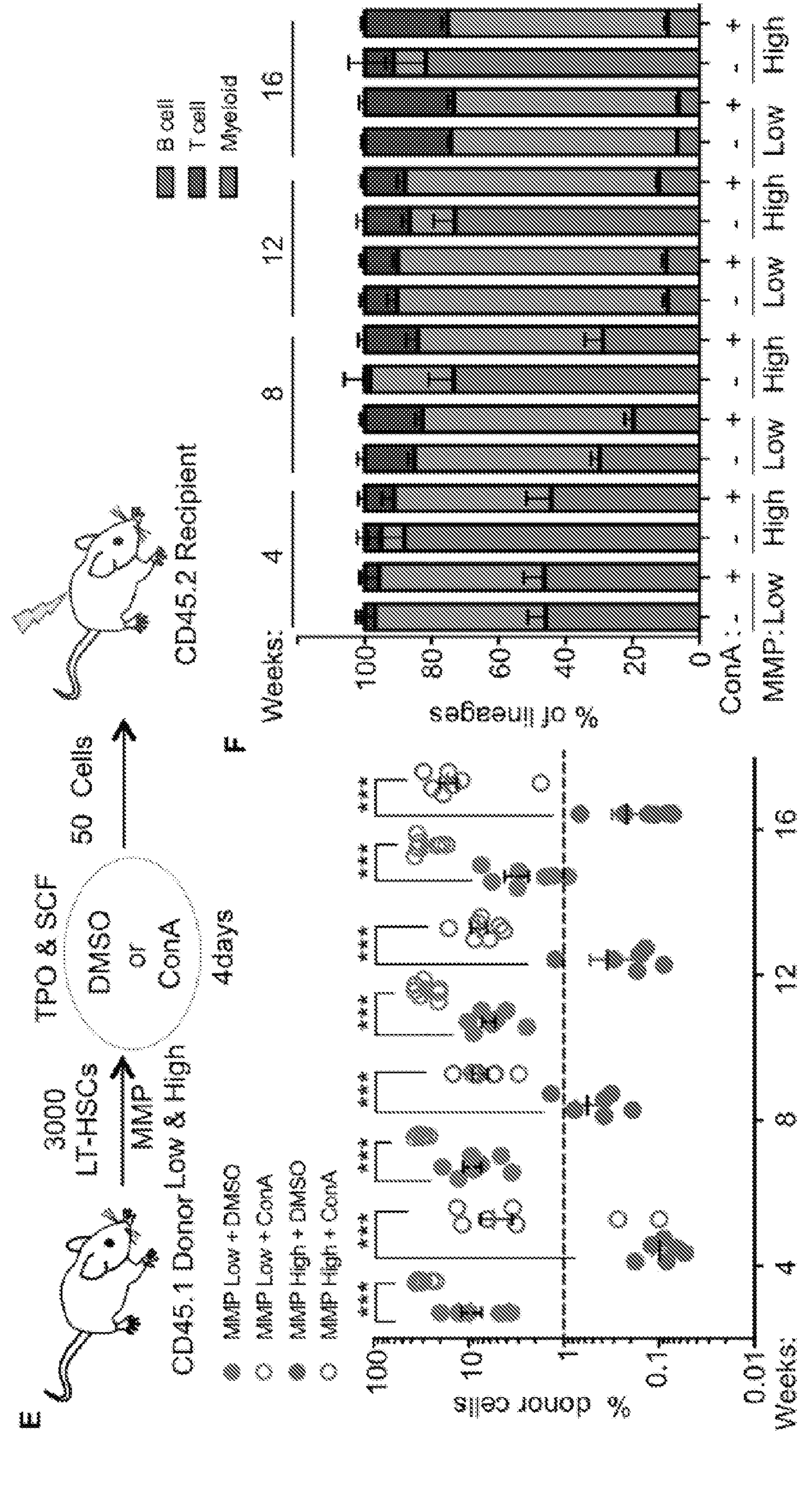

To further probe this lysosomal potential, single MMP-low and MMP-high $GFP^+$ HSCs treated with ConA or vehicle control were cultured and their cell divisions were tracked for up to 60 hours. Consistent with previous results (FIG. 3B), over 70% of MMP-low $GFP^+$ HSCs did not divide during this time, whereas the majority (>85%) of MMP-high $GFP^+$HSCs divided at least once (FIG. 11C). While ConA treatment had only a slight effect on non-dividing MMP-low HSCs in culture, it significantly increased the frequency of non-dividing MMP-high $GFP^+$ HSCs (FIG. 11C; Table 3). Importantly, a 48-hour or a 4-day ConA treatment led to enhanced frequency of LTC-ICs recovered in limiting dilution analysis of both MMP-low (1.5-fold) and MMP-high HSCs (2.5-fold) ex vivo (FIGS. 11D, 10H) associated with an increased size of colonies that were more prominent when derived from MMP-low rather than MMP-high LTC-ICs (FIG. 10H). These findings together indicate that the inhibition of lysosomal activation improves the maintenance of functional HSC ex vivo. Remarkably, it was also found that a 4-day inhibition of lysosomal activity ex vivo increased by over 90-fold (MMP-high) and 9-fold (MMP-low) the in vivo competitive repopulation ability of HSCs (FIG. 11E). ConA treatment also balanced the production of lineages down- stream of MMP-high HSCs (FIG. 11F). These unexpected findings suggested that the inhibition of lysosomal activity enhances HSC function in vivo. Consistent with these findings, expression of Ki67 (FIG. 10I) as well as CDK6 (FIG. 10J) (both associated with activated HSCs) was restored in ConA-treated MMP-high HSCs to the levels of the untreated MMP-low HSCs levels (FIG. 10J), suggesting that ConA treatment promotes quiescence in HSCs.

TABLE 3

Single hematopoietic stem cell division with or without ConA

| Division | MMP Low | MMP Low + Con A (40 nM) | p value | MMP High | MMP High + Con A (40 nM) | p value |
|---|---|---|---|---|---|---|
| Dead | 6.0 ± 1.58 | 7 ± 1.51 | ns | 6.2 ± 2.05 | 14.4 ± 0.92 | ns |
| 0 | 31.8 ± 8.21 | 35.8 ± 8.89 | ns | 8.4 ± 2.99 | 23.8 ± 1.33 | 0.01 |
| 1 | 9.6 ± 0.93 | 7.4 ± 1.24 | ns | 9.2 ± 1.88 | 8.8 ± 0.84 | ns |
| ≥2 | 7.8 ± 2.45 | 4.6 ± 1.53 | ns | 30.4 ± 5.87 | 7.4 ± 2.62 | 0.001 |

Figures 12A, 12B, 12C:
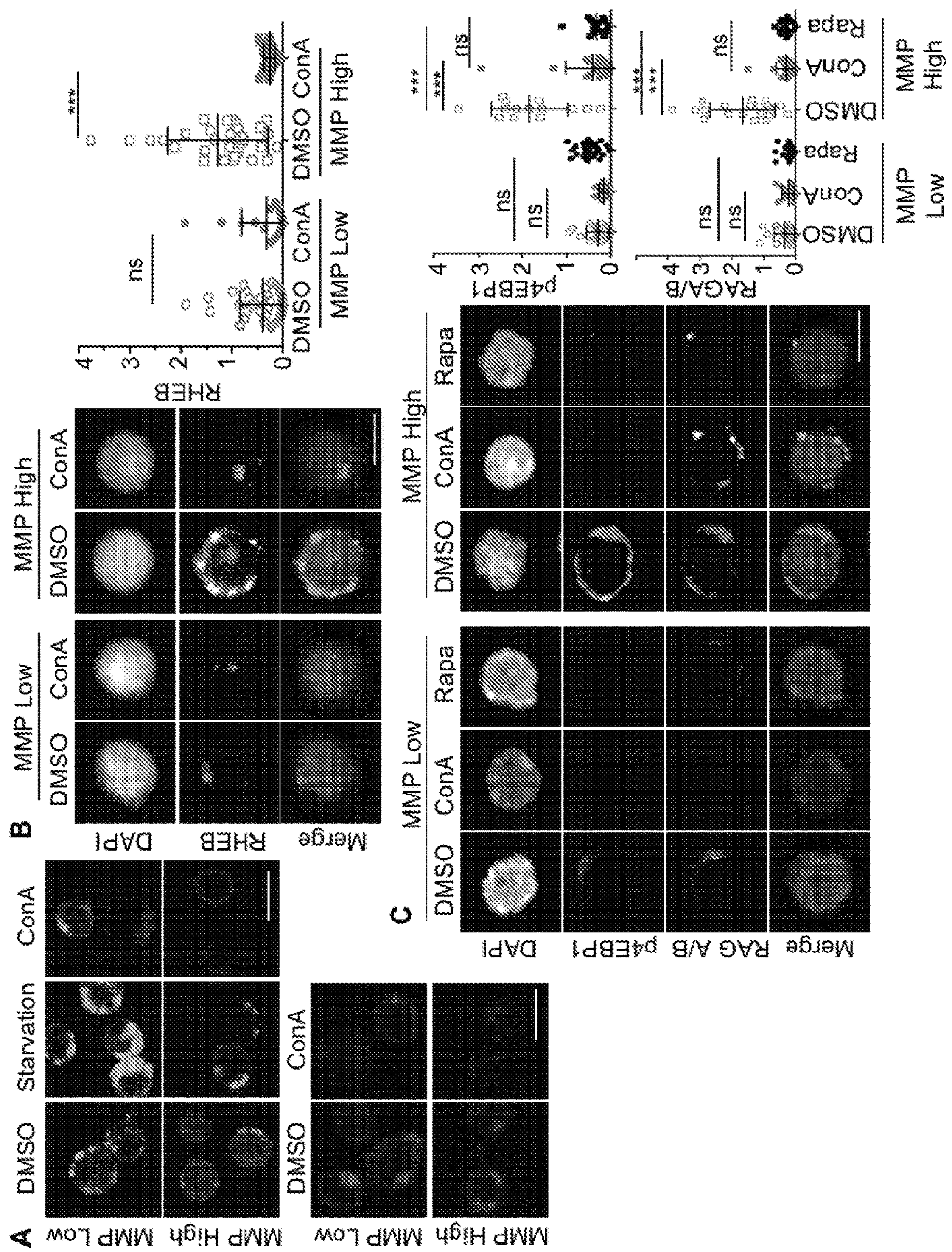
FIGS. 12A-12E demonstrate that repression of lysosomal activation, retains autolysosomes and suppresses mTOR signaling pathway in HSCs.

Number of wells with each number of cell division are shown; ns: non-significant The lysosomal response to ConA treatment was further examined (FIG. 10K). As anticipated, lysosomal acidity was reduced in response to ConA inhibition of v-ATPase, manifested by decreased fluorescence of two pH-sensitive probes, Lyso-Tracker green and LysoSensor blue (FIG. 12A). Consistent with ensuing reduced lysosomal degradation potential (FIGS. 9D-9E) (Xu & Ren, "Lysosomal Physiology," *Annu. Rev. Physiol.* 77: 57-80 (2015), which is hereby incorporated by reference in its entirety), ConA treatment led to a bloated lysosomal phenotype in HSCs (FIGS. 13A, 10K).

Figures 13A, 13B, 13C:
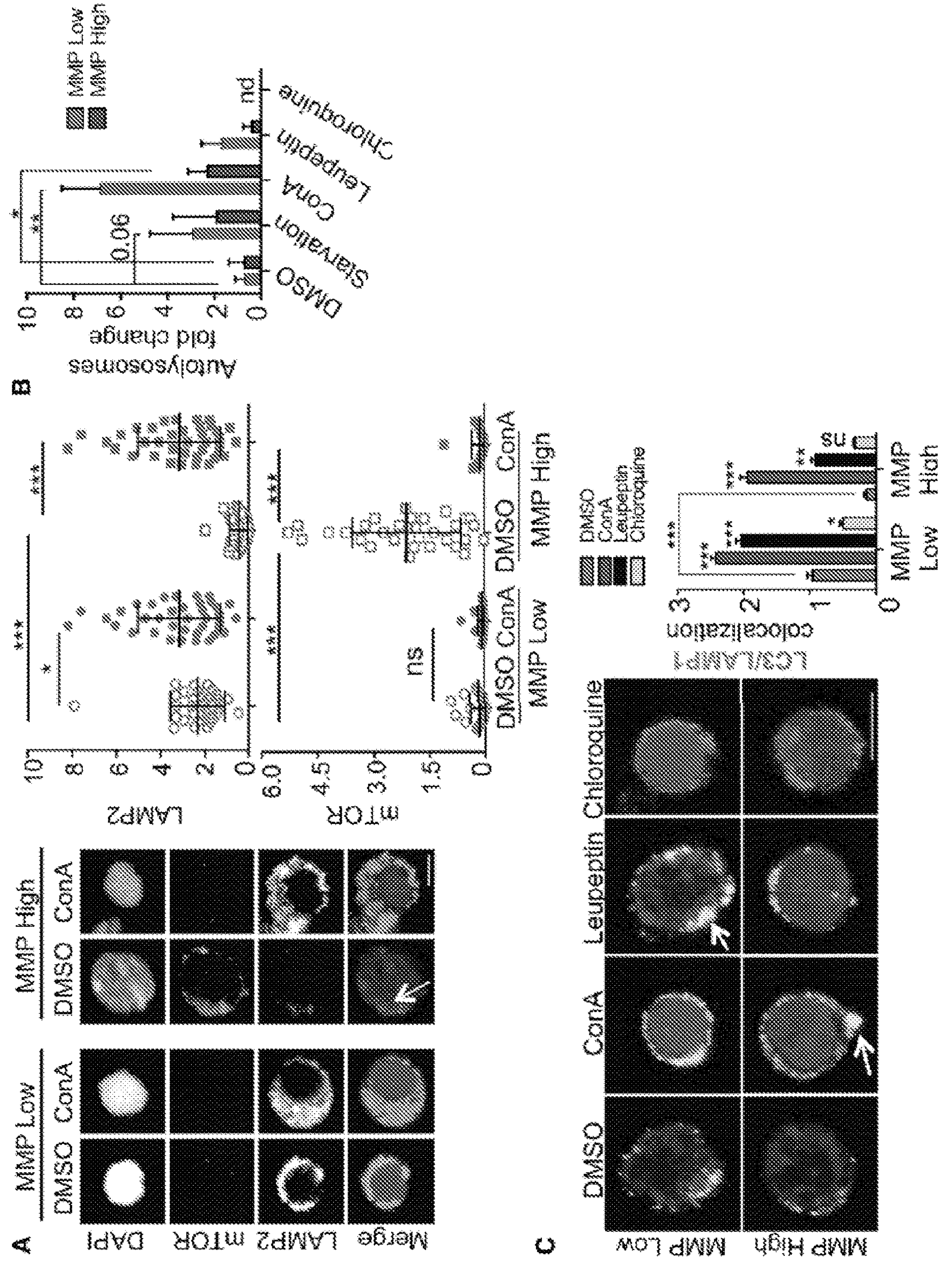
FIGS. 13A-13F demonstrate that inhibition of lysosomal activity enlarges lysosomal networks, retains autolysosomes and the engulfed mitochondria, and inhibits glycolysis in HSCs.

ConA treatment also led to the repression of mTOR signaling, as evidenced by reduced expression of mTOR, its upstream activators (RHEB and RAGA/B), and the phosphorylation of its downstream effector (4EBP1) in MMP-high HSCs almost to the same levels as in rapamycin-treated HSCs (FIGS. 13A, 12B-12C). This was further evident as mTOR co-localization with lysosomes was lost in ConA-treated MMP-high HSCs (FIG. 13A).

Figures 12D, 12E:
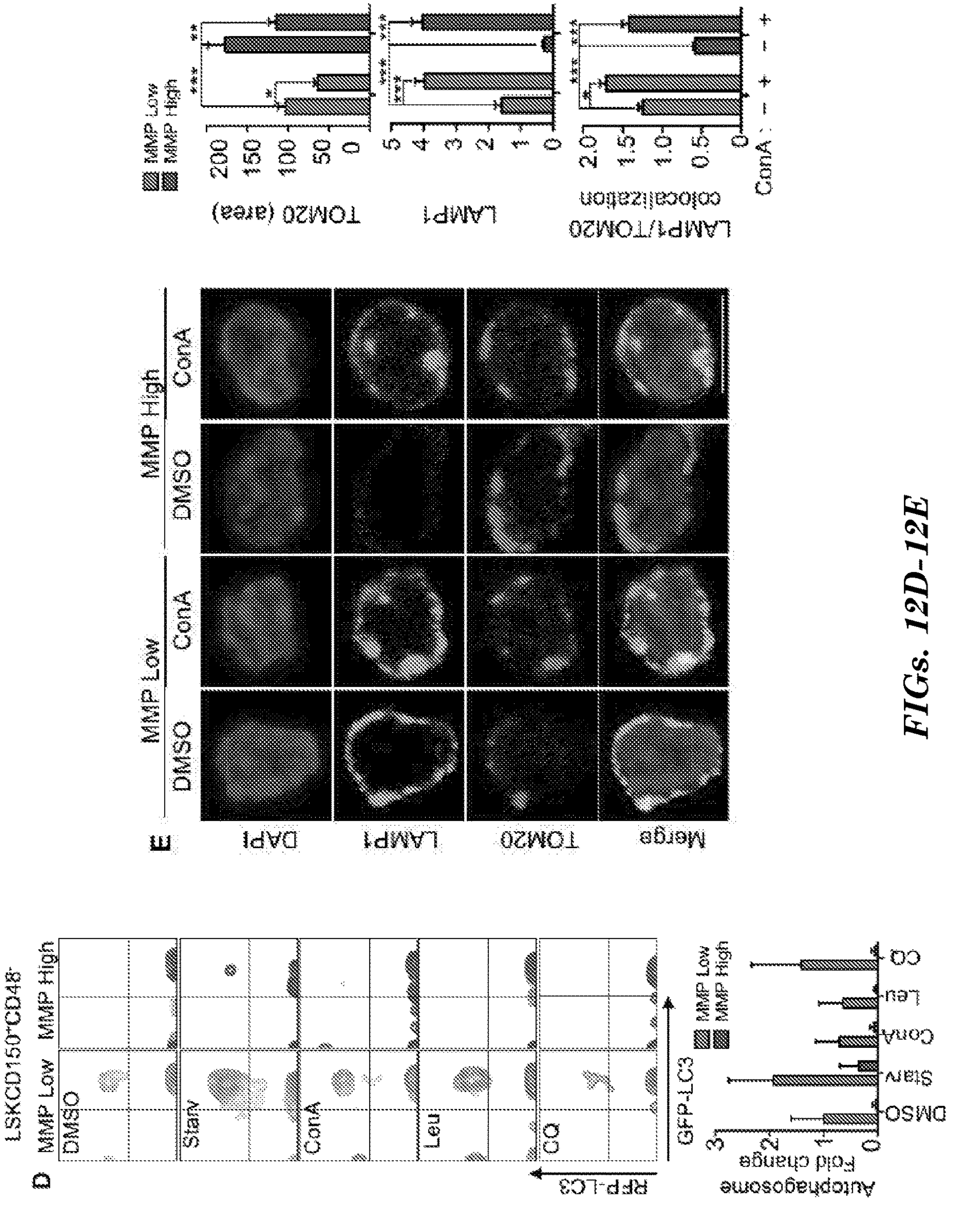

Given that ConA, despite repressing autophagy, had a positive effect on HSC function (FIGS. 11A-11F), its effect using CAG-RFP-EGF-LC3 reporter mice (Li et al., "New Autophagy Reporter Mice Reveal Dynamics of Proximal Tubular Autophagy," *J. Am. Soc. Nephrol.* 25(2): 305-315 (2014), which is hereby incorporated by reference in its entirety) in which LC3 is fused to both RFP and EGFP was further probed (FIGS. 13B, 12D). Due to the acid lability of GFP, autolysosomes are marked only by RFP and distinguished from autophagosomes that are marked by a combined GFP and RFP yellow signal. Under homeostasis, and consistent with previous findings (FIGS. 9D-9E), autophagic vacuoles were greater in MMP-low than MMP-high HSCs (FIGS. 13B, 12D). ConA specifically promoted the frequency of autolysosome ($RFP^+$)-accumulated MMP-high and MMP-low HSCs in which the effect was even superior to that observed u der a starving condition used as a positive control (FIGS. 13B, 12D). The effect of autophagy inhibitors was relatively similar on HSCs with autophagosome formation (FIG. 12D). Confocal analysis of immunofluorescence staining further confirmed that in contrast to its effect on autophagosomes, ConA, like leupeptin and in contrast to chloroquine, dramatically prevented autolysosomal degradation, as evidenced by greater colocalization of LAMP1 with LC3 in both MMP-low and MMP- high HSCs (FIGS. 13C, 12D). Importantly, the increase in LC3-positive puncta in response to ConA was by 3-fold (±0.24-fold) in MMP-high versus only 1.33-fold (±0.09-fold) in MMP-low HSCs, further suggesting (FIG. 9E) that lysosomal degradation is slower (p<0.00024) in ConA-treated MMP-low HSCs (FIG. 13C).

Figures 13D, 13E:
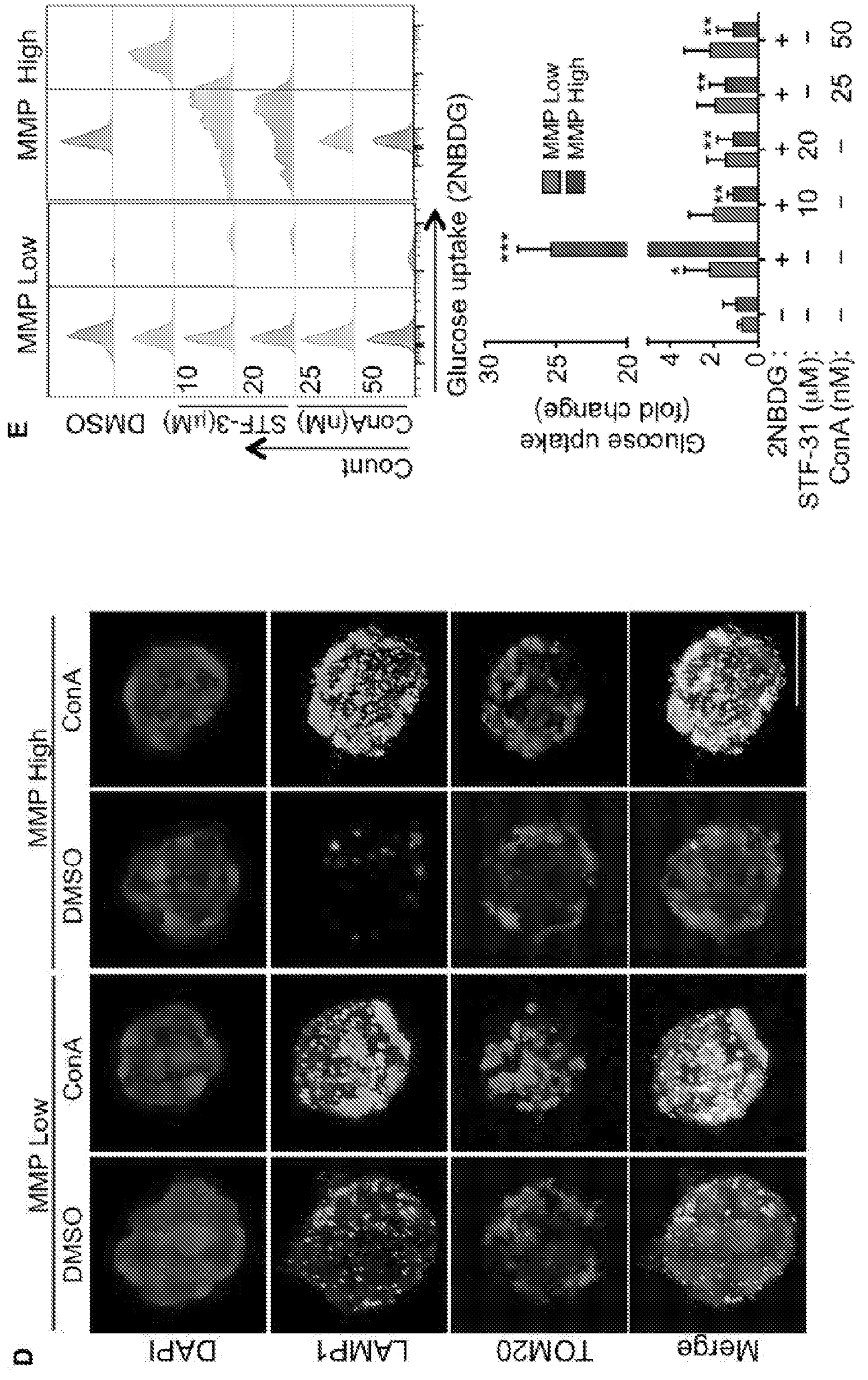

As ConA treatment results in lysosomal enlargement in both MMP-low and MMP-high HSCs, and given the relatively few lysosomes detected by immunofluorescence staining in untreated MMP-high HSCs, it was wondered whether ConA treatment results in the sequestration of cargo (particularly mitochondria) in HSCs. This was confirmed using high-resolution confocal microscopy that a 5-hour ConA treatment led to enlarged lysosomes in both MMP-low and MMP-high HSCs, with greater fold increase in MMP-high (35) than MMP-low (32) HSCs (FIGS. 13D, 12E). It was further found that ConA treatment led to an enhanced mitochondrial fragmentation, similar to that observed in untreated MMP-low HSCs (FIGS. 9A-9D, 13D, 12E), prominently contrasting with hyperfused mitochondria in untreated MMP-high HSCs (FIGS. 9A-9D, 13D, 12E). Furthermore, in response to ConA, localization of TOM20 to LAMP1 was significantly increased in both MMP- low and MMP-high HSCs (FIGS. 13D, 12E). The increase of lysosomal localization of TOM20 was even greater in MMP-high HSCs (~3-fold) than MMP-low HSCs (~1.3-fold) in response to ConA in line with their remarkably improved in vivo function (FIGS. 11E-11F, 12E).

Figure 13F:
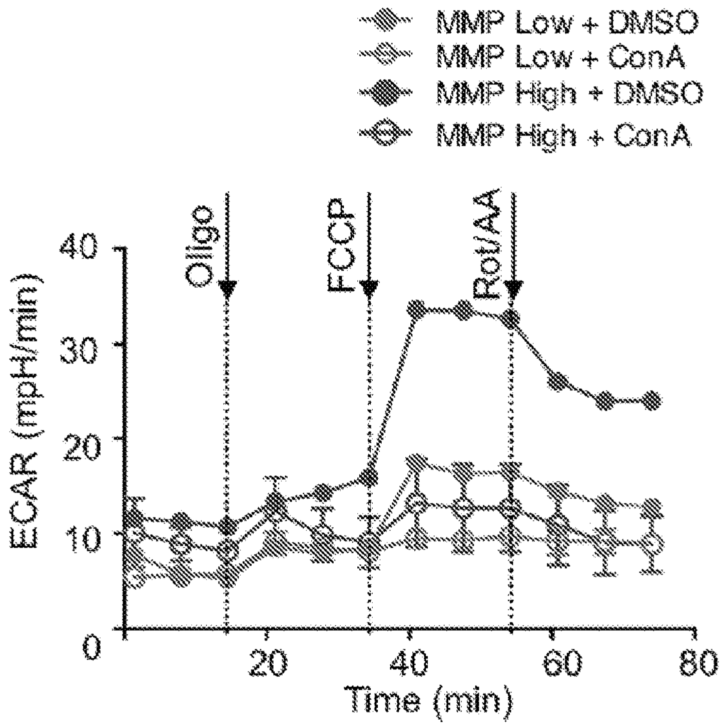
Figure 14A:
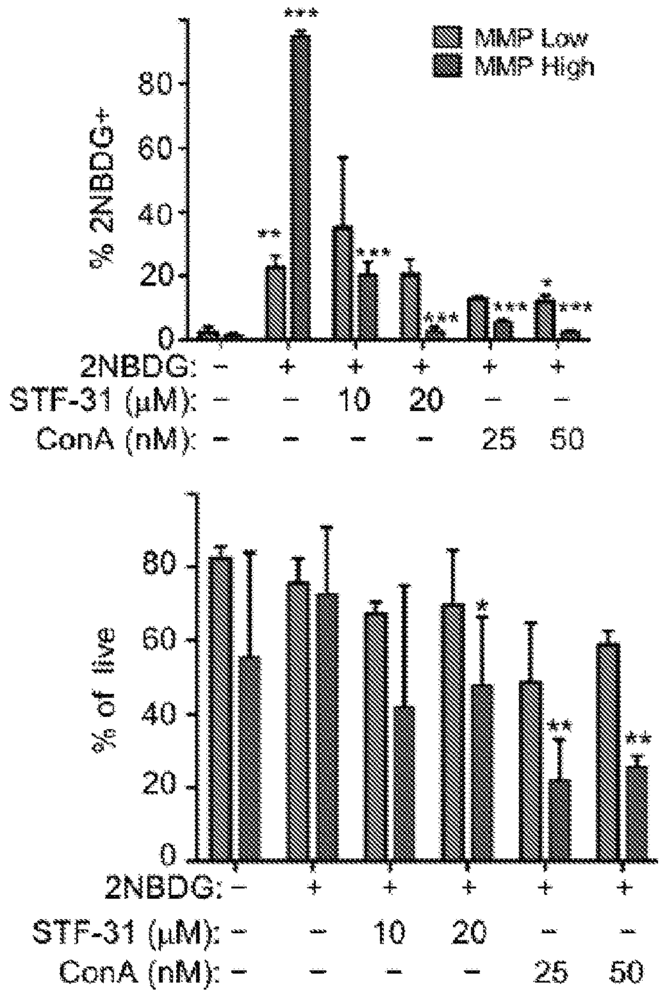
FIGS. 14A-14C demonstrate that repression of lysosomal activity reduces glucose uptake, OXPHOS, and glycolysis - model of lysosomal regulation of HSC quiescence and priming.
Figure 14B:
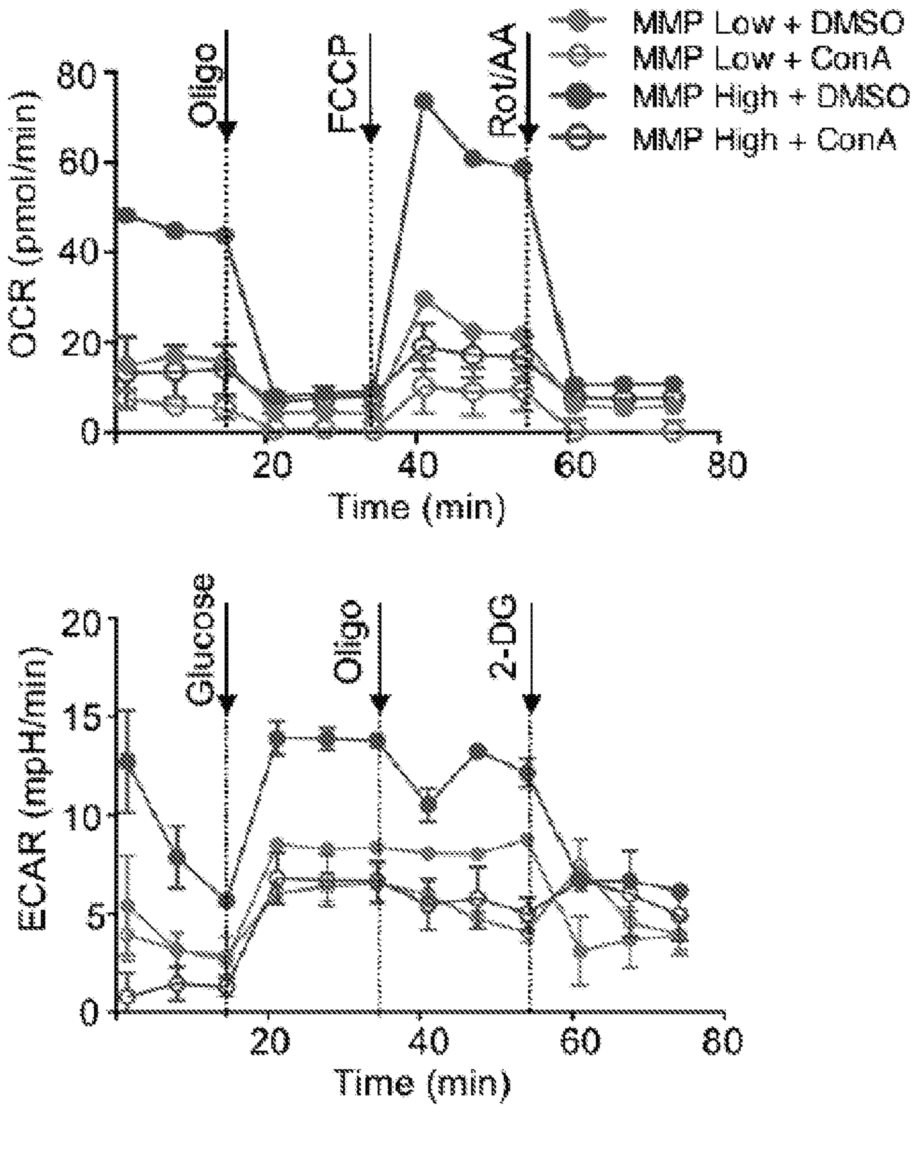

Since a reliance on glycolysis was found to be primarily a property of primed (MMP-high) rather than quiescent (MMP-low) HSCs (FIGS. 4I, 6A-6E, 7A-7E), whether ConA treatment had any impact on glucose uptake was queried. Lysosomal inhibition with ConA, like with Glut1 inhibitor, decreased glucose uptake by 19-fold in MMP-high HSCs, reducing it to the levels observed in MMP-low HSCs (FIGS. 13E, 14A). ConA's effect on reducing the viability under the experimental condition was mostly restricted to MMP-high and subtle in MMP-low HSCs (FIGS. 13A, bottom panel). Using Seahorse, it was confirmed that the basal glycolysis is more elevated in MMP-high HSPCs than MMP-low HSPCs (FIGS. 13F, 14B). It was further found that ConA treatment collapsed glycolysis (extracellular acidification rate ("ECAR")) in both MMP-high and MMP-low HSPCs and drastically decreased oxygen consumption in primed HSPCs, while it had only a relatively small effect on MMP-low HSPCs (FIGS. 13F, 14B). Consistent with previous results (FIGS. 6E, 7C-7E), these findings indicate that ConA treatment improves the potency by reverting activated MMP-high HSCs to a state that resembles quiescent MMP-low HSCs (FIGS. 11A-11F, 13A-13F, 12A-12E, 14A-14C). Collectively, these results show that curbing lysosomal acidification and degradation promotes the sequestration of lysosomal cargo, including mitochondria, and enhances HSC quiescence and potency in vivo (FIGS. 8A-8I, 10A-10J, 111A-11F, 12A-12E, 13A-13F, 14A-14C).

Example 8‡Discussion of Examples 2-7

The results of Examples 2-7 (supra) demonstrate lysosomal regulation as a new unanticipated mode of control of HSC quiescence/cycling and potency. By focusing on minor HSC subsets based on organelle heterogeneity, several fundamental HSC properties were uncovered: (1) primed rather than quiescent HSCs rely readily on glycolysis; (2) lysosomes were identified as key in regulating HSC quiescence/cycling; (3) repression (rather than stimulation) of lysosomal activity was shown to enhance HSC quiescence and potency; and (4) using intrinsic properties of primary HSCs, the similarity of molecular signature of quiescent (MMP-low) HSCs to that of label-retaining cells was exposed. In sum, these findings have broad implications for HSC investigations and may inform HSC-based therapies.

Repression of Lysosomal Activation Maintains HSC Quiescence

Figure 14C:
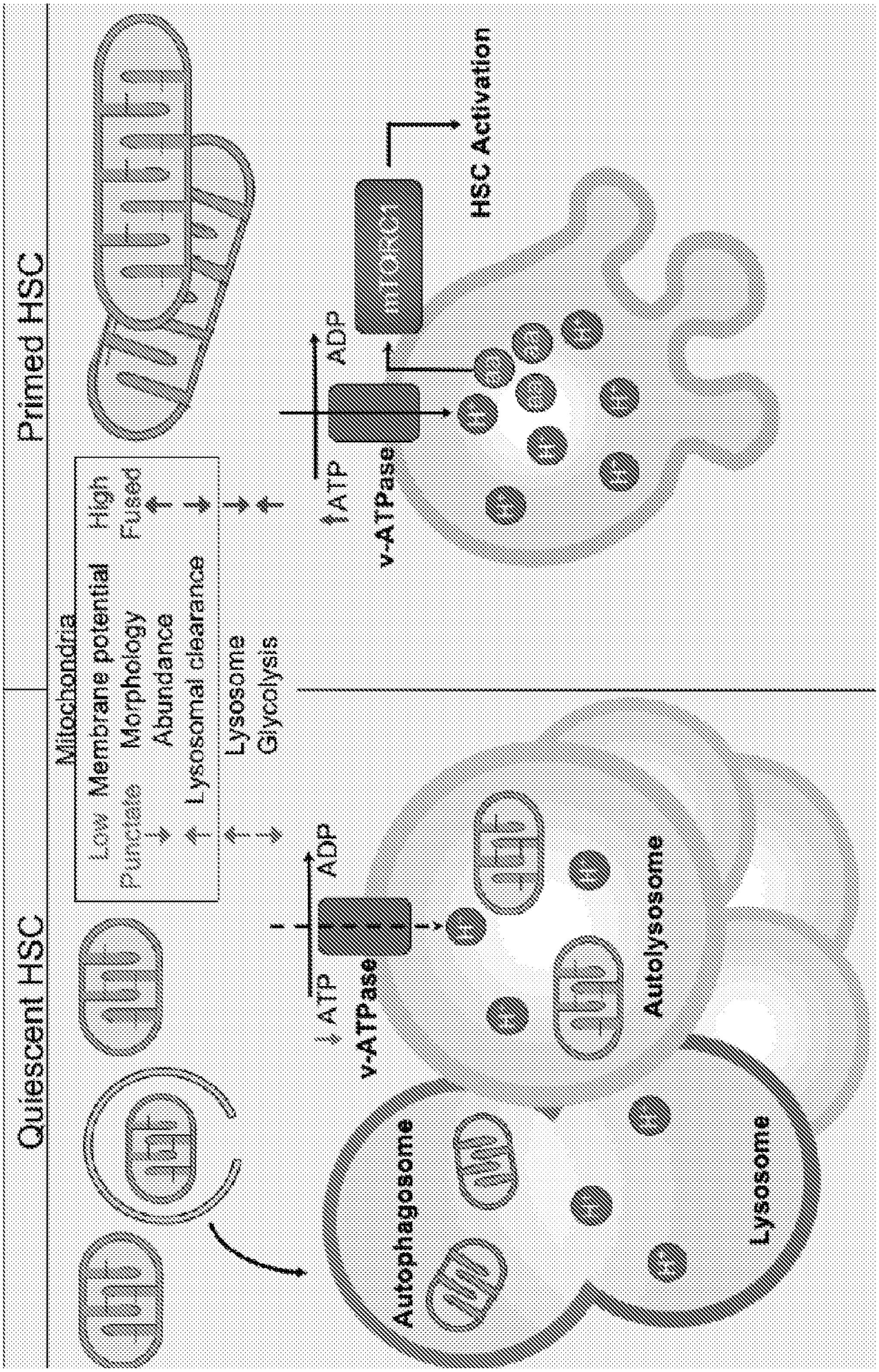

The results presented herein demonstrate that enlarged lysosomes are key in preserving HSC quiescence. The work suggests that enhancing a sluggish lysosomal processing property greatly increases HSC potency (FIGS. 9D-9 E, 13A, 13C-13D, 12F). The slow degradation of lysosomal cargo (i.e., mitochondria in quiescent HSCs) possibly reduces ROS levels, modulates amino acid efflux and mTOR activation toward HSC priming (FIG. 14C, model), and contributes to carbon mass for cell proliferation (Efeyan et al., "Amino Acids and mTORC1: From Lysosomes to Disease," *Trends in Molecular Medicine* 18: 524-533 (2012) and Hosios et al., "Amino Acids Rather Than Glucose Account for the Majority of Cell Mass in Proliferating Mammalian Cells," *Dev. Cell.* 36(5): 540-549 (2016), which are hereby incorporated by reference in their entirety). Based on this work, a model in which quiescence of HSCs is maintained by lysosomes that engulf and degrade (old and damaged) cargo, remove toxins to promote HSC health, and generate and store metabolites whose release primes HSCs is proposed (FIG. 14C). Lysosomal degradation of cargos other than mitochondria might also be involved, which requires further investigation.

It is tempting to speculate that lysosomes function as a hub to control stem cell quiescence; whether lysosomes also regulate quiescence in leukemic stem cells or are altered in aging HSCs as in aged neuro-stem cells requires additional investigations (Leeman et al., "Lysosome Activation Clears Aggregates and Enhances Quiescent Neural Stem Cell Activation During Aging," *Science* 359: 1277-1283 (2018), which is hereby incorporated by reference in its entirety). More broadly, lysosomes might be implicated in hibernation-regulated mitophagy (Remé & Young, "The Effects of Hibernation on Cone Visual Cells in the Ground Squirrel," *Invest. Ophthalmol. Vis. Sci.* 16(9): 815-840 (1977), which is hereby incorporated by reference in its entirety) or contribute to stem cell homeostasis beyond autophagy/mitophagy (Tang et al., "Induction of Autophagy Supports the Bioenergetic Demands of Quiescent Muscle Stem Cell Activation," *EMBO J.* 33: 2782-2797 (2014), which is hereby incorporated by reference in its entirety).

Glycolysis Is Required Mainly for Primed, but Not Quiescent, HSCs

One of the main surprises of the results presented herein challenges the current understanding of metabolism of quiescent HSCs (Filippi & Ghaffari, "Mitochondria in the Maintenance of Hematopoietic Stem Cells: New Perspectives and Opportunities," *Blood* 133(18): 1943-1952 (2019), which is hereby incorporated by reference in its entirety). It was found that the glycolytic pathway is mainly associated with primed, but not quiescent, HSCs under homeostasis (FIGS. 6A-6E, 7A-7E). While quiescent HSCs are equipped to use glycolysis under conditions that enhance TCA cycle activation, their need for using glycolysis at the steady state is limited. The results of in vivo inhibition of glycolysis were intriguing in enhancing the repopulation ability of primed HSCs. This might be through recruiting HSCs with restricted glycolytic requirements. Alternatively, these results may suggest that MMP-high HSCs under restricted glycolytic conditions are reprogrammed to a quiescent state in vivo. The results presented herein also suggests that lysosomal and glycolytic pathways are communicating in regulating HSC.

Overall, the findings presented herein expose the impact of the dynamic in vivo regulation of metabolism on HSCs versus the restricted in vitro conditions, as oxygen-exposure studies of HSCs have shown (Mantel et al., "Enhancing Hematopoietic Stem Cell Transplantation Efficacy by Mitigating Oxygen Shock," *Cell* 161(7): 1553-1565 (2015), which is hereby incorporated by reference in its entirety). These results nonetheless support the notion that like MMP-high HSCs, the majority of phenotypically defined HSCs are glycolytic (Takubo et al., "Regulation of Glycolysis by pdk Functions as a Metabolic Checkpoint for Cell Cycle Quiescence in Hematopoietic Stem Cells," *Cell Stem Cell* 12: 49-61 (2013), which is hereby incorporated by reference in its entirety). Glycolysis is a swift albeit inefficient process for energy production and key in sustaining rapidly dividing cells, including embryonic stem cells and cancer cells (reviewed in Bigarella et al., "Stem Cells and the Impact of ROS Signaling," *Development* 141: 4206-4218 (2014), which is hereby incorporated by reference in its entirety). As such, glycolysis is in line with the metabolic needs in priming HSCs. The findings presented herein also at least partially explain the paradoxical glycolytic phenotype observed in Foxo3$^{-/-}$ HSCs (Rimmele et al., "Mitochondrial Metabolism in Hematopoietic Stem Cells Requires Functional FOXO3," *EMBO Rep.* 16: 1164-1176 (2015), which is hereby incorporated by reference in its entirety). The combined findings further raise the possibility that metabolites generated by lysosomes might nourish quiescent HSCs.

Mitochondrial Shape and Activity Segregate Quiescent from Primed HSCs

Mitochondrial fragmentation via DRP1 and enhanced PINK1-PARKIN activation in MMP-low versus MMP-high HSCs (FIGS. 9A-9F, 8A-8I, 14A-14C, model) suggested that the mitochondrial network is inactive and partially repressed, promoting the initiation of the mitochondrial clearance process in MMP-low (quiescent) HSCs. Whether there is a signal linking lysosomal acidification with mitochondrial fragmentation warrants further investigations (FIGS. 13D, 14E).

Clustering by t-SNE of single HSC identified a path from a dormant state in clusters A and B to a transitional state in cluster C toward activation in clusters D and E (FIGS. 4A-4I, 5A-5J). HSCs in cluster C could potentially represent cells either undergoing self-renewal divisions or committing to activation and subsequent differentiation. The high expression levels of the lysosomal and autophagy pathways in clusters A and E with low levels in cluster B were unanticipated but suggest that a combination of specific catabolic and anabolic pathways are required to support the HSC state (quiescence or activation) in each cluster.

Mitochondrial Activity Provides the First Intrinsic Means to Identify Primary dHSCs The similarity of label-retention-defined dHSCs and aHSCs to MMP-low and MMP-high HSCs, respectively (Liang et al., "Restraining Lysosomal Activity Preserves Hematopoietic Stem Cell Quiescence and Potency," *Cell Stem Cell* 26: 359-376 (2020), Table S3, which is hereby incorporated by reference in its entirety) (Cabezas-Wallscheid et al., "Vitamin A-Retinoic Acid Signaling Regulates Hematopoietic Stem Cell Dormancy," *Cell* 169(5): 807-823 (2017), which is hereby incorporated by reference in its entirety), suggests that MMP-low HSCs may be used in combination with or as an alternative intrinsic strategy to temporally defined, quiescent/dormant label-retaining cells for studies of homeostatic HSCs. This approach would be advantageous as compared to the existing transgenic model system, as it can be applied to human cells and is not limited by the constraints of using a transgenic mouse. Based on these studies, it is proposed that functional attributes of phenotypically defined HSCs may be revisited using the MMP-low HSC subpopulation.

In summary, the results presented herein illuminate several key concepts regarding HSC quiescence and potency. Specifically, the lysosomal regulation of HSC activity may be further explored for therapeutic purposes.

Figure 16:
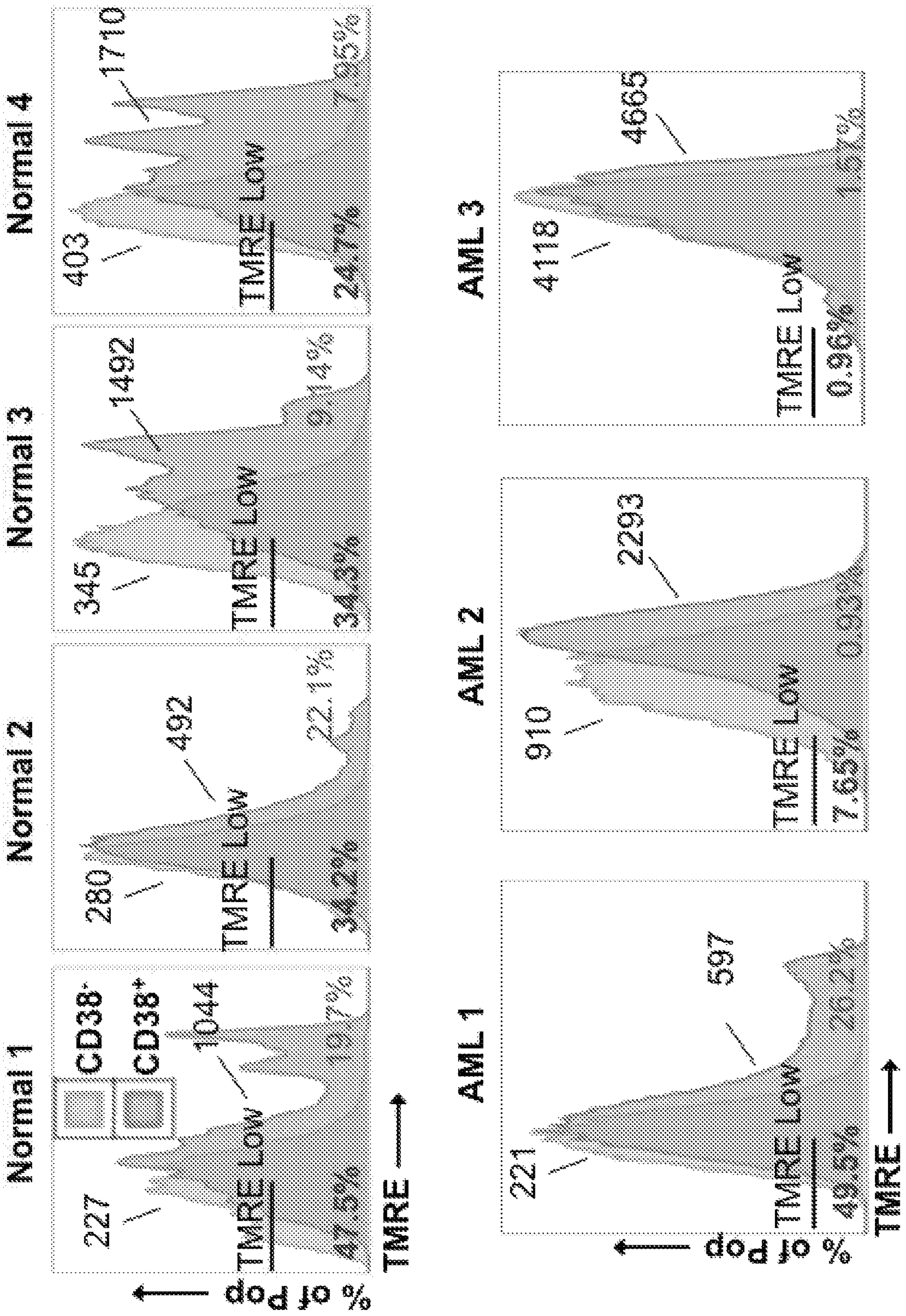
FIG. 16 provides histograms showing mitochondrial heterogeneity in primary human Acute Myeloid Leukemia (AML) stem cells and normal human Lin-CD34$^+$ cells. The histograms compare MMP (based on TMRE fluorescence intensity) between CD38$^-$ (blue) and CD38$^+$ (red) populations of AML or normal Lin-CD34$^+$ cells. Percentages represent the proportion of cells within the TMRE low fraction based on negative controls. Numbers denoted by lines represent the geometric mean of TMRE fluorescence within each population. Note right shift of TMRE in AML versus normal CD34$^+$.

Example 9—Characterization of the MMP of Acute Myeloid Leukemia (AML) Stem Cells Based on TMRE Fluorescence Intensity To test the hypothesis that the MMP of cancer stem cells differs from the MMP of normal human HSCs, the MMP of Lin-CD34$^+$CD38$^+$ and Lin-CD34$^+$CD38$^-$ cells derived from normal human controls was evaluated. The average mean TMRE fluorescence intensity of normal Lin-CD34$^+$CD38$^+$ cells and normal Lin-CD34$^+$CD38$^-$ cells was found to be 1184.5 (n=4) and 313.75 (n=4), respectively (FIG. 16, top panels). Characterization of Lin-CD34$^+$CD38$^+$ and Lin-CD34$^+$CD38$^-$ cells derived from 3 patients diagnosed with AML resulted in a mean TMRE fluorescence intensity of 2518.3 (n=3) and 1749.7 (n=3), respectively (FIG. 16, bottom panels). These results indicate that Lin-CD34$^+$CD38$^+$ and Lin-CD34$^+$CD38$^-$ cells derived from AML patients have a higher MMP than normal Lin-CD34$^+$CD38$^+$ and Lin-CD34$^+$CD38$^-$ cells.

Example 10—MMP-Low (Quiescent) but Not MMP-High (Primed) HSCs Express CD177

Figure 17A:
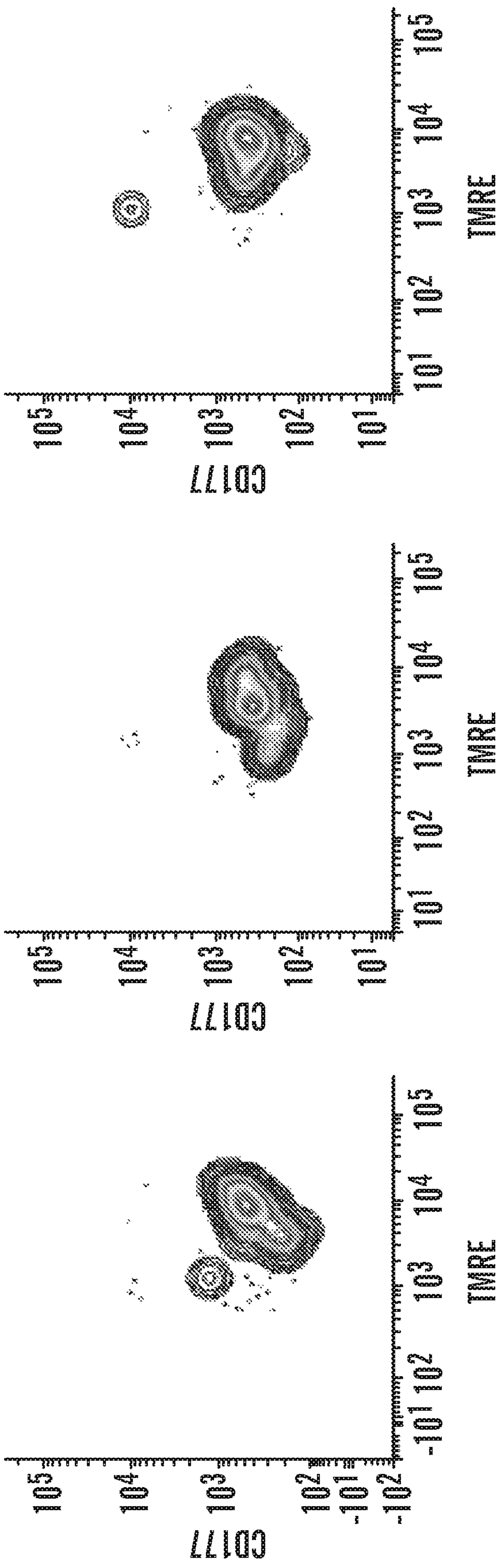
FIGS. 17A-17B are dot plots showing CD177 expression on LSK CD150$^+$CD48$^-$ HSCs probed with TMRE (FIG. 17A) and CD150 (FIG. 17B).
Figure 17B:
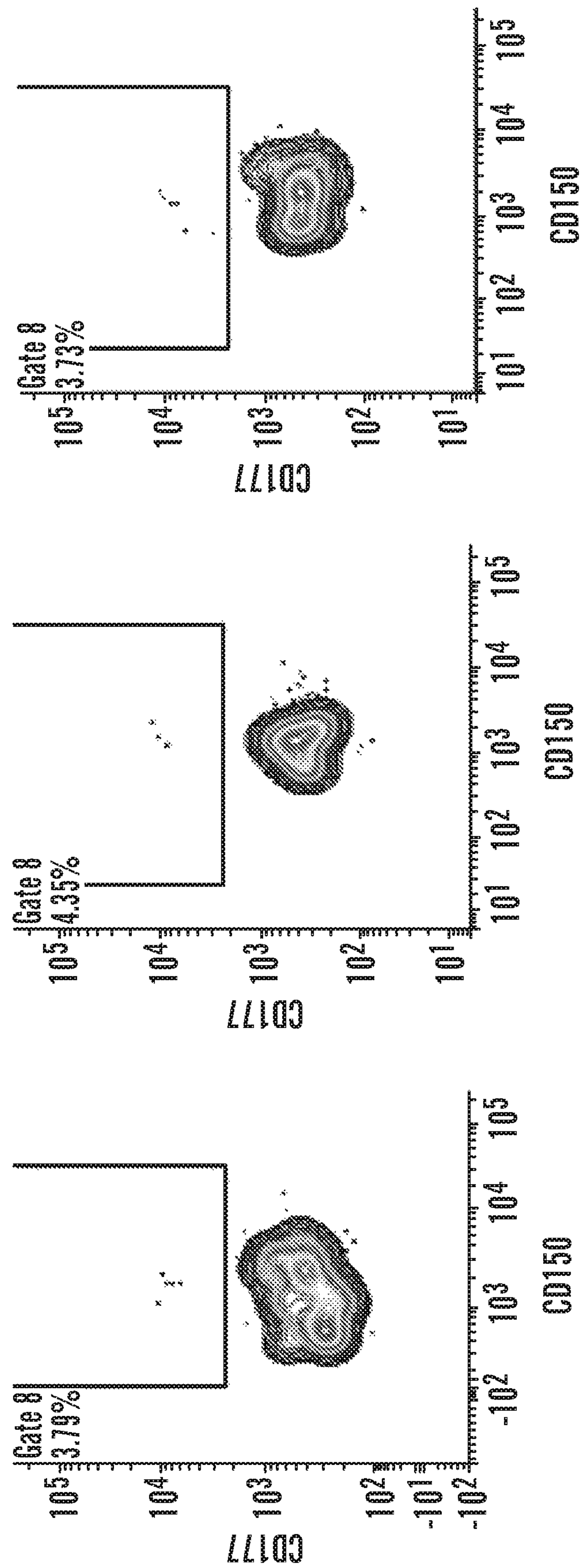
Figure 18A:
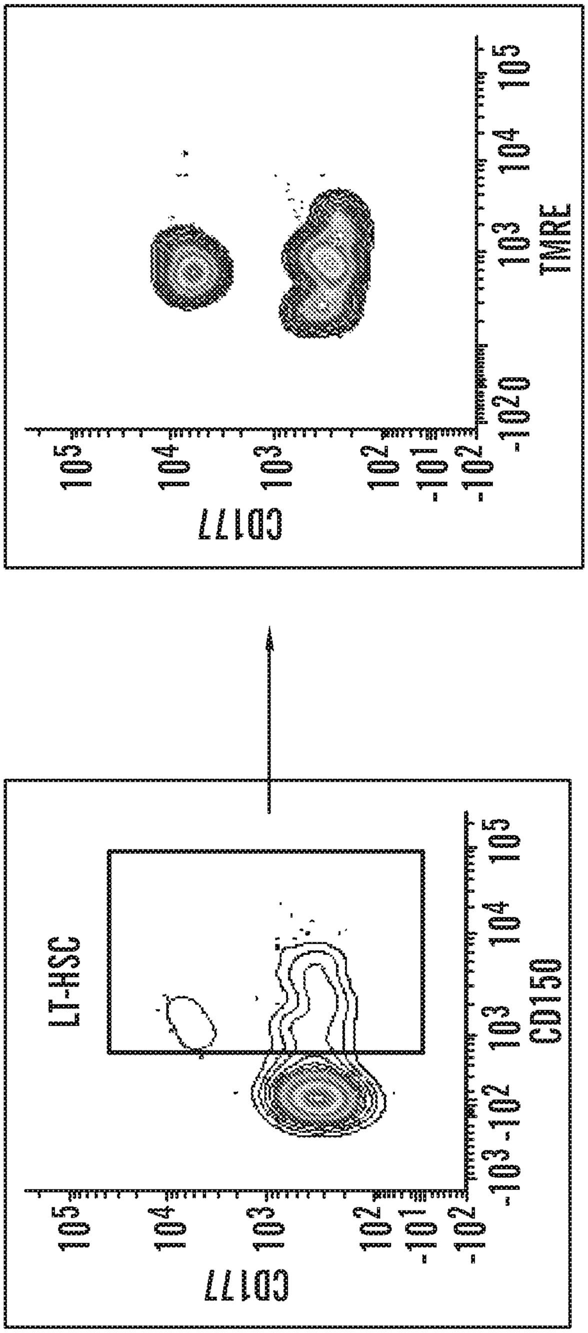
FIGS. 18A-18B are dot plots showing CD177 expression on LSK CD150$^+$CD48$^-$ HSCs.
Figure 18B:
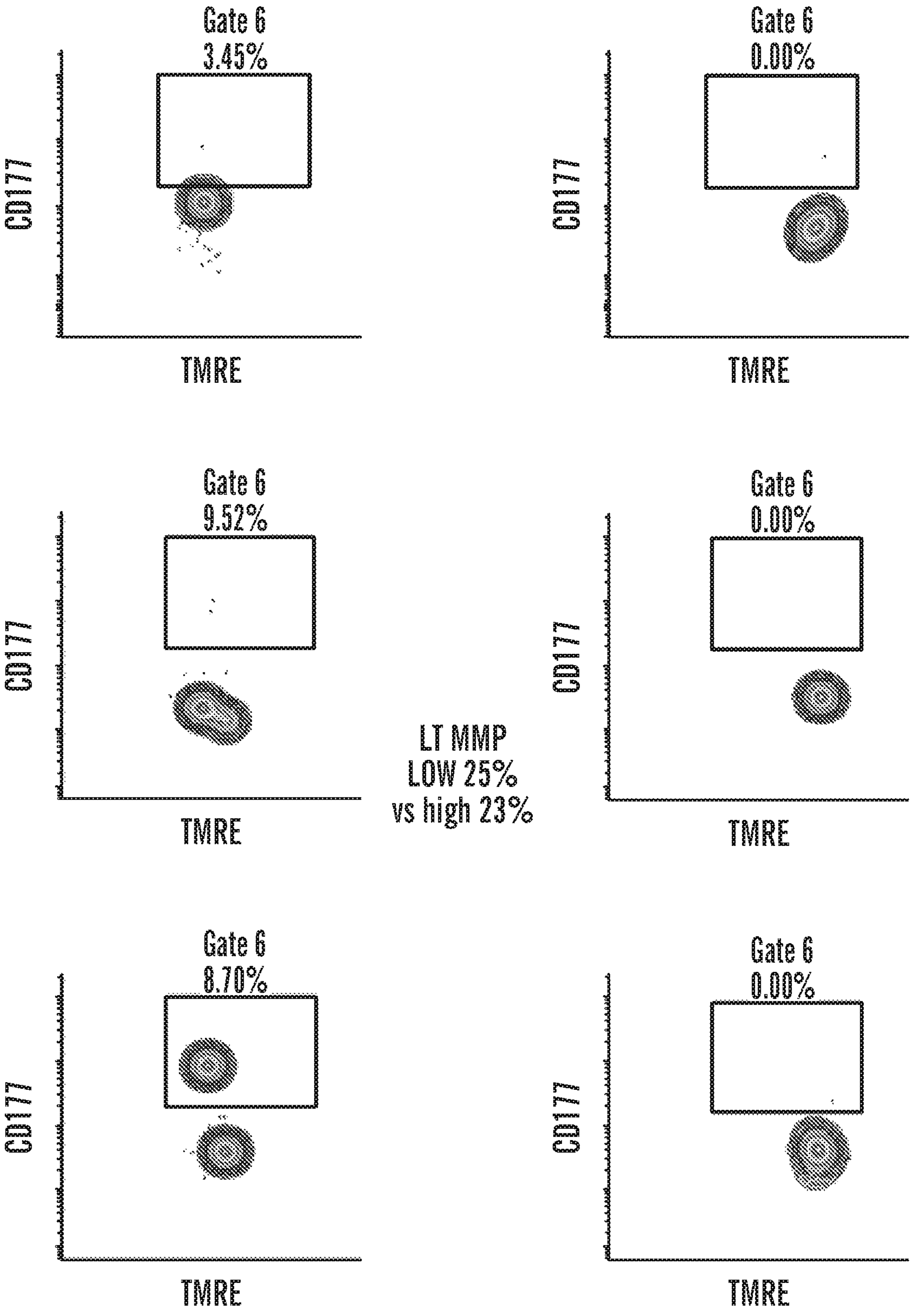

Single-cell RNA-Seq of MMP-low and MMP-high HSCs was used to identify CD177 as a cell surface marker that is present in a sub-population of MMP-low (Quiescent) HSCs but not on MMP-High (Primed HSCs). Flow cytometry analysis of LSK CD150$^+$CD48$^-$ HSCs probed with CD177 and TMRE confirms that the LSK CD150$^+$CD48$^-$ cell population comprises a sub-population of CD117$^+$ cells (FIG. 17A; FIG. 18A-18B). Flow cytometry analysis of LSK CD150$^+$CD48$^-$ HSCs probed with CD150 and CD177 confirms that the LSK CD150$^+$CD48$^-$ cell population comprises a sub-population of CD117$^+$ cells (FIG. 17B; FIG. 18A-18B).

Flow cytometry analysis of LSK CD150$^+$CD48$^-$ HSCs within the 25% MMP-low fraction (FIG. 18B, left panel) and LSK CD150$^+$CD48$^-$ HSCs within the 25% MMP-high fraction (FIG. 18B, right panel) confirmed that CD177 can be used as a marker for a sub-population of MMP-low (Quiescent) HSCs.

Example 11—Lysosomal Inhibition Markedly Improves the Potency of Old HSCs

Figure 19:
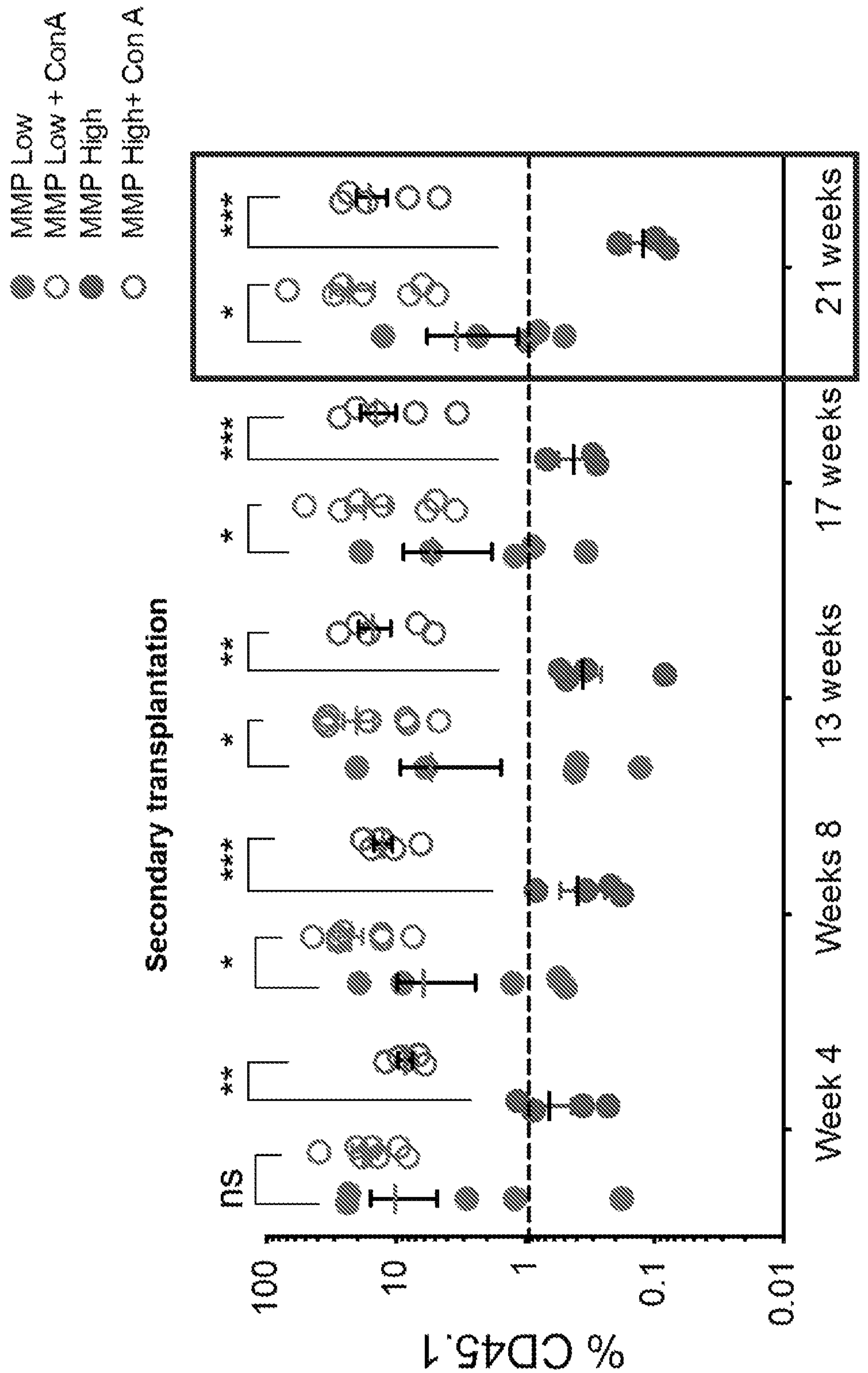
FIG. 19 is a graph showing that repression of lysosomal activity ex vivo greatly improves the in vivo repopulation of young HSCs in secondary transplantations (HSC self-renewal). Contribution of donor-derived (CD45.1) cells to peripheral blood (PB) of secondary transplanted recipient mice (CD45.2) in a long-term competitive repopulation assay. Note ConA treatment leads to increased HSC self-renewal as shown in secondary transplantations.
Figure 20:
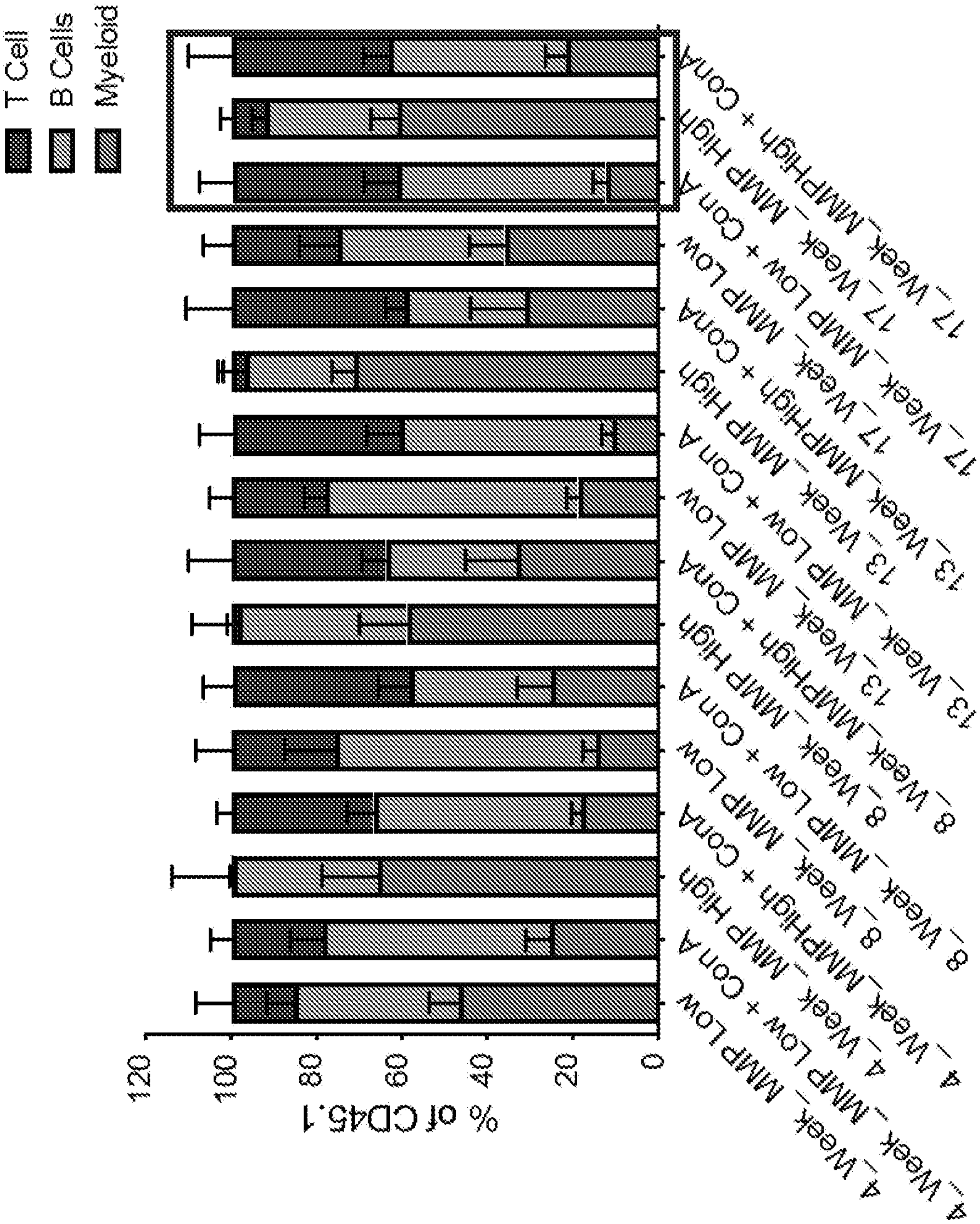
FIG. 20 is a graph showing analysis of peripheral blood cells of secondary transplanted recipients. Contribution of donor-derived (CD45.1) cells to peripheral blood (PB) of secondary recipient mice (CD45.2). Lineage output as a percentage of total CD45.1 donor-derived cells in primary recipients. Note ConA-treated HSCs lead to increased balanced blood production in secondary transplants 38 weeks post-initial transplantation.

FIG. 19 and FIG. 20 show the results of ex vivo ConA treatment, which improves significantly the self-renewal of old HSCs and their balance blood production.

Aging has a damaging impact on the functional capacity of long-lived HSCs (Rossi et al., "Stems Cells and the Pathways to Aging and Cancer," *Cell* 132: 681-696 (2008); Signer & Morrison, "Mechanisms that Regulate Stem Cell Aging and Life Span," *Cell Stem Cell* 12: 152-165 (2013); Beerman & Rossi, "Epigenetic Control of Stem Cell Potential during Homeostasis, Aging, and Disease," *Cell Stem Cell* 16: 613-625 (2015), which are hereby incorporated by reference in their entirety). Quiescence that is essential for the maintenance of HSC function is lost in a significant fraction of old HSCs. As a consequence, old HSCs are activated, engaged in cycling, and compromised in their ability to reconstitute all lineages of blood in a bone marrow transplantation setting. One of the fundamental characteristics of HSC aging is their skewed output towards the myeloid lineage at the expense of lymphoid cells, a process conserved between mouse and human (Signer & Morrison, "Mechanisms that Regulate Stem Cell Aging and Life Span," *Cell Stem Cell* 12: 152-165 (2013); Pang et al., "Human Bone Marrow Hematopoietic Stem Cells are Increased in Frequency and Myeloid-biased with Age," *Proc. Nat'l Acad. Sci. USA* 108: 20012-20017 (2011), which are hereby incorporated by reference in their entirety). This loss of balanced blood production of old HSCs results in immune deficiency of the elderly and may be key to the increased incidence of numerous myeloid malignancies with age (Rossi et al., "Stems Cells and the Pathways to Aging and Cancer," *Cell* 132: 681-696 (2008); Bigarella et al., "Stem Cells and the Impact of ROS Signaling," *Development* 141: 4206-4218 (2014); Dykstra & de Haan, "Hematopoietic Stem Cell Aging and Self-renewal," *Cell and Tissue Research* 331: 91-101 (2008); Snoeck, "Aging of the Hematopoietic System," *Current Opinion in Hematology* 20: 355-361 (2013), which are hereby incorporated by reference in their entirety). Therefore, interventions that may have a positive impact on HSC potency and lineage commitment with age are likely to have significant positive consequence for health and longevity of the elderly.

Figures 15A, 15B, 15C:
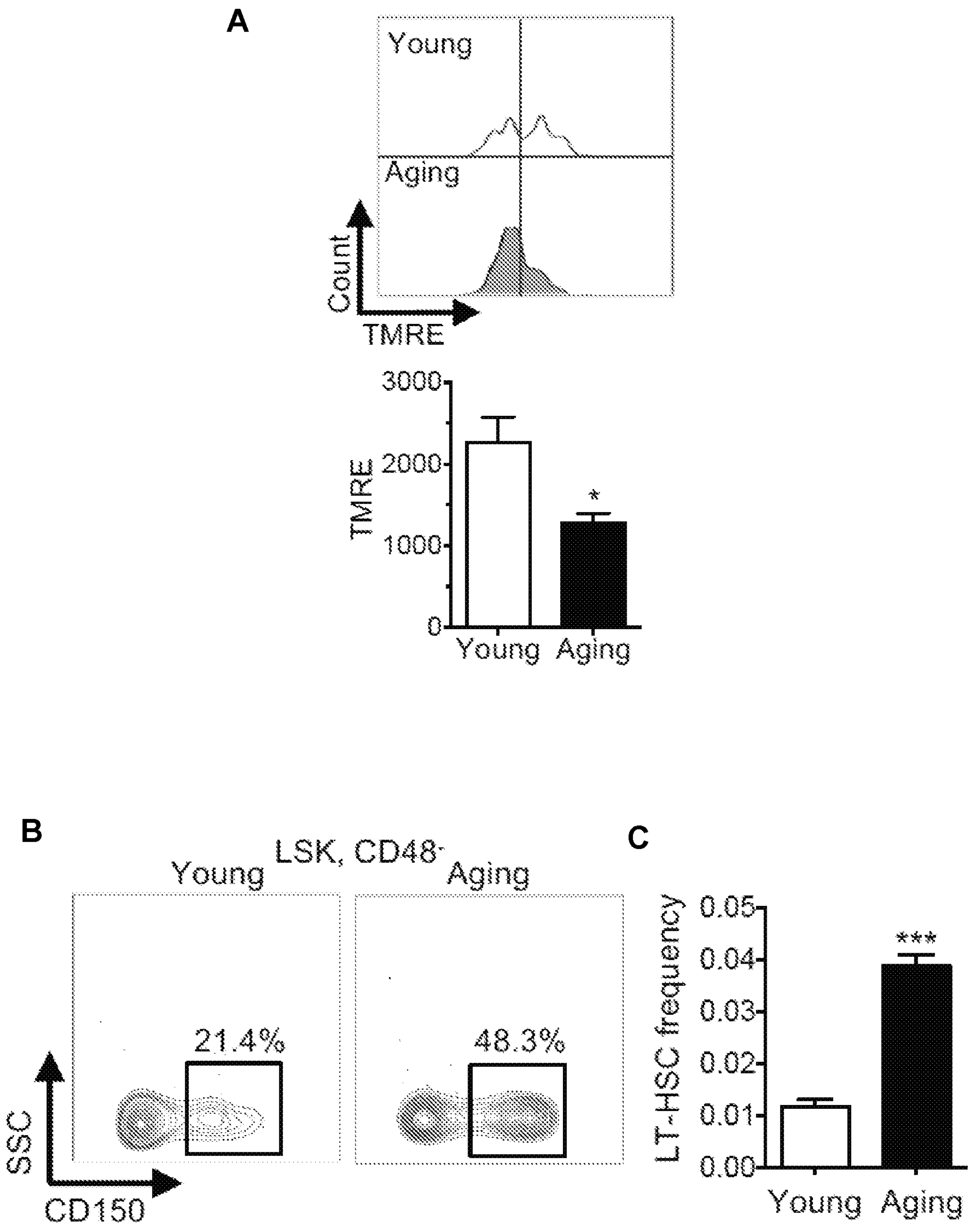
FIGS. 15A-15Q demonstrate that lysosomal inhibition restores quiescence and reduces mTOR activity in aging HSCs.
FIG. 15B shows representative flow plots of HSC compartments (LSK $CD150^{+}CD48^{-}$) in which the frequency of $CD150^{+}$ cells are displayed from young and aging mice (n=3).
FIG. 15C shows the quantification of LT-HSC frequency in total bone marrow cells from four young vs. aging mice.
Figure 15D:
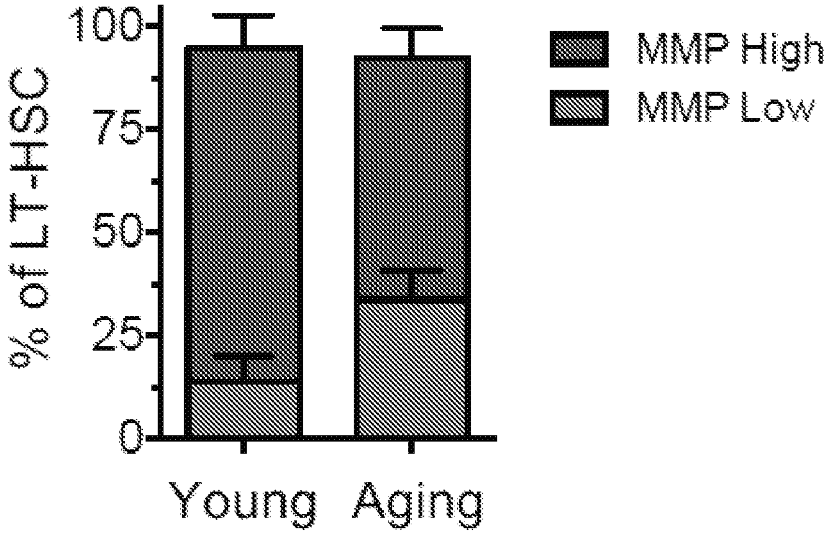
FIG. 15D shows the proportion of immunophenotypically defined LT-HSCs within the MMP-low and MMP-high HSCs (45% lowest and highest MMP respectively) from young vs. aging mice (n=4).
Figure 15E:
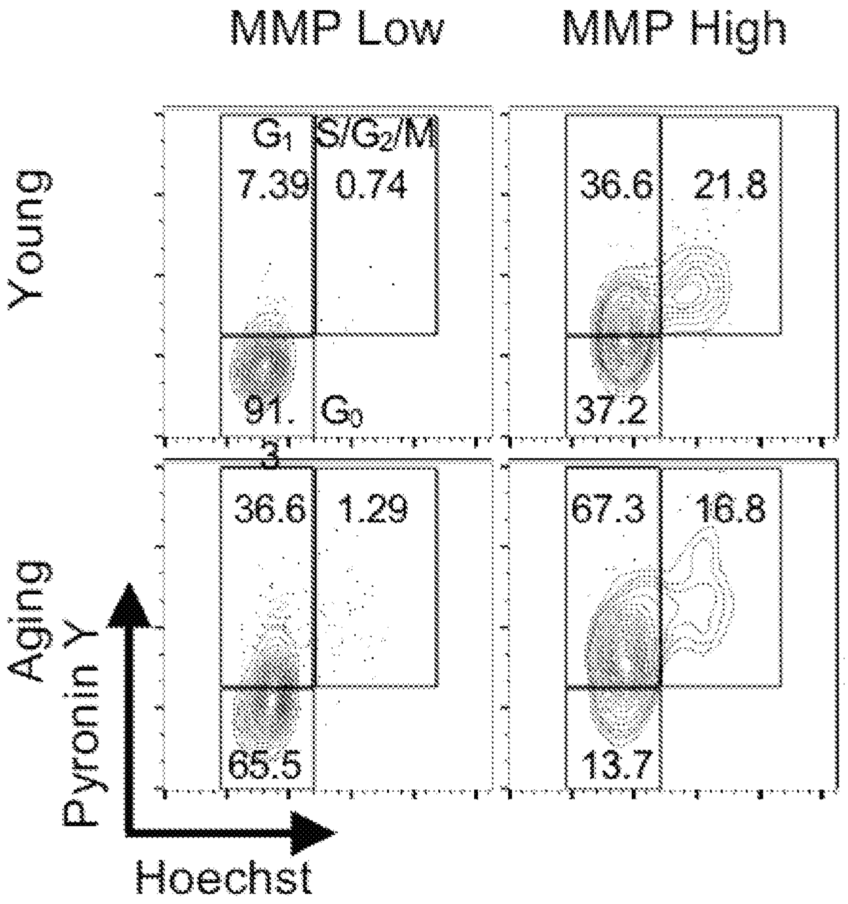
FIG. 15E shows representative flow plots of cell cycle analysis with Pyronin Y and Hoechst staining of live FACS-sorted MMP-low and MMP-high HSCs (LSK $CD150^{+}CD48^{-}$) from young vs. aging mice.
Figure 15F:
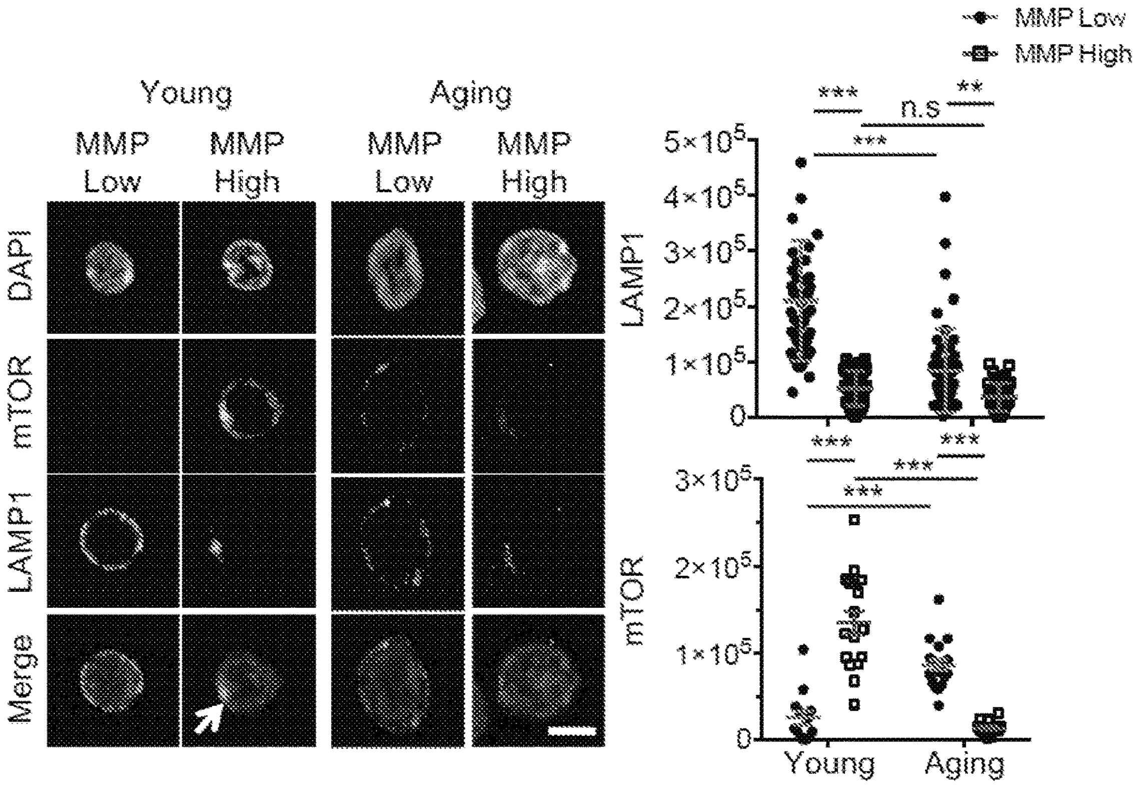
FIG. 15F shows representative confocal images (left, bar=5 μm) and quantification (right) of the indicated proteins in young vs aging MMP-low and MMP-high HSCs; arrow shows colocalization and mTOR (n=3).
Figure 15G:
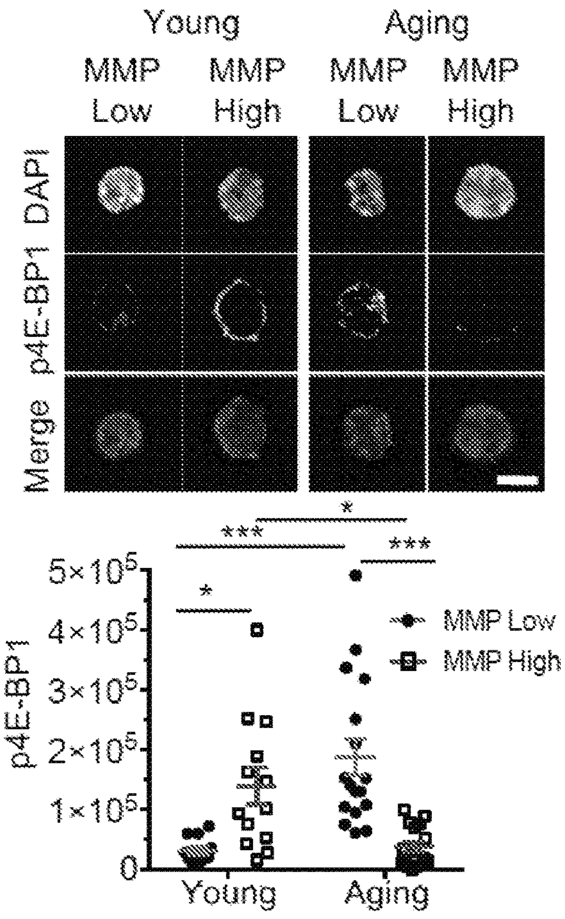
FIG. 15G shows representative confocal images of p4EBP1 downstream to mTOR pathway in young vs. aging HSCs (top, bar=2.5 μm) with quantification of fluorescence intensity (bottom) (n=3).
Figure 15H:
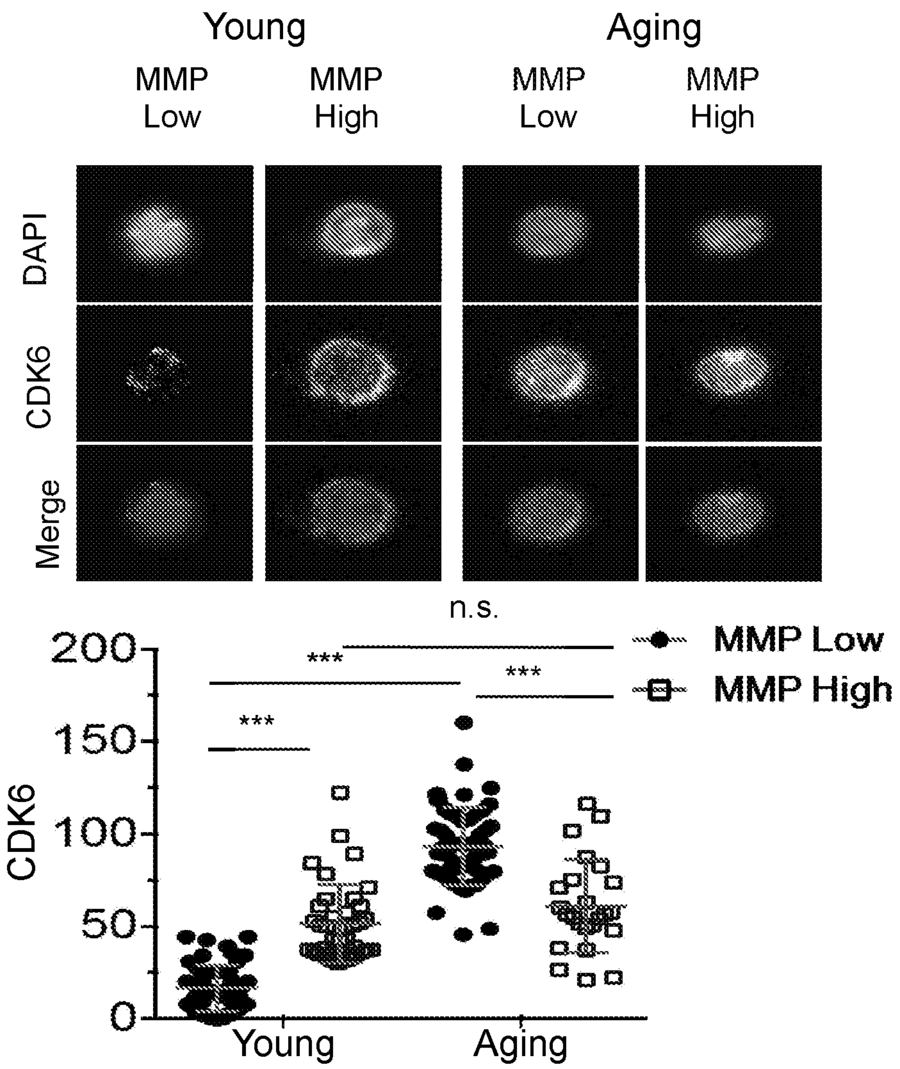
FIG. 15H shows representative confocal images of CDK6 in young vs. aging HSCs (top, bar=2.5 μm) and quantification of nuclear localized CDK6 (bottom) (n=3).

As anticipated aging HSCs exhibited: (i) an elevated expression of the SLAM marker CD150 on their surface (FIG. 15B); (ii) an increased frequency of $CD150^+$ HSCs (FIGS. 15B-15C); and (iii) a higher frequency of phenotypic HSC than young HSC (8-week-old) (FIGS. 15C). The frequency of MMP-low in aging versus young HSCs was also increased more than two-fold (FIG. 15D). These age-associated properties are consistent with the increased cycling of aging HSCs (FIG. 15E). Aging HSCs exhibited aberrant cycling (FIG. 15E). With age, the frequency of HSCs in $G_0$ was reduced and $G_1$ fractions increased substantially in HSCs which was observed in both MMP-low and mmp- high fractions (FIG. 15E). This was associated with increased nuclear expression of CDK6 in MMP low fraction of aging HSCs with no significant CDK6 modulation in MMP-high HSC counterparts (FIG. 15H).

Figure 15I:
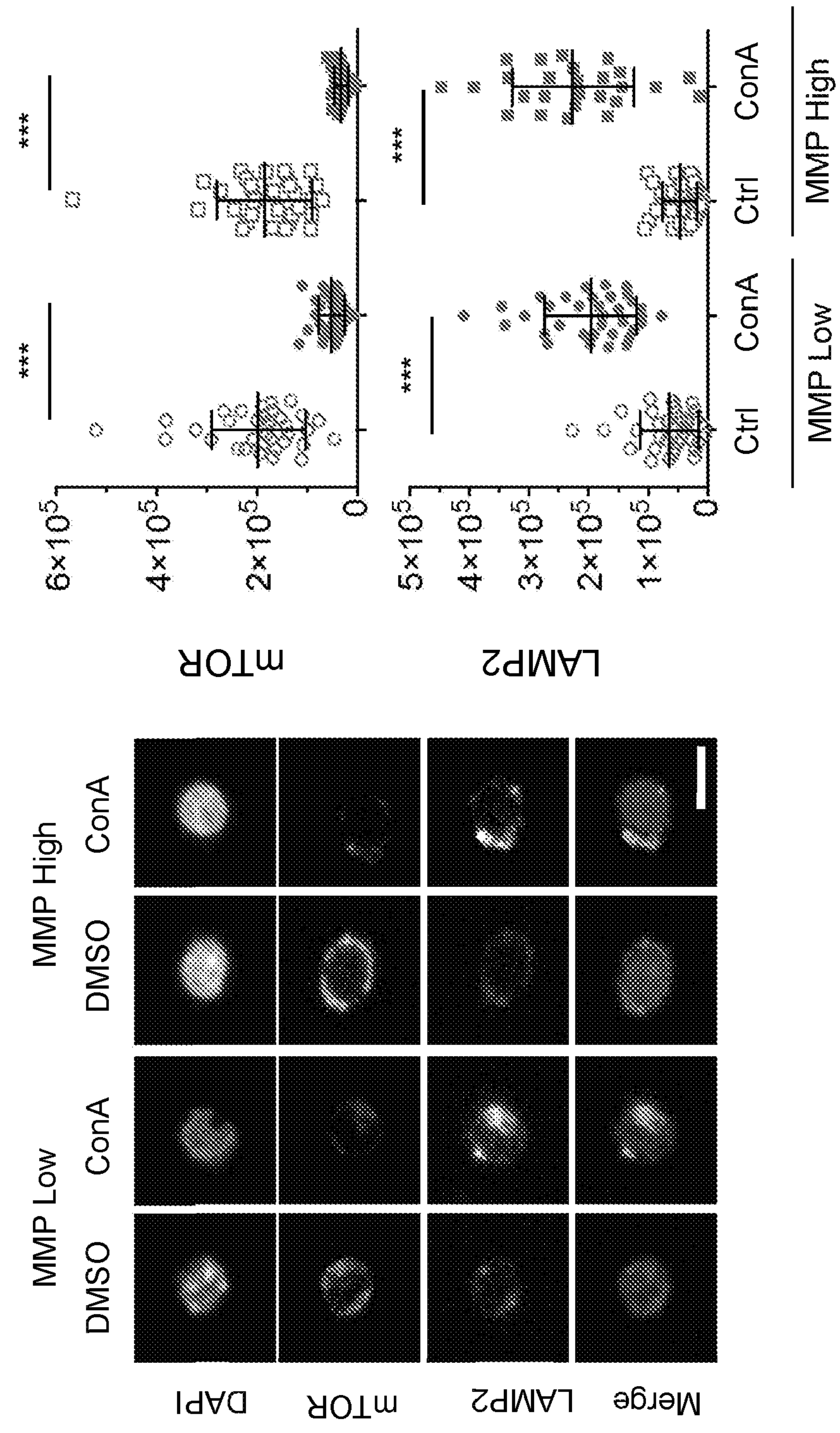
FIGS. 15I, 15J, 15K, 15L, 15M, and 15N show representative confocal microscopy images and quantification of indicated proteins in aging MMP-low and MMP-high HSCs treated with DMSO or ConA (40 nM) for 18 hours.
Figure 15J:
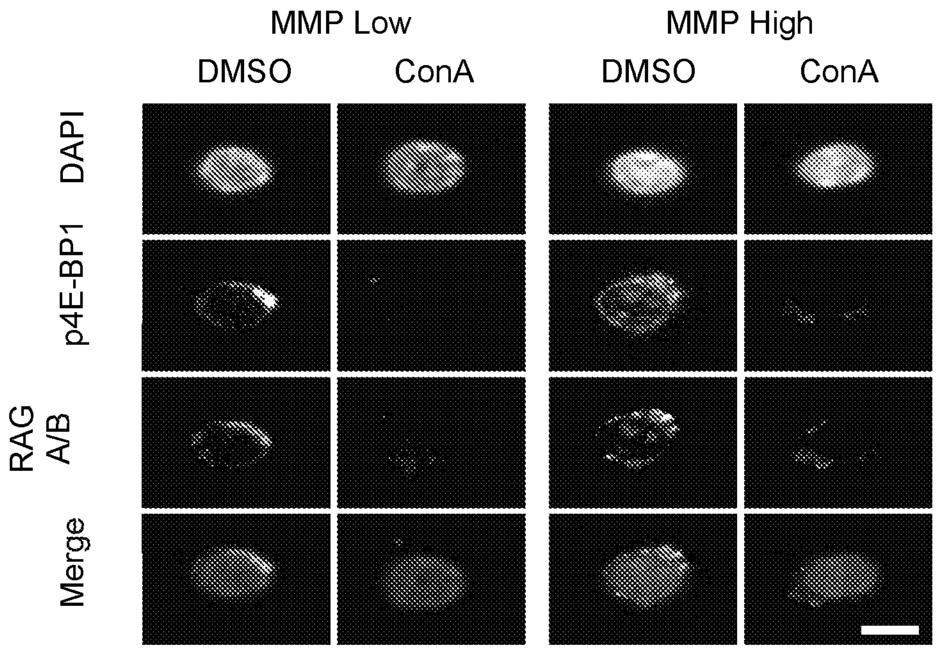
Figure 15K:
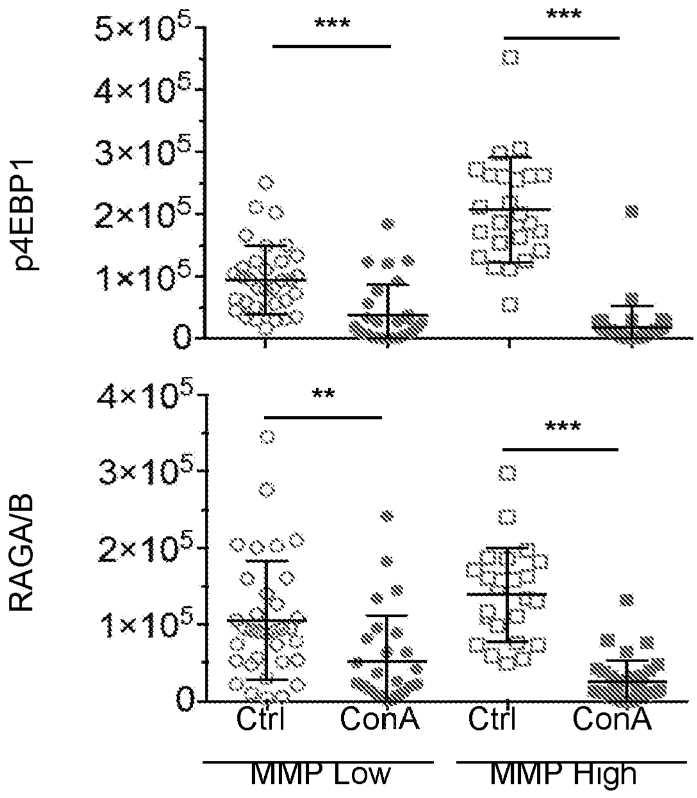
Figures 15L, 15M:
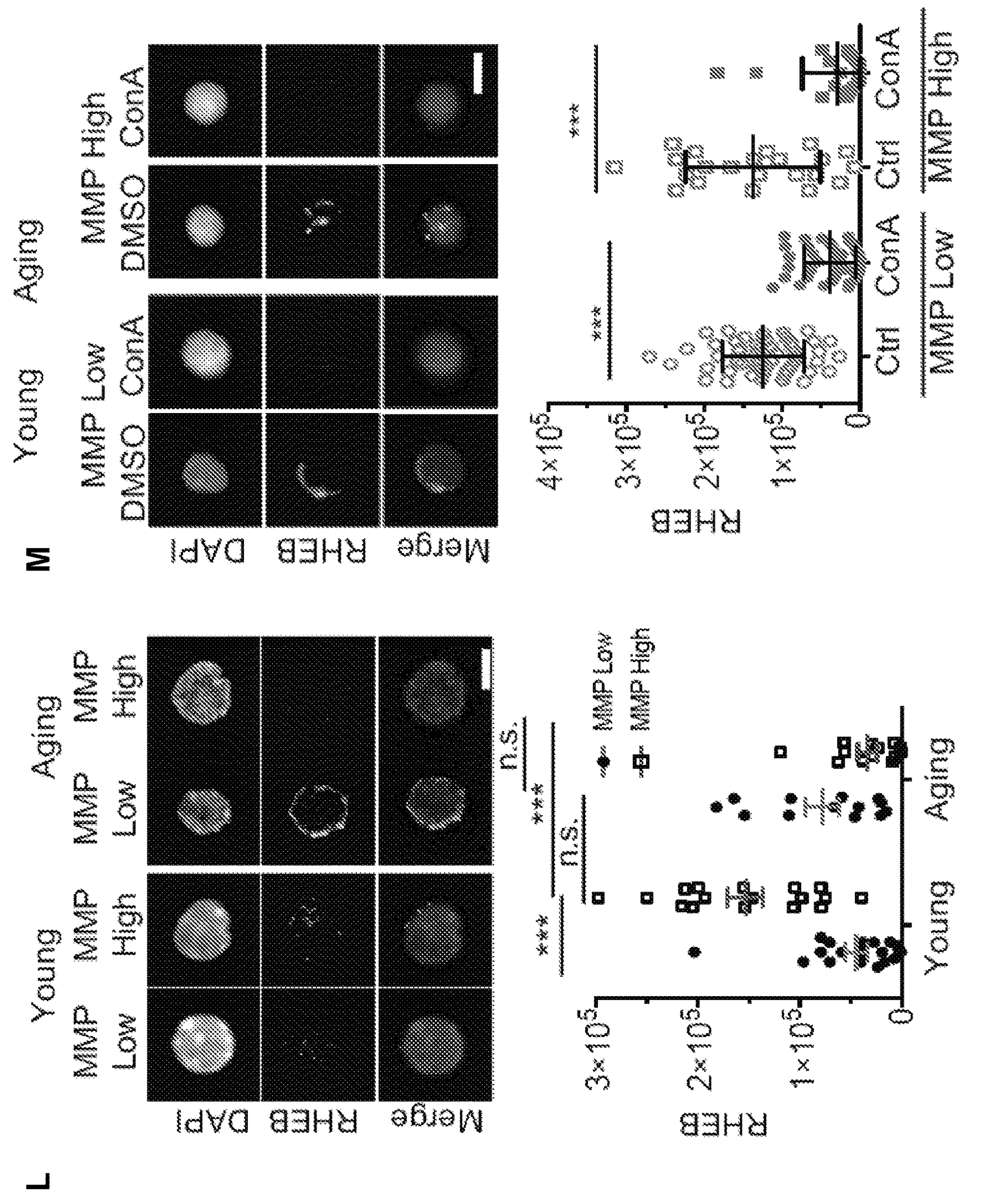
Figure 15N:
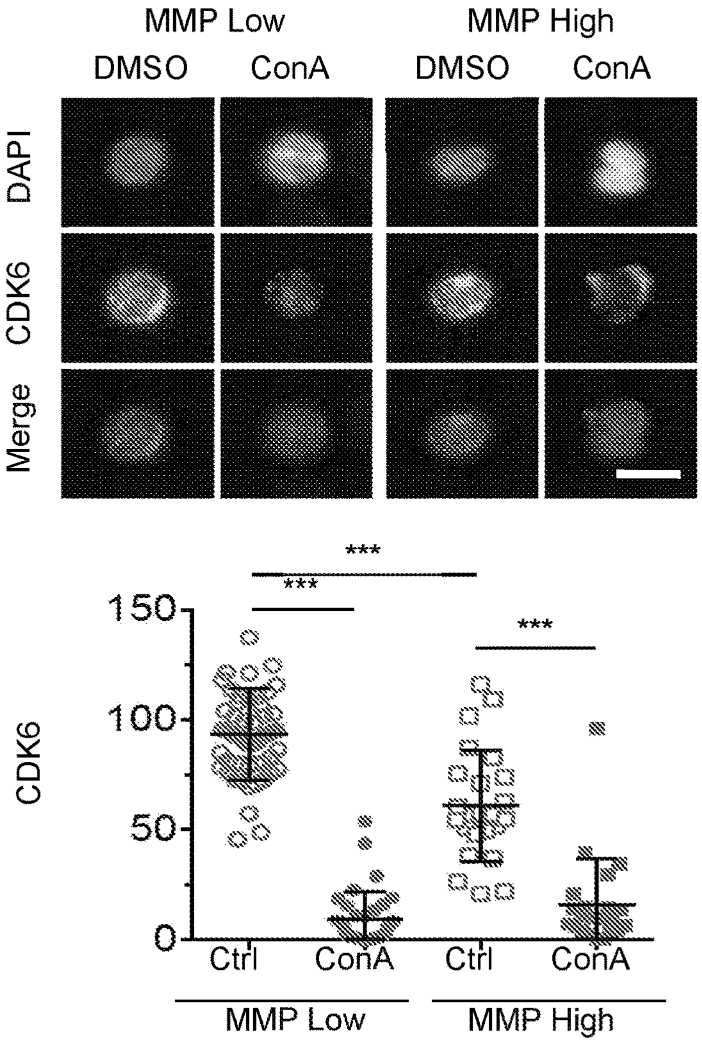
Figure 15O:
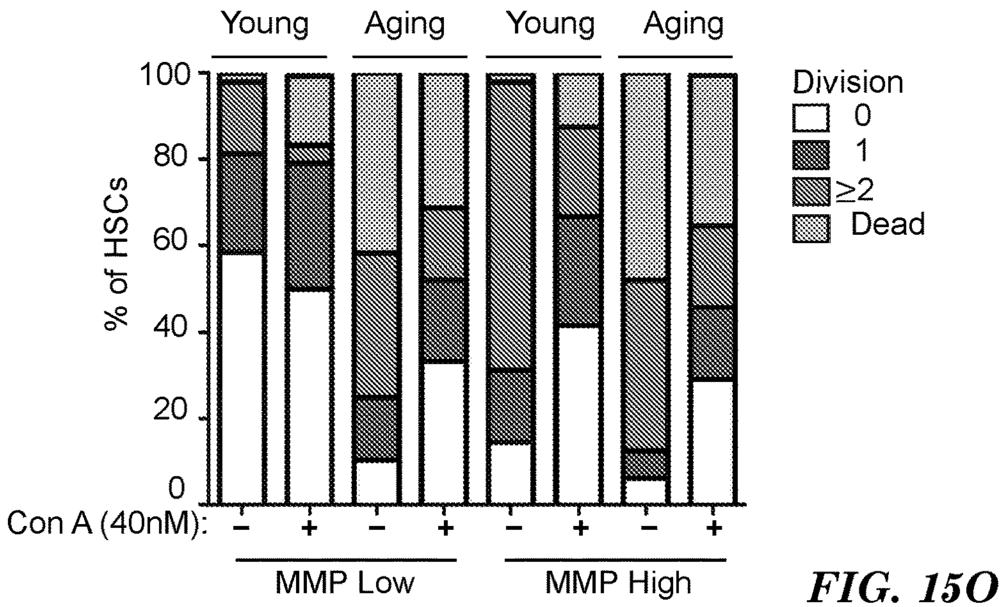
FIG. 15O shows the results of a single-cell division assay (in 96 wells) from young and aging MMP-low and MMP-high HSCs treated with DMSO or ConA (40 nM) for 60 hours (n=3).
Figure 15P:
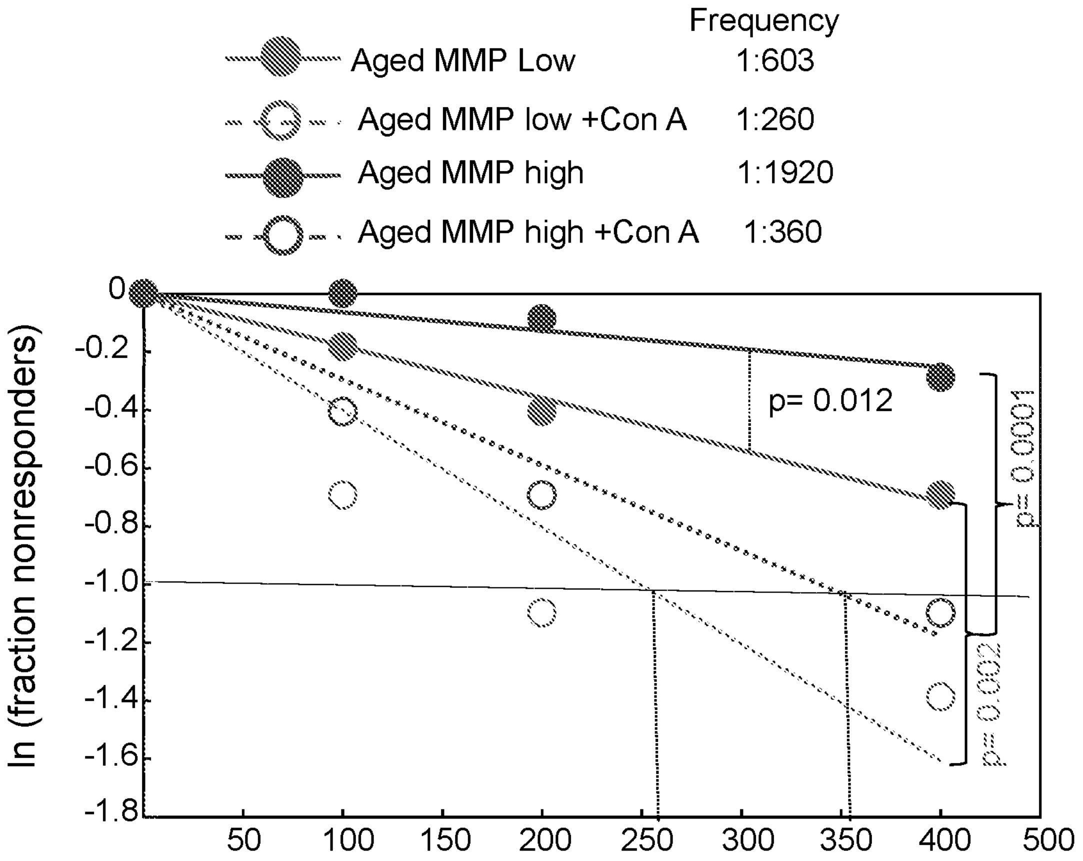
FIG. 15P is a graph showing the results of a limiting dilution analysis of long-term culture-initiated cells (LTC-IC) from decreasing numbers of aged MMP-low and MMP-high cells treated with or without Con A (40 nM) for two days in culture. Aged MMP-low and MMP-high-derived cells were seeded on stroma cells (S17). 12 replicates at 3 dilutions ranging from 100 to 400 cells were deposited on the stromal layer in each well of a 96-well plate. The number of wells containing clonogenic cells was determined by plating the entire content of each well in clonogenic assays after 5 weeks (Purton & Scadden, "Limiting Factors in Murine Hematopoietic Stem Cell Assays," *Cell Stem Cell* 1: 263-270 (2007), which is hereby incorporated by reference in its entirety). The frequency of LTC-ICs was determined after limiting dilution assay using Poisson statistics as described previously (Hu & Smyth, "ELDA: Extreme Limiting Dilution Analysis for Comparing Depleted and Enriched Populations in Stem Cell and Other Assays," *J. Immunol. Methods* 347: 70-78 (2009), which is hereby incorporated by reference in its entirety).
Figure 15Q:
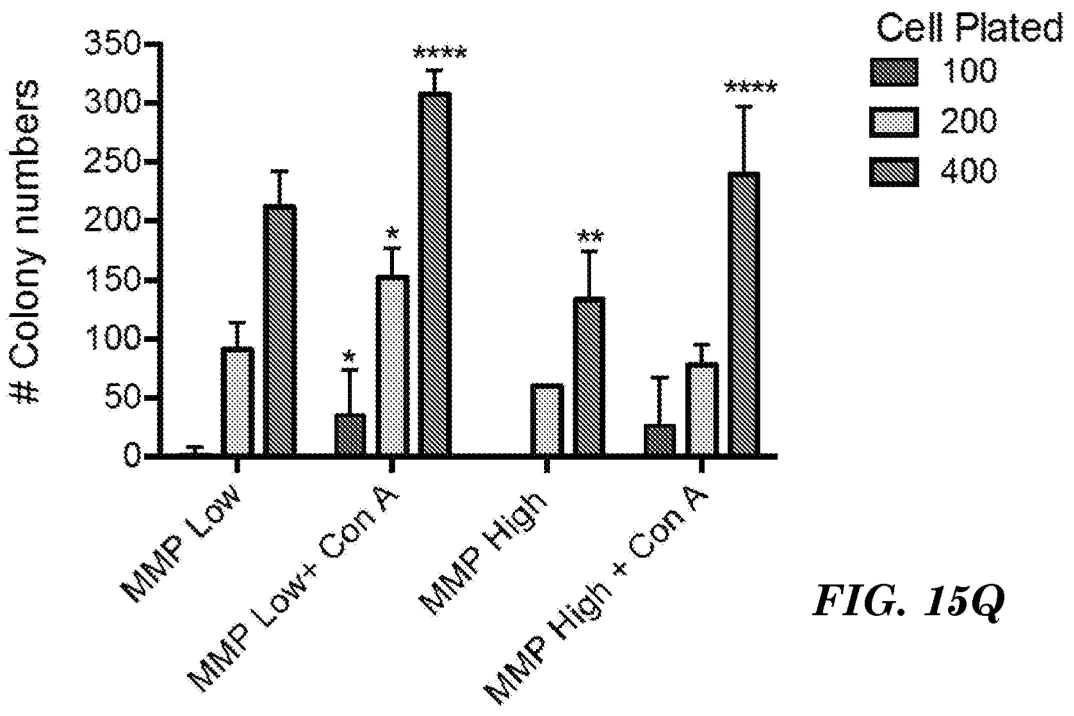
Figure 21A:
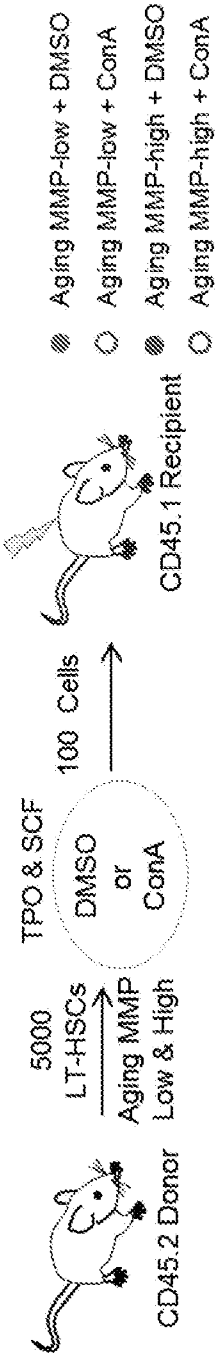
FIGS. 21A-21C show repression of lysosomal activity ex vivo greatly improves in vivo competitive repopulation of old HSCs.
Figure 21B:
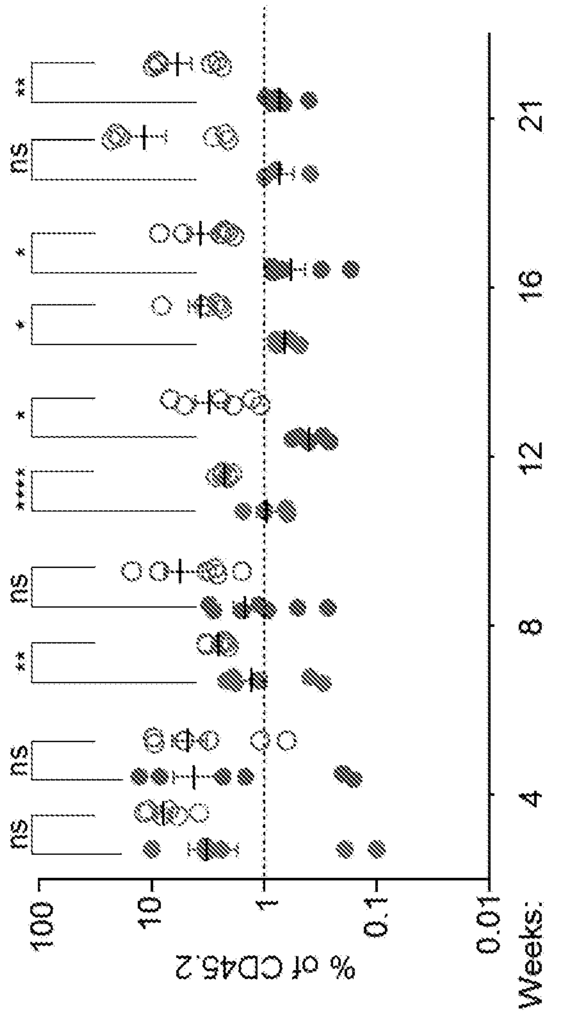
Figure 21C:
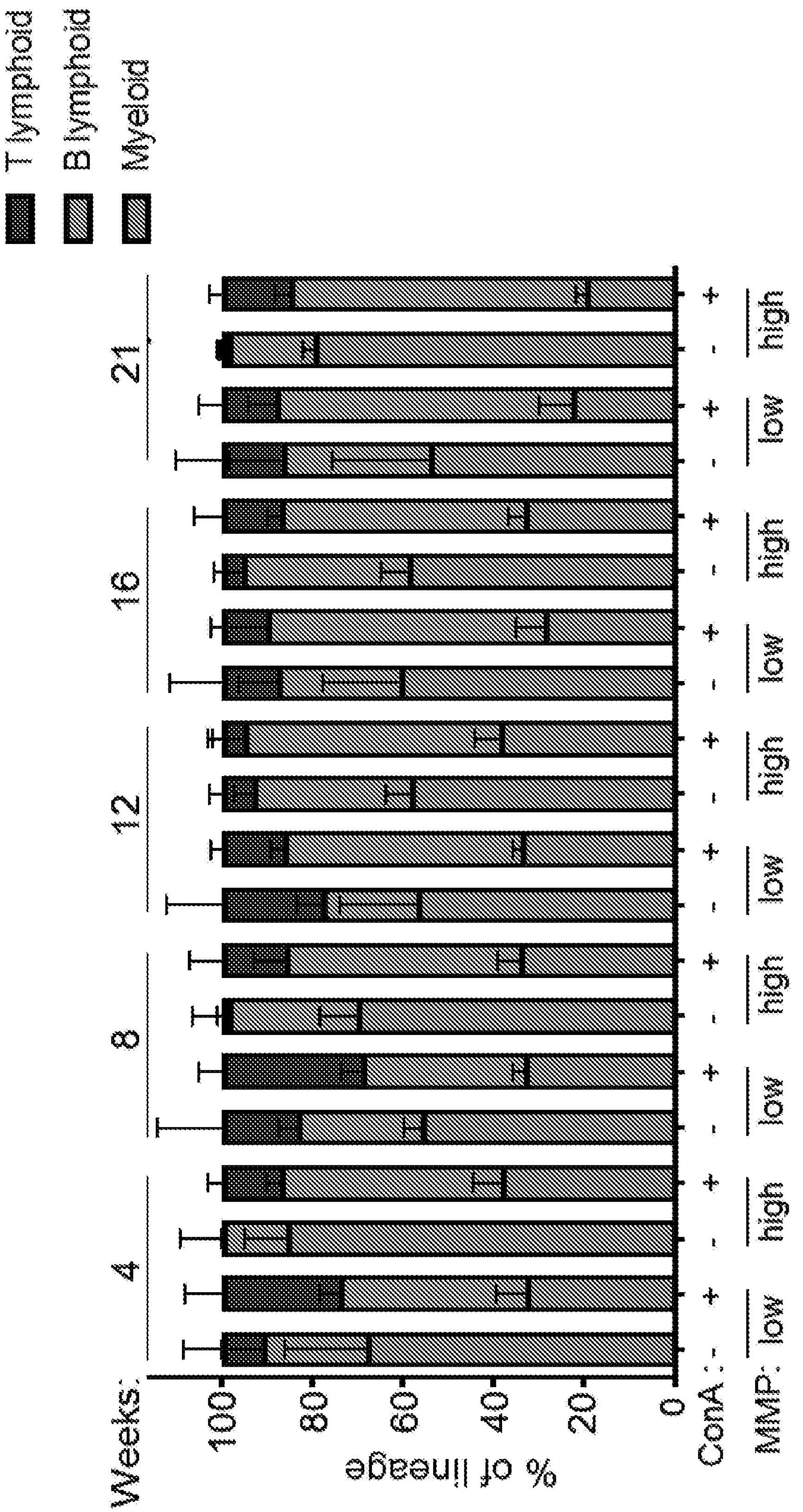
Figure 22:
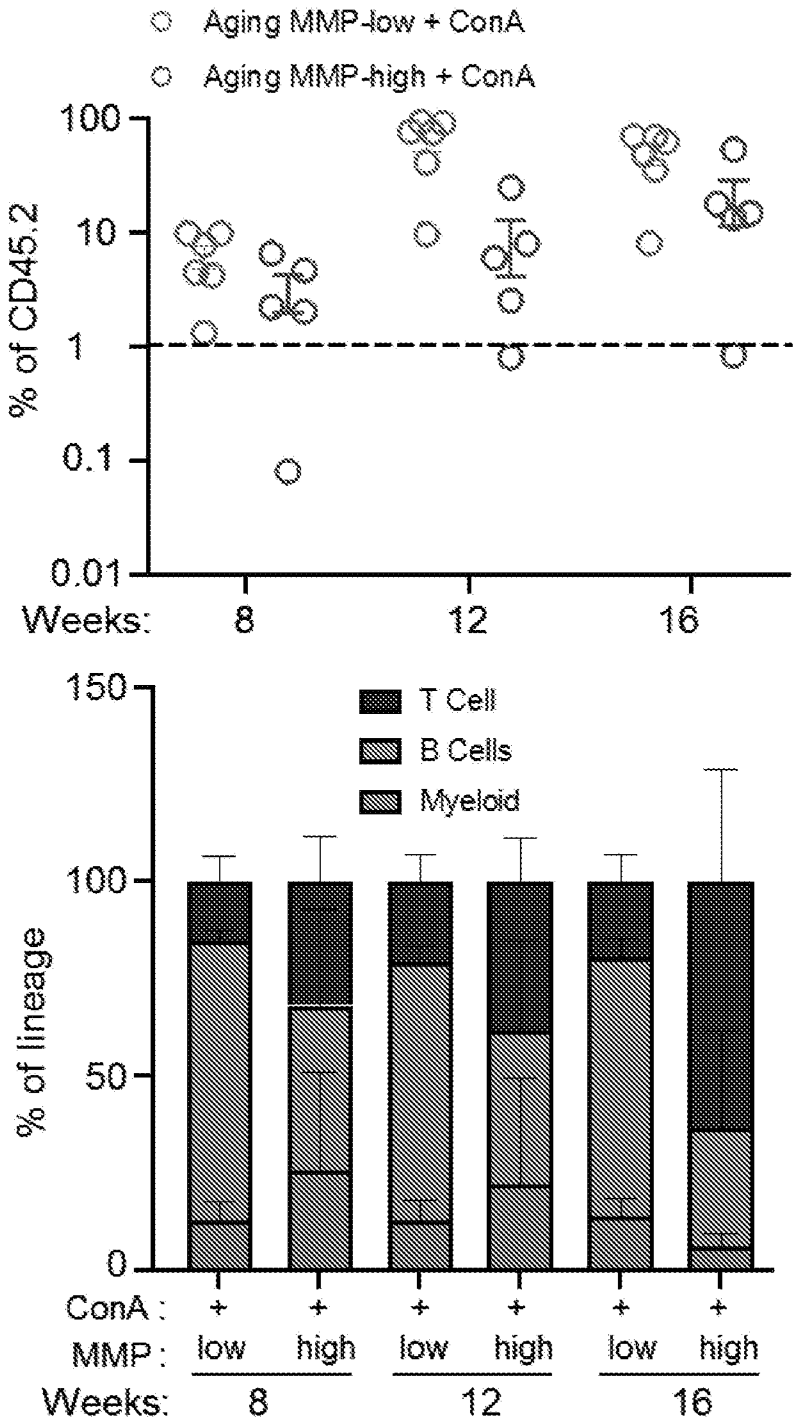
FIG. 22 is a pair of graphs showing that repression of lysosomal activity ex vivo greatly improves self-renewal of old HSCs. Contribution of donor-derived (CD45.2) cells to peripheral blood (PB) of secondary transplanted recipient mice (CD45.2) in a long-term competitive repopulation assay (top). Lineage output as a percentage of total CD45.2 donor-derived cells in recipient mice (bottom). Note only recipients of 4-day ex vivo ConA-treated HSCs and not control-treated HSCs survive in secondary transplantation.
Figure 23:
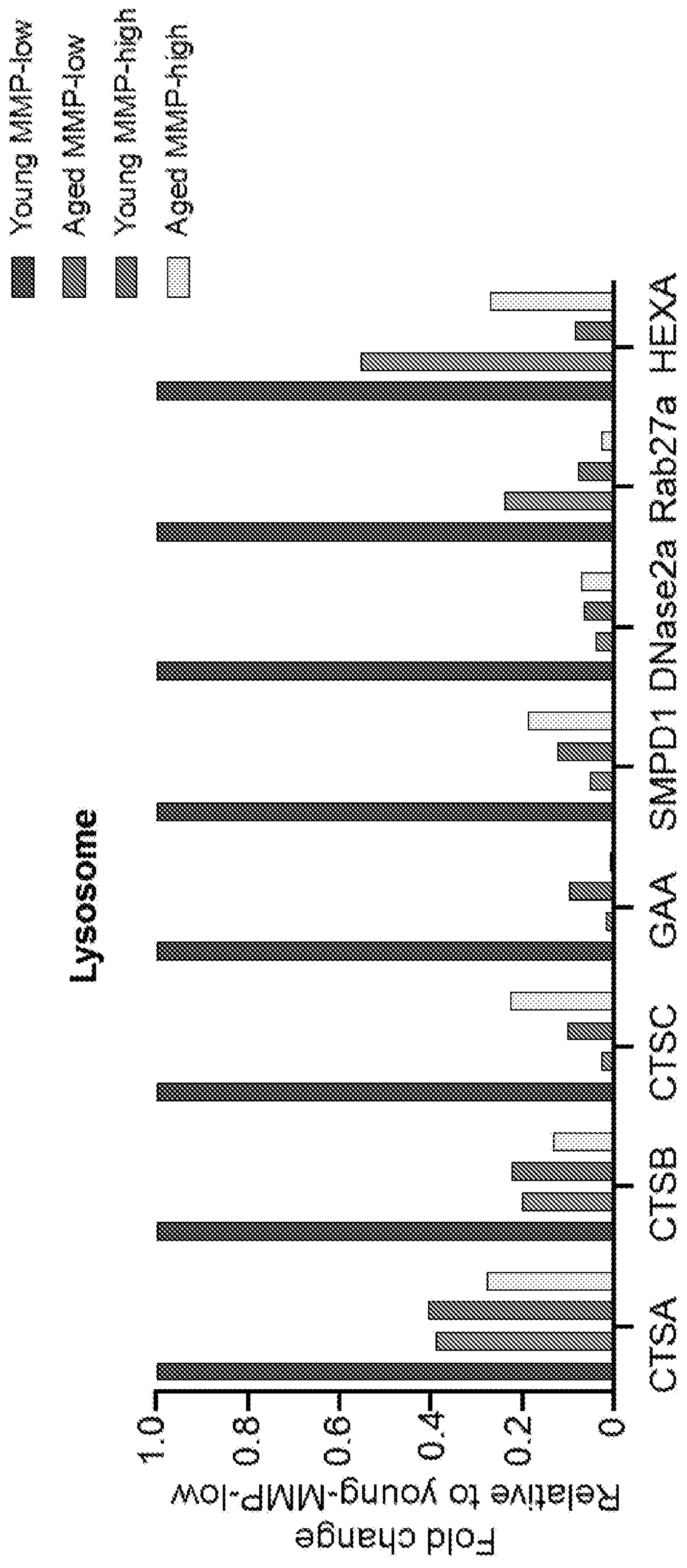
FIG. 23 is a graph showing defective lysosomal gene expression in old HSCs. Fold change of gene expression (qRT-PCR) in freshly isolated FACS-sorted MMP-low and -high HSCs from young vs old mice (normalized to (3-actin in young MMP low).

Lysosomes were found to be greatly depleted in old (20-22 months) quiescent HSCs (FIGS. 15A-15Q). Lysosomal genes were also greatly reduced in old relative to young HSCs (FIG. 23). In addition, mTOR expression and activity (FIGS. 15A-15Q) were abnormally high in the aging quiescent HSC fraction relative to their young counterparts. Notably, inhibition of lysosomal activity using concanamycin A ("ConA"), a specific inhibitor of v-ATPase (Drose et al., "Inhibitory Effect of Modified Bafilomycins and Concanamycins on P- and V-type Adenosinetriphosphatases," *Biochemistry* 32: 3902-3906 (1993), which is hereby incorporated by reference in its entirety) increased restored youthful properties in old HSCs by increasing lysosomal content in both MMP-low and MMP-high fractions (FIG. 15I). This was associated with reduced/abolished mTOR activity (FIGS. 15M, 15J, 15K) ConA treatment also reverted the cycling status of MMP-low and MMP-high aging HSCs, as evidenced by CDK6 staining (FIG. 15N). Importantly, ConA-treated aging HSC divided less than non-treated HSC, as evidenced b y culture over a 60-hour period of time without any increase in cell death (in fact, ConA-treated HSCs appeared to exhibit less death) (FIG. 15O). ConA treatment also improved the number of long-term culture-initiating cells ("LTC-IC") recovered from HSC cultures and increased the LTC-IC-derived colonies (FIGS. 15P-15Q. This treatment also remarkably improved the competitive repopulation ability of (4-day cultured) aged MMP-high HSCs and balanced their lineage output (FIGS. 21A-21C) to similar levels observed with young MMP-low HSCs-transplanted animals (Liang et al., "Restraining Lysosomal Activity Preserves Hematopoietic Stem Cell Quiescence and Potency," *Cell Stem Cell* 26: 359-376 (2020), which is hereby incorporated by reference in its entirety). Furthermore, these ConA-treated HSCs exhibited improved self-renewal in secondary transplants while mice receiving control-treated HSCs died in secondary transplantation (FIG. 22).

The studies here suggest that the slow degradation of lysosomal cargo, i.e., mitochondria in quiescent HSCs, reduces ROS levels, possibly modulates amino acid efflux and mTOR activation towards HSC priming, and contributes to carbon mass for cell proliferation (Efeyan & Sabatini, "Amino Acids and mTORC1: From Lysosomes to Disease," *Trends in Molecular Medicine* 18: 524-533 (2012); Hosios et al., "Amino Acids Rather than Glucose Account for the Majority of Cell Mass in Proliferating Mammalian Cells," *Developmental Cell* 36: 540-549 (2016), which are hereby incorporated by reference in their entirety). Based on this work, a model is proposed in which quiescence of HSCs is maintained by lysosomes that engulf and degrade (old and damaged) cargo, remove toxins to promote HSC health, and generate and store metabolites whose release primes HSCs. Inhibition of lysosomal activity in old HSCs markedly enhances their born marrow transplantation ability and their self-renewal suggesting this ex vivo treatment may have beneficial impact on clinical use of HSCs.

Example 12—Human MMP-Low HSCs Contain the Most Potent HSCs

Figure 24A:
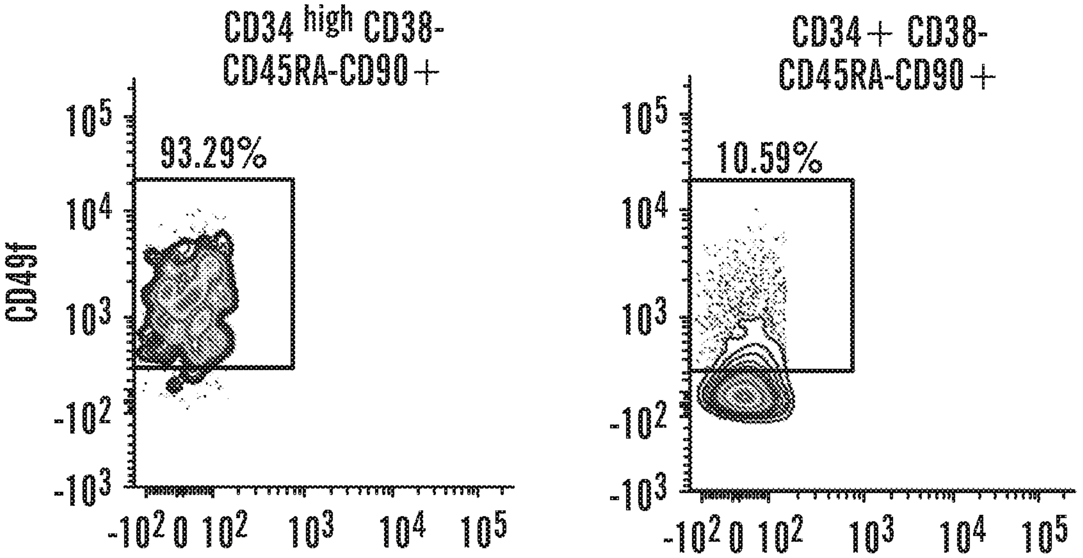
Figure 24B:
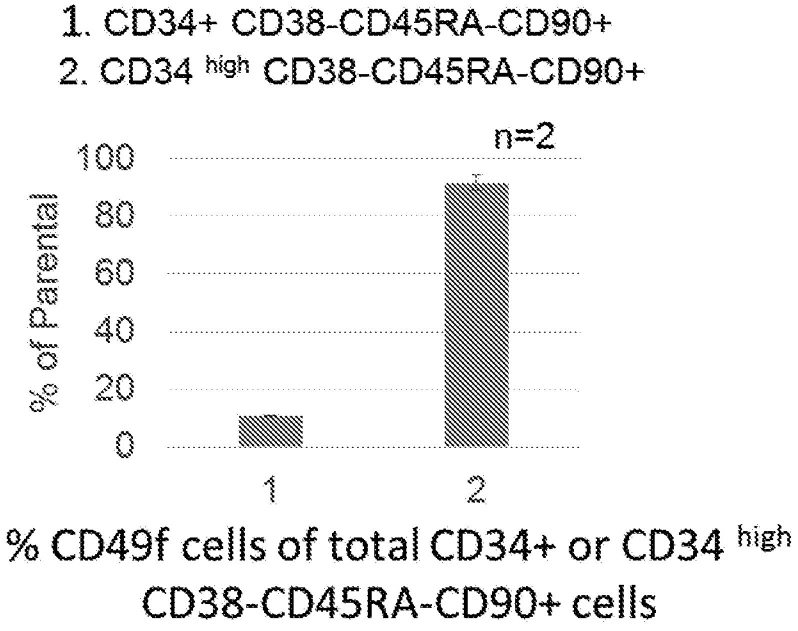
FIG. 24B is a graph showing CD49f$^+$ HSCs are enriched in CD34 high CD38-CD45RA-CD90$^+$.
Figure 24C:
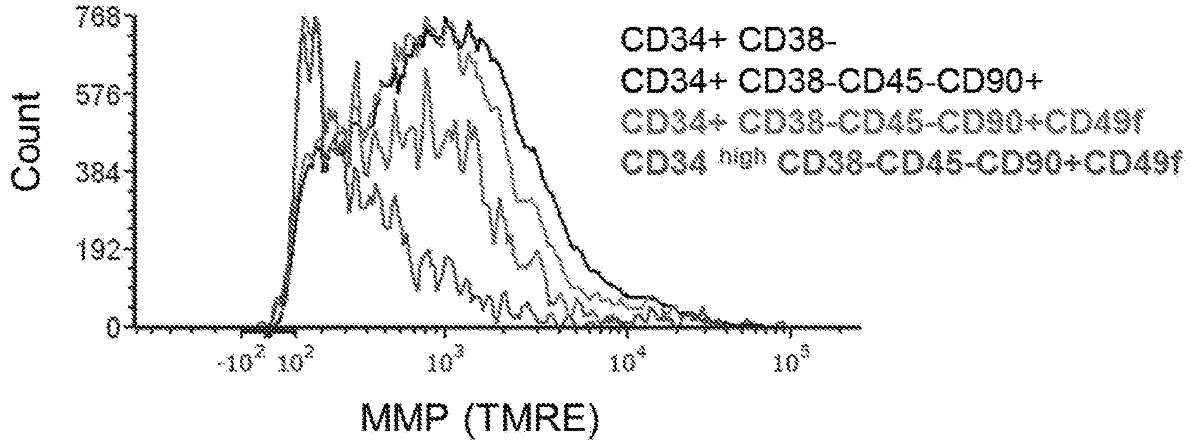
FIG. 24C is a graph showing MMP (TMRE intensity) FACS histogram of CD34+HSPCs, CD38-HSPCs CD90$^+$ HSCs FACS histogram of MMP profiles of CD34$^+$ HSPCs, CD38- HSPCs, CD90$^+$HSCs and CD49f$^+$ LT-HSCs from UCB.

TMRE was used to measure mitochondrial membrane potential ("MMP") levels in phenotypically defined subpopulations of human HSPCs (hematopoietic stem and progenitor cells). $CD34^+$ cells purified from mononuclear cells ("MNCs") of the (un-mobilized) peripheral blood ("PB") under homeostasis were stained with HSPC markers and TMRE, and analyzed by flow cytometry. HSCs of higher hierarchy were enriched in fractions of lower MMPs, while HSPCs of lower hierarchy were enriched in fractions of higher MMPs (FIG. 24A-24C). Specifically, higher percentage of $CD34^+CD38^-CD45RA^-CD90^+$ HSCs (referred to herein as $CD90^+$ HSCs) were observed in $CD34^+CD38^-CD45RA^-$ HSPCs of low MMP as compared to high MMP in PB.

Similar analyses using umbilical cord blood ("UCB") further confirmed these results (FIG. 24A-24C). In addition, in UCBs, $CD90^+$ HSCs of low MMP were further enriched in $CD34^+CD38^-CD45RA^-CD90^+CD49f^+$ long-term repopulating HSCs (referred to herein as $CD49f^+$ HSCs) as compared to high MMP (FIG. 24B). Altogether, these results suggest that even the most primitive subpopulations of HSCs including $CD90^+$ HSCs and in $CD49f^+$ HSCs, are heterogeneous in their MMP levels. Notably, the most primitive human HSCs are contained within the HSC subpopulations with the lowest MMPs.

During these side-by-side studies, it was noticed that $CD34^+$ cells in UBC, in contrast to the ones in PB, were subdivided into two peaks. A major peak containing almost all $CD34^+$ cells, and a small peak encompassing only 1% (1.19% on average) of CD34 with very high expression levels ($CD34^{++}$). The $CD34^{++}$ cells were almost entirely negative for the CD38 marker, suggesting a more primitive subset of these cells. $CD34^{++}CD38^-$ HSPCs were highly enriched for $CD90^+$ HSCs. Furthermore, $CD90^+$ HSCs gated on $CD34^{high}$ fraction significantly enriched for $CD49f^+$ phenotype (above 90% on average). This observation prompted the measurement of the MMP level of $CD34^{high}$ fraction of $CD49f^+$ LT-HSCs. Remarkably, the MMP profile of $CD34^{high}$ compartment shifted to the far-left side of entire $CD49f^+$ LT-HSC population. $CD34^{high}CD49f^+$ LT-HSCs were highly enriched in low MMP cells (FIG. 24B). Furthermore, gating on $CD34^{high}$ alone from total CD34+ cells revealed that its MMP profile extensively shifted to a low level and that $CD34^{high}$ cells enriched for low MMP cells to as close as 30 percent. It was found that in human HSCs using umbilical cord blood ("UCB"), MMP levels progressively decrease in subpopulations with phenotypes of higher hematopoietic hierarchy. These data suggest that the relative activity of mitochondria may be a predictor of the degree of potency of the $CD34^+$ human HSCs.

Lower Mitochondrial Activity Indicates Greater Stem Cell Potential

Figure 25A:
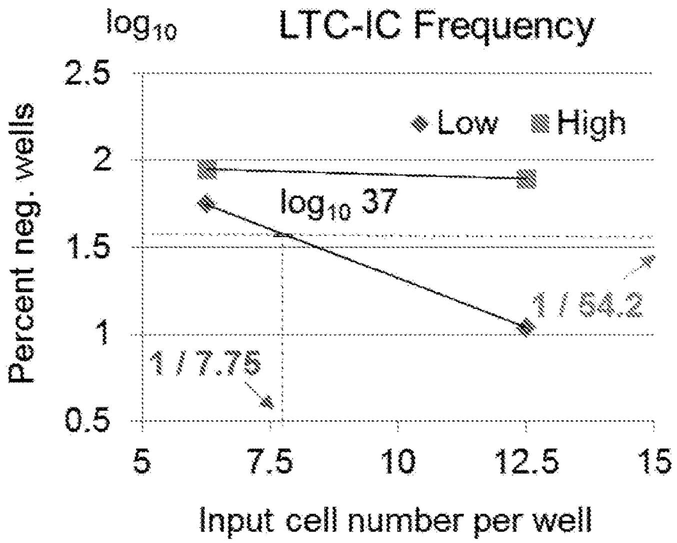
FIGS. 25A-25B show that human MMP-low HSCs are enriched in long-term culture initiating cells (LTC-IC) in vitro.
Figure 25B:
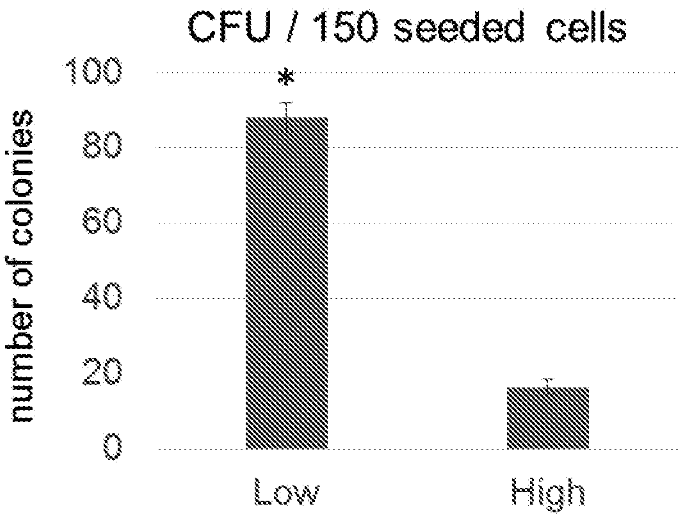
Figure 26A:
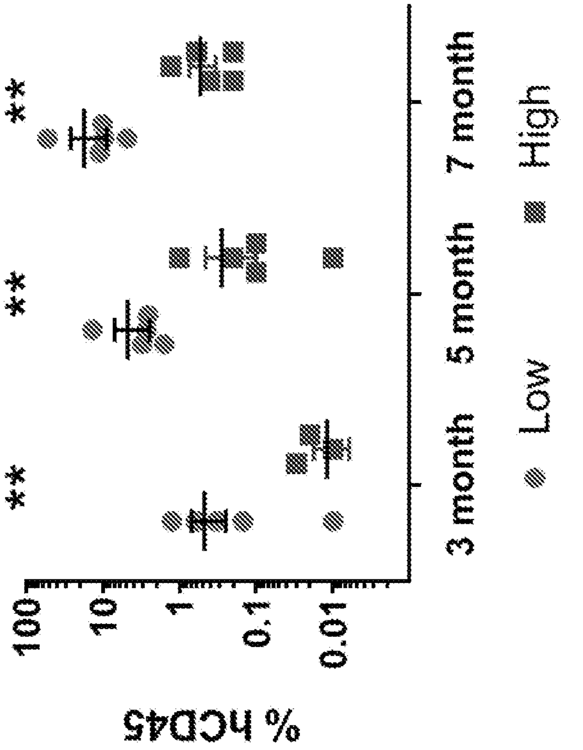
FIGS. 26A-26B show that human MMP-low HSCs contain the most potent HSCs based on results of xenograft transplantations. MMP-low and -high HSCs (800 CD34+ CD38-CD45RA-CD90$^+$) cells were transplanted into NSG mice and contribution of human HSCs to the peripheral blood of mice was evaluated in the primary transplants for 7 months (secondary ongoing).
Figure 26B:
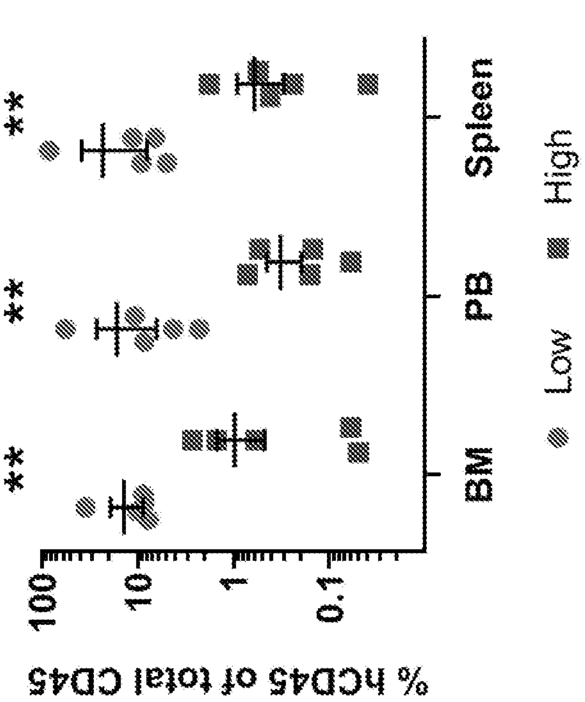

To test this hypothesis, HSC activity was examined within subpopulations of $CD34^+$ human HSCs with distinct MMP levels. Subsets of PB $CD38^-$ HSPCs ($CD34^+CD38^-$) and $CD90^+$ HSCs ($CD34^+CD38^-CD45RA^-CD90^+$) known to be more potent in their functional HSC content within the lowest or the highest 25% TMRE fluorescent intensity (defined as MMP-low and MMP-high) were FACS sorted, and subjected to in vitro long-term culture initiating cell (LTC-IC) assay to identify functional stem cells with the capacity to form colonies in vitro after 5 weeks in liquid culture. Results revealed that $CD90^+$ HSCs further segregate functional stem cells according to MMP levels. By applying limiting dilution analysis it was found that 1 in 7.75 MMP-low $CD90^+$ HSCs contained 7 fold more functional HSCs detectable ex vivo as compared to MMP-high $CD90^+$ HSCs (1 in 54.2 cells) (FIGS. 25A-25B). The average number of LTC-IC-derived colony forming cells ("CFCs") generated from bulk cultures was 9-fold greater in MMP-low vs -high $CD90^+$ HSCs (FIG. 26A-26B). It was further found that the more heterogeneous population of $CD38^-$ HSPCs is also segregated into functionally distinct subsets based on MMP levels. The LTC-IC frequency of MMP-low CD38-HSPCs was 3.3-fold higher as compared to MMP-high HSPCs (1 in 17.7 cells vs 1 in 64.4 cells respectively). Similarly, LTC-IC-derived CFCs was 6.68 fold more elevated in MMP-low as compared to MMP-high CD38- HSPCs. Taken together these studies suggest that the relative mitochondrial activity is an indication of the potency of HSC populations regardless of their phenotypic identification. Interestingly, extending the liquid phase of LTC-IC assay by one and half week, did not have a detectable impact on the frequency of LTC-IC from MMP-low $CD90^+$ HSCs. However this modification greatly decreased the frequency of LTC-IC within MMP-high $CD90^+$ HSCs, to 1 in 269, almost 5 times as low as the LTC-IC in a 5-week culture. These results suggest that MMP-low in contrast to -high HSCs sustain their stem cell activity in culture for an extended time.

It was also observed that human MMP-high $CD90^+$ HSCs were prone to the erythoid lineage specification ex vivo. Specifically, despite the reduction of the total number of CFCs generated from LTC-IC of MMP-high as compared to MMP-low $CD90^+$ HSCs, the ratio of burst-forming unit-erythroid (BFU-E) to granulocyte/macrophage (G/M) colonies was (almost two fold higher) significantly higher, suggesting a tendency of erythroid lineage specification. Similar BFU-E lineage bias was also observed in MMP high $CD38^-$ HSPCs.

Figure 27:
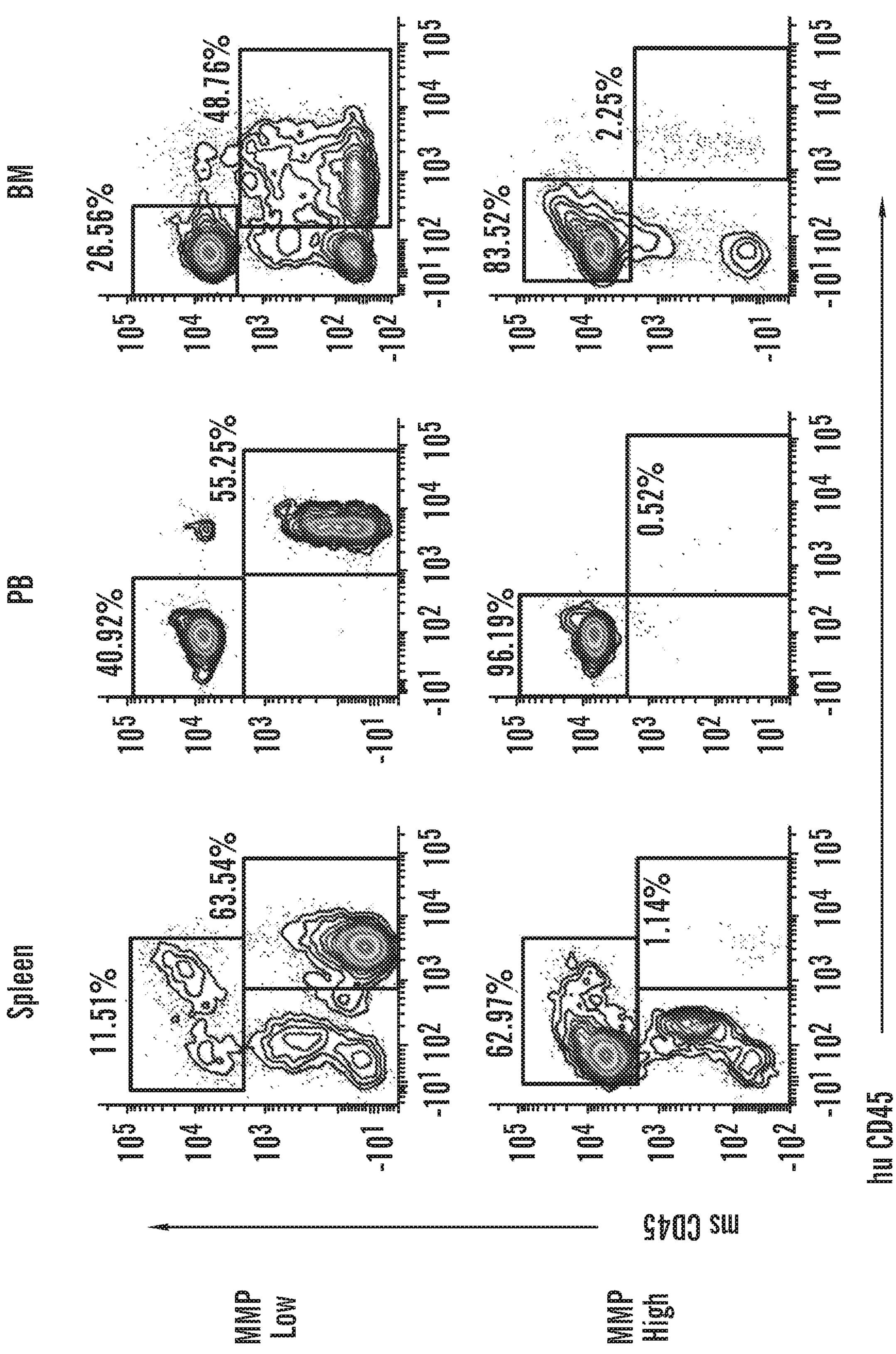
FIG. 27 shows representative FACS profiles of spleen, PB, and BM plotted as human CD45 (X) versus mouse CD45 (Y) from MMP-low or -high recipient mice 7 months post transplantation. Note high detection of human CD45 in mouse hematopoietic organs in transplanted recipients of human MMP-low but not -high HSCs.
Figure 28:
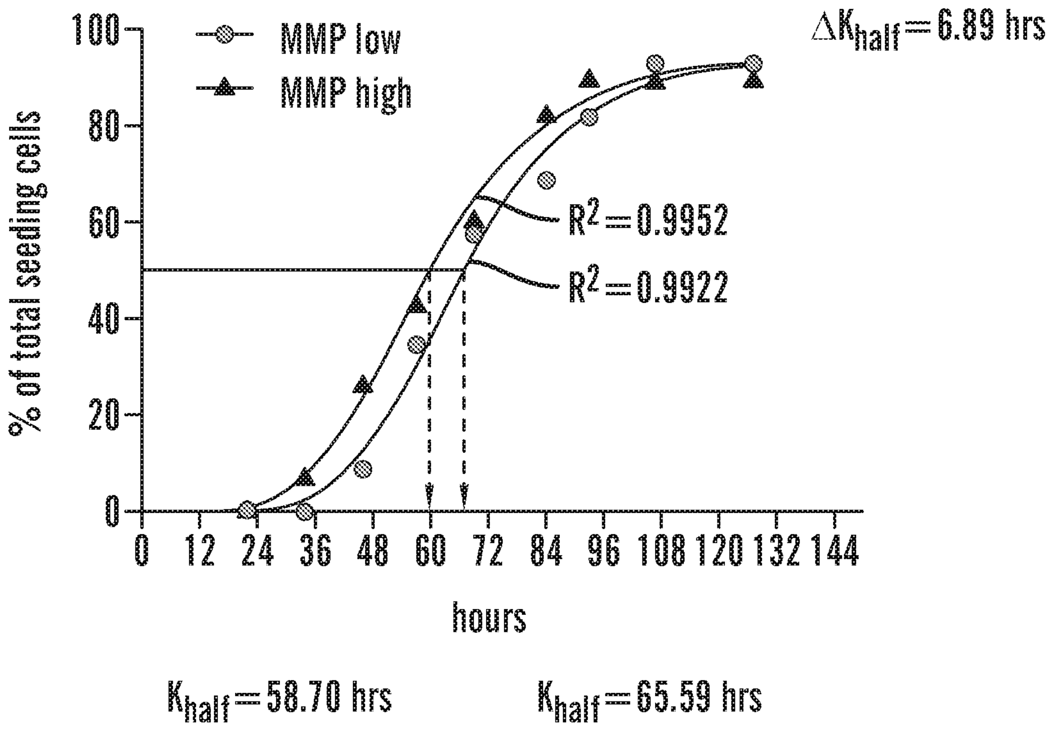
FIG. 28 is a graph showing the percentage of accumulative first cell division of CD38-HSPCs in total single cell cultures. Khalf: hours required for 50% of the cells to finish first division. Cells were cultured in cytokine supplied serum free media (STEM SPAN).

Given the significant difference in the ability of HSCs with low versus high MMP to produce colonies in vitro, the in vivo capacity of these subpopulations of HSCs to repopulate lethally irradiated immunedeficient NSG (NOD/SCID/IL2R$\gamma^{null}$) mice with human blood was next interrogated. The long-term repopulating capacity of these HSCs subpopulations was thus compared by transplanting 800 CB-derived MMP-low vs MMP-high $CD90^+$HSCs. Although the level of chimerism in transplanted animals (measured as percent human $CD45^+$ myelolymphoid cells) continuously increased in recipients of both MMP-low and -high $CD90^+$ HSC during the periods of three to seven months, the level of chimerism in mice that received MMP-low $CD90^+$HSCs was substantially higher than in MMP-high recipients (FIG. 28). The engraftment efficiency of MMP-low $CD90^+$HSCs assessed at the end of 7 months was significantly higher as compared to MMP-high donor cells in the bone marrow ("BM"), spleen and peripheral blood ("PB") (FIG. 27). In addition, $CD45^-$ Glycophorin $A^+$erythroid lineage was detected in the BM of MMP-low but not MMP-high recipient. Although human blood is mostly myeloid (relative to lymphoid), human grafts in NSG mice consist mainly of lymphoid cells given that in the absence of human cytokines, human myelopoiesis in mice is relatively inefficient. Consistent with this, human T-lymphoid or B-lymphoid ($CD3^+$/$CD19^+$) and myeloid ($CD33^+$) lineage distributions were very similar in the PB and spleen of mice recipients of MMP-low and -high $CD90^+$HSCs (FIGS. 26A-26B and FIG. 27). Surprisingly, however, MMP-high donor HSCs gave rise to significantly increased frequency of myeloid cells in the BM (FIG. 27). This finding provided evidence for the possibility that the status of mitochondrial activity might influence the HSCs lineage commitment in vivo; although homing, lodging, and microenvironment may also be involved.

It was then asked to what extent MMP as a single parameter selects for functionally potent HSCs in a total $CD34^+$ population. FACS analysis of UCB profile revealed that MMP-low $CD34^+$ cells are 10-fold enriched for MMP-low $CD90^+$ HSCs relative to total $CD34^+$ cells. These combined results suggest that HSCs with low MMP levels contain the most potent within the entire population. They also support the notion that highly functional human HSCs may be isolated based on their intrinsic metabolic activity reflected in their MMPs.

HSCs with Lower Mitochondrial Activity are Delayed in Entering Cell Cycle

Highly primitive HSCs are known to be mostly quiescent. The quiescence is directly linked to HSC potency. Given that MMP levels predict stem cell potential, it was reasoned that HSC mitochondrial activity should also be linked to their cycling status. To examine this, MMP-low and MMP-high $CD38^-$ HSPCs or $CD90^+$ HSCs were double stained with RNA and DNA dyes, Pyronin Y and Hoechst. Quiescent HSCs are found within Hoechst-low, Pyronin Y-low gate. Above 90% of MMP-low CD38-HSPCs were found in $G_0$ phase as compared to 75% of MMP-high cells. This suggested that low MMP level identifies quiescent cells from a mixed population of both stem and progenitor cells. Consistent with previous reports (Laurenti et al, "CDK6 Levels Regulate Quiescence Exit in Human Hematopoietic Stem Cells," *Cell Stem Cell* 16: 302-313 (2015), which is hereby incorporated by reference in its entirety), it was found that above 90% of both MMP-low and -high CD90+HSCs were in $G_0$ phase. However, an even higher percentage of quiescent cells (95.5%) was present in MMP-low as compared to MMP-high HSCs (90.6%).

Given these results, it was questioned whether MMP levels predict distinct kinetics of HSC cycle entry when activated. To address this, sorted single HSCs were cultured in serum free medium (SFM) supplemented with mitogenic cytokines. The occurrence of cell division in each well was monitored under microscopy every 12 hours for 6 days. These studies found that cell cycle entrance of MMP-low CD38-HSPCs was delayed as compared to MMP-high by 6.89 hrs as measured by the time for accumulative 50% cells to complete their first division (FIG. 28). Notably, even though MMP-low and -high CD90+ HSCs are both mostly in $G_0$ phase and similarly low in CDK6 expression, their cell cycle entry kinetics differed upon cytokine stimulation. The first division of MMP-low CD90+ HSCs was delayed by 1.9 hrs as compared to MMP-high HSCs (FIG. 28). The percentage of newly divided CD90+ HSCs was then plotted at each time point during the first division instead of plotting the accumulative percentage. Two waves of cell cycle entrance were revealed for both MMP-low and -high $CD90^+$ HSCs. In both cell types the majority of the cells divided during the first wave. However, while the first division was observed after 72 hours in MMP-high HSCs, it took 7 hours longer for MMP-low HSCs to undergo their first division under identical cytokine conditions in culture. This difference was even longer (10.6 hours) for the second division of MMP-high versus -low human HSCs. It was also found that MMP-high HSCs proliferate 3.5 times more than MMP-low in culture, further confirming the above results. These combined findings indicate that the subtle but reproducible and significant difference in cell cycle kinetics of MMP-low vs -high CD90+ HSCs translates into a pronounced difference in their functional potential.

These results support the notion that HSCs with higher mitochondrial activity are primed in their response to environmental cues and suggest that MMP may be used for selecting the most potent human HSC for bone marrow transplantation.

Example 13—CD74 in HCS

Figure 29:
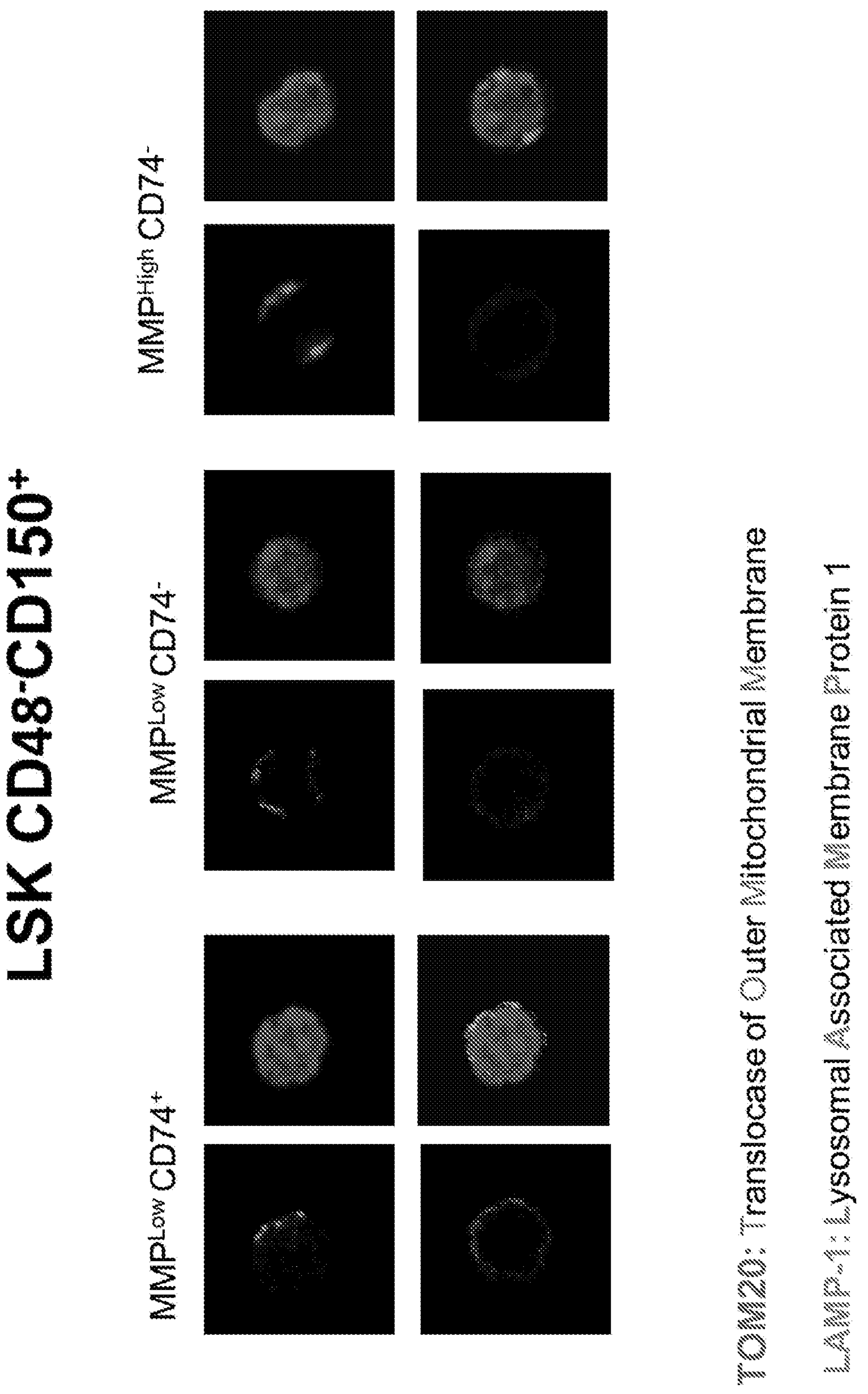
FIG. 29 shows CD74 expression identified subsets of highly potent HSCs (LSKCD150$^+$CD48$^-$, MMP-low) enriched in lysosomes. Mouse: MMP-low but not -high HSCs express CD74. MMP-low CD74+cells are enriched in lysosomes.
Figure 30:
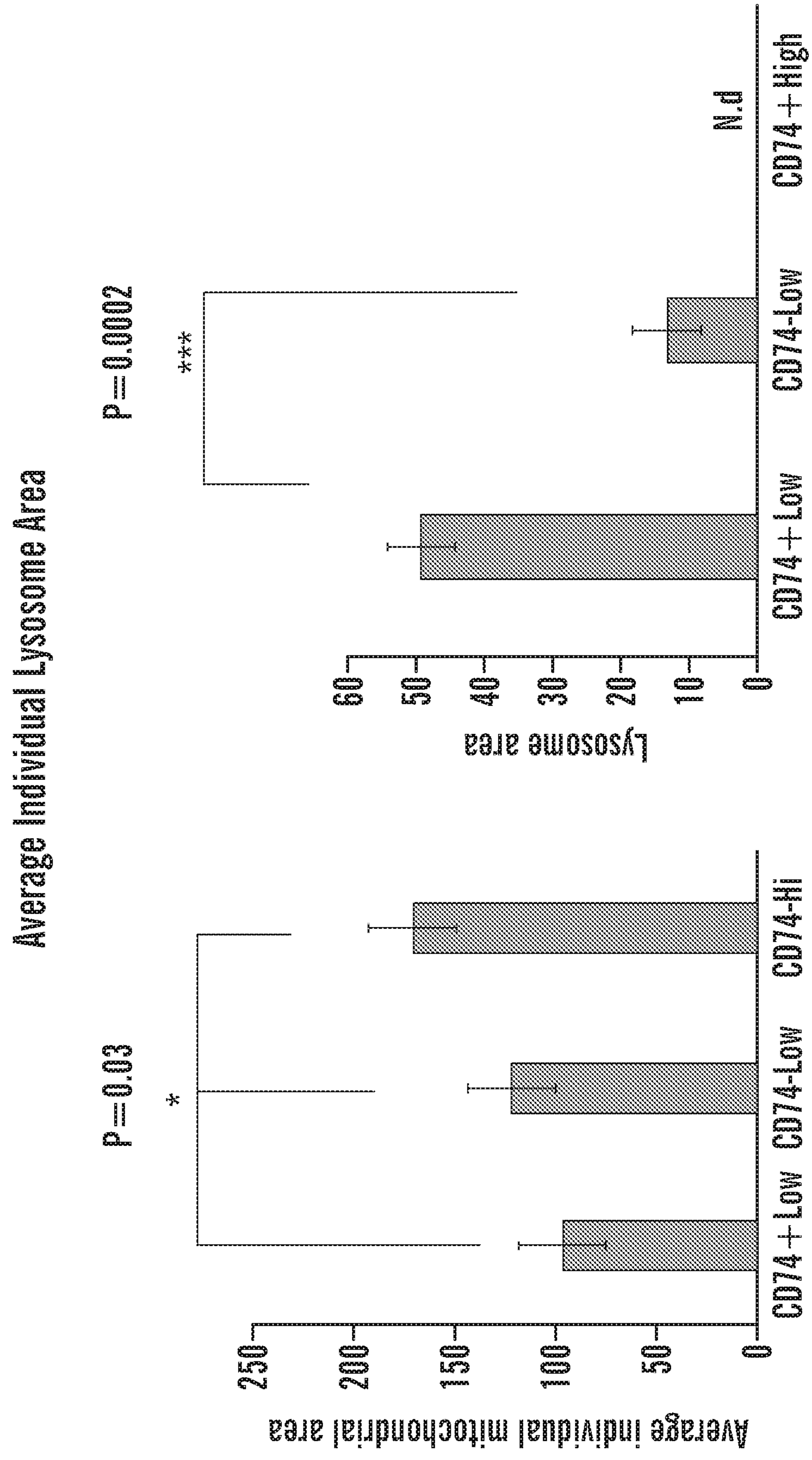
FIG. 30 shows that mouse lysosomes are highly enriched in MMP-low LSKCD150$^+$CD48$^-$CD74$^+$ HSCs. Note CD74$^+$ MMP-low are greatly enriched relative to CD74-MMP-low HSCs in lysosomes.
Figure 31:
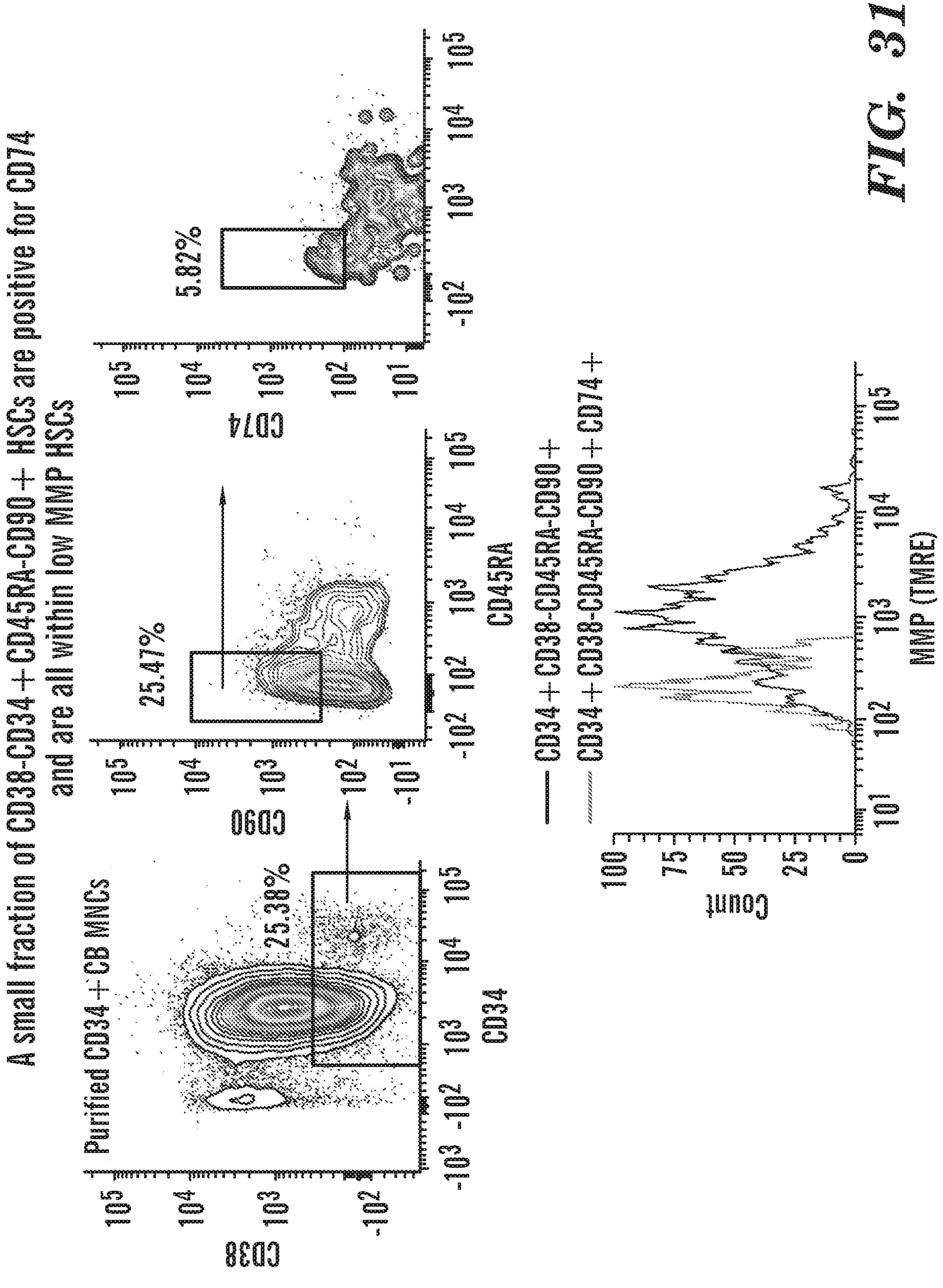
FIG. 31 shows the analysis of CD74 on a highly primitive HSC subset (CD34$^+$CD38$^-$CD45RA$^-$CD90$^+$). CD74 expression detects the most primitive subsets of human HSCs with low MMP levels.

Surprisingly, it was found that CD74, the invariant chain of MHC class II is expressed on a small subset of both mouse (FIGS. 29-30) and human (FIG. 31) HSCs with low MMP. CD74 is only expressed on MMP-low HSCs, suggesting that CD74 may be used as a marker to select for potent HSCs (FIGS. 29-31). CD74 is not expressed on primed MMP-high HSCs. In addition, CD74 expression on HSCs was found to select for a subset of MMP-low HSCs greatly enriched in lysosomes (FIGS. 29-30). These findings suggest that CD74 may be used for selecting lysosome-rich subsets of HSCs (and possibly other hematopoietic cells).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of culturing quiescent hematopoietic stem cells, said method comprising:

providing a serum-free culture medium comprising a vacuolar-H$^{+}$ adenosine triphosphate ATPase (v-ATPase) inhibitor;

introducing into the serum-free culture medium quiescent hematopoietic stem cells, wherein the stem cells are mitochondrial membrane potential (MMP)-low, lineage negative (Lin$^{-}$), stem cell antigen 1 positive (Sca$^{+}$), cKit$^{30}$ , Signaling Lymphocyte Activation Molecule 1 positive (CD150$^{+}$), and Signaling Lymphocyte Activation Molecule 2 negative (CD48$^{-}$) cells; and culturing the quiescent hematopoietic stem cells in the serum-free culture medium to produce cultured quiescent hematopoietic stem cells, wherein said culturing is effective to maintain and promote the quiescence of the cultured quiescent hematopoietic stem cells.

2. The method of claim 1, wherein the quiescent hematopoietic stem cells are mammalian stem cells.

3. The method of claim 1, wherein the quiescent hematopoietic stem cells are human stem cells.

4. The method of claim 1, wherein the quiescent hematopoietic stem cells are peripheral blood cells, cord blood cells, bone marrow cells, amniotic fluid cells, placental blood cells, aorta-gonad mesonephros (AGM), or mixtures thereof.

5. The method of claim 1, wherein the v-ATPase inhibitor is selected from the group consisting of bafilomycin A1, bafilomycin B1, bafilomycin C1, bafilomycin D, concanamycin A, concanamycin C, disulfiram, and combinations thereof.

6. The method of claim 1, wherein the culture medium further comprises a cytokine selected from the group consisting of stem cell factor (SCF), flk2/flt3 ligand (Flt3), thrombopoietin (TPO), interleukin-3 (IL3), and combinations thereof.

7. The method of claim 1, wherein at least 90% of the cultured quiescent hematopoietic stem cells are in Go phase.

8. The method of claim 1, wherein at least 99% of the cultured quiescent hematopoietic stem cells are in $G_0$ phase.

9. The method of claim 1, wherein the hematopoietic stem cells are human umbilical cord blood hematopoietic stem cells.

10. The method of claim 9, wherein the v-ATPase inhibitor is concanamycin A.

11. The method of claim 1, wherein the hematopoietic stem cells are human peripheral blood hematopoietic stem cells.

12. The method of claim 11, wherein the v-ATPase inhibitor is concanamycin A.

13. The method of claim 1, wherein the hematopoietic stem cells are human bone marrow hematopoietic stem cells.

14. The method of claim 13, wherein the v-ATPase inhibitor is concanamycin A.

15. The method of claim 1, wherein said culturing increases the percentage of cultured hematopoietic stem cells in $G_0$ phase.

16. The method of claim 1, wherein the v-ATPase inhibitor is concanamycin A.

* * * * *